US009555191B2

(12) United States Patent
Edwards et al.

(10) Patent No.: US 9,555,191 B2
(45) Date of Patent: Jan. 31, 2017

(54) APPARATUS AND METHODS FOR SELF-ADMINISTRATION OF VACCINES AND OTHER MEDICAMENTS

(71) Applicant: kaleo, Inc., Richmond, VA (US)

(72) Inventors: Eric S. Edwards, Moseley, VA (US); Evan T. Edwards, Charlottesville, VA (US); Mark J. Licata, Doswell, VA (US); Paul F. Meyers, Fishers, IN (US); David A. Weinzierl, Andover, MN (US)

(73) Assignee: kaleo, Inc., Richmond, VA (US)

( * ) Notice: Subject to any disclaimer, the term of this patent is extended or adjusted under 35 U.S.C. 154(b) by 0 days.

(21) Appl. No.: 15/044,337

(22) Filed: Feb. 16, 2016

(65) Prior Publication Data

US 2016/0166768 A1    Jun. 16, 2016

Related U.S. Application Data

(63) Continuation of application No. 13/748,733, filed on Jan. 24, 2013, now abandoned, which is a continuation
(Continued)

(51) Int. Cl.
*G06F 19/00* (2011.01)
*A61M 5/20* (2006.01)
(Continued)

(52) U.S. Cl.
CPC ........... *A61M 5/2033* (2013.01); *A61M 5/002* (2013.01); *A61M 5/19* (2013.01); *A61M 5/2053* (2013.01);
(Continued)

(58) Field of Classification Search
CPC .................. G07F 17/0092; G06F 19/3462
See application file for complete search history.

(56) References Cited

U.S. PATENT DOCUMENTS

| | | |
|---|---|---|
| 2,960,087 A | 11/1960 | Uytenbogaart |
| 3,055,362 A | 9/1962 | Uytenbogaart |

(Continued)

FOREIGN PATENT DOCUMENTS

| | | |
|---|---|---|
| AU | 2004231230 | 6/2006 |
| EP | 1043037 A2 | 10/2000 |

(Continued)

OTHER PUBLICATIONS

"Solutions for Medical Devices," 3M Brochure, ©3M, (2006), 80/6201-3490-0, 8 pages.
(Continued)

*Primary Examiner* — Timothy Waggoner

(57) ABSTRACT

A medicament delivery device includes a housing, a medicament container disposed within the housing, an activation mechanism, a cover and an electronic circuit system. The activation mechanism includes an energy storage member configured to produce a force to deliver the dose of a medicament and/or vaccine. The cover is configured to receive at least a portion of the housing. The electronic circuit system is coupled to the housing such that a protrusion of the cover electrically isolates a battery from a portion of the electronic circuit system when the portion of the housing is received by the cover. The electronic circuit system is configured to be electrically coupled to the battery and to produce a recorded speech output when the portion of the housing is at least partially removed from the cover. The electronic circuit system configured to produce a signal when the activation mechanism is actuated.

24 Claims, 67 Drawing Sheets

Related U.S. Application Data of application No. 12/615,636, filed on Nov. 10, 2009, now Pat. No. 8,361,026, and a continuation-in-part of application No. 12/017,405, filed on Jan. 22, 2008, now Pat. No. 8,226,610, which is a continuation-in-part of application No. 11/671,025, filed on Feb. 5, 2007, now Pat. No. 8,172,082.

(60) Provisional application No. 61/113,368, filed on Nov. 11, 2008.

(51) Int. Cl.

| | | |
|---|---|---|
| *A61M 5/00* | (2006.01) | |
| *A61M 5/19* | (2006.01) | |
| *A61M 5/32* | (2006.01) | |
| *A61M 15/00* | (2006.01) | |
| *A61M 5/50* | (2006.01) | |
| *A61M 5/315* | (2006.01) | |
| *A61M 5/24* | (2006.01) | |
| *A61M 5/31* | (2006.01) | |

(52) U.S. Cl.
CPC ....... *A61M 5/31525* (2013.01); *A61M 5/3202* (2013.01); *A61M 5/5086* (2013.01); *A61M 15/009* (2013.01); *A61M 15/0025* (2014.02); *G06F 19/3468* (2013.01); *A61M 5/24* (2013.01); *A61M 5/2448* (2013.01); *A61M 5/3129* (2013.01); *A61M 5/3204* (2013.01); *A61M 5/326* (2013.01); *A61M 2005/206* (2013.01); *A61M 2005/2013* (2013.01); *A61M 2005/2026* (2013.01); *A61M 2205/13* (2013.01); *A61M 2205/14* (2013.01); *A61M 2205/18* (2013.01); *A61M 2205/332* (2013.01); *A61M 2205/3317* (2013.01); *A61M 2205/3368* (2013.01); *A61M 2205/3553* (2013.01); *A61M 2205/3561* (2013.01); *A61M 2205/3569* (2013.01); *A61M 2205/3576* (2013.01); *A61M 2205/3592* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/583* (2013.01); *A61M 2205/6018* (2013.01); *A61M 2205/6036* (2013.01); *A61M 2205/8206* (2013.01); *A61M 2209/01* (2013.01); *A61M 2209/086* (2013.01)

(56) References Cited

U.S. PATENT DOCUMENTS

| | | | |
|---|---|---|---|
| 3,115,133 A | | 12/1963 | Morando |
| 3,426,448 A | | 2/1969 | Sarnoff |
| 3,688,765 A | | 9/1972 | Gasaway |
| 3,768,472 A | | 10/1973 | Hodosh et al. |
| 3,795,061 A | | 3/1974 | Sarnoff et al. |
| 3,945,379 A | | 3/1976 | Pritz et al. |
| 4,108,177 A | | 8/1978 | Pistor |
| 4,149,394 A | | 4/1979 | Sornes |
| 4,186,741 A | | 2/1980 | Cesaro |
| 4,226,235 A | | 10/1980 | Sarnoff et al. |
| 4,360,019 A | | 11/1982 | Portner et al. |
| 4,424,057 A | | 1/1984 | House |
| 4,441,629 A | | 4/1984 | Mackal |
| 4,484,910 A | | 11/1984 | Sarnoff |
| 4,524,243 A | | 6/1985 | Shapiro |
| 4,573,976 A | | 3/1986 | Sampson et al. |
| 4,596,556 A | | 6/1986 | Morrow et al. |
| 4,610,666 A | | 9/1986 | Pizzino |
| 4,613,328 A | | 9/1986 | Boyd |
| 4,617,557 A | | 10/1986 | Gordon |
| 4,624,660 A | | 11/1986 | Mijers et al. |
| 4,640,686 A | | 2/1987 | Dalling et al. |
| 4,643,721 A | | 2/1987 | Brunet |
| 4,666,430 A | | 5/1987 | Brown et al. |
| 4,673,657 A | | 6/1987 | Christian |
| 4,689,042 A | | 8/1987 | Sarnoff et al. |
| 4,693,708 A | | 9/1987 | Wanderer et al. |
| 4,781,697 A | | 11/1988 | Slaughter |
| 4,782,841 A | | 11/1988 | Lopez |
| 4,784,652 A | | 11/1988 | Wikstrom |
| 4,795,433 A | | 1/1989 | Sarnoff |
| 4,822,340 A | | 4/1989 | Kamstra |
| 4,826,489 A | | 5/1989 | Haber |
| 4,853,521 A | | 8/1989 | Claeys et al. |
| 4,865,582 A | | 9/1989 | Sibalis |
| 4,874,382 A | | 10/1989 | Lindemann et al. |
| 4,894,054 A | | 1/1990 | Miskinyar |
| 4,906,235 A | | 3/1990 | Roberts |
| 4,915,695 A | | 4/1990 | Koobs |
| 4,941,880 A | | 7/1990 | Burns |
| 4,959,056 A | | 9/1990 | Dombrowski et al. |
| 4,968,302 A | | 11/1990 | Schluter et al. |
| 4,983,164 A | | 1/1991 | Hook et al. |
| 5,000,736 A | | 3/1991 | Kaufhold, Jr. et al. |
| 5,024,656 A | | 6/1991 | Gasaway et al. |
| 5,037,306 A | | 8/1991 | van Schoonhoven |
| 5,038,023 A | | 8/1991 | Saliga |
| 5,041,088 A | | 8/1991 | Ritson et al. |
| 5,062,603 A | | 11/1991 | Smith et al. |
| 5,064,413 A | | 11/1991 | McKinnon et al. |
| 5,071,353 A | | 12/1991 | van der Wal |
| 5,085,642 A | | 2/1992 | Sarnoff et al. |
| 5,092,843 A | | 3/1992 | Monroe et al. |
| 5,125,898 A | | 6/1992 | Kaufhold, Jr. et al. |
| 5,167,625 A | | 12/1992 | Jacobsen et al. |
| 5,167,641 A | | 12/1992 | Schmitz |
| 5,199,949 A | | 4/1993 | Haber et al. |
| 5,224,936 A | | 7/1993 | Gallagher |
| 5,240,146 A | | 8/1993 | Smedley et al. |
| 5,281,198 A | | 1/1994 | Haber et al. |
| 5,286,258 A | | 2/1994 | Haber et al. |
| 5,298,023 A | | 3/1994 | Haber et al. |
| 5,312,326 A | | 5/1994 | Myers et al. |
| 5,314,412 A | | 5/1994 | Rex |
| 5,314,502 A | | 5/1994 | McNichols et al. |
| 5,343,519 A | | 8/1994 | Feldman |
| 5,344,407 A | | 9/1994 | Ryan |
| 5,354,284 A | | 10/1994 | Haber et al. |
| 5,356,376 A | | 10/1994 | Milijasevic et al. |
| 5,363,842 A | | 11/1994 | Mishelevich et al. |
| 5,380,281 A | | 1/1995 | Tomellini et al. |
| 5,383,851 A | | 1/1995 | McKinnon, Jr. et al. |
| 5,394,866 A | | 3/1995 | Ritson et al. |
| 5,399,163 A | | 3/1995 | Peterson et al. |
| 5,405,362 A | | 4/1995 | Kramer et al. |
| 5,417,660 A | | 5/1995 | Martin |
| 5,466,217 A | | 11/1995 | Myers et al. |
| 5,505,192 A | | 4/1996 | Samiotes et al. |
| 5,514,135 A | | 5/1996 | Earle |
| 5,558,679 A | | 9/1996 | Tuttle |
| 5,567,160 A | | 10/1996 | Massino |
| 5,568,555 A | | 10/1996 | Shamir |
| 5,569,192 A | | 10/1996 | van der Wal |
| 5,584,815 A | | 12/1996 | Pawelka et al. |
| 5,615,771 A | | 4/1997 | Hollister |
| 5,616,132 A | | 4/1997 | Newman |
| 5,642,731 A | * | 7/1997 | Kehr ..................... A61J 7/0481 600/300 |
| 5,645,534 A | | 7/1997 | Chanoch |
| 5,662,612 A | | 9/1997 | Niehoff |
| 5,681,291 A | | 10/1997 | Galli |
| 5,692,492 A | | 12/1997 | Bruna et al. |
| 5,695,476 A | | 12/1997 | Harris |
| 5,697,916 A | | 12/1997 | Schraga |
| 5,716,338 A | | 2/1998 | Hjertman et al. |
| 5,728,074 A | | 3/1998 | Castellano et al. |
| 5,740,794 A | | 4/1998 | Smith et al. |
| 5,752,235 A | * | 5/1998 | Kehr ..................... A61J 7/0481 340/309.4 |

(56) References Cited

U.S. PATENT DOCUMENTS

| | | |
|---|---|---|
| 5,772,635 A | 6/1998 | Dastur et al. |
| 5,792,190 A | 8/1998 | Olson et al. |
| 5,800,397 A | 9/1998 | Wilson et al. |
| 5,805,423 A | 9/1998 | Wever et al. |
| 5,809,997 A | 9/1998 | Wolf |
| 5,813,397 A | 9/1998 | Goodman et al. |
| 5,814,020 A | 9/1998 | Gross |
| 5,823,346 A | 10/1998 | Weiner |
| 5,823,363 A | 10/1998 | Cassel |
| 5,832,488 A | 11/1998 | Eberhardt |
| 5,837,546 A | 11/1998 | Allen et al. |
| RE35,986 E | 12/1998 | Ritson et al. |
| 5,846,089 A | 12/1998 | Weiss et al. |
| 5,848,988 A | 12/1998 | Davis |
| 5,852,590 A | 12/1998 | de la Huerga |
| 5,853,292 A | 12/1998 | Eggert et al. |
| 5,868,713 A | 2/1999 | Klippenstein |
| 5,868,721 A | 2/1999 | Marinacci |
| D407,487 S | 3/1999 | Greubel et al. |
| 5,905,653 A | 5/1999 | Higham et al. |
| 5,925,021 A | 7/1999 | Castellano et al. |
| 5,928,195 A | 7/1999 | Malamud |
| 5,941,857 A | 8/1999 | Nguyen et al. |
| 5,954,641 A * | 9/1999 | Kehr .................. A61B 5/0002 128/920 |
| 5,964,739 A | 10/1999 | Champ |
| 5,970,457 A | 10/1999 | Brant et al. |
| 5,971,953 A | 10/1999 | Bachynsky |
| 5,991,655 A | 11/1999 | Gross et al. |
| 6,015,438 A | 1/2000 | Shaw |
| 6,030,363 A | 2/2000 | Kriesel |
| 6,039,713 A | 3/2000 | Botich et al. |
| 6,045,534 A | 4/2000 | Jacobsen et al. |
| 6,062,901 A | 5/2000 | Liu et al. |
| 6,063,053 A | 5/2000 | Castellano et al. |
| 6,074,213 A | 6/2000 | Hon |
| 6,077,106 A | 6/2000 | Mish |
| 6,084,526 A | 7/2000 | Blotky et al. |
| 6,086,562 A | 7/2000 | Jacobsen et al. |
| 6,096,002 A | 8/2000 | Landau |
| 6,099,504 A | 8/2000 | Gross et al. |
| 6,102,896 A | 8/2000 | Roser |
| 6,119,684 A | 9/2000 | Nöhl et al. |
| 6,149,626 A | 11/2000 | Rachynsky et al. |
| 6,158,613 A | 12/2000 | Novosel et al. |
| 6,161,281 A | 12/2000 | Dando et al. |
| 6,165,155 A | 12/2000 | Jacobsen et al. |
| 6,175,752 B1 | 1/2001 | Say |
| 6,179,812 B1 | 1/2001 | Botich et al. |
| 6,190,326 B1 | 2/2001 | McKinnon et al. |
| 6,192,891 B1 | 2/2001 | Gravel et al. |
| 6,193,695 B1 | 2/2001 | Rippstein, Jr. |
| 6,202,642 B1 | 3/2001 | McKinnon et al. |
| 6,210,359 B1 | 4/2001 | Patel et al. |
| 6,210,369 B1 | 4/2001 | Wilmot et al. |
| 6,219,587 B1 | 4/2001 | Ahlin et al. |
| 6,221,045 B1 | 4/2001 | Duchon et al. |
| 6,221,055 B1 | 4/2001 | Shaw et al. |
| 6,245,046 B1 | 6/2001 | Sibbitt |
| 6,249,717 B1 | 6/2001 | Nicholson et al. |
| 6,258,063 B1 | 7/2001 | Haar et al. |
| 6,259,654 B1 | 7/2001 | de la Huerga |
| 6,264,629 B1 | 7/2001 | Landau |
| 6,270,455 B1 | 8/2001 | Brown |
| 6,284,765 B1 | 9/2001 | Caffrey |
| 6,285,757 B1 | 9/2001 | Carroll et al. |
| 6,312,412 B1 | 11/2001 | Saied et al. |
| 6,317,630 B1 | 11/2001 | Gross et al. |
| 6,321,654 B1 | 11/2001 | Robinson |
| 6,334,070 B1 | 12/2001 | Nova et al. |
| 6,364,866 B1 | 4/2002 | Furr et al. |
| 6,371,939 B2 | 4/2002 | Bergens et al. |
| 6,377,848 B1 | 4/2002 | Garde et al. |
| 6,387,078 B1 | 5/2002 | Gillespie, III |
| 6,398,760 B1 | 6/2002 | Danby |
| 6,405,912 B2 | 6/2002 | Giannou |
| 6,411,567 B1 | 6/2002 | Niemiec et al. |
| 6,413,236 B1 | 7/2002 | Van Dyke |
| 6,425,897 B2 | 7/2002 | Overes et al. |
| 6,428,517 B1 | 8/2002 | Hochman et al. |
| 6,428,528 B2 | 8/2002 | Sadowski |
| 6,475,181 B1 | 11/2002 | Potter et al. |
| 6,478,769 B1 | 11/2002 | Parker |
| 6,478,771 B1 | 11/2002 | Lavi et al. |
| 6,482,185 B1 | 11/2002 | Hartmann |
| 6,494,863 B1 | 12/2002 | Shaw et al. |
| 6,500,150 B1 | 12/2002 | Gross et al. |
| 6,514,230 B1 | 2/2003 | Munk et al. |
| 6,529,446 B1 * | 3/2003 | de la Huerga ........ A61J 7/0084 368/10 |
| 6,530,900 B1 | 3/2003 | Daily et al. |
| 6,530,904 B1 | 3/2003 | Edwards et al. |
| 6,535,714 B2 | 3/2003 | Melker et al. |
| 6,539,281 B2 * | 3/2003 | Wan ..................... G07F 9/026 700/236 |
| 6,540,672 B1 | 4/2003 | Simonsen et al. |
| 6,540,675 B2 | 4/2003 | Aceti et al. |
| 6,544,234 B1 | 4/2003 | Gabriel |
| 6,551,276 B1 | 4/2003 | Mann et al. |
| 6,551,298 B1 | 4/2003 | Zhang |
| 6,554,798 B1 | 4/2003 | Mann et al. |
| 6,558,320 B1 | 5/2003 | Causey, III et al. |
| 6,560,471 B1 | 5/2003 | Heller |
| 6,565,533 B1 | 5/2003 | Smith et al. |
| 6,569,123 B2 | 5/2003 | Alchas |
| 6,572,584 B1 | 6/2003 | Shaw et al. |
| 6,574,166 B2 | 6/2003 | Niemiec |
| 6,575,939 B1 | 6/2003 | Brunel |
| RE38,189 E | 7/2003 | Walker et al. |
| 6,585,685 B2 | 7/2003 | Staylor et al. |
| 6,585,698 B1 | 7/2003 | Packman et al. |
| 6,589,158 B2 | 7/2003 | Winkler |
| 6,595,956 B1 | 7/2003 | Gross et al. |
| 6,633,796 B1 | 10/2003 | Pool et al. |
| 6,641,566 B2 | 11/2003 | Douglas et al. |
| 6,645,181 B1 | 11/2003 | Lavi et al. |
| 6,648,850 B2 | 11/2003 | Landau |
| 6,659,980 B2 | 12/2003 | Moberg et al. |
| 6,676,630 B2 | 1/2004 | Landau et al. |
| 6,679,862 B2 | 1/2004 | Diaz et al. |
| 6,689,093 B2 | 2/2004 | Landau |
| 6,702,778 B2 | 3/2004 | Hill et al. |
| 6,707,763 B2 | 3/2004 | Osberg et al. |
| 6,708,050 B2 | 3/2004 | Carim |
| 6,722,916 B2 | 4/2004 | Buccinna et al. |
| 6,723,077 B2 | 4/2004 | Pickup et al. |
| 6,726,661 B2 | 4/2004 | Munk et al. |
| 6,736,796 B2 | 5/2004 | Shekalim |
| 6,743,635 B2 | 6/2004 | Neel et al. |
| 6,749,437 B2 | 6/2004 | Chan |
| 6,752,781 B2 | 6/2004 | Landau et al. |
| 6,767,336 B1 | 7/2004 | Kaplan |
| 6,770,052 B2 | 8/2004 | Hill et al. |
| 6,770,056 B2 | 8/2004 | Price et al. |
| 6,783,509 B1 | 8/2004 | Landau et al. |
| 6,786,875 B2 | 9/2004 | Barker et al. |
| 6,786,885 B2 | 9/2004 | Hochman et al. |
| 6,793,646 B1 | 9/2004 | Giambattista et al. |
| 6,803,856 B1 | 10/2004 | Murphy et al. |
| 6,805,686 B1 | 10/2004 | Fathallah et al. |
| 6,808,514 B2 | 10/2004 | Schneider et al. |
| 6,809,653 B1 | 10/2004 | Mann et al. |
| 6,817,986 B2 | 11/2004 | Slate et al. |
| 6,830,560 B1 | 12/2004 | Gross et al. |
| 6,839,304 B2 | 1/2005 | Niemiec et al. |
| 6,872,200 B2 | 3/2005 | Mann et al. |
| 6,875,195 B2 | 4/2005 | Choi |
| 6,883,222 B2 | 4/2005 | Landau |
| 6,923,764 B2 | 8/2005 | Aceti et al. |
| 6,936,029 B2 | 8/2005 | Mann et al. |
| 6,937,150 B2 | 8/2005 | Medema et al. |
| 6,942,646 B2 | 9/2005 | Langley et al. |
| 6,946,299 B2 | 9/2005 | Neel et al. |
| 6,949,082 B2 | 9/2005 | Langley et al. |

(56) References Cited

U.S. PATENT DOCUMENTS

| | | |
|---|---|---|
| 6,950,028 B2 | 9/2005 | Zweig |
| 6,952,604 B2 | 10/2005 | DeNuzzio et al. |
| 6,953,445 B2 | 10/2005 | Wilmot et al. |
| 6,953,693 B2 | 10/2005 | Neel et al. |
| 6,958,691 B1 | 10/2005 | Anderson et al. |
| 6,959,247 B2 | 10/2005 | Neel et al. |
| 6,961,285 B2 | 11/2005 | Niemiec et al. |
| 6,964,650 B2 | 11/2005 | Alexandre et al. |
| 6,969,259 B2 | 11/2005 | Pastrick et al. |
| 6,979,316 B1 | 12/2005 | Rubin et al. |
| 6,979,326 B2 | 12/2005 | Mann et al. |
| 6,985,870 B2 | 1/2006 | Martucci et al. |
| 6,997,911 B2 | 2/2006 | Klitmose |
| 7,014,470 B2 | 3/2006 | Vann |
| 7,048,141 B2 | 5/2006 | Abdulhay |
| 7,072,738 B2 | 7/2006 | Bonney et al. |
| 7,093,595 B2 | 8/2006 | Nesbitt |
| 7,102,526 B2 | 9/2006 | Zweig |
| 7,104,972 B2 | 9/2006 | Moller et al. |
| 7,113,101 B2 | 9/2006 | Petersen et al. |
| 7,116,233 B2 | 10/2006 | Zhurin |
| 7,126,879 B2 | 10/2006 | Snyder |
| 7,158,011 B2 | 1/2007 | Brue |
| 7,191,916 B2 | 3/2007 | Clifford et al. |
| 7,229,458 B2 | 6/2007 | Boecker et al. |
| 7,278,983 B2 | 10/2007 | Ireland et al. |
| 7,287,031 B1 | 10/2007 | Karpf |
| 7,299,981 B2 | 11/2007 | Hickle et al. |
| 7,343,914 B2 | 3/2008 | Abrams et al. |
| 7,351,223 B2 | 4/2008 | Call |
| 7,416,540 B2 | 8/2008 | Edwards et al. |
| 7,469,213 B1 | 12/2008 | Rao |
| 7,544,188 B2 | 6/2009 | Edwards et al. |
| 7,630,788 B1 | 12/2009 | Reese |
| 7,648,482 B2 | 1/2010 | Edwards et al. |
| 7,648,483 B2 | 1/2010 | Edwards et al. |
| 7,670,328 B2 | 3/2010 | Miller et al. |
| 7,674,246 B2 | 3/2010 | Gillespie et al. |
| 7,689,318 B2 | 3/2010 | Draper |
| 7,731,686 B2 | 6/2010 | Edwards et al. |
| 7,731,690 B2 | 6/2010 | Edwards et al. |
| 7,749,194 B2 | 7/2010 | Edwards et al. |
| 7,806,866 B2 | 10/2010 | Hommann et al. |
| 7,871,393 B2 | 1/2011 | Monroe |
| 7,938,802 B2 | 5/2011 | Bicknell et al. |
| 7,947,017 B2 | 5/2011 | Edwards et al. |
| 7,996,106 B2 | 8/2011 | Ervin |
| 8,021,344 B2 | 9/2011 | Edwards et al. |
| 8,099,301 B2 | 1/2012 | Keresman |
| 8,123,719 B2 | 2/2012 | Edwards et al. |
| 8,149,111 B2 | 4/2012 | Monroe |
| 8,172,082 B2 | 5/2012 | Edwards et al. |
| 8,206,360 B2 | 6/2012 | Edwards et al. |
| 8,212,658 B2 | 7/2012 | Monroe |
| 8,226,610 B2 | 7/2012 | Edwards et al. |
| 8,231,573 B2 | 7/2012 | Edwards et al. |
| 8,424,517 B2 | 4/2013 | Sutherland et al. |
| 8,544,645 B2 | 10/2013 | Edwards et al. |
| 8,556,865 B2 | 10/2013 | Krulevitch et al. |
| 8,556,867 B2 | 10/2013 | Krulevitch et al. |
| 8,622,973 B2 | 1/2014 | Edwards et al. |
| 8,627,816 B2 | 1/2014 | Edwards et al. |
| 8,670,865 B2 | 3/2014 | Coe |
| 8,690,827 B2 | 4/2014 | Edwards et al. |
| 8,751,039 B1 | 6/2014 | Macoviak et al. |
| 8,789,748 B2 | 7/2014 | Waugh et al. |
| 8,849,449 B2 | 9/2014 | Waugh et al. |
| 8,899,987 B2 | 12/2014 | Edwards et al. |
| 8,926,594 B2 | 1/2015 | Edwards et al. |
| 8,932,252 B2 | 1/2015 | Edwards et al. |
| 8,939,943 B2 | 1/2015 | Edwards et al. |
| 9,022,980 B2 | 5/2015 | Edwards et al. |
| 9,084,849 B2 | 7/2015 | Edwards et al. |
| 9,173,999 B2 | 11/2015 | Edwards et al. |
| 2001/0005781 A1 | 6/2001 | Bergens et al. |
| 2002/0072784 A1 | 6/2002 | Sheppard, Jr. et al. |
| 2002/0074345 A1 | 6/2002 | Schneider et al. |
| 2002/0076679 A1 | 6/2002 | Aman |
| 2002/0090601 A1 | 7/2002 | Strupat et al. |
| 2002/0096543 A1 | 7/2002 | Juselius |
| 2002/0169439 A1 | 11/2002 | Flaherty |
| 2002/0183721 A1 | 12/2002 | Santini, Jr. et al. |
| 2003/0028145 A1 | 2/2003 | Duchon et al. |
| 2003/0040717 A1 | 2/2003 | Saulenas et al. |
| 2003/0060765 A1 | 3/2003 | Campbell et al. |
| 2003/0106824 A1 | 6/2003 | Wilmot et al. |
| 2003/0120212 A1 | 6/2003 | Dedig et al. |
| 2003/0130853 A1 | 7/2003 | Maire |
| 2003/0132128 A1 | 7/2003 | Mazur |
| 2003/0135388 A1 | 7/2003 | Martucci et al. |
| 2003/0171717 A1 | 9/2003 | Farrugia et al. |
| 2003/0233070 A1 | 12/2003 | De La Serna et al. |
| 2004/0015125 A1 | 1/2004 | Alexandre et al. |
| 2004/0019326 A1 | 1/2004 | Gilbert et al. |
| 2004/0039336 A1 | 2/2004 | Amark et al. |
| 2004/0039337 A1 | 2/2004 | Letzing |
| 2004/0039368 A1 | 2/2004 | Reilly et al. |
| 2004/0042596 A1 | 3/2004 | Kim et al. |
| 2004/0054327 A1 | 3/2004 | Gillespie, III |
| 2004/0069667 A1 | 4/2004 | Tomellini et al. |
| 2004/0078001 A1 | 4/2004 | Langley et al. |
| 2004/0116854 A1 | 6/2004 | Abulhaj et al. |
| 2004/0138611 A1 | 7/2004 | Griffiths et al. |
| 2004/0143298 A1 | 7/2004 | Nova et al. |
| 2004/0159364 A1 | 8/2004 | Landau et al. |
| 2004/0164146 A1 | 8/2004 | Rosenblum |
| 2004/0210199 A1 | 10/2004 | Atterbury et al. |
| 2004/0215369 A1 | 10/2004 | Rosenblum |
| 2004/0220524 A1 | 11/2004 | Sadowski et al. |
| 2004/0225255 A1 | 11/2004 | Ono |
| 2004/0249358 A1 | 12/2004 | McWethy et al. |
| 2004/0267204 A1 | 12/2004 | Brustowicz |
| 2005/0020969 A1 | 1/2005 | Slate et al. |
| 2005/0027255 A1 | 2/2005 | Lavi et al. |
| 2005/0033234 A1 | 2/2005 | Sadowski et al. |
| 2005/0033386 A1 | 2/2005 | Osborn et al. |
| 2005/0055014 A1 | 3/2005 | Coppeta et al. |
| 2005/0062603 A1 | 3/2005 | Fuerst et al. |
| 2005/0088289 A1 | 4/2005 | Rochkind |
| 2005/0090781 A1 | 4/2005 | Baba et al. |
| 2005/0134433 A1 | 6/2005 | Sweeney, II |
| 2005/0137530 A1 | 6/2005 | Campbell et al. |
| 2005/0148931 A1 | 7/2005 | Juhasz |
| 2005/0148945 A1 | 7/2005 | Chen |
| 2005/0150488 A1 | 7/2005 | Dave |
| 2005/0159705 A1 | 7/2005 | Crawford et al. |
| 2005/0165360 A1 | 7/2005 | Stamp |
| 2005/0168337 A1 | 8/2005 | Mahoney |
| 2005/0171477 A1 | 8/2005 | Rubin et al. |
| 2005/0182358 A1 | 8/2005 | Veit et al. |
| 2005/0183982 A1 | 8/2005 | Giewercer |
| 2005/0186221 A1 | 8/2005 | Reynolds et al. |
| 2005/0192530 A1 | 9/2005 | Castellano |
| 2005/0197654 A1 | 9/2005 | Edman et al. |
| 2005/0209569 A1 | 9/2005 | Ishikawa et al. |
| 2005/0261742 A1 | 11/2005 | Nova et al. |
| 2005/0267403 A1 | 12/2005 | Landau et al. |
| 2005/0277891 A1 | 12/2005 | Sibbitt |
| 2006/0030819 A1 | 2/2006 | Young et al. |
| 2006/0053036 A1 | 3/2006 | Coffman et al. |
| 2006/0058848 A1 | 3/2006 | Piraino et al. |
| 2006/0074519 A1 | 4/2006 | Barker et al. |
| 2006/0089592 A1 | 4/2006 | Kadhiresan et al. |
| 2006/0111666 A1 | 5/2006 | Hommann et al. |
| 2006/0111671 A1 | 5/2006 | Klippenstein |
| 2006/0116639 A1 | 6/2006 | Russell |
| 2006/0129090 A1 | 6/2006 | Moberg et al. |
| 2006/0169611 A1 | 8/2006 | Prindle |
| 2006/0189938 A1 | 8/2006 | Hommann et al. |
| 2006/0200077 A1 | 9/2006 | Righi et al. |
| 2006/0204939 A1 | 9/2006 | Bardsley et al. |
| 2006/0247578 A1 | 11/2006 | Arguedas et al. |
| 2006/0247579 A1 | 11/2006 | Friedman |
| 2006/0265186 A1 | 11/2006 | Holland et al. |

(56) References Cited

U.S. PATENT DOCUMENTS

| | | |
|---|---|---|
| 2007/0008113 A1 | 1/2007 | Spoonhower et al. |
| 2007/0074722 A1 | 4/2007 | Giroux et al. |
| 2007/0094048 A1 | 4/2007 | Grichnik |
| 2007/0111175 A1 | 5/2007 | Raven et al. |
| 2007/0129686 A1 | 6/2007 | Daily et al. |
| 2007/0135767 A1 | 6/2007 | Gillespie et al. |
| 2007/0149954 A1 | 6/2007 | Hood et al. |
| 2007/0184847 A1 | 8/2007 | Hansen et al. |
| 2007/0185053 A1 | 8/2007 | Linn |
| 2007/0186923 A1* | 8/2007 | Poutiatine ............ A61J 7/0038 128/200.14 |
| 2007/0203247 A1 | 8/2007 | Phillips et al. |
| 2007/0210147 A1 | 9/2007 | Morrone et al. |
| 2007/0213598 A1 | 9/2007 | Howard et al. |
| 2007/0233001 A1 | 10/2007 | Burroughs et al. |
| 2007/0239116 A1 | 10/2007 | Follman et al. |
| 2007/0239140 A1 | 10/2007 | Chechelski et al. |
| 2007/0260210 A1 | 11/2007 | Conroy |
| 2007/0260480 A1 | 11/2007 | Cederlund |
| 2007/0271117 A1 | 11/2007 | Klein |
| 2007/0285238 A1 | 12/2007 | Batra |
| 2007/0293826 A1 | 12/2007 | Wall et al. |
| 2008/0097311 A1 | 4/2008 | Dacquay et al. |
| 2008/0111685 A1 | 5/2008 | Olson et al. |
| 2008/0160492 A1 | 7/2008 | Campbell et al. |
| 2008/0230057 A1 | 9/2008 | Sutherland |
| 2009/0030285 A1 | 1/2009 | Andersen |
| 2009/0062728 A1 | 3/2009 | Woo |
| 2009/0131875 A1 | 5/2009 | Green |
| 2009/0143761 A1 | 6/2009 | Cantor et al. |
| 2009/0176834 A1 | 7/2009 | Kottayil et al. |
| 2009/0194104 A1 | 8/2009 | Van Sickle |
| 2009/0240200 A1 | 9/2009 | Heneveld et al. |
| 2010/0111066 A1 | 5/2010 | Mehta |
| 2010/0160894 A1 | 6/2010 | Julian et al. |
| 2010/0169111 A1 | 7/2010 | Brue et al. |
| 2010/0185148 A1 | 7/2010 | Gillespie, III et al. |
| 2010/0192948 A1 | 8/2010 | Sutherland et al. |
| 2010/0211005 A1 | 8/2010 | Edwards et al. |
| 2010/0250280 A1 | 9/2010 | Sutherland |
| 2010/0268303 A1 | 10/2010 | Mitchell et al. |
| 2010/0286612 A1 | 11/2010 | Cirillo |
| 2011/0046698 A1 | 2/2011 | Kivi et al. |
| 2011/0144574 A1 | 6/2011 | Kamen et al. |
| 2011/0264033 A1 | 10/2011 | Jensen et al. |
| 2011/0295215 A1 | 12/2011 | Nielsen et al. |
| 2012/0015335 A1 | 1/2012 | Smith et al. |
| 2012/0046613 A1 | 2/2012 | Plumptre |
| 2012/0052837 A1 | 3/2012 | Reich et al. |
| 2012/0071819 A1 | 3/2012 | Bruggemann et al. |
| 2012/0079718 A1 | 4/2012 | Singer et al. |
| 2012/0081225 A1 | 4/2012 | Waugh et al. |
| 2012/0083666 A1 | 4/2012 | Waugh et al. |
| 2012/0101444 A1 | 4/2012 | Muller-Pathle et al. |
| 2012/0107783 A1 | 5/2012 | Julian et al. |
| 2012/0165747 A1 | 6/2012 | Lanin et al. |
| 2012/0233834 A1 | 9/2012 | Szechinski et al. |
| 2012/0238960 A1 | 9/2012 | Smith et al. |
| 2012/0253288 A1 | 10/2012 | Dasbach et al. |
| 2012/0259285 A1 | 10/2012 | Schabbach et al. |
| 2012/0271243 A1 | 10/2012 | Plumptre et al. |
| 2013/0060231 A1 | 3/2013 | Adlon et al. |
| 2013/0060232 A1 | 3/2013 | Adlon et al. |
| 2013/0079725 A1 | 3/2013 | Shang |
| 2013/0184649 A1 | 7/2013 | Edwards et al. |
| 2013/0190692 A1 | 7/2013 | Edwards et al. |
| 2013/0266919 A1 | 10/2013 | Baker et al. |
| 2013/0317477 A1 | 11/2013 | Edwards et al. |
| 2014/0243749 A1 | 8/2014 | Edwards et al. |
| 2014/0276385 A1 | 9/2014 | Buchine et al. |
| 2014/0296824 A1 | 10/2014 | Edwards et al. |
| 2014/0309616 A1 | 10/2014 | Edwards et al. |
| 2014/0371714 A1 | 12/2014 | Edwards et al. |
| 2015/0011973 A1 | 1/2015 | Edwards et al. |
| 2015/0174323 A1 | 6/2015 | Edwards et al. |
| 2015/0190591 A1 | 7/2015 | Edwards et al. |
| 2015/0196711 A1 | 7/2015 | Edwards et al. |
| 2015/0294551 A1 | 10/2015 | Edwards et al. |
| 2015/0302779 A1 | 10/2015 | Edwards et al. |
| 2016/0121056 A1 | 5/2016 | Edwards et al. |
| 2016/0184535 A1 | 6/2016 | Edwards et al. |

FOREIGN PATENT DOCUMENTS

| | | |
|---|---|---|
| EP | 1287840 A1 | 3/2003 |
| EP | 1462134 A1 | 9/2004 |
| EP | 1712178 A2 | 10/2006 |
| FR | 2509615 | 1/1983 |
| JP | 55-75335 | 5/1980 |
| JP | 2006-034845 | 2/2006 |
| MX | PA04009276 | 1/2005 |
| WO | WO 91/04760 | 4/1991 |
| WO | WO 93/02720 | 2/1993 |
| WO | WO 95/26009 | 9/1995 |
| WO | WO 96/25965 | 8/1996 |
| WO | WO 97/30742 | 8/1997 |
| WO | WO 98/52632 | 11/1998 |
| WO | WO 99/07425 | 2/1999 |
| WO | WO 99/10031 | 3/1999 |
| WO | WO 99/43283 | 9/1999 |
| WO | WO 01/03758 | 1/2001 |
| WO | WO 01/24690 | 4/2001 |
| WO | WO 01/26020 | 4/2001 |
| WO | WO 01/41849 | 6/2001 |
| WO | WO 01/88828 | 11/2001 |
| WO | WO 01/93926 | 12/2001 |
| WO | WO 02/24257 | 3/2002 |
| WO | WO 02/051471 | 7/2002 |
| WO | WO 03/057283 | 7/2003 |
| WO | WO 03/095001 | 11/2003 |
| WO | WO 03/097133 | 11/2003 |
| WO | WO 2004/041330 | 5/2004 |
| WO | WO 2005/050526 | 6/2005 |
| WO | WO 2005/074790 | 8/2005 |
| WO | WO 2005/077441 | 8/2005 |
| WO | WO 2006/045525 | 5/2006 |
| WO | WO 2006/085175 | 8/2006 |
| WO | WO 2006/109778 | 10/2006 |
| WO | WO 2006/123956 | 11/2006 |
| WO | WO 2006/125692 | 11/2006 |
| WO | WO 2007/088444 | 8/2007 |
| WO | WO 2008/005315 | 1/2008 |
| WO | WO 2008/008451 | 1/2008 |
| WO | WO 2008/148864 | 12/2008 |
| WO | WO 2010/114392 | 10/2010 |
| WO | WO 2013/043063 | 3/2013 |
| WO | WO 2013/044172 | 3/2013 |

OTHER PUBLICATIONS

Tingelstad, M., "Revolutionary Medical Technology Increases Demand for Flexible Interconnects," [online] May 15, 2006 [retrieved on Nov. 15, 2006] Retrieved from the Internet <URL: http://www.ecnmag.com/index.asp?layout=articlePrint& ArticleID=CA6332947>, 3 pages.

"Flexible circuits / Flex circuits / Flexible Technology Ltd.," Flexible Technology Limited [online] [retrieved on Aug. 28, 2006] Retrieved from the Internet <URL: http://www.flexibletechnology.com/ >, 2 pages.

"Flexible circuits capabilities of Flexible Technology Limited," Our Flexible Circuits Capabilities [online] [retrieved on Aug. 28, 2006] Retrieved from the Internet <URL: http://www.flexibletechnology.com/Flexible circuits Capability.htm >, 2 pages.

"Flex Circuits/flexible circuits design guide," [online] [retrieved on Aug. 28, 2006] Retrieved from the Internet <URL: http://flexiblecircuit.co.uk/Flex Circuits Design Guide.htm >, 7 pages.

"Insect Stings Auto-injector Pouches and Carry Cases," The Insect Stings On-Line Shop, [online] [retrieved on Jan. 24, 2007] Retrieved from the Internet <URL: http://www.insectstings.co.uk/acatalog/Auto Injector Pouches.html >, 3 pages.

(56) References Cited

OTHER PUBLICATIONS

"Anaphylaxis Canada Product Catalogue," Anaphylaxis Canada > Living with Anaphylaxis > Tools and Resources [online] [retrieved on Jan. 24, 2007] Retrieved from the Internet <URL: http://anaphylaxis.org/content/livingwith/product catalogue.asp >, 9 pages.
"Microfluidics Device Provides Programmed, Long-Term Drug Dosing," nano techwire.com [online] [retrieved on Nov. 28, 2006] Retrieved from the Internet <URL: http://nanotechwire.com/news.asp?nid=3141&ntid=124&pg=1 >, 3 pages.
Allan, R., "Medical Electronics: Technology Advances Will Revolutionize Healthcare," Sep. 30, 2002 [online] [retrieved on Nov. 28, 2006] Retrieved from the Internet <URL: http://www.elecdesign.com/Articles/Index.cfm?AD=1&ArticleID=2041>, 3 pages.
RFID Gazette, "Smart Labels in Healthcare," Sep. 29, 2005 [online] [retrieved on Nov. 28, 2006] Retrieved from the Internet <URL: http://www.rfidagazeete.org/2005/09/smart labels in.html >, 2 pages.
"Merck Serono Launches easypod(R), First Electronic Growth Hormone Injection Device," Jan. 30, 2007 [online] [retrieved on Feb. 5, 2007] Retrieved from the Internet <URL: http://www.biz.yahoo.com/prnews/070130/ukm028.html?.v=8>, 3 pages.
Scholz, O., "Drug depot in a tooth," [online] [retrieved on Feb. 6, 2007] Retrieved from the Internet <URL: http://www.fraunhofer.de/fhg/EN/press/pi/2007/02Mediendienst22007Thema2.jsp?print=true>, 1 page.
Heartsine Technology, samaritan™ Pad Accessories [online] [retrieved on Jun. 1, 2007] Retrieved from the Internet <URL: http://www.heartsine.com/aboutsam-accessories.htm>, 4 pages.
CliniSense Corporation, "Drug delivery devices a potentially harsh environment for drugs," Stability [online] [retrieved on Jun. 1, 2007] Retrieved from the Internet <URL: http://www.clinisense.com/devices.htm>, 2 pages.
CliniSense Corporation, "LifeTrack Technology a new method to detect improper storage." Stability [online] [retrieved on Jun. 1, 2007] Retrieved from the Internet <URL: http://www.clinisense.com/tech.htm>, 2 pages.
AED Professionals™ Brochure [online] [retrieved on Jun. 1, 2007] Retrieved from the Internet <URL: http://www.aedprofessionals.com>, 4 pages.
Ruppar, D., "Implant Technologies Expected to Remain a Niche but Effective Method of Drug Delivery," Drug Delivery Technology, Feb. 2007, vol. 7, No. 2 [online] [retrieved on Jun. 1, 2007] Retrieved from the Internet <URL: http://www.drugdeliverytech-online.com/drugdelivery/200702/templates/pageviewer_print?pg=44&pm=8 >, 8 pages.
O'Hagan, D. et al., "Novel approaches to pediatric vaccine delivery," Advanced Drug Delivery Reviews, 58:29-51 (2006).
Gosbee, L. L., "Nuts! I Can't Figure Out How to Use My Life-Saving Epinephrine Auto-Injector," Joint Commision Journal on Quality and Safety, 30(4):220-223 (Apr. 2004).
Apple, Inc., "Bluetooth Accessory Design Guidelines for Apple Products," Release R7, (Sep. 18, 2013), 40 pages.
Stuart, M., "Cellnovo's Mobile Health Approach to Diabetes Care," In Vivo: The Business & Medicine Report, (Dec. 2010), pp. 40-44.
Office Action for Israel Patent Application No. 184552, mailed Jul. 28, 2011.
International Search Report and Written Opinion for International Patent Application No. PCT/US06/03415, mailed Jul. 13, 2006, 10 pages.
Search Report for European Patent Application No. 09150135.3, mailed Mar. 15, 2010.
Office Action for European Patent Application No. 09150135.3, mailed Jul. 11, 2011.
Combined Search and Examination Report for British Patent Application 0818178.6, mailed Dec. 1, 2008.
Examination Report for British Patent Application No. 0818178.6, mailed Mar. 23, 2009.
Examination Report for British Patent Application No. 0818178.6, mailed Jul. 9, 2009.
Examination Report for British Patent Application No. 0905194.7, mailed May 8, 2009.
Office Action for U.S. Appl. No. 10/572,148, mailed Feb. 3, 2010.
Office Action for Japanese Patent Application No. 2009-502964, mailed May 23, 2011.
Office Action for Japanese Patent Application No. 2009-502964, mailed May 21, 2012 (English Translation).
International Search Report and Written Opinion for International Patent Application No. PCT/US07/007626, mailed Sep. 29, 2008.
Search and Examination Report for British Patent Application No. 1104754.5, mailed May 18, 2011.
Office Action for U.S. Appl. No. 11/621,236, mailed Feb. 3, 2009.
Office Action for U.S. Appl. No. 11/621,236, mailed Jul. 1, 2009.
Office Action for U.S. Appl. No. 11/621,236, mailed Jan. 11, 2010.
Search and Examination Report for British Patent Application No. 1108993.5, mailed Jun. 17, 2011.
Office Action for U.S. Appl. No. 11/671,025, mailed Mar. 24, 2011.
Office Action for U.S. Appl. No. 11/671,025, mailed Sep. 8, 2011.
Examination Report for British Patent Application No. 1019599.8, mailed Feb. 7, 2012.
Office Action for U.S. Appl. No. 12/119,016, mailed Nov. 3, 2011.
Search Report and Written Opinion for International Patent Application No. PCT/US2009/043578, mailed Aug. 27, 2009.
Office Action for U.S. Appl. No. 12/794,020, mailed Oct. 25, 2011.
Office Action for U.S. Appl. No. 12/017,405, mailed Dec. 7, 2011.
International Search Report and Written Opinion for International Patent Application No. PCT/US2008/051612, mailed Dec. 9, 2008, 7 pages.
Office Action for U.S. Appl. No. 12/180,708, mailed Feb. 28, 2011.
International Search Report and Written Opinion for International Patent Application No. PCT/US09/63983, mailed Feb. 25, 2010.
Non-Final Office Action for U.S. Appl. No. 13/036,720, mailed May 17, 2013.
International Preliminary Report on Patentability for International Patent Application No. PCT/US2013/077996, mailed Jun. 30, 2015.

* cited by examiner

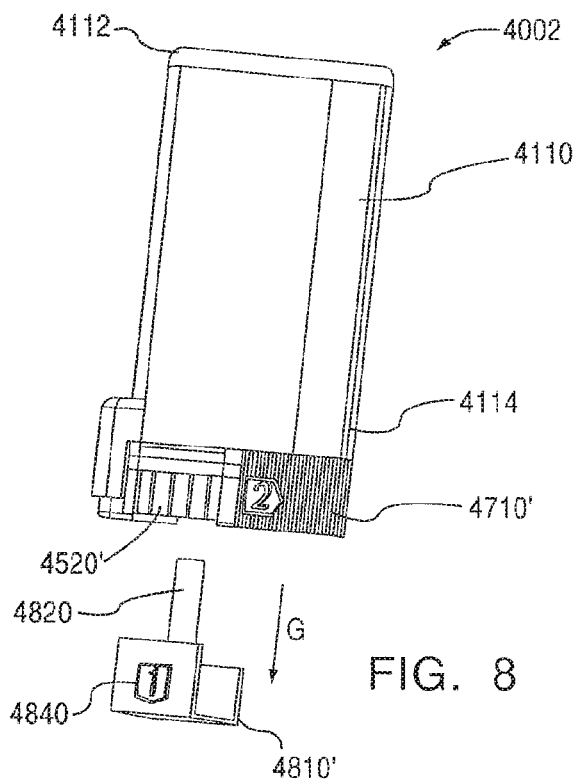
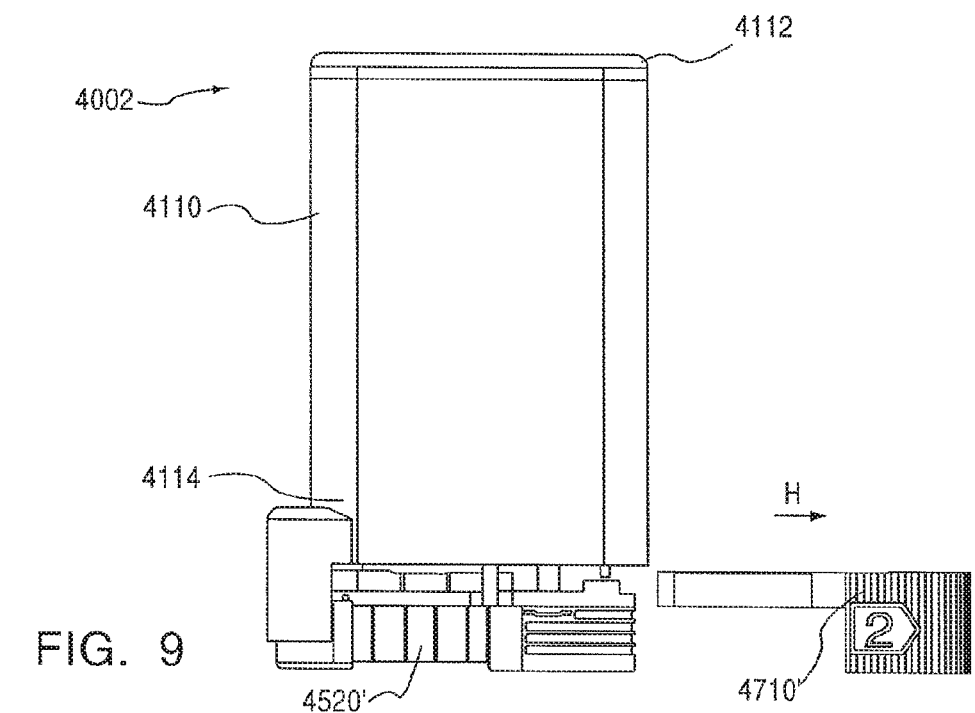

APPARATUS AND METHODS FOR SELF-ADMINISTRATION OF VACCINES AND OTHER MEDICAMENTS

CROSS-REFERENCE TO RELATED APPLICATIONS

This application is a continuation of U.S. patent application Ser. No. 13/748,733, now abandoned, entitled "Apparatus and Methods for Self-Administration of Vaccines and Other Medicaments," filed Jan. 24, 2013, which is a continuation of U.S. patent application Ser. No. 12/615,636, now U.S. Pat. No. 8,361,026, entitled "Apparatus and Methods for Self-Administration of Vaccines and Other Medicaments," filed Nov. 10, 2009, which claims priority to U.S. Provisional Application Ser. No. 61/113,368, entitled "Apparatus and Methods for Self-Administration of Vaccines and Other Medicaments," filed Nov. 11, 2008, each which is incorporated herein by reference in its entirety.

U.S. patent application Ser. No. 13/748,733 and U.S. patent application Ser. No. 12/615,636 are related to U.S. patent application Ser. No. 11/621,236, now U.S. Pat. No. 7,731,686, entitled "Devices, Systems and Methods for Medicament Delivery," filed Jan. 9, 2007, which is a continuation-in-part of U.S. patent application Ser. No. 10/572,148, now U.S. Pat. No. 7,749,194, entitled "Devices, Systems and Methods for Medicament Delivery," filed Mar. 16, 2006, which is a national stage filing under 35 U.S.C. §371 of International Patent Application No. PCT/US2006/003415, entitled "Devices, Systems and Methods for Medicament Delivery," filed Feb. 1, 2006, which claims priority to U.S. Provisional Application Ser. No. 60/648,822, entitled "Devices, Systems and Methods for Medicament Delivery," filed Feb. 1, 2005 and U.S. Provisional Application Ser. No. 60/731,886, entitled "Auto-Injector with Feedback," filed Oct. 31, 2005, each of which is incorporated herein by reference in its entirety. U.S. patent application Ser. No. 11/621,236 now U.S. Pat. No. 7,731,686, also claims priority to U.S. Provisional Application Ser. No. 60/787,046, entitled "Devices, Systems and Methods for Medicament Delivery," filed Mar. 29, 2006, which is incorporated herein by reference in its entirety.

U.S. patent application Ser. No. 12/615,636 is a continuation-in-part of U.S. patent application Ser. No. 12/017,405, now U.S. Pat. No. 8,226,610, entitled "Medical Injector with Compliance Tracking and Monitoring," filed Jan. 22, 2008, which is a continuation-in-part of U.S. patent application Ser. No. 11/671,025, now U.S. Pat. No. 8,172,082, entitled "Devices, Systems and Methods for Medicament Delivery," filed Feb. 5, 2007, which is incorporated herein by reference in its entirety.

U.S. patent application Ser. No. 13/748,733 and U.S. patent application Ser. No. 12/615,636 are related to U.S. patent application Ser. No. 12/119,016, now U.S. Pat. No. 8,231,573, entitled "Medicament Delivery Device Having an Electronic Circuit System," filed May 12, 2008, which is a continuation-in-part of U.S. patent application Ser. No. 11/679,331, now U.S. Pat. No. 9,022,980, entitled "Medical Injector Simulation Device," filed Feb. 27, 2007, which is a continuation-in-part of U.S. patent application Ser. No. 11/671,025, now U.S. Pat. No. 8,172,082, entitled "Devices, Systems and Methods for Medicament Delivery," filed Feb. 5, 2007, which is a continuation-in-part of U.S. patent application Ser. No. 11/621,236, now U.S. Pat. No. 7,731,686, entitled "Devices, Systems and Methods for Medicament Delivery," filed Jan. 9, 2007, which is a continuation-in-part of U.S. patent application Ser. No. 10/572,148, now U.S. Pat. No. 7,749,194, entitled "Devices, Systems and Methods for Medicament Delivery," filed Mar. 16, 2006, which is a national stage filing under 35 U.S.C. §371 of International Patent Application No. PCT/US2006/003415, entitled "Devices, Systems and Methods for Medicament Delivery," filed Feb. 1, 2006, which claims priority to U.S. Provisional Application Ser. No. 60/648,822, entitled "Devices, Systems and Methods for Medicament Delivery," filed Feb. 1, 2005 and U.S. Provisional Application Ser. No. 60/731,886, entitled "Auto-Injector with Feedback," filed Oct. 31, 2005, each of which is incorporated herein by reference in its entirety.

BACKGROUND

The invention relates generally to medical devices, and more particularly to medical systems, medicament delivery devices and methods for delivering a vaccine and/or other medicaments into a body of a patient.

Vaccination is the administration of antigenic material (the vaccine) to produce immunity to a disease. Many known vaccines are given by hypodermic injection and/or are stored under controlled conditions, and are thus often administered by a medical professional. Known vaccination procedures, therefore, are performed at a physician's office, a clinic and/or some other location where a medical professional can administer the vaccine. Known vaccination procedures can include validating the stability of the vaccine, administering the dose of the vaccine and/or monitoring the patient at the physician's office for a period of time after administering the vaccine to ensure that the patient does not have an adverse reaction to the vaccine. Visitations by a patient to a physician's office, however, are costly, inconvenient and can result in the patient being exposed to an infectious disease. Moreover, the administration of vaccines at a central location (clinic, physician's office or the like) can pose logistical issues during vaccination campaigns, such as, for example, vaccination campaigns during which a large number of individuals are vaccinated during a short period of time (e.g., vaccination during a pandemic).

Additionally, many known vaccines are administered via multiple doses over a period of time. Multiple doses can be used to produce a sufficient initial immune response and/or to boost a response that declines over time. Thus, some known vaccination procedures include multiple visits by the patient to the medical professional after a period of time to receive subsequent doses of the vaccine. For example, a vaccine against human papillomavirus (HPV) is administered in three doses: an initial dose followed up by a second dose two months after the initial dose is administered, and a third dose six months after the initial dose is administered. In certain instances, a patient may forget or decline to return to the medical professional, and therefore may not receive the subsequent doses of the vaccine. In such instances, the effectiveness of the vaccine can be diminished.

Thus, a need exists for methods and apparatus to provide self-administration of vaccines and/or other medicaments. A need further exists for methods and apparatus to ensure correct administration of the vaccine. Additionally, a need exists for method and apparatus that can track and/or enhance patient compliance and/or adherence in self-administering vaccinations.

SUMMARY

Medicament delivery systems and devices are described herein. In some embodiments, a medicament delivery device includes a housing, a medicament container disposed within the housing, an activation mechanism, a cover and an electronic circuit system. The medicament container is configured to contain a medicament, such as, for example, a vaccine. The activation mechanism includes an energy storage member configured to produce a force to deliver the dose of the medicament into a body. The cover, which can be, for example, a protective sheath, is configured to receive at least a portion of the housing. The electronic circuit system is coupled to the housing such that a protrusion of the cover electrically isolates a battery from a portion of the electronic circuit system when the portion of the housing is received by the cover. The electronic circuit system is configured to be electrically coupled to the battery and to produce a recorded speech output when the portion of the housing is at least partially removed from the cover. The electronic circuit system configured to produce a signal, such as, for example, a wireless validation signal, when the activation mechanism is actuated.

BRIEF DESCRIPTION OF THE DRAWINGS

FIG. 8 is a perspective view of the auto-injector illustrated in FIG. 6 showing an assembly according to an embodiment of the invention being removed.

FIG. 9 is a front view of the auto-injector illustrated in FIG. 6 showing a member according to an embodiment of the invention being removed.

DETAILED DESCRIPTION

Figure 1:
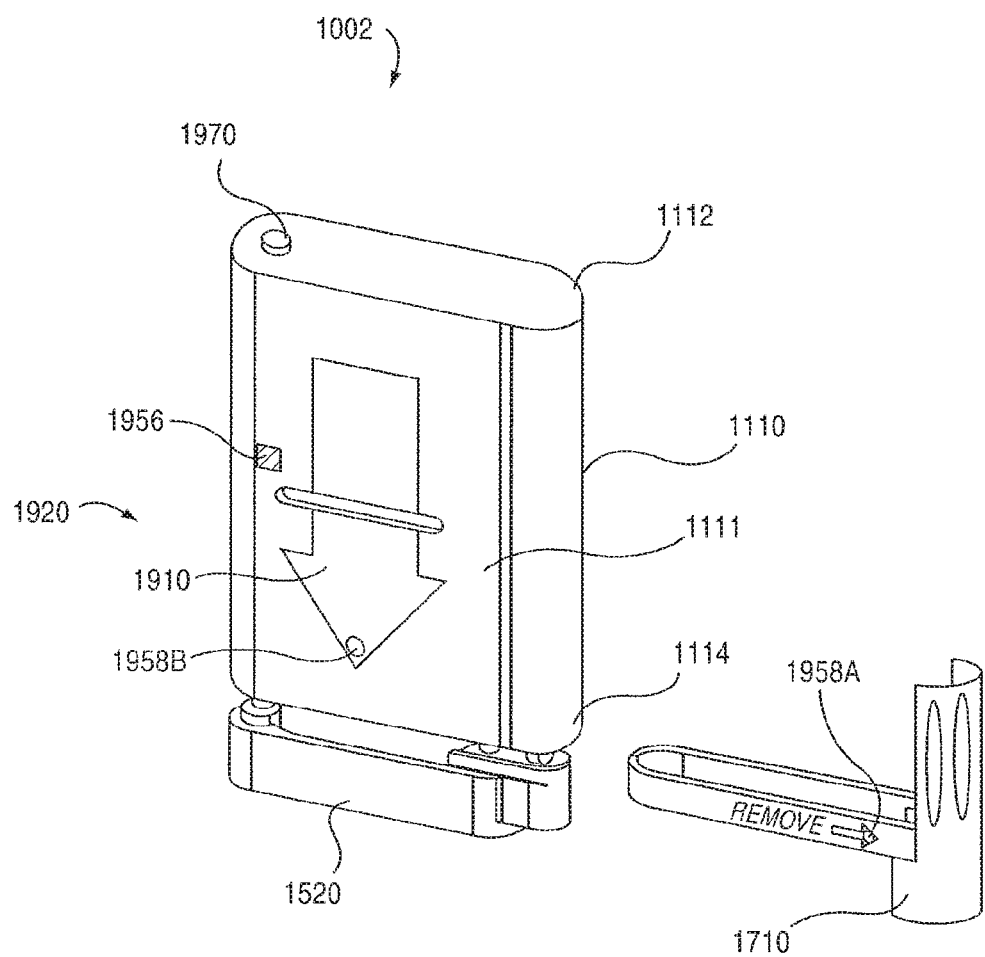
FIG. 1 is a perspective view of an auto-injector according to an embodiment.

Medicament delivery systems and devices are described herein. In some embodiments, a medicament delivery device includes a housing, a medicament container disposed within the housing, an activation mechanism, a cover and an electronic circuit system. The medicament container is configured to contain a medicament, such as, for example, a vaccine. The activation mechanism includes an energy storage member configured to produce a force to deliver the dose of the medicament into a body. The cover, which can be, for example, a protective sheath, is configured to receive at least a portion of the housing. The electronic circuit system is coupled to the housing such that a protrusion of the cover electrically isolates a battery from a portion of the electronic circuit system when the portion of the housing is received by the cover. The electronic circuit system is configured to be electrically coupled to the battery and to produce a recorded speech output when the portion of the housing is at least partially removed from the cover. The electronic circuit system configured to produce a signal, such as, for example, a wireless validation signal, when the activation mechanism is actuated.

In some embodiments, a medicament delivery device includes a housing, a medicament container disposed within the housing, an activation mechanism and an electronic circuit system. The medicament container can contain, for example, a dose of a vaccine. The activation mechanism includes an energy storage member configured to produce a force to deliver the dose of the vaccine into a body. The electronic circuit system, which is coupled to the housing, is configured to calculate a stability parameter associated with the vaccine. The electronic circuit system is configured to produce a recorded speech output associated with the stability parameter when the electronic circuit system is actuated.

In some embodiments, a method of self-administering a vaccine includes actuating an electronic circuit system coupled to a first auto-injector containing a first dose of a vaccine. In response to a recorded speech output produced by the first auto-injector, a delivery mechanism is actuated such that the first dose of the vaccine is delivered into a portion of a body of a patient. The actuating is performed by the patient, and the recorded speech output provides instructions associated with a stability of the first dose of the vaccine, an instruction for using the first auto-injector, an instruction for following a regimen associated with the vaccine, an instruction for using a second auto-injector containing a second dose of the vaccine and/or a post-injection instruction.

In some embodiments, a method includes providing a first set of instructions to a patient. The first set of instructions is associated with the administration of a vaccine and is provided to the patient at a first location. The method can optionally include verifying that the patient has received and/or understood the first set of instructions. A first dose of the vaccine is delivered to the patient at the first location. The first location can be, for example, a physician's office, and in some embodiments, the first dose can be delivered by the physician or another medical professional. A second set of instructions is provided to the patient at a second location different from the first location. The second location can be, for example, the patient's home. The second set of instructions is associated with the administration of a second dose of the vaccine, and can include, for example, instructions for using a medicament delivery device. The second dose of the vaccine is delivered to the patient at the second location. In some embodiments, the second dose can be self-administered using the medicament delivery device. In some embodiments, any number of additional doses can be delivered at the second location. For example in some embodiments, the method includes delivering one or more doses after the second dose, each of the subsequent doses can be delivered at a predetermined time interval after the first dose and/or the second dose. In some embodiments, the method optionally includes outputting a signal associated with the delivery of the second dose and/or any subsequent doses of the vaccine. In this manner, the patient's compliance and/or adherence with the vaccination regimen can be tracked.

In some embodiments, a system includes a medicament delivery device and a container configured to receive at least a portion of the medicament delivery device. The medicament delivery device, which can be, for example, a single-use medical injector, includes an actuator and a first electronic circuit system. The actuator is configured to initiate delivery of a medicament (such as a vaccine) into a body when the actuator is moved from a first position to a second position. The first electronic circuit system is configured to output a first electronic signal when the actuator is moved from the first position to the second position. The first electronic signal can be, for example, a short-range radio frequency signal having a range of approximately 100 meters or less. The container includes a second electronic circuit system configured to receive the first electronic signal. The second electronic circuit system is configured to output a second electronic signal associated with the first electronic signal.

In some embodiments, an apparatus includes a medicament delivery device and an electronic circuit system coupled to the medicament delivery device. The medicament delivery device includes an actuator configured to initiate delivery of a medicament into a body when the actuator is moved from a first position to a second position. The electronic circuit system includes a first radio frequency identification tag configured to output a first electronic signal and a second radio frequency identification tag configured to output a second electronic signal. The second electronic signal has a characteristic (e.g., a frequency) different than a characteristic of the first electronic signal. The actuator is configured to prevent the second radio frequency identification tag from outputting the second electronic signal when the actuator is moved from the first position to the second position. In some embodiments, for example, the actuator is configured to sever at least a portion of the second radio frequency identification tag when the actuator is moved from the first position to the second position.

In some embodiments, an apparatus includes a housing, a medicament container disposed within the housing, a needle, and an electronic circuit system. The needle has a proximal end and a distal end, and is configured to be in fluid communication with the medicament container. The needle is configured to be moved between a first position and a second position. The distal end of the needle is disposed within the housing when the needle is in the first position. At least a portion of the distal end of the needle is disposed outside of the housing when the needle is in the second position. The electronic circuit system is configured to be coupled to the housing. The electronic circuit system is configured to output an electronic signal associated with an impedance between the distal end of the needle and a portion of the housing.

In some embodiments, a method includes moving an actuator of a medicament delivery device to initiate delivery of a medicament into a body. The actuator can be, for example, a mechanical actuator configured to release a spring, an energy storage member, or the like to initiate medicament delivery when the actuator is moved from the first position to the second position. A first electronic signal is output from a first electronic circuit system in response to the movement of the actuator between the first position and the second position. The first electronic signal is a short-range radio frequency signal having a range of approximately 100 meters or less. A second electronic signal associated with the first electronic signal is output from a second electronic circuit system.

As used herein, the term "regimen" or "medication regimen" can include any program, schedule and/or procedure to enhance, improve, sustain, alter, and/or maintain a patient's well-being. A regimen can include, for example, a schedule of medicament delivery events (e.g., injections, oral doses, etc.) that are prescribed or otherwise suggested for the patient. For example, a regimen can include daily insulin injections. A regimen can also include a single medicament delivery event that can be prescribed or otherwise suggested for the patient to administer in response to given a set of circumstances. For example, a regimen can include an injection of epinephrine in response to an allergic reaction. A regimen can also include the delivery of a placebo or inactive ingredient. For example, a clinical trial can include a regimen including various injections of a placebo. Finally, a regimen can also include activities other than the delivery of drugs to the patient. For example, a regimen can include certain procedures to be followed to enhance the patient's well-being (e.g., a schedule of rest, a dietary plan, etc.).

Figure 2:
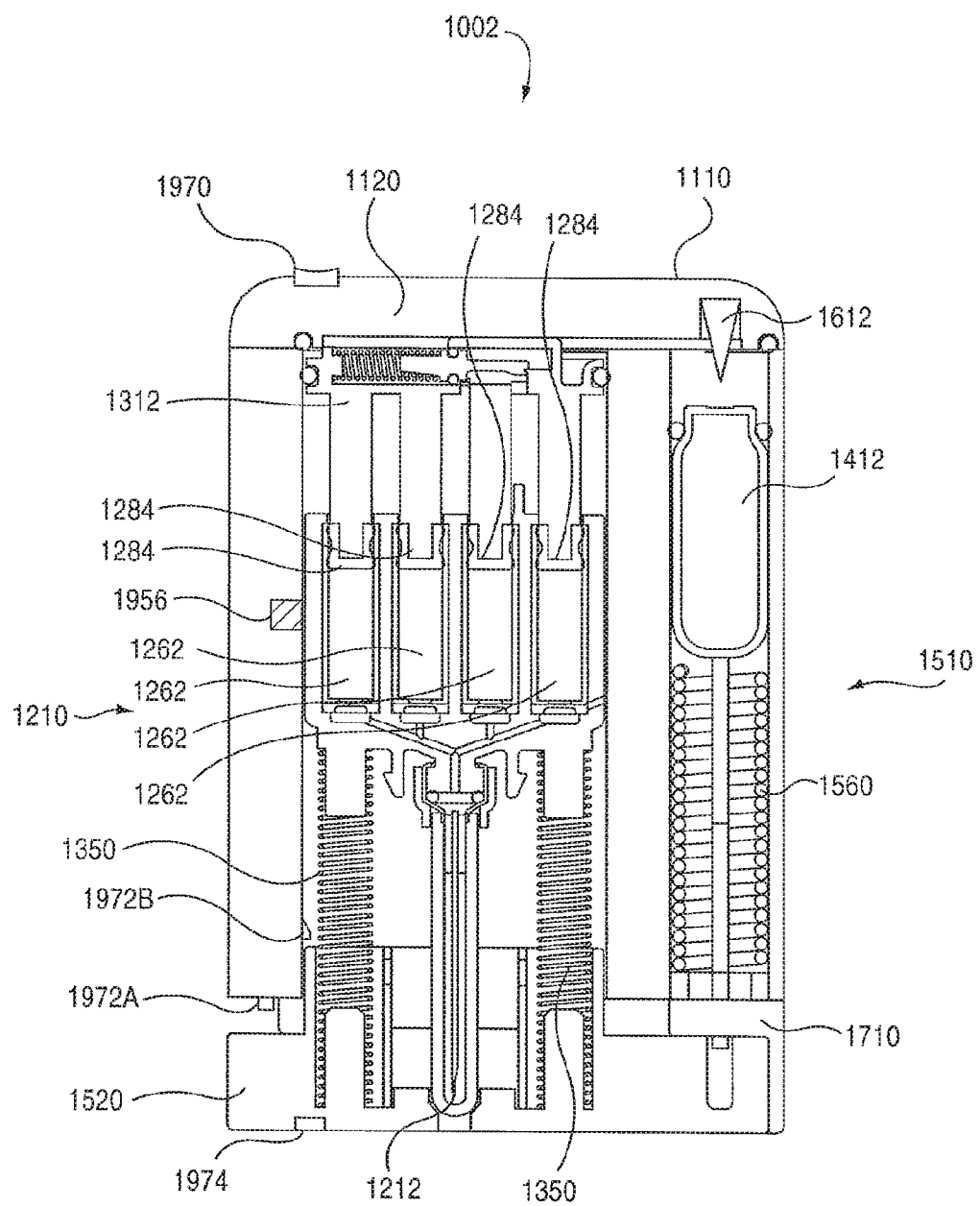
FIG. 2 is a front cross-sectional view of the auto-injector shown in FIG. 1.

FIGS. 1 and 2 are a perspective view and a partial cutaway front view, respectively, of an auto-injector 1002 according to an embodiment. The auto-injector 1002 is similar to the auto-injectors described in U.S. patent application Ser. No. 11/562,061, entitled "Devices, Systems and Methods for Medicament Delivery," filed Nov. 21, 2006, which is incorporated herein by reference in its entirety. Accordingly, only an overview of the mechanical components and related operation of the auto-injector 1002 is included below.

The auto-injector 1002 includes a housing 1110 that defines a gas chamber 1120. The housing 1110 has a proximal end portion 1112 and a distal end portion 1114. A base 1520 is movably coupled to the distal end portion 1114 of the housing 1110. A safety lock 1710 is removably coupled to the base 1520. As discussed in more detail herein, when the safety lock 1710 is coupled to the base 1520, the auto-injector 1002 cannot be actuated. When the safety lock 1710 is removed from the base 1520, the base 1520 can be moved relative to the housing 1110, thereby actuating the auto-injector 1002. Accordingly, to inject a medicament into the body, the distal end portion 1114 of the housing 1110 is oriented towards the user such that the base 1520 is in contact with the portion of the body where the injection is to be made. The base 1520 is then moved towards the proximal end 1112 of the housing 1110 to actuate the auto-injector 1002.

The auto-injector 1002 includes a medicament injector 1210 and a system actuator 1510 disposed non-coaxially within the housing 1110. The medicament injector 1210 includes multiple medicament vials 1262, a plunger 1284 movably disposed within each medicament vial 1262, a movable member 1312 engaged with each plunger 1284 and a needle 1212. Retraction springs 1350 located within a portion of the base 1520 and the housing 1110 can push the needle 1212 back within the housing 1110 after injection. The system actuator 1510 includes a compressed spring 1560, a compressed gas cylinder 1412, and a puncturing mechanism 1612 to dispel the contents of the compressed gas cylinder 1412.

In use, when the auto-injector 1002 is actuated, the puncturing mechanism 1612 punctures the compressed gas cylinder 1412 allowing a pressurized gas to flow into the gas chamber 1120. In response to a force produced by the pressurized gas on the movable member 1312, the movable member 1312 moves distally within the housing 1110. As a result, the needle 1212 is extended through the housing 1110. The movement of the movable member 1312 also causes the plungers 1284 to move within the vials 1262, thereby expelling a medicament from the vials 1262.

The auto-injector 1002 includes an electronic circuit system 1920 configured to provide a predetermined sequence of electronic outputs and/or electronic signals during the use of the auto-injector 1002. The electronic circuit system 1920 is powered by a battery (not shown in FIGS. 1 and 2) and includes a processor (see e.g., FIG. 3), a start button 1970, two switches 1972A and 1972B, a proximity sensor 1974, two visual output devices 1958A and 1958B, an audio output device 1956, and a network interface device 1953. The components of the electronic circuit system 1920 are operatively coupled by any suitable mechanism, such as, for example, a printed circuit board (not shown in FIGS. 1 and 2) having conductive traces.

The start button 1970 is disposed on the proximal end of the housing 1110 and can be manually actuated by the user to begin the sequence of electronic outputs. The first switch 1972A is disposed on the distal portion 1114 of the housing 1110 adjacent the base 1520 and the locking member 1710. The locking member 1710 is configured to engage the first switch 1972A such that when the locking member 1710 is removed, as shown in FIG. 1, the first switch 1972A changes states. In this manner, removal of the locking member 1710 can trigger the processor to output a predetermined electronic output. Said another way, the electronic circuit system 1920 can produce and/or output an electronic signal and/or an electronic output when the auto-injector 1002 is moved from a "storage" configuration (i.e., a configuration in which the locking member 1710 will prevent the actuation of the auto-injector 1002) to a "ready" configuration (i.e., a configuration in which the auto-injector 1002 can be actuated).

The proximity sensor 1974 is disposed on the base 1520 and is configured to produce an output when the base 1520 engages the body. The proximity sensor can be, for example, a temperature sensor, an optical sensor, pressure sensor, impedance sensor or the like. In this manner, the processor can be prompted to output a predetermined electronic output when the base 1520 is positioned against the body.

Similarly, the second switch 1972B is disposed on the housing 1110 adjacent the medicament injector 1210. The medicament injector 1210 is configured to engage the second switch 1972B such that when the medicament injector 1210 is moved distally within the housing 1110 the second switch 1972B changes states. In this manner, the processor can be prompted to output a predetermined electronic output based on the position of the medicament injector 1210. Said another way, the electronic circuit system 1920 can produce and/or output an electronic signal and/or an electronic output in response to the actuation of the auto-injector 1002.

In some embodiments, the electronic circuit system 1920 can be configured to output an electronic signal and/or an electronic output based on the output of the proximity sensor 1974 and the output from the second switch 1972B. For example, in some embodiments, the electronic circuit system 1920 can output a first electronic signal when the output from the proximity sensor 1974 indicates that the base 1520 of the auto-injector 1002 is in contact with the body when the second switch 1972B changes states, and a second electronic signal when the output from the proximity sensor 1974 indicates that the base 1520 of the auto-injector 1002 is disposed apart from the body when the second switch 1972B changes states. Said another way, in some embodiments, the electronic circuit system 1920 can be configured to output a first electronic signal associated with the occurrence of a valid injection event (i.e., an injection event during which there was a high likelihood that the medicament was properly injected into the body) and a second electronic signal associated with the occurrence of an invalid injection event (i.e., an injection event during which there was a high likelihood that the medicament was not injected into the body).

The first visual output device 1958A is disposed on the locking member 1710. Similarly, the second visual output device 1958B is disposed on the outer surface 1111 of the housing 1110. The visual output devices 1958A and 1958B are in electronic communication with the processor and are configured to produce an output in response to an electronic signal output by the processor. The visual output devices 1958A and 1958B, as well as any other visual output devices referenced herein, can be any suitable visual indicia, such as, light-emitting diodes (LEDs), liquid-crystal display (LCD) screens, optical polymers, fiber optic components or the like. In some embodiments, the visual output devices 1958A and 1958B can be coupled to the housing 1110 and/or the locking member 1710 by a label 1910.

The audio output device 1956 is disposed within the housing 1110 such that it can project sound outside of the housing 1110. The audio output device 1956, as well as any other audio output devices referenced herein, can be any suitable device for producing sound, such as a microspeaker a piezo-electric transducer or the like. Such sound output can include, for example, an alarm, a series of beeps, recorded speech or the like. The audio output device 1956 is in electronic communication with the processor and is configured to produce an output in response to an electronic signal output by the processor.

Figure 3:
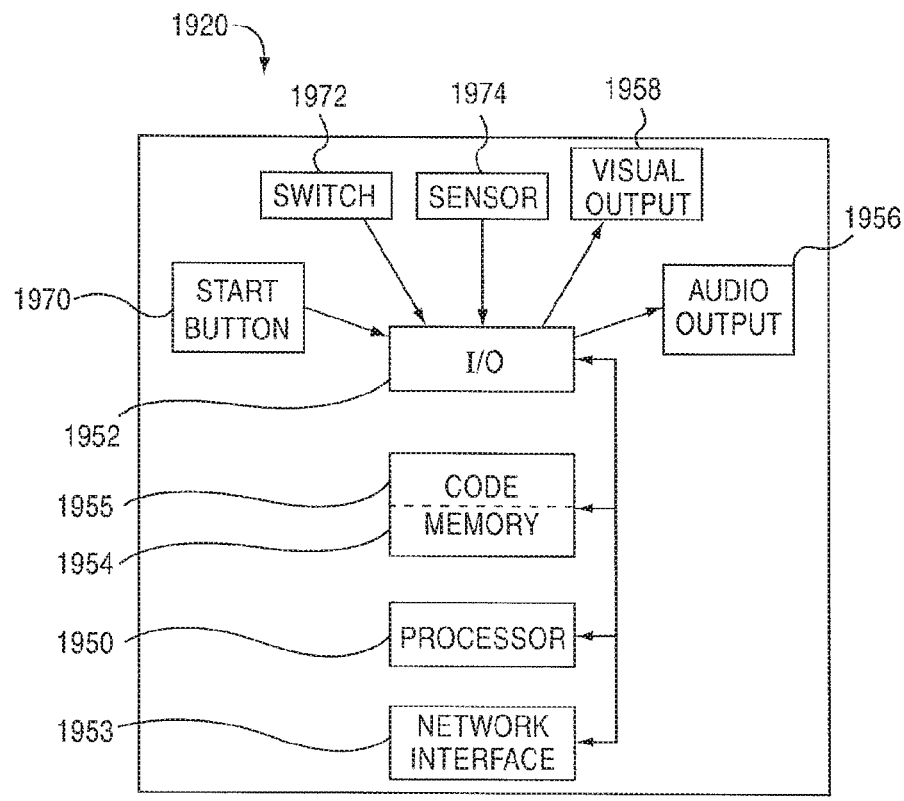
FIG. 3 is a schematic illustration of a portion of the auto-injector shown in FIG. 1.

The network interface device 1953 is configured to operatively connect the electronic circuit system 1920 to a remote device 1941 (see FIG. 3) and/or a communications network (not shown in FIGS. 1-3). In this manner, the electronic circuit system 1920 can send information to and/or receive information from the remote device 1941. The remote device 1941 can be, for example, a remote communications network, a computer, a compliance monitoring device, a cell phone, a personal digital assistant (PDA) or the like. Such an arrangement can be used, for example, to download replacement processor-readable code 1955 (see FIG. 3) from a central network to the memory device 1954 (see FIG. 3). In some embodiments, for example, the electronic circuit system 1920 can download information associated with a medicament delivery device 1002, such as an expiration date, a recall notice, updated use instructions or the like. Similarly, in some embodiments, the electronic circuit system 1920 can upload compliance and/or adherence information associated with the use of the medicament delivery device 1002 via the network interface device 1953.

In use, the user activates the electronic circuit system by pushing the start button 1970 to activate the processor, thereby causing the processor to output a predetermined sequence of electronic outputs. In some embodiments, the start button 1970 can activate the processor by providing an input to the processor. In other embodiments, the start button 1970 can activate the processor by placing the battery (not shown in FIGS. 1 and 2) in electronic communication with the processor.

In some embodiments, upon activation, the processor can output an electronic signal to the audio output device 1956 thereby producing a first electronic output instructing the user in how to use the auto-injector 1002. Such a message can state, for example, "please remove the safety tab."

Additionally, the first visual output device 1958A can produce a flashing light to further indicate to the user where the locking member 1710 is located. The processor can be configured to repeat the first audible instruction if the locking member 1710 is not removed within a predetermined time period.

When the user removes the locking member 1710, the first switch 1972A changes states thereby triggering the processor to output an electronic output providing a second instruction to the user. The second instruction can be, for example, an audible speech output instructing the user to "please place the base of the device on the outer portion of your thigh." The first visual output device 1958A can produce a lighted output during this audible instruction, thereby visually indicating where the base 1520 is located and/or what portion of the base 1520 should be placed on the thigh.

When the user places the base 1520 against the body, the proximity sensor 1974 provides an input to the processor, thereby triggering the processor to output an electronic output providing a third instruction to the user. The third instruction can be, for example, an audible speech output instructing the user to "push down on the top of the device to activate the injector."

When the injection is completed, the medicament injector 1210 is configured to engage the second switch 1972B, thereby triggering the processor to output an electronic output providing a fourth instruction to the user. Such a post-use instruction can be, for example, an audible speech output instructing the user to seek further medical attention, providing instructions for the safe disposal of the auto-injector 1002 or the like.

In some embodiments, the processor 1950 can output an electrical signal associated with the second switch 1972B that is received by a remote device 1941, which can be, for example, a compliance tracking device. Said another way, in some embodiments, the electronic circuit system 1920 can output, to the remote device 1941, an electrical signal associated with the end of the injection event. In this manner the electronic circuit system 1920 on the auto-injector 1002 can cooperate with the remote device 1941 to electronically and/or automatically track the details of the use of the auto-injector 1002. Similarly stated, the electronic circuit system 1920 on the auto-injector 1002 and the remote device 1941 can electronically and/or automatically track the patient compliance and/or adherence data associated with the use of the auto-injector 1002.

FIG. 3 is a schematic illustration of the electronic circuit system 1920 of the auto-injector 1002. The electronic circuit system 1920 includes a processor 1950 operatively coupled to a memory device 1954. The memory device 1954 can be configured to store processor-readable code 1955 instructing the processor 1950 to perform the functions described above. In some embodiments, the processor-readable code 1955 can be modified and/or updated as circumstances dictate. The electronic circuit system 1920 includes an input/output device 1952 configured to receive electronic inputs from the switches 1972A and 1972B, the proximity sensor 1974 and/or the start button 1970. The input/output device 1952 is also configured to provide electronic signals to the various output devices, such as the visual output devices 1958A and 1958B and the audio output device 1956.

As described above, the electronic circuit system 1920 also includes a network interface 1953 configured to couple the electronic circuit system 1920 to a remote device 1941 and/or a communications network (not shown in FIG. 3). Such an arrangement can be used, for example, to download replacement processor-readable code 1955 from a central network (not shown) to the memory device 1954. The network interface 1953 can also be configured to transmit information from the electronic circuit system 1920 to a central network and/or the remote device 1941 (e.g., the user's home computer, the user's cell phone or the like). The network interface 1953 can include any hardware, software and/or firmware suitable for establishing communication between the electronic circuit system 1920 and the remote device 1941. For example, in some embodiments, the network interface 1953 can include a microprocessor, a transmitter, a receiver, a transceiver, a microchip, a radio chipset, a wireless interface card (WIC), a host controller interface (HCI), a universal asynchronous receiver/transmitter (UART), a power source (e.g., a battery), one or more sensors, a transponder, an antenna, a crystal, a circuit board, a liquid crystal display (LCD), a Small Computer System Interface (SCSI and ports), a FireWire (or other IEEE 1394 interfaces), a data uplink, a data downlink, a point-to-point link, a fiber optic link, a storage device (e.g., hard drive, flash drive or the like), a personal computer cards, a docking stations, a parallel and/or bit-serial connections, a Universal Serial Bus (USB) port or other serial ports, radiofrequency identification (RFID) devices and/or other common electronic components used to establish electronic communication.

Figure 4:
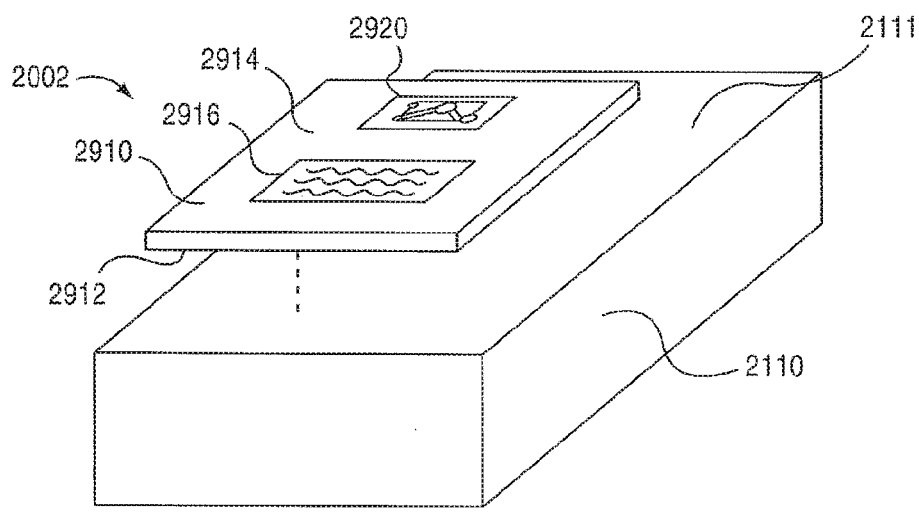
FIG. 4 is a schematic illustration of a medicament delivery device according to an embodiment.

FIG. 4 is a schematic illustration of a medical device 2002 according to an embodiment. The medical device 2002, which can be, for example, a medicament delivery device such as an auto-injector, a pen injector, an inhaler, a transdermal delivery system or the like, includes a housing 2110 and a label 2910. The label 2910 is coupled to an outer surface 2111 of the housing 2110. The label 2910 includes a first surface 2912, a second surface 2914 and an electronic circuit system 2920. The first surface 2912 is configured to engage the outer surface 2111 of the housing 2110 to couple the label 2910 to the housing 2110. In some embodiments, the first surface 2912 can include an adhesive to fixedly couple the label 2910 to the housing 2110. The second surface 2914 includes a textual indicia 2916. The textual indicia 2916 can include, for example, a description of the medicament delivery device, a source of the medicament delivery device and/or an instruction associated with the use of the medicament delivery device. Although the first surface 2912 is shown as being opposite the second surface 2914, in other embodiments, the first surface 2912 and the second surface 2914 can be adjacent each other and/or co-planar.

The electronic circuit system 2920 is configured to output an electronic signal of the types shown and described herein. As discussed in more detail herein, the electronic circuit system 2920 can include many components, such as, for example, a processor, a switch, a visual output device and/or an audio output device. The electronic signal can be, for example, an electronic signal communicated to an output device, such as, for example, a visual output device, an audio output device, a haptic output device or the like. In some embodiments, the electrical signal can be a communications signal configured to be received by a remote device, in a manner similar to that described herein.

In some embodiments, the electronic signal can be associated with an aspect of the medical device 2002, such as an instruction associated with an initial use of the medical device 2002. For example, in some embodiments, the electronic circuit system 2920 can output a text message to a display screen (not shown) disposed on the medical device 2002 instructing the user in the use of the medical device 2002. In other embodiments, the electronic circuit system 2920 can produce an audio output, such as recorded speech, instructing the user in the use of the medical device 2002. In yet other embodiments, the electronic circuit system 2920 can produce and/or transmit an electrical signal associated with a medicament delivery event. In this manner, the electronic circuit system 2920 can be used to track the patient compliance and/or adherence data associated with the use of the medicament delivery device 2002.

Although the electronic circuit system 2920 is shown as being disposed on the second surface 2914 of the label 2910, in other embodiments, the electronic circuit system can be disposed on the first surface 2912 of the label 2910. In yet other embodiments, the electronic circuit system 2920 can be disposed between the first surface 2912 and the second surface 2914 of the label 2910. In yet other embodiments, the label 2910 can include multiple discrete layers coupled together, within which portions of the electronic circuit system can be disposed.

Figure 5:
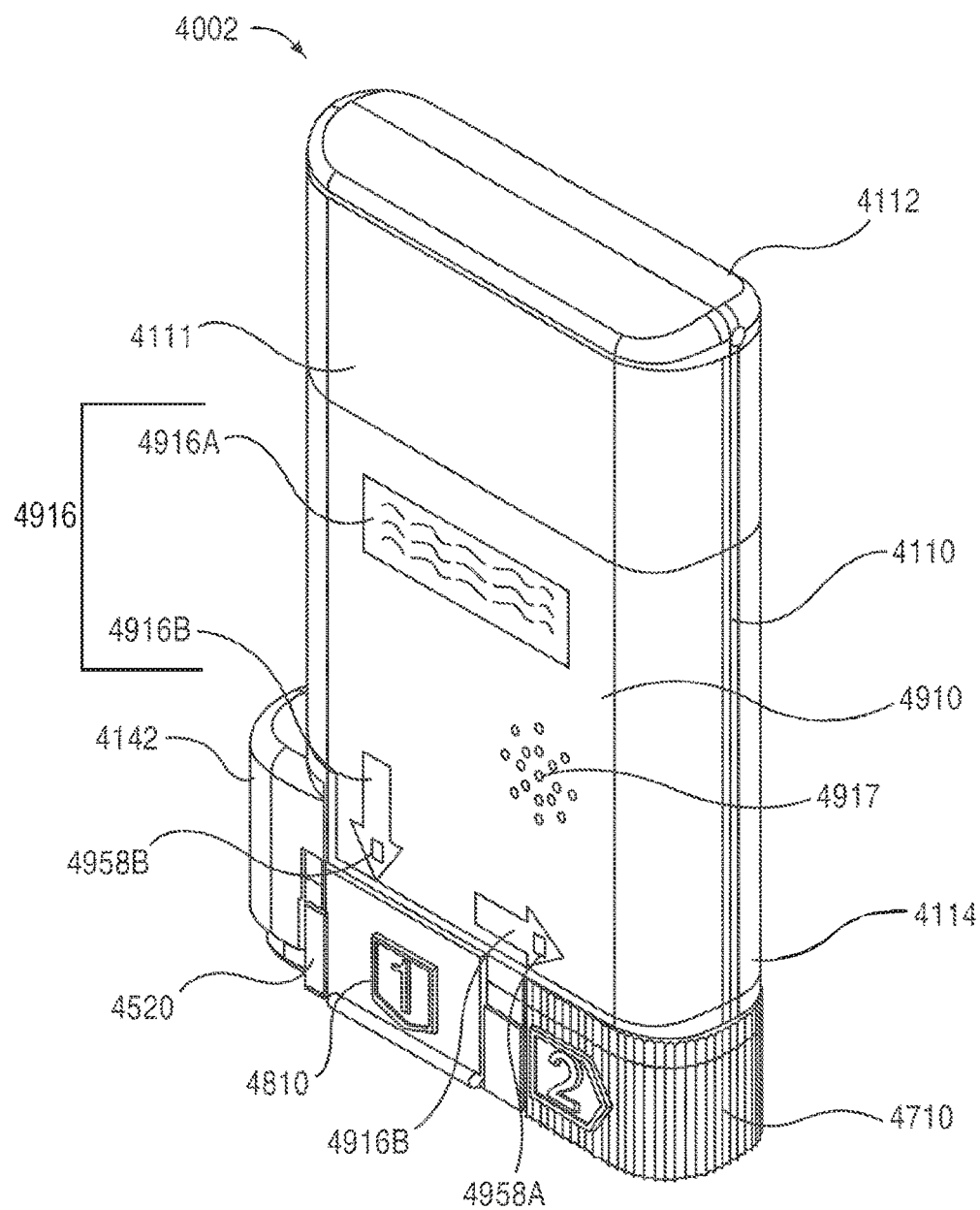
FIG. 5 is a perspective view of an auto-injector according to an embodiment.

FIG. 5 is a perspective view of an auto-injector 4002 according to an embodiment. The auto-injector 4002 is similar to the auto-injectors described in U.S. patent application Ser. No. 11/562,061, entitled "Devices, Systems and Methods for Medicament Delivery," filed Nov. 21, 2006, which is incorporated herein by reference in its entirety. Accordingly, the mechanical components and operation of the auto-injector 4002 are not described in detail herein.

The auto-injector 4002 includes a housing 4110 having a proximal end portion 4112 and a distal end portion 4114. The distal end portion 4114 of the housing 4110 includes a protrusion 4142 to help a user grasp and retain the housing 4110 when using the auto-injector 4002. Said another way, the protrusion 4142 is configured to prevent the auto-injector 4002 from slipping from the user's grasp during use. A base 4520 is movably coupled to the distal end portion 4114 of the housing 4110. A needle guard assembly 4810 is removably coupled to the base 4520. Similarly, a safety lock 4710 is removably coupled to the base 4520. To inject a medicament into the body, the distal end portion 4114 of the housing is oriented towards the user such that the base 4520 is in contact with the portion of the body where the injection is to be made. The base 4520 is then moved towards the proximal end 4112 of the housing 4110 to actuate the auto-injector 4002.

Figure 6:
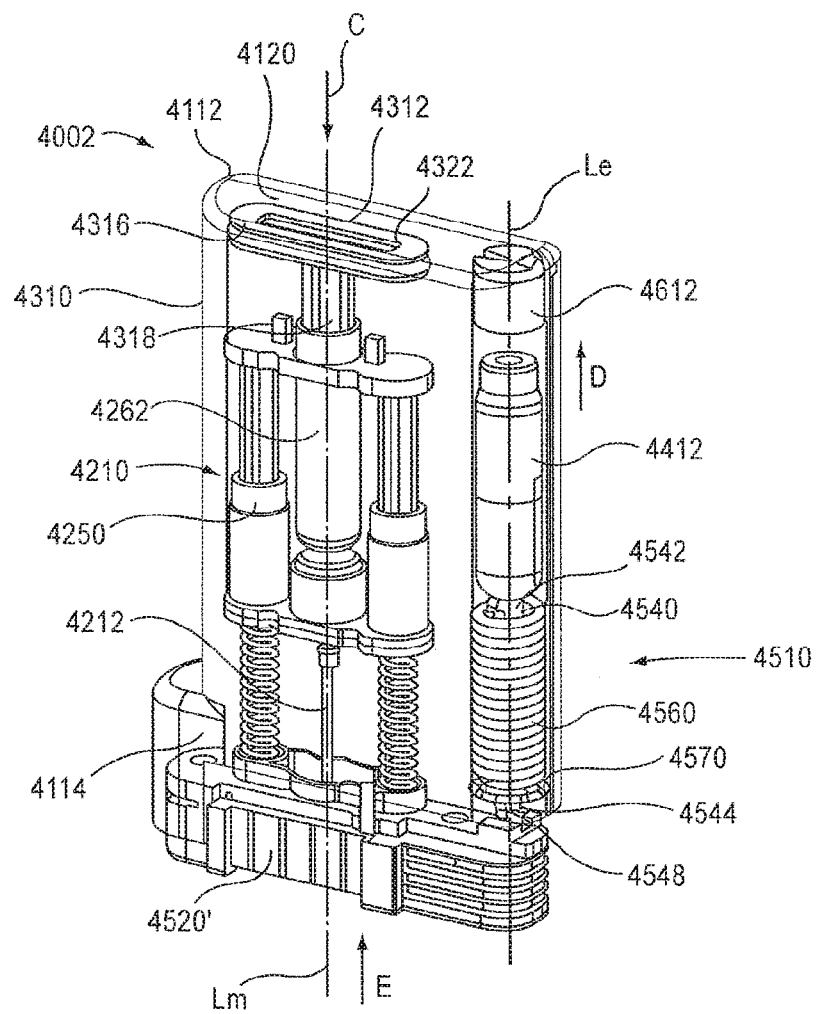
FIG. 6 is a perspective view of the auto-injector illustrated in FIG. 5 in a first configuration, with at least a portion of the auto-injector illustrated in phantom lines for ease of reference.
Figure 7:
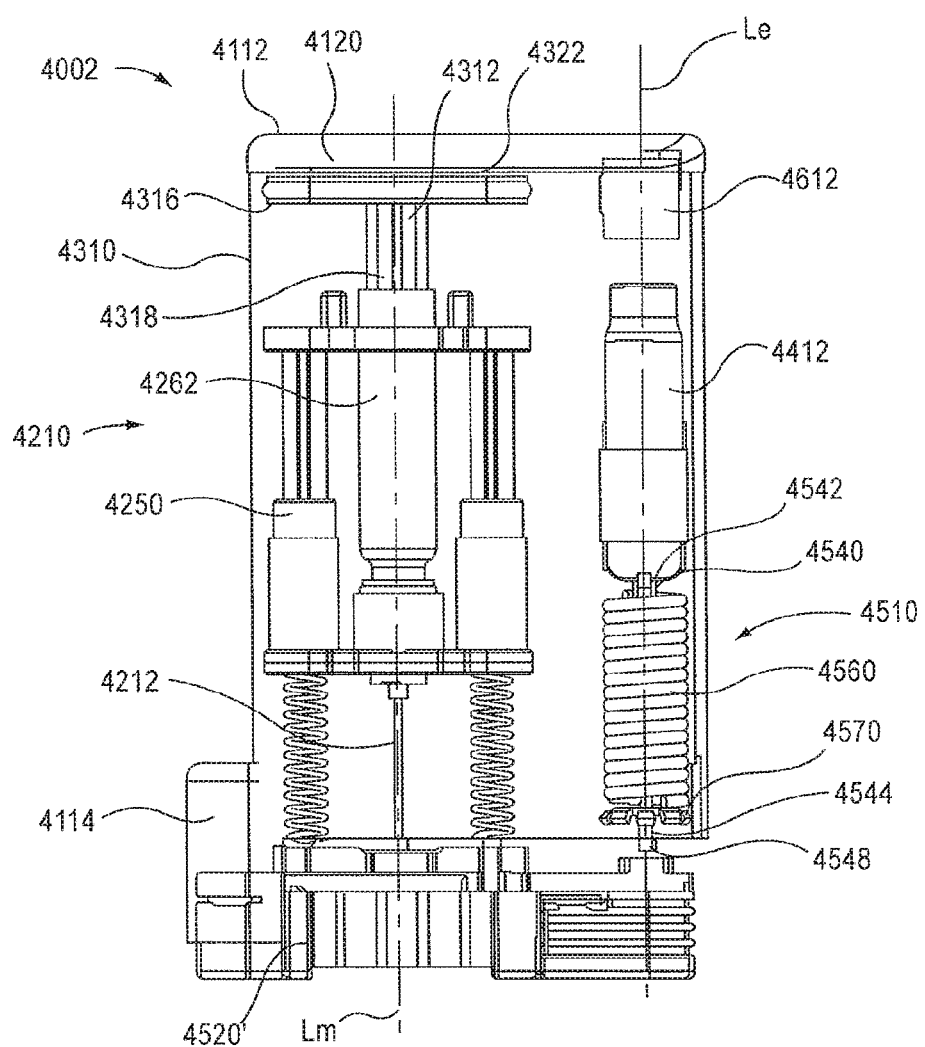
FIG. 7 is a front view of the auto-injector illustrated in FIGS. 5 and 6 in a first configuration.

FIG. 6 is a perspective view of the auto-injector 4002 showing the housing 4110 in phantom lines so that the components contained within the housing 4110 can be more clearly seen. Similarly, FIG. 7 is a front view of the auto-injector 4002 showing the housing 4110 in phantom lines. For clarity, the auto-injector 4002 shown in FIGS. 6 and 7 show the auto-injector 4002 without the needle guard assembly 4810', the safety lock 4710' and the electronic circuit system 4920. Additionally, the auto-injector 4002 shown and described with reference to FIGS. 6-14 is presented to describe the mechanical components and operation of the device. Accordingly, the auto-injector 4002 shown and described with reference to FIGS. 6-14 includes a needle guard assembly 4810' that does not include a battery isolation tab 4860 (see e.g. FIG. 21), a safety lock 4710' that does not include an actuator 4732 (see e.g., FIG. 22), and a base 4520' that does not include an actuator 4538 (see e.g., FIG. 23).

The auto-injector 4002 includes a medicament injector 4210 and a movable member 4312 engaged with the medicament injector 4210, each of which are disposed within the housing 4110. The auto-injector 4002 also includes a system actuator 4510, a compressed gas container 4412 and a gas release mechanism 4612. The medicament injector 4210 includes a carrier 4250 that is movable within the housing 4110, a medicament container 4262 and a needle 4212. The medicament container 4262 is coupled to the carrier 4250. The needle 4212 is disposed within a needle hub portion of the carrier to allow the needle 4212 to be placed in fluid communication with the medicament container 4262 during an injection event.

The movable member 4312 includes a proximal end portion 4316 and a distal end portion 4318. The proximal end portion 4316 includes a surface 4322 that, together with the housing 4110, defines a gas chamber 4120. Said another way, the surface 4322 defines a portion of a boundary of the gas chamber 4120. The distal end portion 4318 is disposed within the medicament container 4262. In use, the movable member 4312 moves towards the distal end portion 4114 of the housing 4110, as indicated by arrow C in FIG. 6, in response to a force produced by a pressurized gas on the surface 4322 of the movable member 4312. As a result, the movable member 4312 and the medicament injector 4250 are moved towards the distal end portion 4114 of the housing 4110, thereby exposing the needle 4212 from the housing 4110. The movable member 4312 then continues to move within the medicament container 4262 to expel a medicament from the medicament container 4262 through the needle 4212.

The auto-injector 4002 is actuated by the system actuator 4510, which is configured to move the compressed gas container 4412 into contact with the gas release mechanism 4612. The gas release mechanism 4612 punctures a portion of the compressed gas container 4412 to release the pressurized gas contained therein into the gas chamber 4120 defined by the housing 4110. The system actuator 4510 includes a rod 4540, a spring 4560 and a spring retainer 4570. The rod 4540 has a proximal end portion 4542 and a distal end portion 4544. The proximal end portion 4542 of the rod 4540 is coupled to the compressed gas container 4412. The distal end portion 4544 of the rod 4540 is coupled to the spring retainer 4570 by two projections 4548, which can be moved inwardly towards each other to decouple the rod 4540 from the spring retainer 4570, as discussed below.

The spring 4560 is disposed about the rod 4540 in a compressed state such that the spring 4560 is retained by the proximal end portion 4542 of the rod 4540 and the spring retainer 4570. In this manner, the rod 4540 is spring-loaded such that when the distal end portion 4544 of the rod 4540 is decoupled from the spring retainer 4570, the force of the spring 4560 causes the rod 4540, and therefore the compressed gas container 4412, to move proximally as indicated by arrow D in FIG. 6 and into contact with the gas release mechanism 4612.

The base 4520' defines an opening 4522 configured to receive a portion of the projections 4548 when the base is moved towards the proximal end 4112 of the housing 4110, as indicated by arrow E in FIG. 6. When the projections 4548 are received within the opening 4522, they are moved together causing the distal end portion 4544 of the rod 4540 to be released from the spring retainer 4570.

As shown in FIGS. 6 and 7, the medicament injector 4210 defines a longitudinal axis Lm that is non-coaxial with the longitudinal axis Le defined by the compressed gas container 4412. Accordingly, the medicament injector 4210, the compressed gas container 4412 and the system actuator 4510 are arranged within the housing 4110 such that the housing has a substantially rectangular shape. Moreover, the non-coaxial relationship between the medicament injector 4210 and the compressed gas container 4412 allows the auto-injector 4002 to be actuated by manipulating the base 4520', which is located at the distal end portion 4114 of the housing 4110.

Prior to use, the auto-injector 4002 must first be enabled by first removing the needle guard 4810' and then removing the safety lock 4710'. As illustrated by arrow G in FIG. 8, the needle guard 4810' is removed by pulling it distally. As described in more detail below, removal of the needle guard 4810' also removes the isolation tab 4860 (see FIG. 21), thereby placing the batteries 4962 into electrical connection with the electronic circuit system 4910 (not shown in FIGS. 6-14, for purposes of clarity). Similarly, as illustrated by arrow H in FIG. 9, the safety lock 4710' is removed by pulling it substantially normal to the longitudinal axis Le of the compressed gas container 4412. Said another way, the safety lock 4710' is removed by moving it in a direction substantially normal to the direction that the needle guard 4810' is moved. As described below, removal of the safety lock 4710' also actuates the electronic circuit system 4920 (not shown in FIGS. 6-14, for purposes of clarity). The needle guard 4810' and the safety lock 4710' are cooperatively arranged to prevent the safety lock 4710' from being removed before the needle guard 4810' has been removed. Such an arrangement prevents the auto-injector 4002 from being actuated while the needle guard 4810' is in place.

Figure 10:
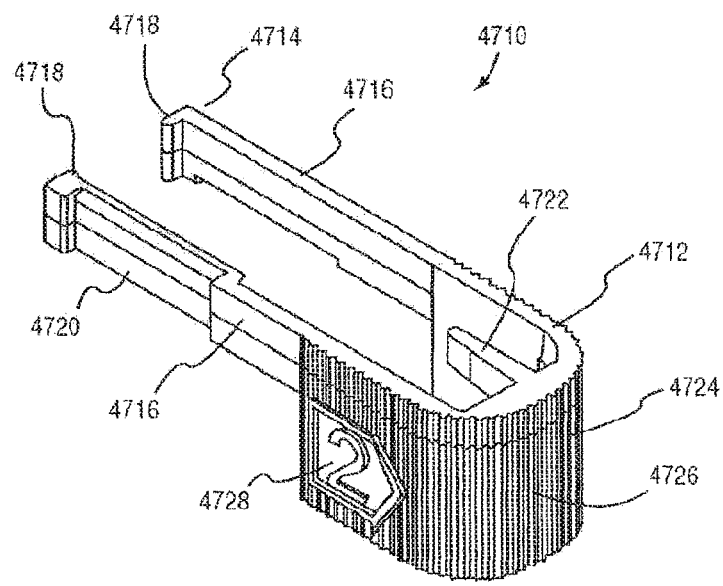
FIG. 10 is a perspective view of a member of the auto-injector illustrated in FIG. 9.
Figure 11:
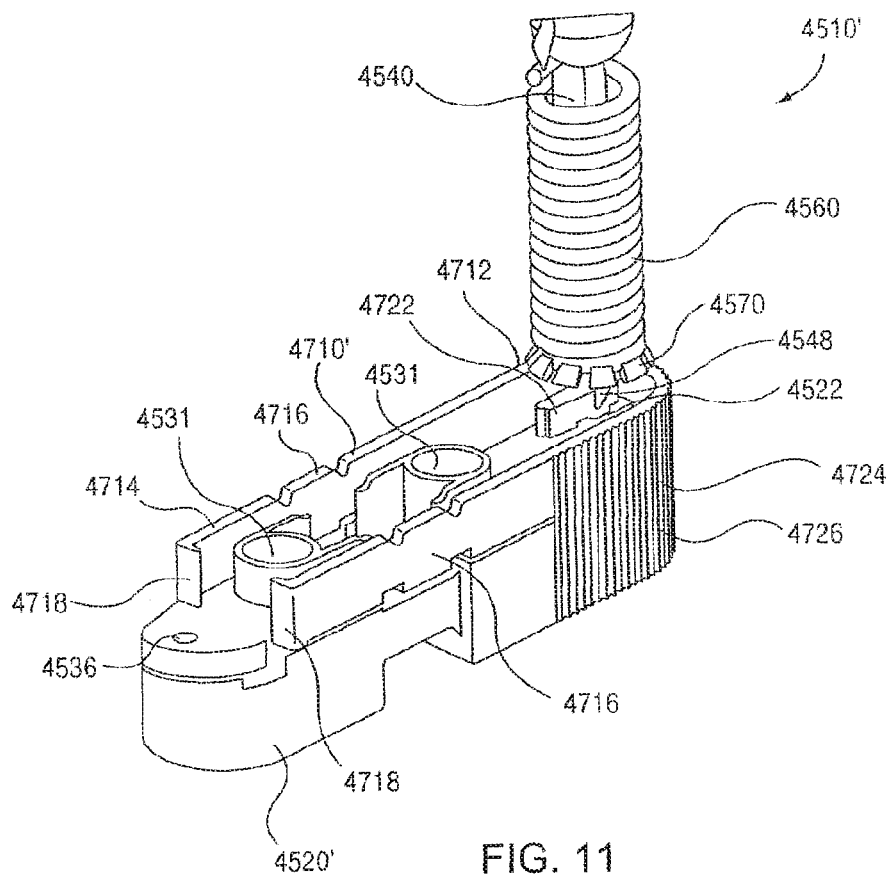
FIG. 11 is a perspective view of a portion of the auto-injector illustrated in FIG. 9.

As shown in FIG. 10, the safety lock 4710' is a U-shaped member having a first end 4712 and a second end 4714. The second end 4714 of the safety lock 4710' includes two extended portions 4716, each of which includes an inwardly facing protrusion 4718. When the safety lock 4710' is in its first (or locked) position, the extended portions 4716 extend around a portion of the base 4520' to space the base 4520' apart from the distal end portion 4114 of the housing 4110. As shown in FIG. 11, the protrusions 4718 are configured engage a portion of the base 4520' to removably couple the safety lock 4710' in its first position. Additionally, one of the extended portions 4716 defines a recess 4720 that receives the sheath retainer 4840 when the needle guard 4810' is in its first position.

The first end 4712 of the safety lock 4710' includes a locking protrusion 4722 that extends inwardly. As shown in FIG. 11, when the safety lock 4710' is in its first position, the locking protrusion 4722 extends between the projections 4548 of the rod 4540 and obstructs the opening 4522 of the base 4520'. In this manner, when the safety lock 4710' is in its first position, the base 4520' cannot be moved proximally to allow the projections 4548 to be received within the opening 4522. The arrangement of the locking protrusion 4722 also prevents the projections 4548 from being moved inwardly towards each other. Accordingly, when the safety lock 4710' is in its first position, the auto-injector 4002 cannot be actuated.

The outer surface 4724 of the first end 4712 of the safety lock 4710' includes a series of ridges 4726 to allow the user to more easily grip the safety lock 4710'. The outer surface 4724 of the first end 4712 of the safety lock 4710' also includes an indicia 4728 to instruct the user in operating the auto-injector 4002. As shown in FIG. 10, the indicia 4728 includes a numeral to indicate the order of operation and an arrow to indicate the direction in which the safety lock 4710' should be moved. In some embodiments, the indicia 4728 can include different colors, detailed instructions or any other suitable indicia to instruct the user. In other embodiments, the indicia 4728 can protrude from the safety lock 4710' to aid the user when grasping the safety lock 4710'.

Figure 12:
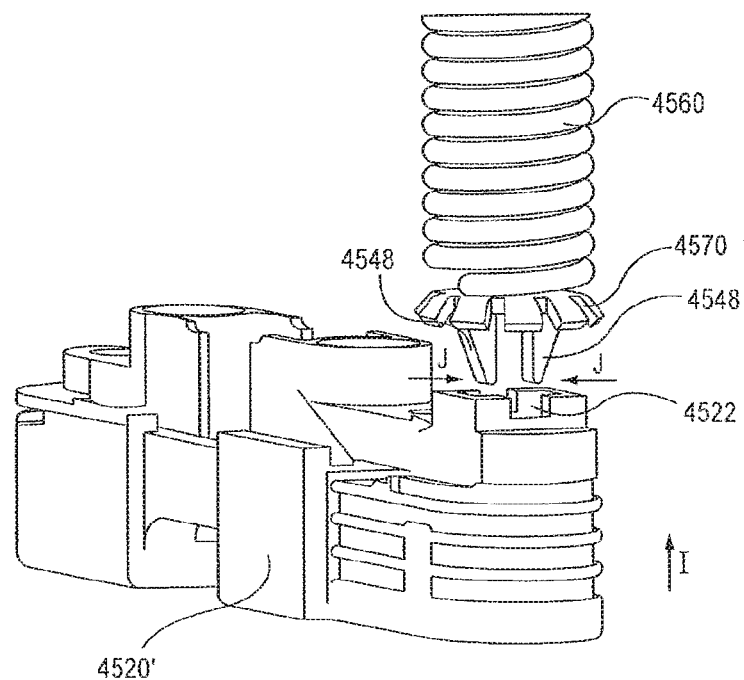
FIG. 12 is a perspective view of a portion of the auto-injector illustrated in FIG. 11.
Figure 13:
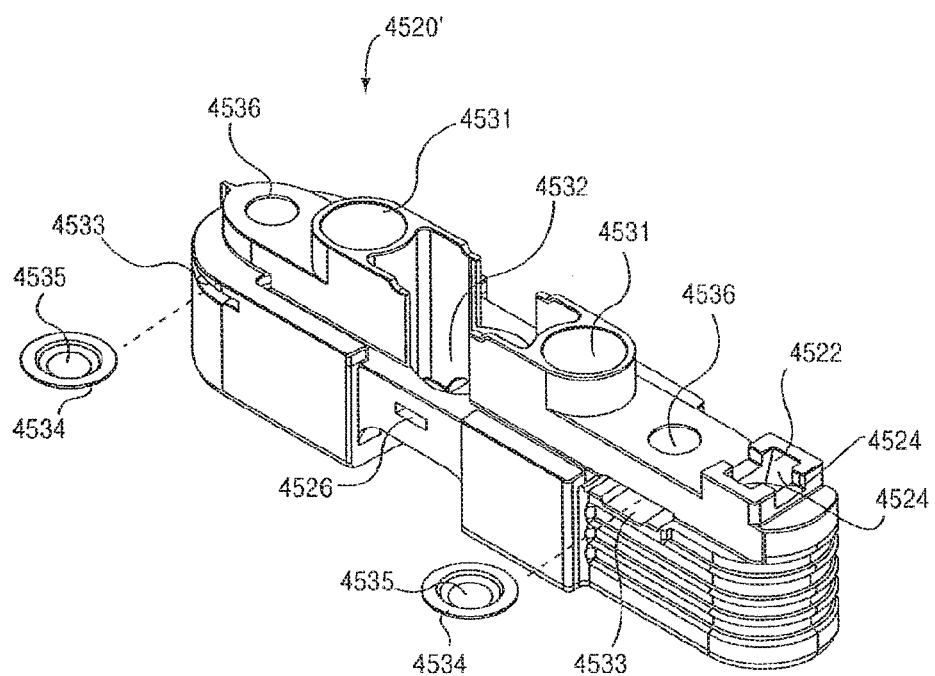
FIG. 13 is a partially exploded perspective view of a base of the auto-injector illustrated in FIG. 11.

After being enabled, the auto-injector 4002 can then be actuated by moving the base 4520' proximally towards the housing 4110, as indicated by arrow I in FIG. 12. Additionally, as described below, movement of the base 4520' actuates the electronic circuit system 4920 (not shown in FIGS. 6-14, for purposes of clarity). As shown in FIG. 13, the base 4520' defines two openings 4536 that receive corresponding attachment protrusions 4150 disposed on the distal end portion 4114 of the housing 4110. In this manner, the movement and/or alignment of the base 4520' relative to the housing 4110 is guided by the attachment protrusions 4150 and the openings 4536. Each attachment protrusion 4150 is secured within its corresponding opening 4536 by a lock washer 4534. The lock washers 4534 each define an opening 4535 that receives a portion of the attachment protrusion 4150. The lock washers 4534 are disposed within slots 4533 defined by the base 4520' so that the openings 4535 are aligned with the attachment protrusions 4150. The openings 4535 are configured to allow the lock washers 4534 to move proximally relative to the attachment protrusions 4150, but to prevent movement of the lock washers 4534 distally relative to the attachment protrusions 4150. In this manner, when the attachment protrusions 4150 are disposed within the openings 4535 of the lock washers 4534, the base 4520' becomes fixedly coupled to the housing 4110. Moreover, after the base 4520' is moved proximally relative to the housing 4110, the lock washers 4534 prevent the base 4520' from returning to its initial position.

The base 4520' also defines a needle opening 4532, a recess 4526 and two retraction spring pockets 4531. The needle opening 4532 receives a portion of the needle guard 4810' when the needle guard is in its first position. Additionally, when the auto-injector 4002 is actuated, the needle 4212 extends through the needle opening 4532. The retraction spring pockets 4531 receive a portion of the retraction springs.

As shown in FIG. 13, the base 4520' includes two opposing tapered surfaces 4524 that define an opening 4522 configured to receive a corresponding tapered surface 4550 of the projections 4548 when the base 4520' is moved proximally towards the housing 4110. When the projections 4548 are received within the tapered opening 4522, they are moved together as indicated by arrows J in FIG. 12. The inward movement of the projections 4548 causes the rod 4540 to become disengaged from the spring retainer 4570, thereby allowing the rod 4540 to be moved proximally along its longitudinal axis as the spring 4560 expands.

Figure 14:
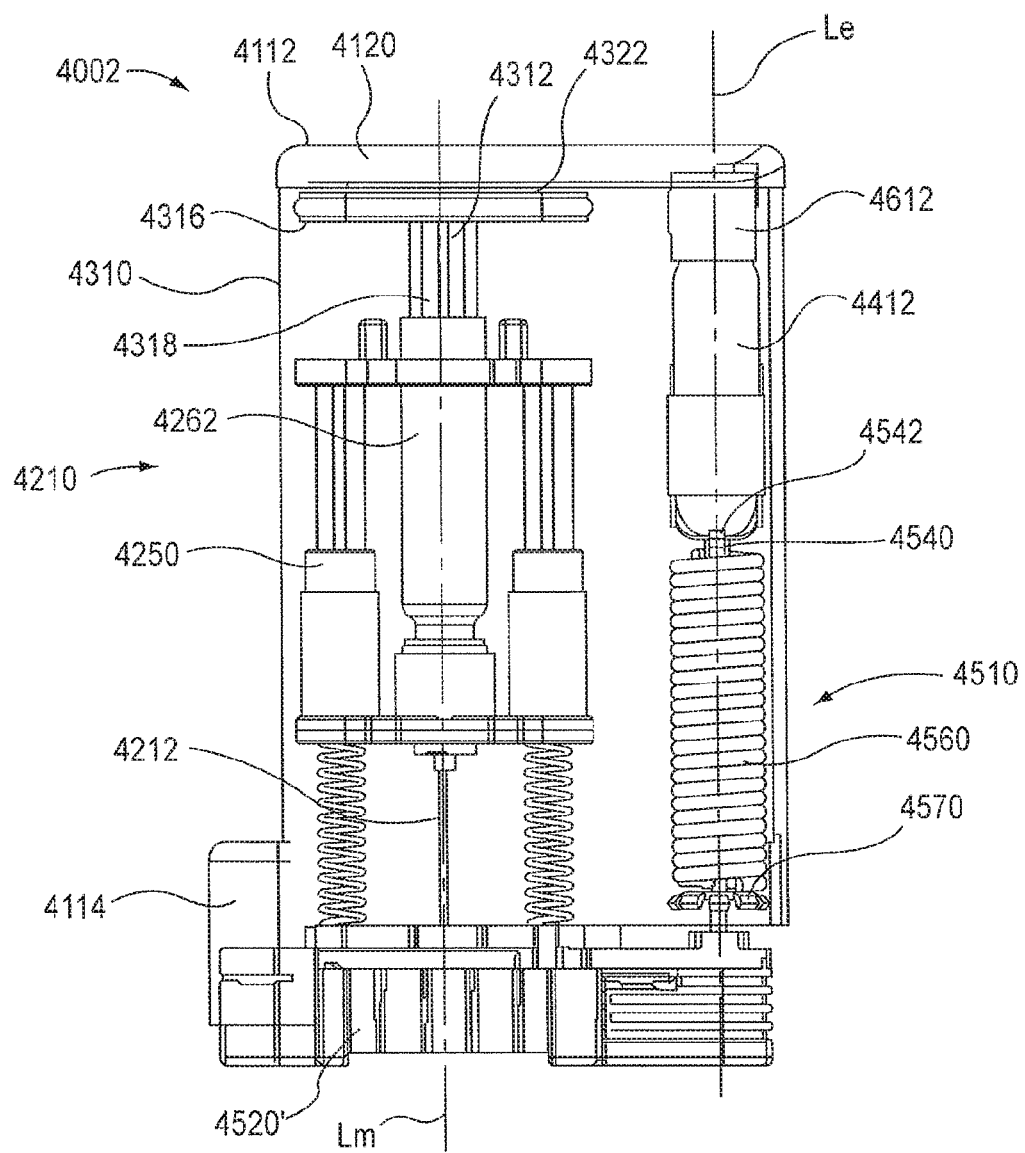
FIG. 14 is a front view of the auto-injector illustrated in FIG. 7 in a second configuration.

Because the rod 4540 is coupled to the compressed gas container 4412, when the rod 4540 is moved from its first (engaged) position to its second (actuated) position, the compressed gas container 4412 is moved proximally within the housing 4110 into engagement with the gas release mechanism 4612. FIG. 14 shows the auto-injector in a second configuration, in which the compressed gas container 4412 is engaged with the gas release mechanism 4612. When in the second configuration, the compressed gas contained within the compressed gas container 4412 is released to actuate the medicament injector 4210. Although the system actuator 4510 is shown and described as moving the gas container 4412 into contact with the gas release mechanism 4612, in other embodiments, a system actuator can move a gas release mechanism into contact with a gas container. For example, the auto-injector 4000' shown and described below with reference to FIGS. 26-57 includes a moving puncturer (see e.g., FIG. 35).

The pressurized gas produces a force that causes the movable member 4312 and the medicament injector 4210 to move distally within the housing 4110. The movement of the medicament injector 4210 causes the needle 4212 to extend from distal end portion 4114 of the housing 4110 and the base 4520. This operation can be referred to as the "needle insertion" operation. When the medicament injector 4210 has completed its movement (i.e., the needle insertion operation is complete), the movable member 4312 continues to move the medicament container 4262 distally within the carrier 4250. The continued movement of the medicament container 4262 places the needle 4212 in fluid communication with the medicament container 4262, thereby allowing the medicament to be injected. The force from the pressurized gas also causes the movable member 4312 to move within the medicament container 4262, thereby expelling the medicament through the needle 4212. This operation can be referred to as the "injection operation." Upon completion of the injection, the pressurized gas is released from the gas chamber 4120, thereby allowing the medicament injector 4210 and the movable member 4312 to be moved proximally within the housing. This operation can be referred to as the "retraction operation."

Figure 15:
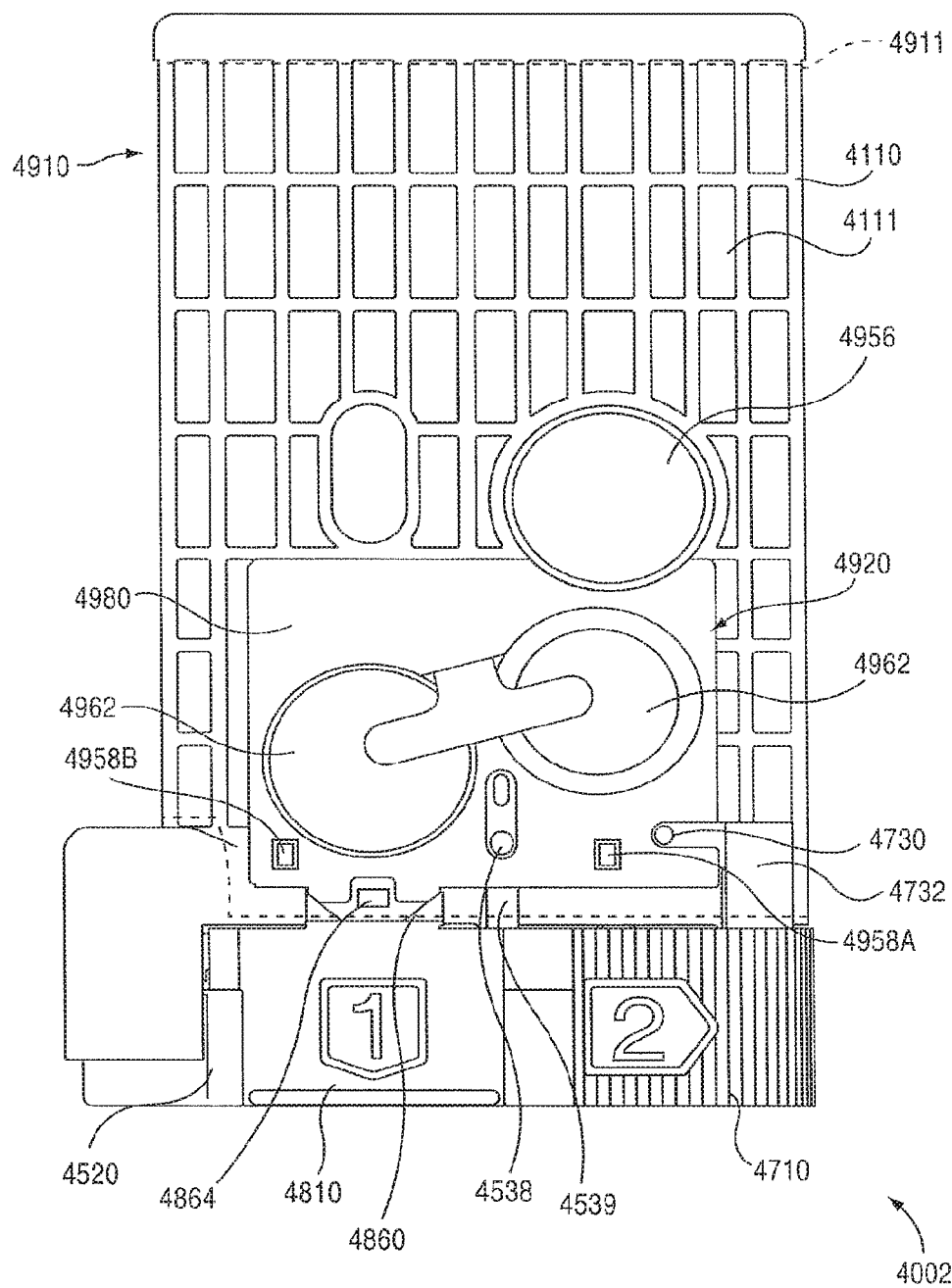
FIG. 15 is a front view of the auto-injector illustrated in FIG. 5, with a portion of the auto-injector illustrated in phantom lines for ease of reference.
Figure 16:
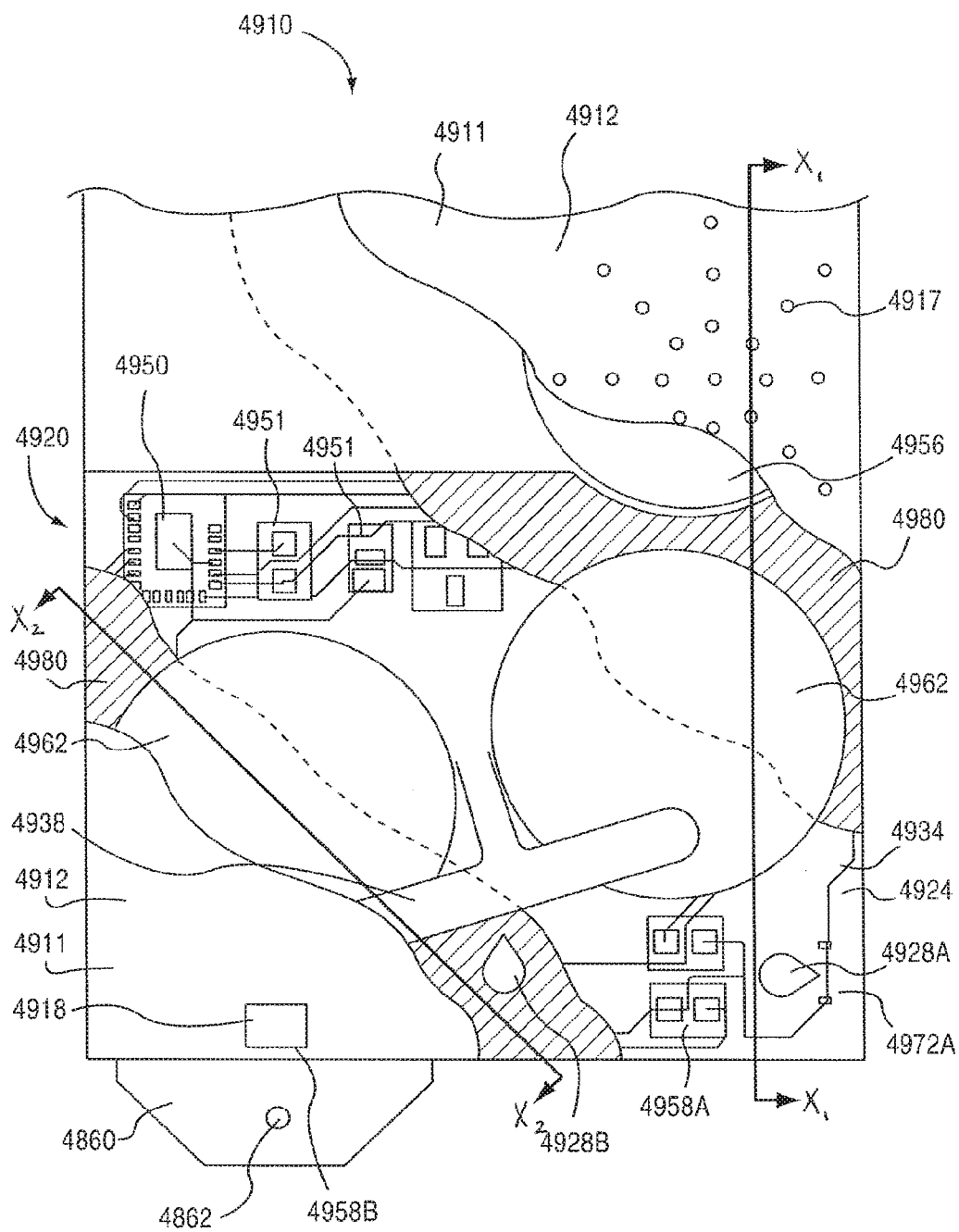
FIG. 16 is a partial cut-away front view of a portion of the auto-injector illustrated in FIG. 15.
Figure 17:
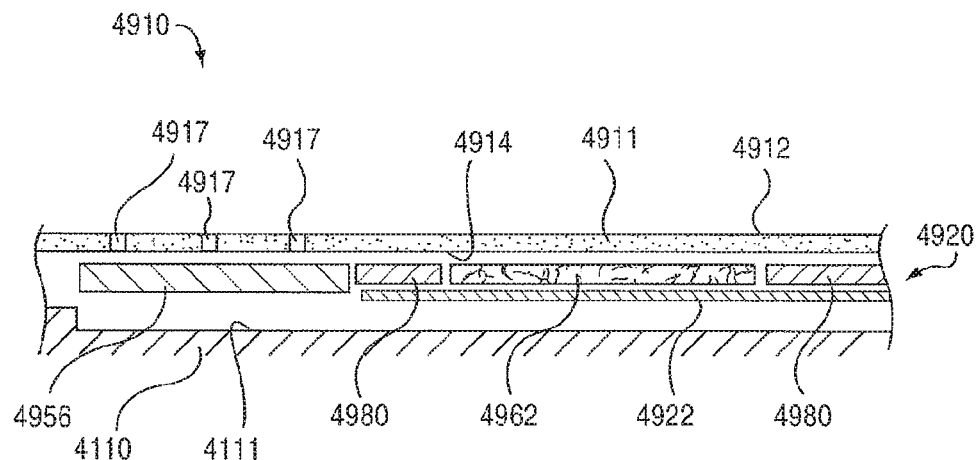
FIG. 17 is a cross-sectional view of a portion of the auto-injector illustrated in FIG. 15 taken along line $X_1$-$X_1$ in FIG. 16.
Figure 18:
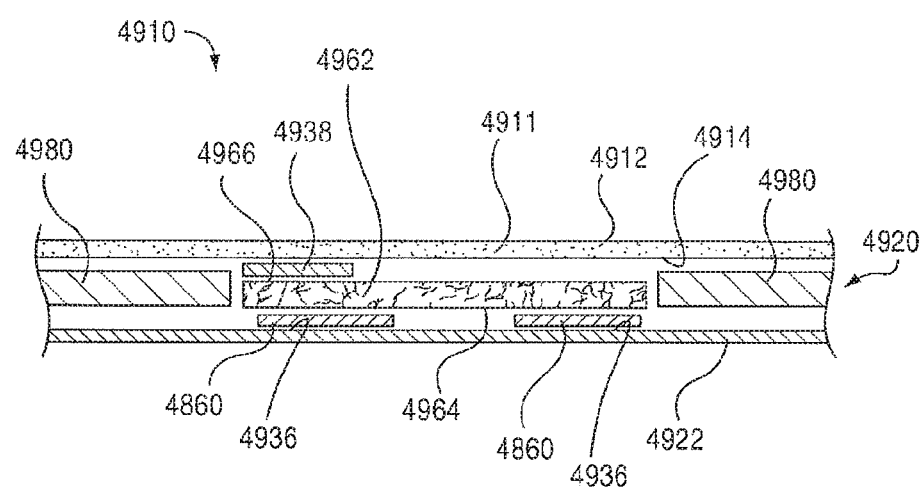
FIG. 18 is a cross-sectional view of a portion of the auto-injector illustrated in FIG. 15 taken along line $X_2$-$X_2$ in FIG. 16.

As shown in FIG. 5, the auto-injector 4002 includes a label 4910 coupled to an outer surface 4111 of the housing 4110. The label 4910 includes an outer layer 4911, an intermediate layer 4980 and an electronic circuit system 4920 (see FIGS. 16-18). FIG. 15 is a front view of the auto-injector 4002 showing the outer layer 4911 of the label 4910 in phantom lines so that the intermediate layer 4980 and an electronic circuit system 4920 can be more clearly seen. As shown in FIGS. 16-18, the outer layer 4911, which, in some embodiments, can be constructed from paper, has a first surface 4912 and a second surface 4914 opposite the first surface 4912. Multiple indicia 4916 are disposed on the first surface 4912. The indicia 4916 include a textual indicia 4916A and two symbolic indicia 4916B. The textual indicia 4916B can be written text describing the medicament delivery device, indicating a source of the medicament delivery device and/or instructing a user in the use of the medicament delivery device. The symbolic indicia 4916B can include, for example, arrows, pointers, trademarks, symbols describing the use of the medicament delivery device or the like. The label 4910 is coupled to the outer surface 4111 of the housing 4110 such that the portion of the first surface 4912 including the indicia 4916 is visible.

A portion of the second surface 4914 of the outer layer 4911 can be coupled to the outer surface 4111 of the housing 4110 by any suitable method. For example, in some embodiments, the second surface 4914 of the outer layer 4911 includes an adhesive configured to bond the outer layer 4911 to the outer surface 4111 of the housing 4110. Other portions of the second surface 4914 of the outer layer 4911 are adjacent the intermediate layer 4980 and portions of the electronic circuit system 4920. In this manner, the outer layer 4911 of the label 4910 retains the intermediate, or spacer, layer 4980 and the electronic circuit system 4920 in a predetermined position against the outer surface 4111 of the housing 4110.

The outer layer 4911 of the label 4910 includes multiple openings 4917 adjacent the audio output device 4956. In this manner, sound waves produced by the audio output device 4956 can be transmitted to an area outside of the housing 4110. Similarly, the outer layer 4911 of the label 4910 includes openings 4918 adjacent the light emitting diodes (LEDs) 4958A and 4958B to allow the user to see the visual output. In some embodiments, the outer layer 4911 of the label 4910 can include a transparent portion adjacent the LEDs 4958A and 4958B to allow the user to see the visual output.

The electronic circuit system 4920 includes a printed circuit board 4922 upon which a microprocessor 4950, two LEDs 4958A and 4958B, two switches 4972A and 4972B and various electronic components 4951, such as, for example, resistors, capacitors and diodes, are mounted. The electronic circuit system 4920 also includes an audio output device 4956, such as, for example, a micro-speaker, coupled to the outer surface 4111 of the housing 4110 adjacent the printed circuit board 4922. The printed circuit board 4922 includes a substrate 4924 upon which a series of electrical conductors 4934, such as for example, copper traces, are etched. The substrate 4924 can be constructed from any material having suitable electrical properties, mechanical properties and flexibility, such as, for example Mylar®, Kapton® or impregnated paper.

A mask layer (not shown) is disposed over the substrate 4924 to electrically isolate selected portions of the electrical conductors 4934 from adjacent components. The electrical conductors 4934 operatively couple the above-mentioned circuit components in a predetermined arrangement. In this manner, the electronic circuit system 4920 can be configured to output, via the LEDs 4958A and 4958B and/or the audio output device 4956, a predetermined sequence of electronic outputs during the use of the auto-injector 4002.

Power is supplied to the electronic circuit system 4920 by two batteries 4962 connected in series. The batteries can be, for example, three volt, "watch-style" lithium batteries. As shown in FIG. 18, each of the batteries 4962 has a first surface 4964 and a second surface 4966 opposite the first surface. The first surface 4964 can be, for example, an electrically negative terminal. Similarly, the second surface 4966 can be an electrically positive terminal. As discussed in more detail herein, the batteries 4962 are positioned such that a first electrical contact portion 4936 of the printed circuit board 4922 can be placed in contact with the first surface 4964 of the battery 4962 and a second electrical contact portion 4938 of the printed circuit board 4922 can be placed in contact with the second surface 4966 of the battery 4962. In this manner, the batteries 4962 can be operatively coupled to the electronic circuit system 4920.

As shown in FIGS. 16 and 18, a battery isolation tab 4860 is movably disposed between the first electrical contact portion 4936 of the printed circuit board 4922 and the first surface 4964 of one of the batteries 4962. The battery isolation tab 4860 can be constructed from any electrically isolative material, such as, for example, Mylar®. As discussed in more detail herein, in this manner, the batteries 4962 can be selectively placed in electronic communication with the electronic circuit system 4920.

The intermediate, or spacer, layer 4980 is disposed between the outer layer 4911 and the electronic circuit system 4920. The intermediate layer 4980 includes openings (not shown) within which various components of the electronic circuit system, such as, for example, the batteries 4962 are disposed. The intermediate layer 4980 is sized to maintain a predetermined spacing between the various components included in the label 4910. The intermediate layer can be constructed from any suitable material, such as, for example, flexible foam having an adhesive surface, polycarbonate or the like.

Figure 19:
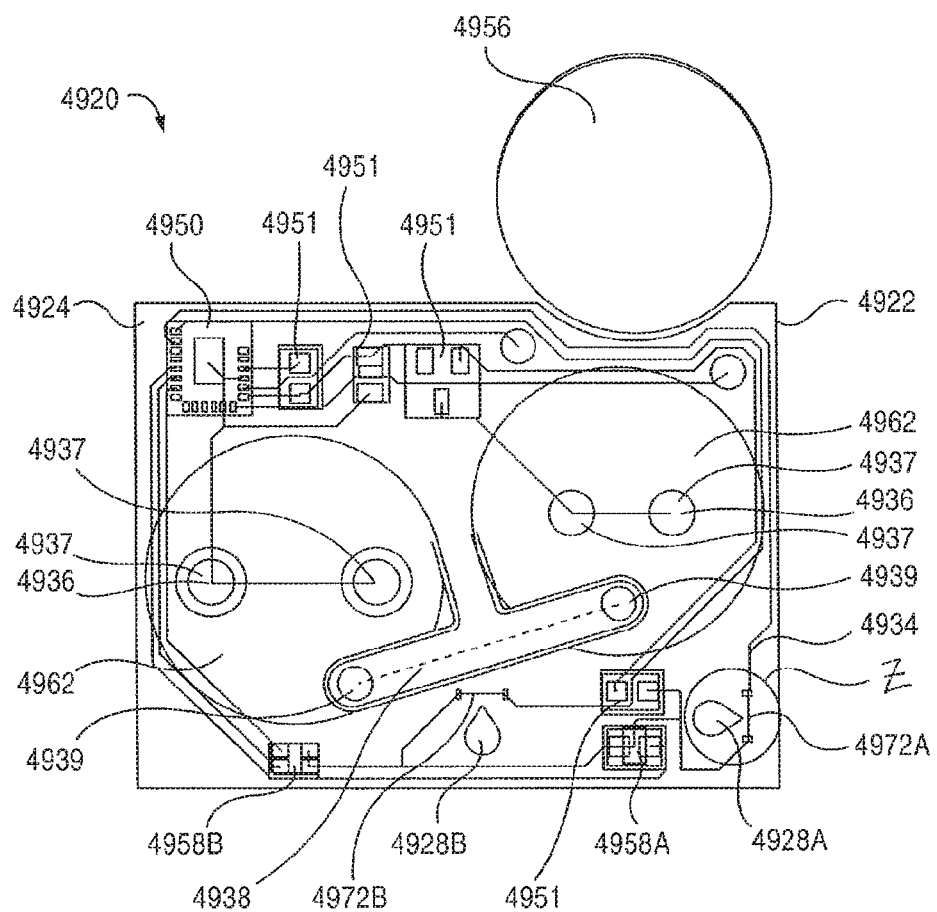
FIG. 19 is a front view of a portion of the auto-injector illustrated in FIG. 15.
Figure 20:
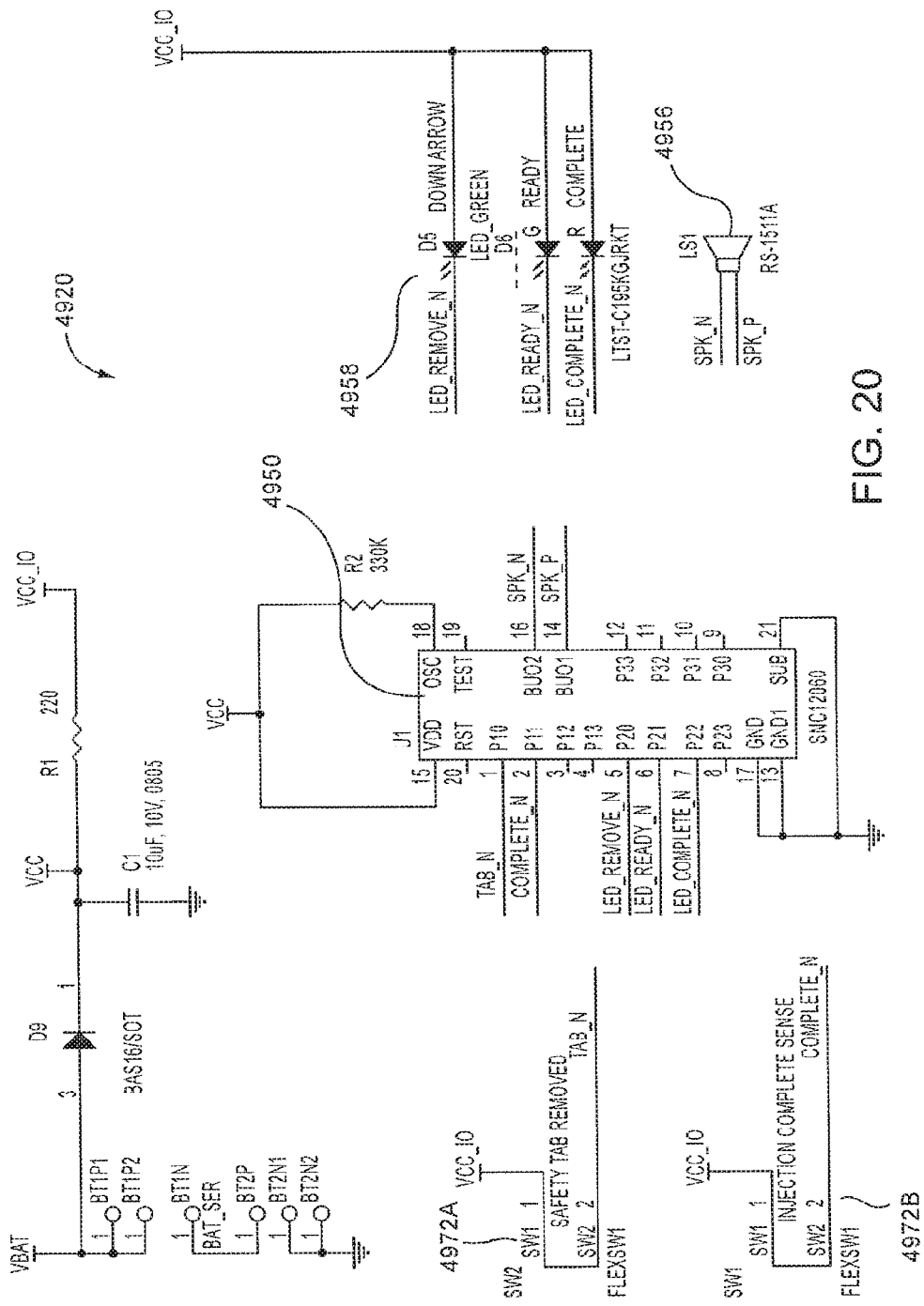
FIG. 20 is a schematic illustration of a portion of the auto-injector illustrated in FIG. 15.

FIG. 19 is a front view of the electronic circuit system 4920 showing the arrangement of the various components (i.e., the microprocessor 4950, LEDs 4958A and 4958B, switches 4972A and 4972B, audio output device 4956 or the like). FIG. 20 is a schematic illustration of the electronic circuit system 4920.

The operation of the auto-injector 4002 and the electronic circuit system 4920 is now discussed with reference to FIGS. 21-23. The actuation of the electronic circuit system 4920 is performed in multiple steps that correspond to operations that are incorporated into the procedures for using the auto-injector 4002. In this manner, the user can actuate various portions and/or functions of the electronic circuit system 4920 without completing any additional operations. Similarly stated, the electronic circuit system 4920 can produce and/or transmit electronic outputs in response to the various stages of operation of the auto-injector 4002. Although not explicitly shown in FIGS. 5-25, in some embodiments, the electronic circuit system 4920 can include a network interface device, as described herein. In this manner, the electronic outputs produced and/or transmitted by the electronic circuit system 4920 can be used to track the patient compliance and/or adherence associated with the use of the auto-injector 4002.

Figure 21:
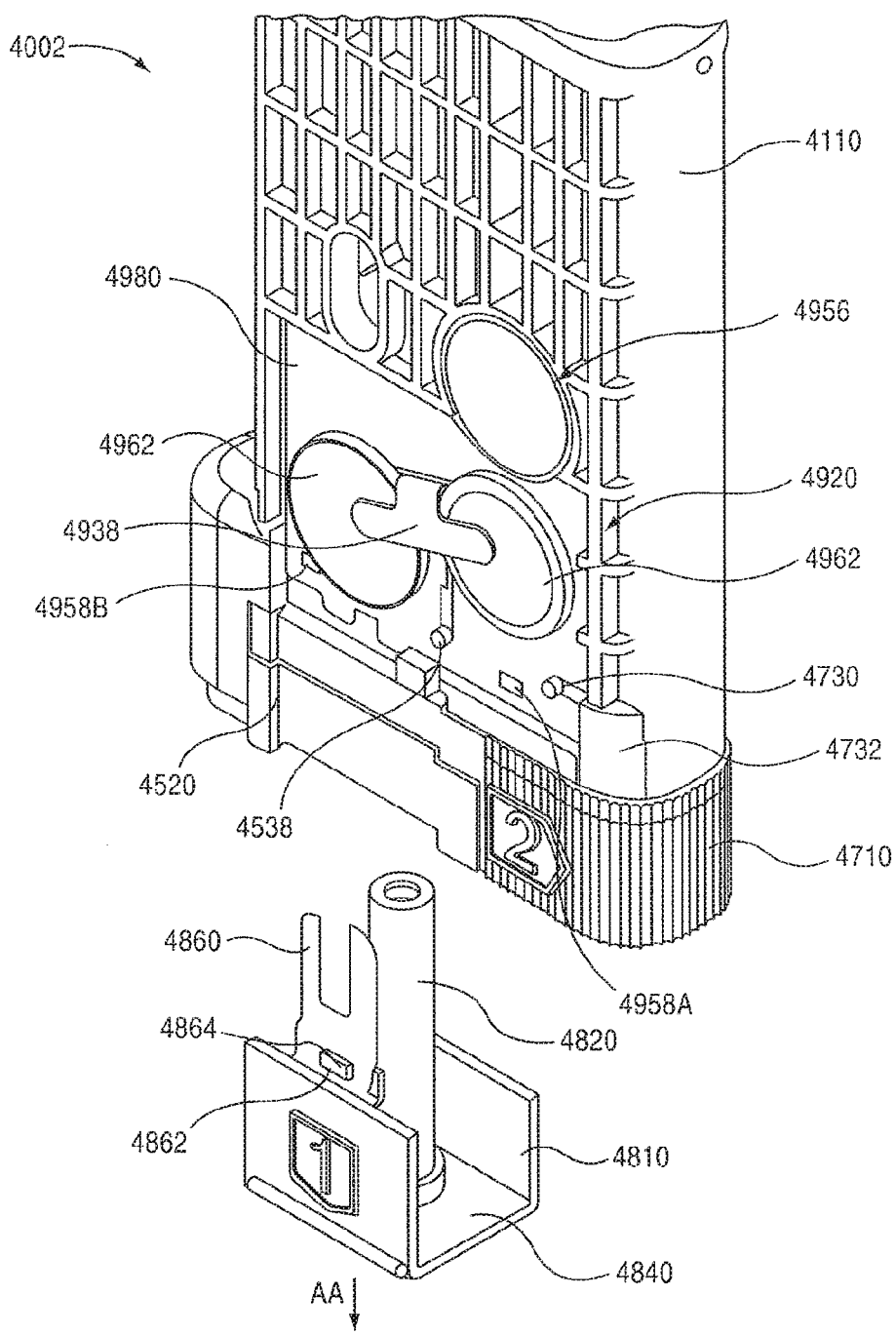
FIG. 21 is a perspective view of a portion of the auto-injector illustrated in FIG. 15 in a second configuration.
Figure 22:
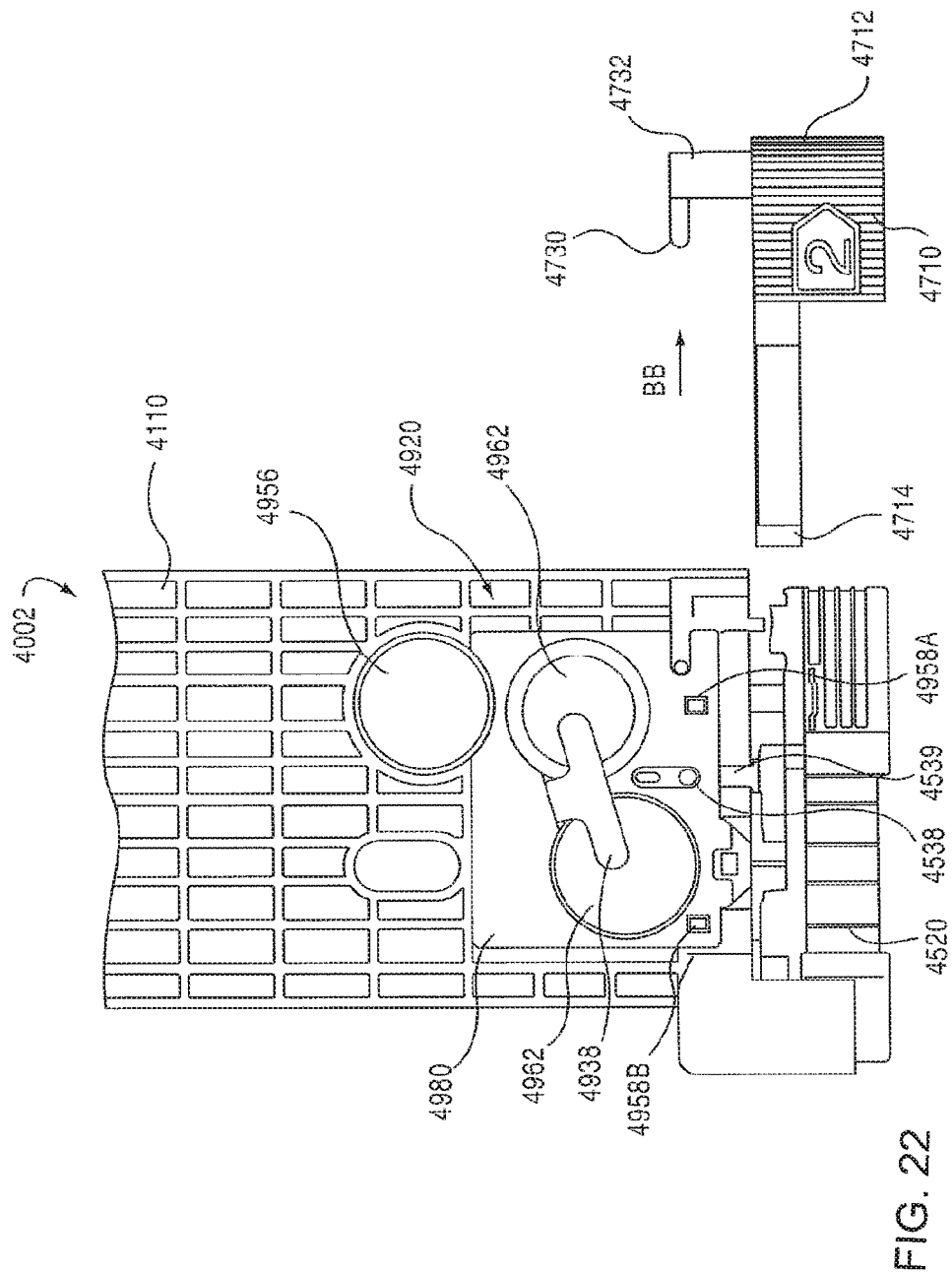
FIG. 22 is a front plan view of a portion of the auto-injector illustrated in FIG. 15 in a third configuration.

Prior to use, the auto-injector 4002 is first enabled by removing the needle guard 4810 and the safety lock 4710 (see FIGS. 21 and 22). As illustrated by arrow AA in FIG. 21, the needle guard 4810 is removed by moving it distally. The needle guard 4810 includes a sheath retainer 4840 and a sheath 4820. The sheath 4820 is configured to receive a portion of the needle (not shown) when the needle guard 4810 is in a first (or installed) position. The sheath retainer 4840 is coupled to the sheath 4820 such that when the sheath retainer 4840 is moved distally away from the base 4520 into a second (or removed) position, the sheath 4820 is removed from the needle.

The sheath retainer 4840 includes an actuator 4864 that is received by an opening 4862 in the isolation tab 4860. Accordingly, when the sheath retainer 4840 is moved distally away from the base 4520, the isolation tab 4860 is removed from the area between the first electrical contact portion 4936 of the printed circuit board 4922 and the first surface 4964 of one of the batteries 4962. In this manner, the batteries 4962 can be operatively coupled to the electronic circuit system 4920 when the needle guard 4810 is removed, thereby actuating the electronic circuit system 4920.

When actuated, the electronic circuit system 4920 can output one or more predetermined electronic outputs. For example, in some embodiments, the processor 4950 can output an electronic signal associated with recorded speech to the audible output device 4956. Such an electronic signal can be, for example, associated with a .WAV file that contains a recorded instruction instructing the user in the operation of the auto-injector 4002. Such an instruction can state, for example, "remove the blue safety tab near the base of the auto-injector." The processor can simultaneously output an electronic signal to the first LED 4958A, thereby causing the first LED 4958A, which is located near the safety lock 4710, to flash a particular color. In this manner, the electronic circuit system 4920 can provide both audible and visual instructions to assist the user in the initial operation of the auto-injector 4002.

In other embodiments, the electronic circuit system 4920 can output an electronic output associated with a description and/or status of the auto-injector 4002 and/or the medicament contained therein. For example, in some embodiments, electronic circuit system 4920 can output an audible message indicating the type of medicament contained in the auto-injector, the expiration date of the medicament, the dosage of the medicament or the like.

As illustrated by arrow BB in FIG. 22, the safety lock 4710 is removed by moving it substantially normal to the longitudinal axis of the housing 4110. The safety lock 4710 has a first end 4712 and a second end 4714. When the safety lock 4710 is in its first (or locked) position, the second end 4714 extends around a portion of the base 4520 to space the base 4520 apart from the distal end portion 4114 of the housing 4110. Additionally, the first end 4714 includes a locking protrusion (not shown) that obstructs portions of the system actuator (not shown) further preventing the base 4520 from being moved proximally towards the housing 4110. Accordingly, when the safety lock 4710 is in its first position, the auto-injector 4002 cannot be actuated.

Figure 24:
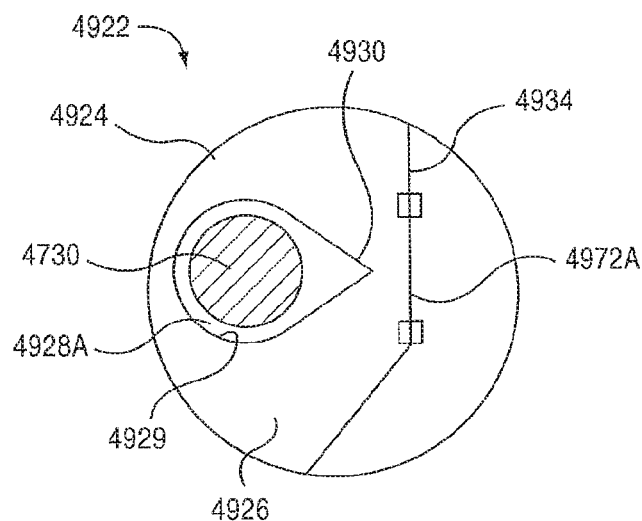
FIGS. 24 and 25 are front plan views of a portion of the auto-injector labeled as region Z in FIG. 19, in a first configuration and a second configuration, respectively.
Figure 25:
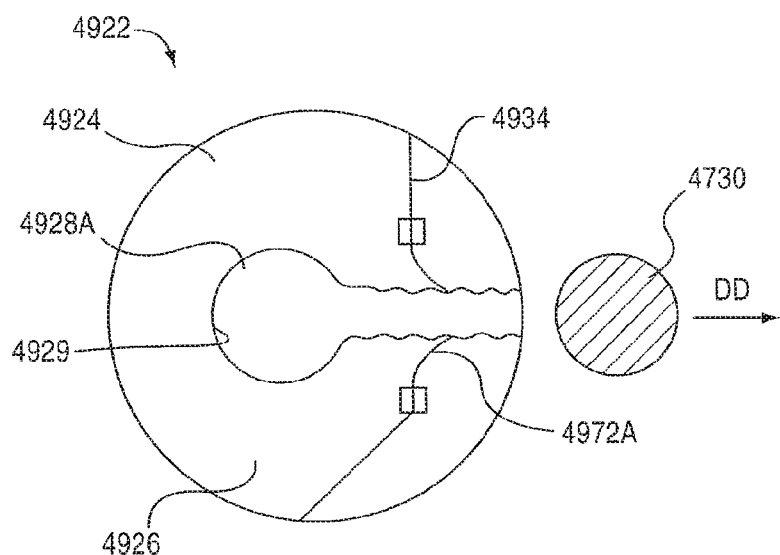

In some embodiments, the safety lock 4710 includes an actuator 4732 that actuates the electronic circuit 4920 to trigger a predetermined output or sequence of outputs when the safety lock 4710 is moved from the first position to a second (or unlocked) position, as shown in FIG. 22. More particularly, as shown in FIGS. 19, 24 and 25, the actuator 4732 includes a protrusion 4730 that is received within a first opening 4928A defined by an actuation portion 4926 of the substrate 4924 when the safety lock 4710 is in the first position. The boundary 4929 of the first opening 4928A has a discontinuous shape, such as, for example, a teardrop shape, that includes a stress concentration riser 4930. The discontinuity and/or the stress concentration riser 4930 of the boundary 4929 can be of any suitable shape to cause the substrate 4924 to deform in a predetermined direction when the protrusion 4730 is moved relative to the first opening 4928A.

As shown in FIGS. 24 and 25, the first opening 4928A is defined adjacent an electrical conductor 4934 that, as discussed above, electronically couples the components included in the electronic circuit system 4920. The electrical conductor 4934 includes a first switch 4972A, which can be, for example a frangible portion of the electrical conductor 4934. In use, when the safety lock 4710 is moved from the first position to the second position, the actuator 4732 moves in a direction substantially parallel to a plane defined by a surface of the actuation portion 4926 of the substrate 4924. The movement of the actuator 4732 causes the protrusion 4730 to move within the first opening 4928A, as indicated by the arrow DD in FIG. 25. The movement of the protrusion 4730 tears the actuation portion 4926 of the substrate 4924, thereby separating the portion of the electrical conductor 4934 including the first switch 4972A. Said another way, when the safety lock 4710 is moved to the second position, the actuator 4732 moves irreversibly the first switch 4972A from a first state (e.g., a state of electrical continuity) to a second state (e.g., a state of electrical discontinuity).

When the actuator 4732 actuates the electronic circuit system 4920 as described above, the electronic circuit system 4920 can output one or more predetermined electronic outputs. For example, in some embodiments, the processor 4950 can output an electronic signal associated with recorded speech to the audible output device 4956. Such an electronic signal can be, for example, associated with a recorded message notifying the user of the status of the auto-injector 4002. Such a status message can state, for example, "The auto-injector is now enabled." The processor can also simultaneously output an electronic signal to the first LED 4958A, thereby causing the first LED 4958A to stop flashing, change color or the like.

In some embodiments, the electronic circuit system 4920 can be configured to output the status message for a predetermined time period, such as, for example, five seconds. After the predetermined time period has elapsed, the electronic circuit system 4920 can output an audible message further instructing the user in the operation of the autoinjector 4002. Such an instruction can state, for example, "Place the base of the auto-injector against the patient's thigh. To complete the injection, press the base firmly against the patient's thigh." In some embodiments, the processor can simultaneously output an electronic signal to the second LED 4958B, thereby causing the second LED 4958B, which is located near the base 4520, to flash a particular color. In this manner, the electronic circuit system 4920 can provide both audible and visual instructions to assist the user in the placement and actuation of the auto-injector 4002. In some embodiments, the electronic circuit system 4920 can be configured to repeat the instructions after a predetermined time period has elapsed.

Figure 23:
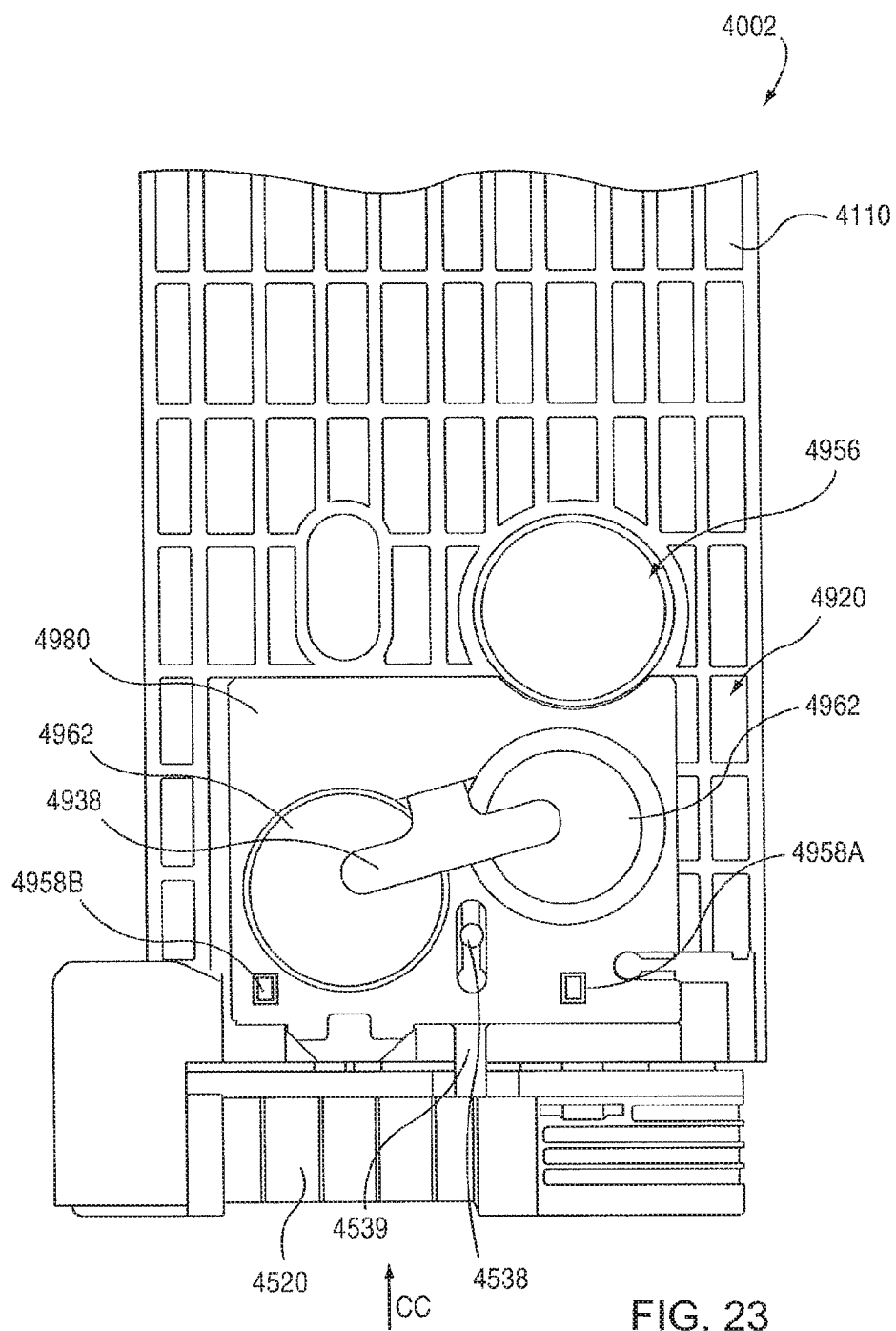
FIG. 23 is a front plan view of a portion of the auto-injector illustrated in FIG. 15 in a fourth configuration.

After the auto-injector 4002 is enabled and placed against the body of the patient, the auto-injector 4002 is actuated by moving the base 4520 proximally towards the housing 4110, as illustrated by arrow CC in FIG. 23. The base 4520 includes an actuator 4538 that actuates the electronic circuit 4920 to trigger a predetermined output or sequence of outputs when the base 4520 is moved from a first position to a second position, as shown in FIG. 22. The actuator 4538 includes a protrusion 4539 that is received within a second opening 4928B (see FIG. 19) defined by the substrate 4924 when the base 4520 is in the first position. The configuration and operation of the protrusion 4539, the second opening 4928B and the second switch 4972B are similar to the configuration and operation of the protrusion 4730, the first opening 4928A and the first switch 4972A, and are therefore not described in detail.

When the actuator 4538 actuates the electronic circuit system 4920, the electronic circuit system 4920 can output one or more predetermined electronic outputs. For example, in some embodiments, the processor 4950 can output an electronic signal associated with recorded speech to the audible output device 4956. Such an electronic signal can be, for example, associated with a recorded message notifying the user that the injection is complete, instructing the user on post-injection disposal and safety procedures, instructing the user on post-injection medical treatment or the like. Such a status message can state, for example, "The injection is now complete. Please seek further medical attention from a doctor." The processor can also simultaneously output an electronic signal to the first LED 4958A, thereby causing the first LED 4958A to stop flashing, change color or the like, to provide a visual indication that the injection is complete.

As described above, the audio output device 4956, can include, for example, a micro-speaker. In some embodiments, for example, the audio output device 4956 can include an RS-1511A micro-speaker manufactured by Regal Electronics, Inc.

Similarly, the microprocessor 4950 can be a commercially-available processing device dedicated to performing one or more specific tasks. For example, in some embodiments, the microprocessor 4950 can be a commercially-available microprocessor, such as the Sonix SNC 12060 voice synthesizer. Alternatively, the microprocessor 4950 can be an application-specific integrated circuit (ASIC) or a combination of ASICs, which are designed to perform one or more specific functions. In yet other embodiments, the microprocessor 4950 can be an analog or digital circuit, or a combination of multiple circuits.

The microprocessor 4950 can include a memory device (not shown) configured to receive and store information, such as a series of instructions, processor-readable code, a digitized signal, or the like. The memory device can include one or more types of memory. For example, the memory device can include a read only memory (ROM) component and a random access memory (RAM) component. The memory device can also include other types of memory suitable for storing data in a form retrievable by the microprocessor 4950, for example, electronically-programmable read only memory (EPROM), erasable electronically-programmable read only memory (EEPROM), or flash memory.

Figure 26:
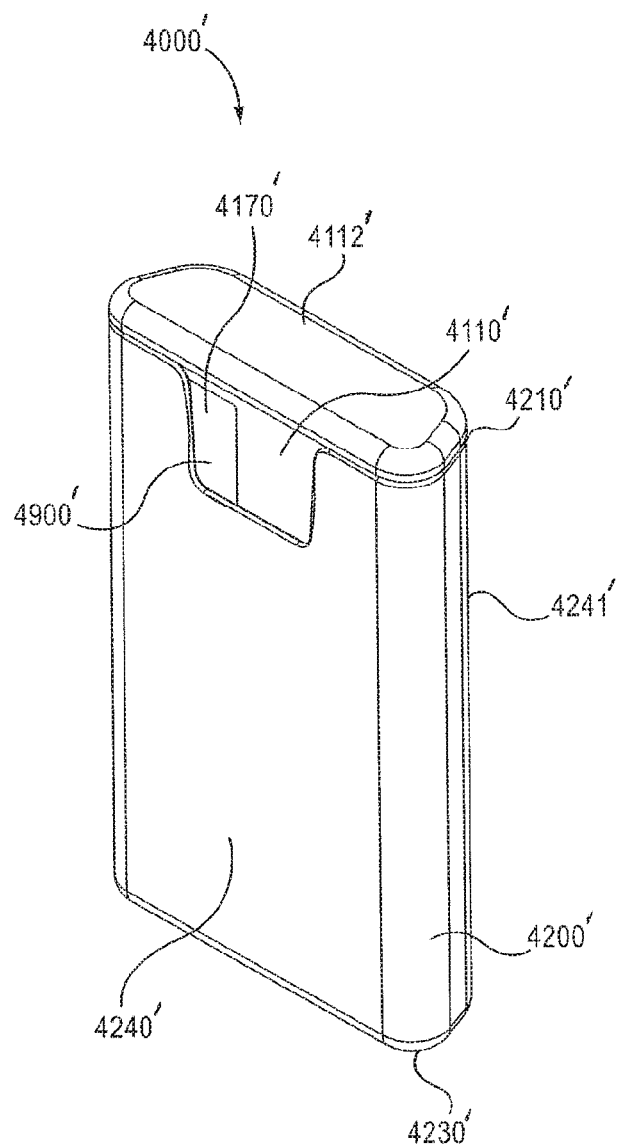
FIGS. 26 and 27 are perspective views of a medical injector according to an embodiment of the invention, in a first configuration.
Figure 27:
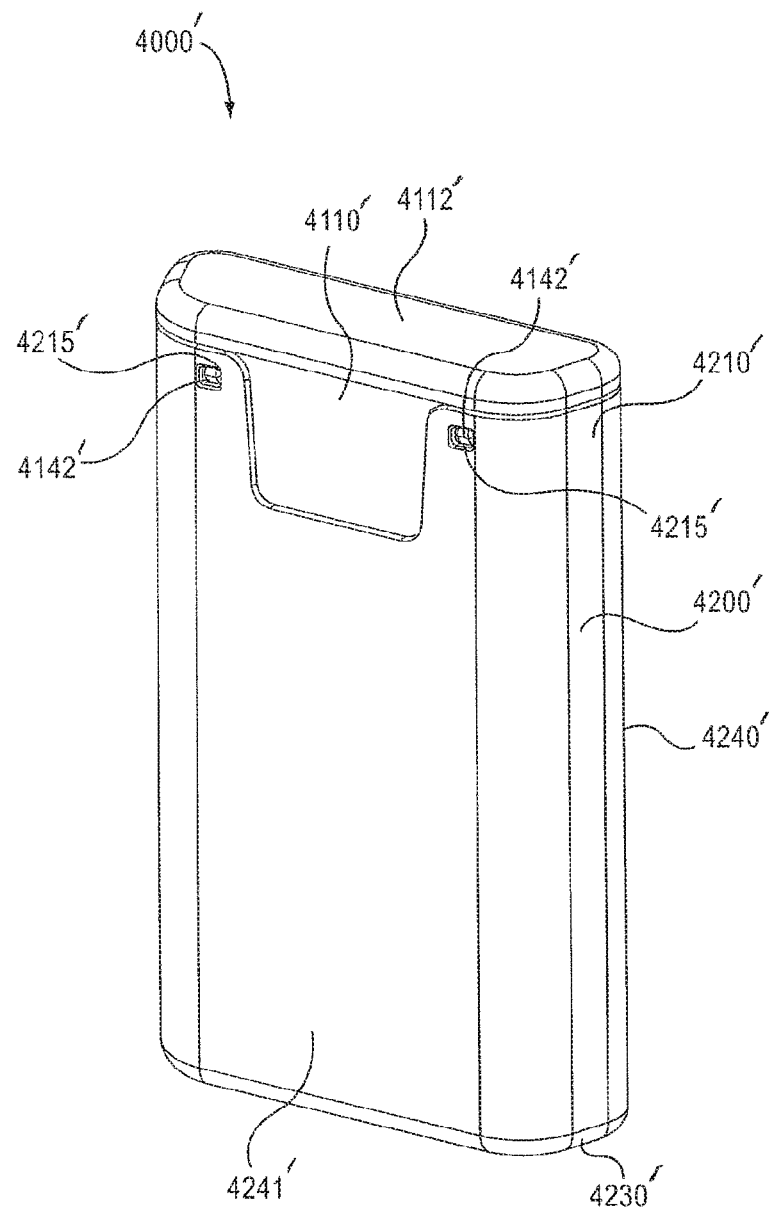
Figure 28:
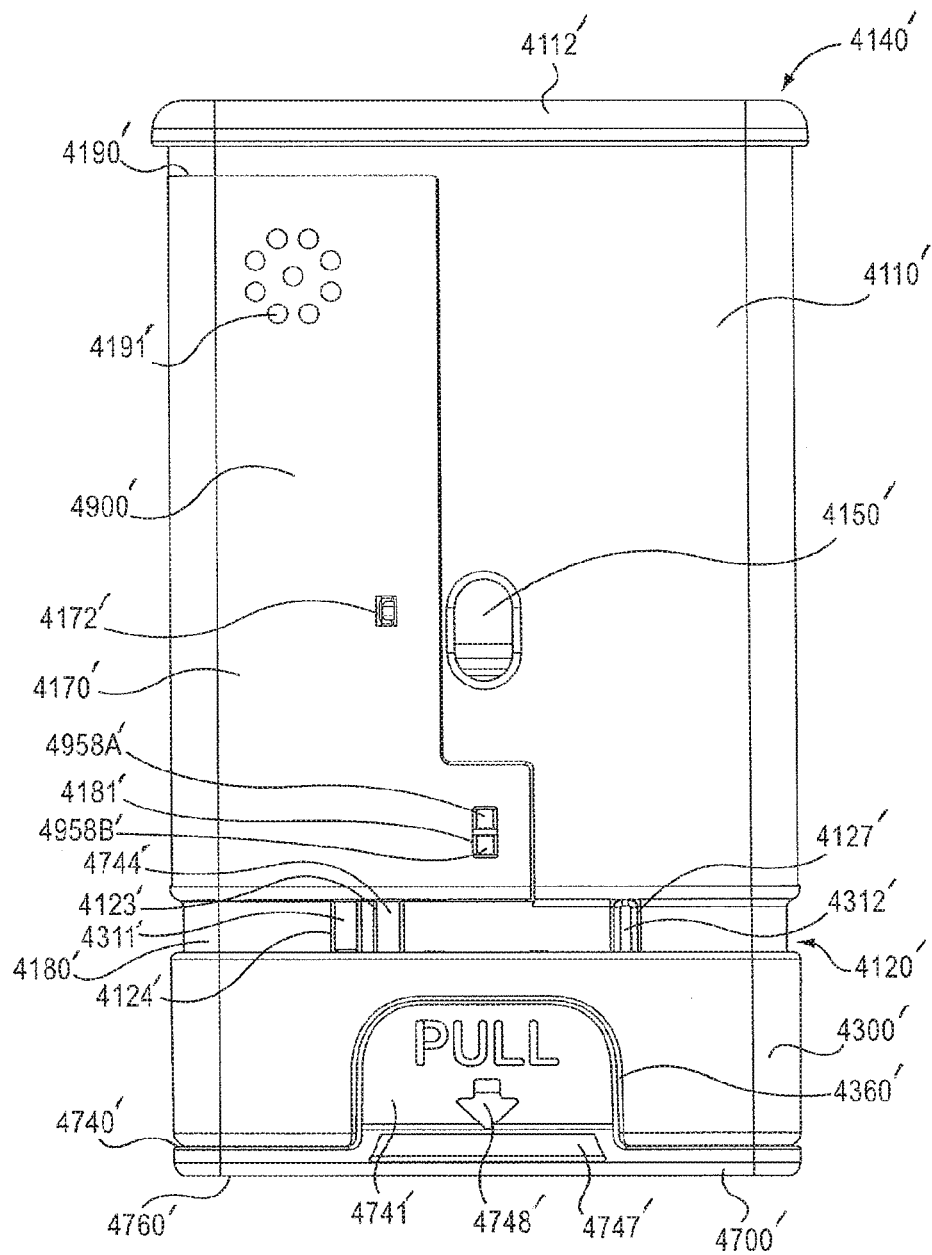
FIG. 28 is a front view of the medical injector illustrated in FIG. 26 with the cover removed.

Although not shown in FIGS. 5-25, in some embodiments, an auto-injector can include a protective cover, container and/or sheath. The cover can prevent the auto-injector from being inadvertently actuated or exposed to non-sterile conditions, actuate portion of the electronic circuit system, include portions of the electronic circuit system and/or provide a barrier to prevent the medicament or vaccine from being exposed to light. For example, FIGS. 26-57 show a medical injector 4000', according to an embodiment of the invention. FIGS. 26 and 27 are perspective views of the medical injector 4000' in a first configuration (i.e., prior to use). The medical injector 4000' includes a housing 4110', a delivery mechanism 4500' (see e.g., FIG. 35), an electronic circuit system 4900' (see e.g., FIGS. 36-46), a cover 4200' (see e.g., FIGS. 47-48), a safety lock 4700' (see e.g., FIGS. 49-52) and a base 4300' (see e.g., FIGS. 53-54). A discussion of the components of the medical injector 4000' will be followed by a discussion of the operation of the medical injector 4000'.

As shown in FIGS. 28-34, the housing 4110' has a proximal end portion 4140' and a distal end portion 4120'. The housing 4110' defines a first status indicator aperture 4150' and a second status indicator aperture 4151'. The first status indicator aperture 4150' defined by the housing 4110' is located on a first side of the housing 4110', and the second status indicator aperture 4151' of the housing 4110' is located on a second side of the housing 4110'. The status indicator apertures 4150', 4151' can allow a patient to monitor the status and/or contents of a medicament container 4560'. For example, by visually inspecting the status indicator apertures 4150', 4151', a patient can determine whether the medicament container 4560' contains a medicament and/or whether a medicament has been dispensed.

Figure 32:
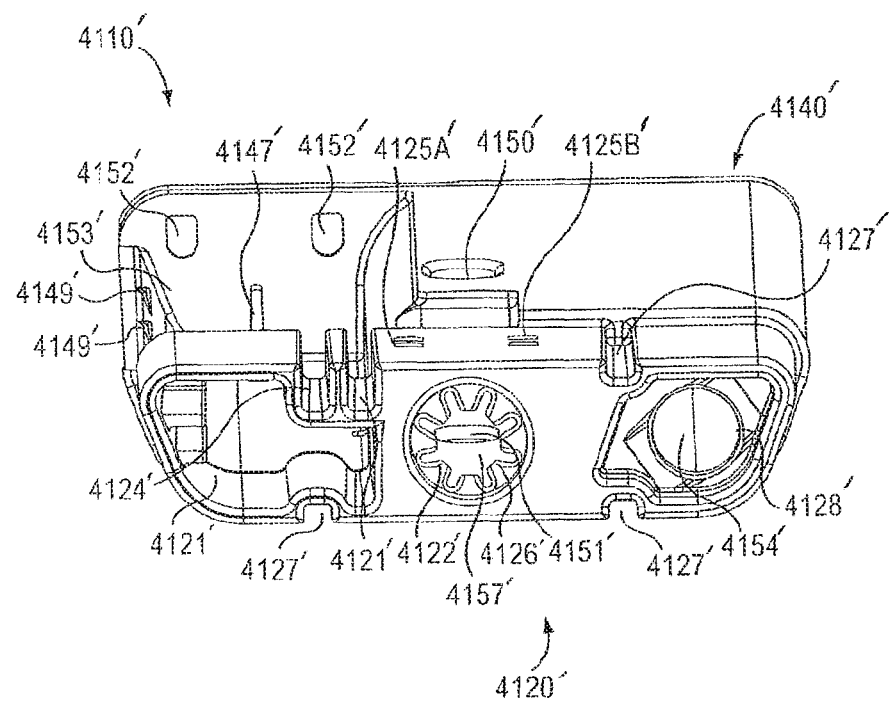
FIG. 32 is a bottom perspective view of a housing of the medical injector illustrated in FIG. 26.
Figure 33:
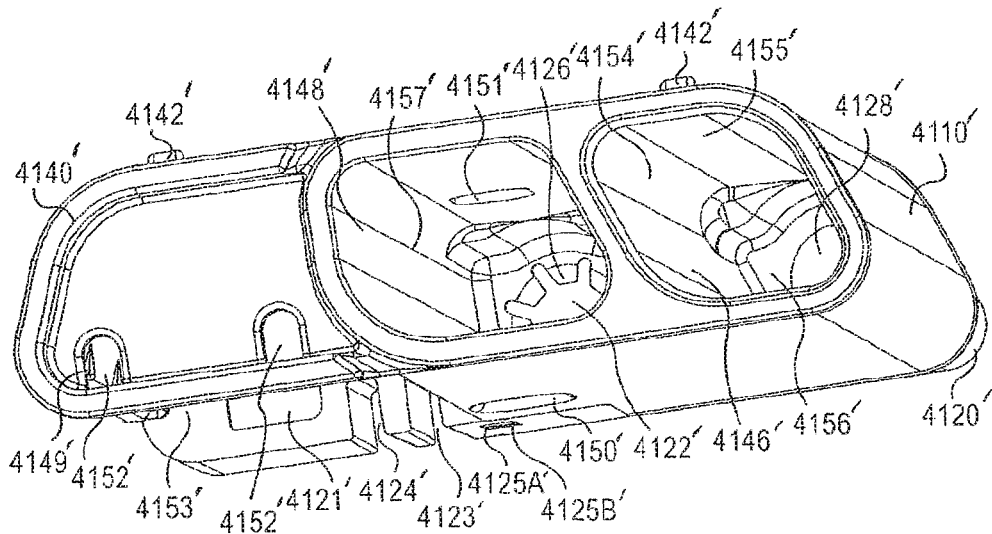
FIG. 33 is a top perspective view of a housing of the medical injector illustrated in FIG. 26.

As shown in FIGS. 32 and 33, the housing 4110' defines a gas cavity 4154', a medicament cavity 4157' and an electronic circuit system cavity 4153'. The gas cavity 4154' has a proximal end portion 4155' and a distal end portion 4156'. The gas cavity 4154' is configured to receive the gas container 4570' and the release member 4540' of the medicament delivery mechanism 4500' (see e.g., FIG. 35) as described in further detail herein. The proximal end portion 4155' of the gas cavity 4154' is configured to receive the gas container retention member 4580' of the proximal cap 4112' of the housing 4110', as described in further detail herein. The gas cavity 4154' is in fluid communication with the medicament cavity 4157' via a gas passageway 4144', as described in further detail herein, and the gas cavity 4154' is in fluid communication with a region outside the housing 4110' via a safety lock aperture 4128'.

The medicament cavity 4157' is configured to receive a portion of the delivery mechanism 4500'. In particular, the carrier 4520', the moveable member 4530' and the needle 4512' of the medicament delivery mechanism 4500' are movably disposed in the medicament cavity 4157'. The medicament cavity 4157' is in fluid communication with a region outside the housing 4110' via a needle aperture 4122'.

The electronic circuit system cavity 4153' is configured to receive the electronic circuit system 4900'. The housing 4110' has protrusions 4149' (see e.g., FIG. 31) configured to stabilize the electronic circuit system 4900' when the electronic circuit system 4900' is disposed within the electronic circuit system cavity 4153'. The housing 4110' also defines connection apertures 4152' configured to receive connection protrusions 4171' of the electronic circuit system 4900', and aperture 4145' (see e.g., FIG. 29) configured to receive a portion of a protrusion 4174' of the electronic circuit system 4900'. In this manner, the electronic circuit system 4900' can be coupled to the housing 4110' within the electronic circuit system cavity 4153'. In other embodiments, the electronic circuit system 4900' can be coupled within the electronic circuit system cavity 4153' by other suitable means such as an adhesive, a clip and/or the like.

The electronic circuit system cavity 4153' is fluidically and/or physically isolated from the gas cavity 4154' and/or the medicament cavity 4157' by a sidewall 4148'. The sidewall 4148' can be any suitable structure to isolate the electronic circuit system cavity 4153' within the housing 4110' from the gas cavity 4154' and/or the medicament cavity 4157' within the housing 4110'. Similarly, the gas cavity 4154' and the medicament cavity 4157' are separated by a sidewall 4146'. In some embodiments, sidewall 4146' can be similar to the sidewall 4148', which isolates the gas cavity 4154' and the medicament cavity 4157' from the electronic circuit system cavity 4153'. In other embodiments the gas cavity 4154' can be fluidically and/or physically isolated from the medicament cavity 4157'.

Figure 29:
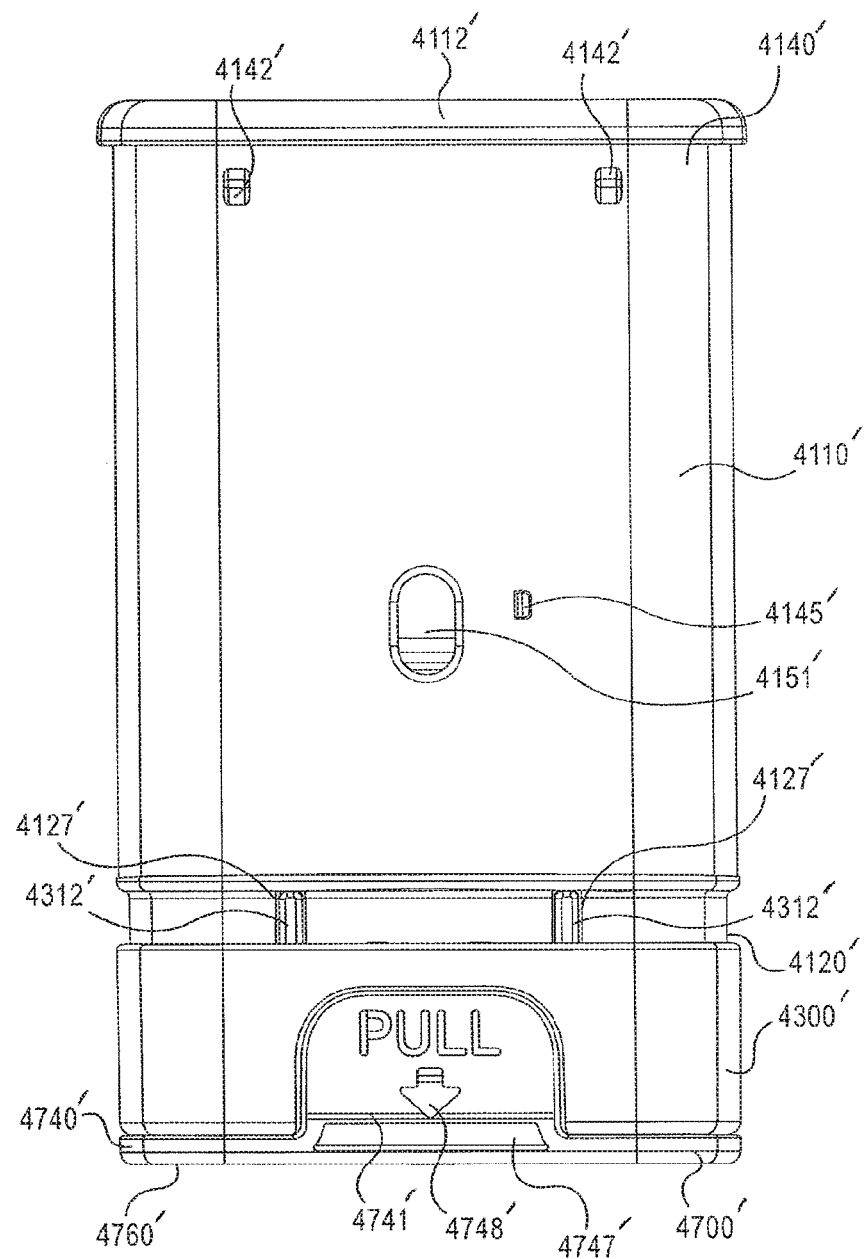
FIG. 29 is a back view of the medical injector illustrated in FIG. 26 with the cover removed.

The proximal end portion 4140' of the housing 4110' includes a proximal cap 4112', a speaker protrusion 4147' (see e.g., FIGS. 31 and 32), and cover retention protrusions 4142' (see e.g., FIGS. 27 and 29). The speaker protrusion 4147' is configured to maintain a position of an audio output device 4956' of the electronic circuit system 4900' relative to the housing 4110' when the electronic circuit system 4900' is attached to the housing 4110', as described herein. Cover retention protrusions 4142' are configured to be received within corresponding openings 4215' on the cover 4200'. In this manner, as described in more detail herein, the cover 4200' can be removably coupled to and disposed about at least a portion of the housing 4110'.

Figure 34:
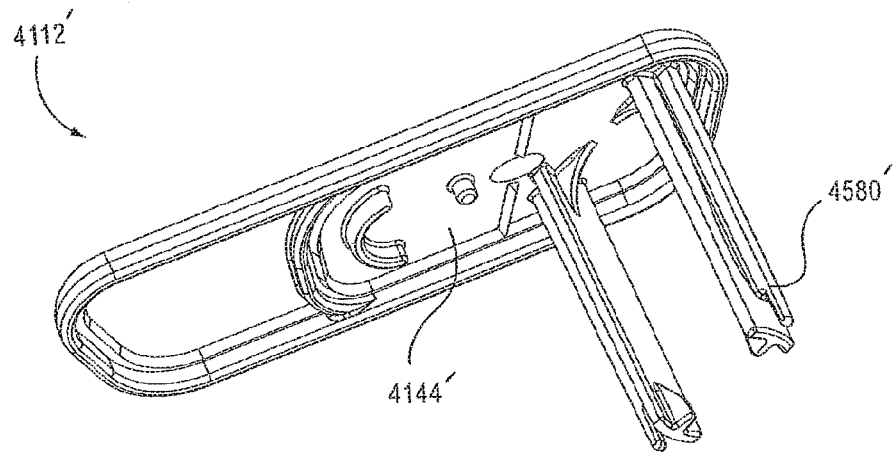
FIG. 34 is a perspective view of a proximal cap of the medical injector illustrated in FIG. 26.
Figure 37:
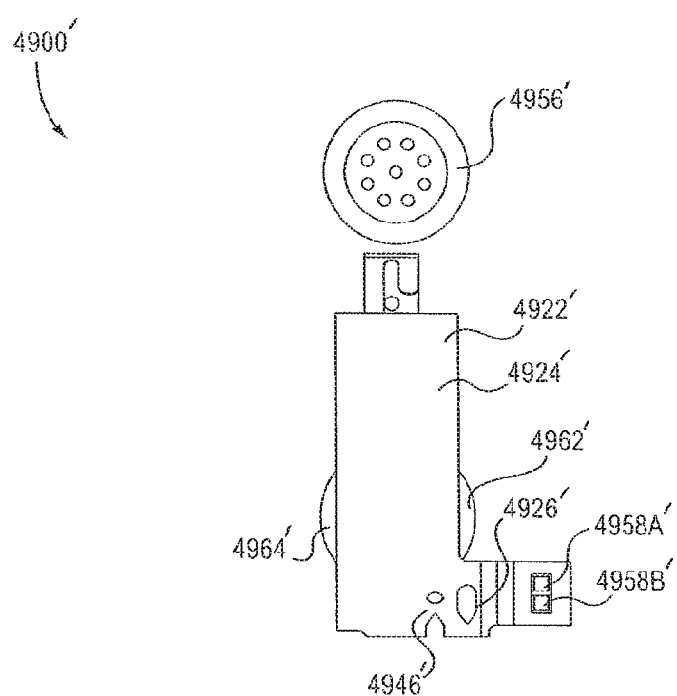
FIG. 37 is a front view of a portion of the electronic circuit system of the medical injector illustrated in FIG. 36.

As shown in FIG. 34, the proximal cap 4112' includes a gas container retention member 4580' and defines a gas passageway 4144'. The gas container retention member 4580' is configured to receive and/or retain a gas container 4570' that can contain a pressurized gas. The gas passageway 4144' is configured to allow for the passage of gas contained in the gas container 4570' from the gas cavity 4154' to the medicament cavity 4157', as further described herein. Said another way, the gas passageway 4144' places the gas cavity 4154' in fluid communication with the medicament cavity 4157'.

Figure 30:
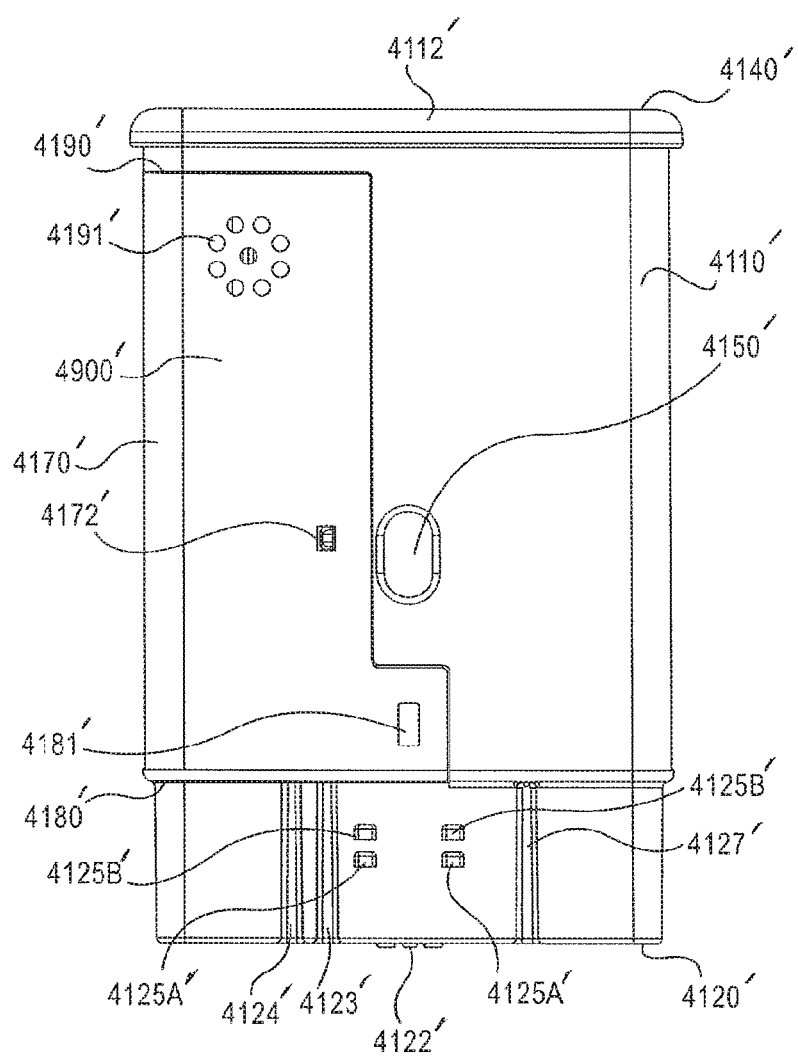
FIG. 30 is a front view of a portion of the medical injector illustrated in FIG. 26.
Figure 31:
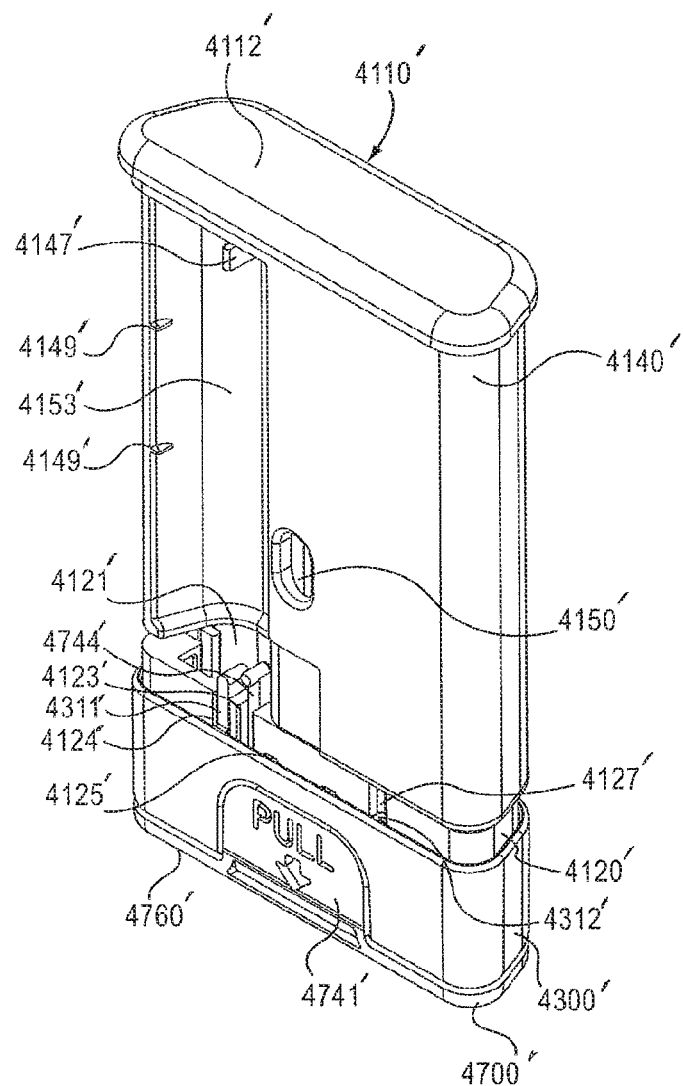
FIG. 31 is a perspective view of a portion of the medical injector illustrated in FIG. 26.

As shown in FIGS. 30 and 32, the distal end portion 4120' of the housing 4110' defines a battery isolation protrusion aperture 4121', a needle aperture 4122', a safety lock actuator groove 4123', a safety lock aperture 4128', a base actuator groove 4124', base retention recesses 4125A, 4125B, and base rail grooves 4127'. The battery isolation protrusion aperture 4121' is configured to receive the battery isolation protrusion 4235' of the cover 4200' (see e.g., FIG. 48), as described in further detail herein.

The needle aperture 4122' is configured to allow the needle 4512' (see e.g., FIG. 35) to exit the housing 4110' when the medical injector 4000' is actuated. The portion of the sidewall of the housing 4110' that defines the needle aperture 4122' includes multiple sheath retention protrusions 4126'. In some embodiments, the sheath retention protrusions can interact with the a plurality of ribs 4728' of the needle sheath 4720' (see e.g. FIG. 52) to maintain a position of the needle sheath 4720' relative to the safety lock 4700' when the safety lock 4700' is coupled to the housing 4110' and/or when the safety lock 4700' is being removed from the housing 4110'.

The safety lock actuator groove 4123' is configured to receive an actuator 4744' of the safety lock 4700'. As described in more detail herein, the actuator 4744' is configured to engage and/or activate the electronic circuit system 4900' when the safety lock 4700' is moved with respect to the housing 4110'. The safety lock aperture 4128' is configured to receive a safety lock protrusion 4742' (see e.g., FIGS. 48 and 49). As described in more detail below, the safety lock protrusion 4742' is received within an opening 4554' between extensions 4552' of a release member 4540' such that activation of the medical injector 4000' is prevented when the safety lock 4700' is in place. The safety lock 4700', its components and functions are further described herein.

The distal base retention recesses 4125A are configured to receive the base connection knobs 4358' of the base 4300' (see e.g., FIG. 53) when the base 4300' is in a first position relative to the housing 4110'. The proximal base retention recesses 4125B are configured to receive the base connection knobs 4358' of the base 4300' when the base 4300' is in a second position relative to the housing 4110'. The base retention recesses 4125A, 4125B have a tapered proximal sidewall and a non-tapered distal sidewall. This allows the base retention recesses 4125A, 4125B to receive the base connection knobs 4358' such that the base 4300' can move proximally relative to the housing 4110', but cannot move distally relative to the housing 4110'. Said another way, the distal base retention recesses 4125A are configured to prevent the base 4300' from moving distally when the base 4300' is in a first position and the proximal base retention recesses 4125B are configured to prevent the base 4300' from moving distally when the base 4300' is in a second position. Similarly stated, the proximal base retention recesses 4125B and the base connection knobs 4358' cooperatively prevent "kickback" after the medical injector 4000' is actuated.

The base actuator groove 4124' is configured to receive an actuator 4311' of the base 4300'. As described in more detail herein, the actuator 4311' of the base 4300' is configured to engage the electronic circuit system 4900' when the base 4100' is moved with respect to the housing 4110'. The base rail grooves 4127' are configured to receive the guide members 4312' of the base 4300'. The guide members 4312' of the base 4300' and the base rail grooves 4127' of the housing 4110' engage each other in a way that allows the guide members 4312' of the base 4300' to slide in a proximal and/or distal direction within the base rail grooves 4127' while limiting lateral movement of the guide members 4312'. This arrangement allows the base 4300' to move in a proximal and/or distal direction with respect to the housing 4110' but prevents the base 4300' from moving in a lateral direction with respect to the housing 4110'.

Figure 35:
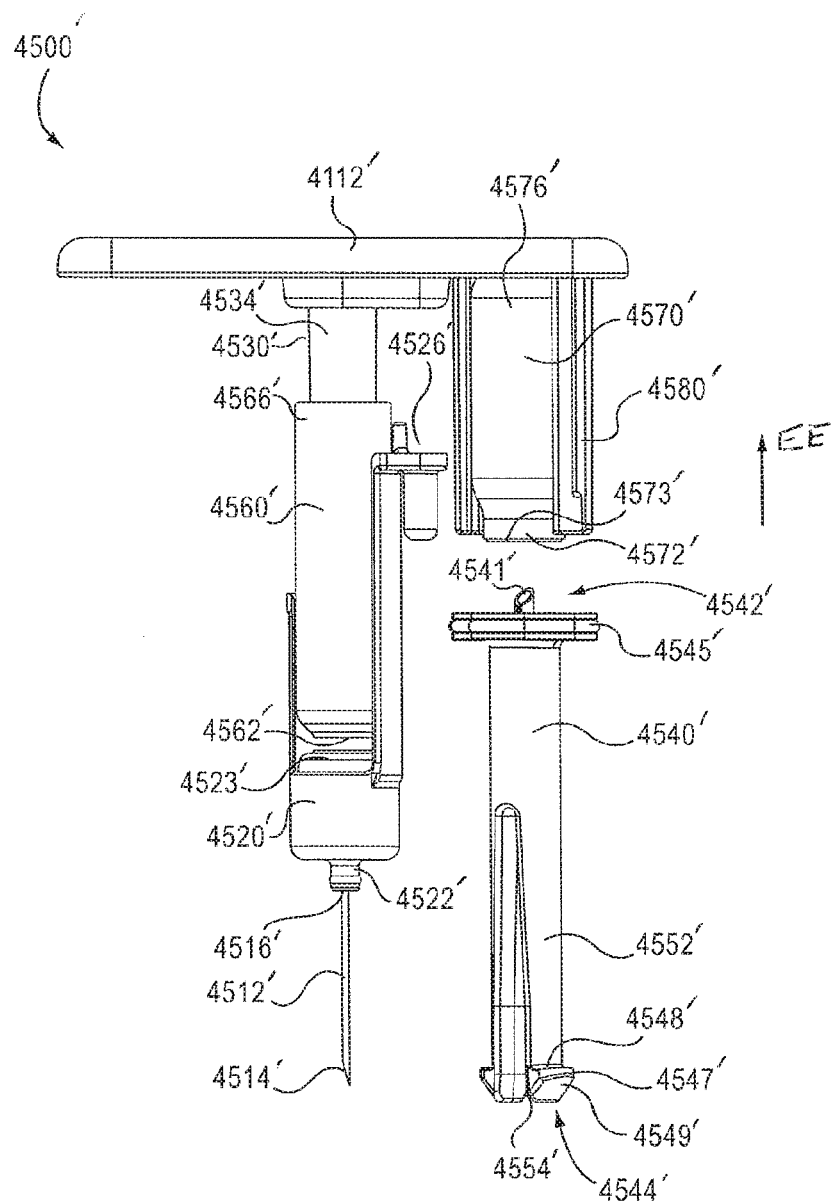
FIG. 35 is a front view of a medicament delivery mechanism of the medical injector illustrated in FIG. 26.
Figure 36:
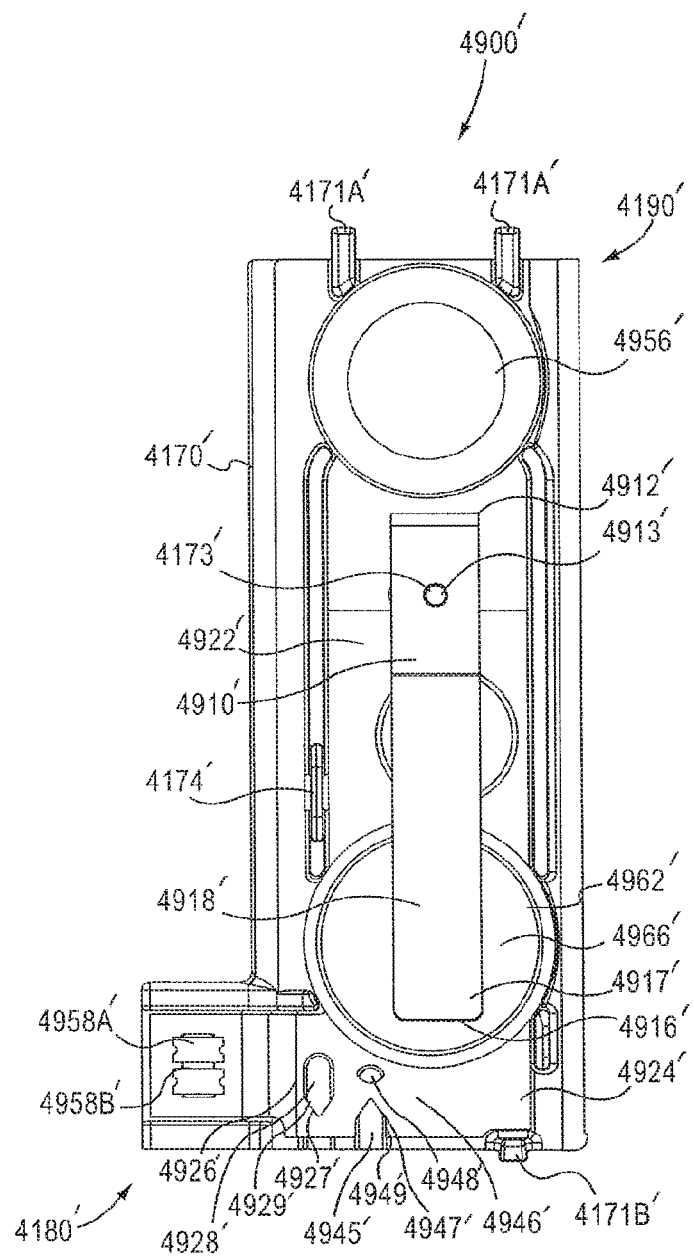
FIG. 36 is a back view of an electronic circuit system of the medical injector illustrated in FIG. 26.
Figure 38:
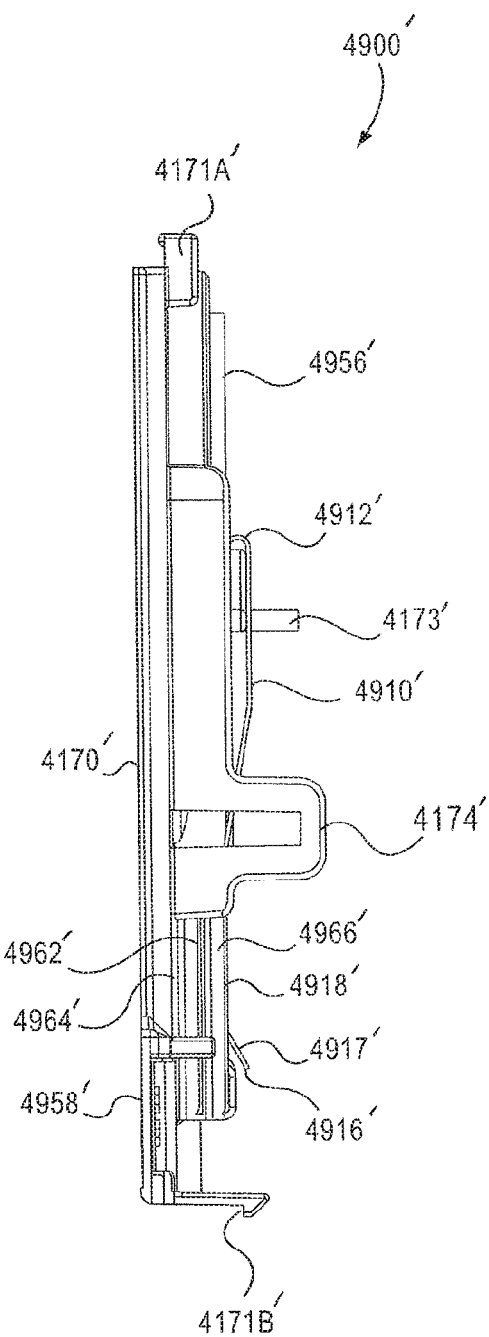
FIG. 38 is a side view of the electronic circuit system of the medical injector illustrated in FIG. 36.

FIG. 35 shows the medicament delivery mechanism 4500' of the medical injector 4000'. The medicament delivery mechanism 4500' includes a needle 4512', a carrier 4520', a movable member 4530', a medicament container 4560', a gas container 4570', and a release member 4540'. As described above, the needle 4512', carrier 4520', movable member 4530' and medicament container 4560' are disposed within the medicament cavity 4157' of the housing 4110'. The gas container 4570' and the release member 4540' are disposed within the gas cavity 4154' of the housing 4110'.

The release member 4540' has a proximal end portion 4542' and a distal end portion 4544', and is movably disposed within the distal end portion 4156' of the gas cavity 4154'. The proximal end portion 4542' of the release member 4540' includes a sealing member 4545' and a puncturer 4541'. The sealing member 4545' is configured to engage the sidewall of the housing 4110' defining the gas cavity 4154' such that the proximal end portion 4155' of the gas cavity 4154' is fluidically isolated from the distal end portion 4156' of the gas cavity 4154'. In this manner, when gas is released from the gas container 4570', the gas contained in the proximal end portion 4155' of the gas cavity 4154' is unable to enter the distal end portion 4156' of the gas cavity 4154'. The puncturer 4541' of the proximal end portion 4542' of the release member 4540' is configured to contact and puncture a frangible seal 4573' on the gas container 4570' when the release member 4540' moves proximally within the gas cavity 4154', as shown by the arrow EE in FIG. 35.

The distal end portion 4544' of the release member 4540' includes extensions 4552'. The extensions 4552' include projections 4547' that include tapered surfaces 4549' and engagement surfaces 4548'. Further, the extensions 4552' define an opening 4554' between the extensions 4552'. The tapered surfaces 4549' of the projections 4547' are configured to contact protrusions 4313' on a proximal surface 4310' of the base 4300' (see e.g., FIG. 53). The engagement surfaces 4548' of the projections 4547' are configured to extend through the safety lock aperture 4128' of the housing 4110' and contact a distal surface of the housing 4110'. In this manner, the engagement surfaces 4548' of the projections 4547' limit proximal movement of the release member 4540' when the engagement surfaces 4548' are in contact with the distal surface of the housing 4110'.

Figure 50:
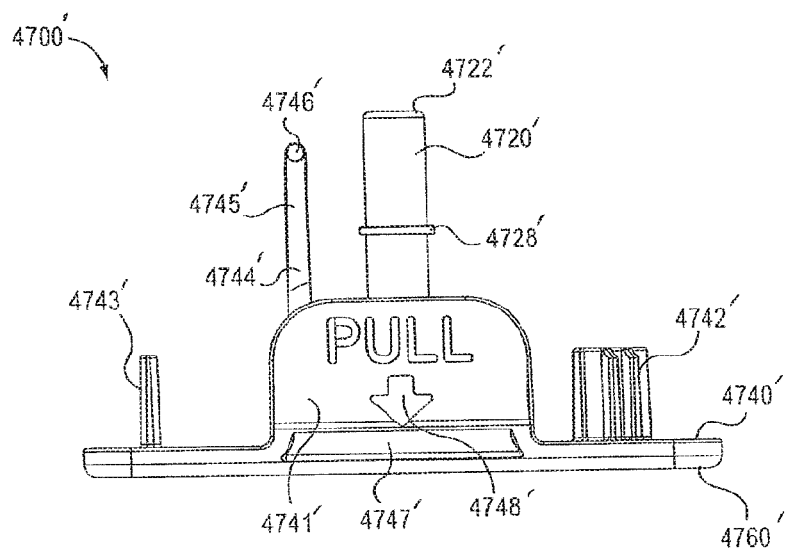
FIG. 50 is a front view of the safety lock of the medical injector illustrated in FIG. 49.

The opening 4554' defined by the extensions 4552' is configured to receive the safety lock protrusion 4742' of the safety lock 4700' (see e.g., FIG. 50). The safety lock protrusion 4742' is configured to prevent the extensions 4552' from moving closer to each other. Said another way, the safety lock protrusion 4742' is configured to ensure that the extensions 4552' remain apart and the engagement surfaces 4548' of the projections 4547' remain in contact with the distal end portion 4120' of the housing 4110'. In some embodiments, for example, the release member 4540' and/or the extensions 4552' can be constructed from any suitable material configured to withstand deformation that may occur when exposed to a load over an extended period of time. In some embodiments, for example, the release member 4540' and/or the extensions 4552' can be constructed from brass.

The gas container 4570' includes a distal end portion 4572' and a proximal end portion 4576', and is configured to contain a pressurized gas. The distal end portion 4572' of the gas container 4570' contains a frangible seal 4573' configured to break when the puncturer 4541' of the proximal end portion 4542' of the release member 4540' contacts the frangible seal 4573'. The gas container retention member 4580' of the proximal cap 4112' of the housing 4110' is configured to receive and/or retain the proximal end portion 4576' of the gas container 4570'. Said another way, the position of the gas container 4570' within the gas cavity 4154' is maintained by the gas container retention member 4580'.

The medicament container 4560' of the medicament delivery mechanism 4500' has a distal end portion 4562' and a proximal end portion 4566', and is configured to contain a medicament. The distal end portion 4562' of the medicament container 4560' contains a seal 4523'. The seal 4523' is configured to burst when punctured by the proximal end 4516' of the needle 4512', as described below. The proximal end portion 4566' of the medicament container 4560' is configured to receive a piston portion 4534' of the movable member 4530'.

The movable member 4530' of the medicament delivery mechanism 4500' is movably disposed within the medicament cavity 4157'. The movable member 4530' includes a piston portion 4534' having a plunger at the distal end portion of the piston portion 4534'. The piston portion 4534' is configured to move within the medicament container 4560'. In this manner, the piston portion 4534' of the movable member 4530' can apply pressure to a medicament contained in the medicament container 4560'. The piston portion 4534' can be constructed of a resilient, durable, and/or sealing material, such as a rubber.

The carrier 4520' of the medicament delivery mechanism 4500' includes a distal end portion 4522' and a proximal end portion 4526'. The medicament container 4560' is coupled to the carrier 4520' via a "snap-fit" connection (not shown) such that the medicament container 4560' can move relative to the carrier 4520' between a first configuration and a second configuration during an injection event. In the first configuration, the carrier 4520' is configured to move within the medicament cavity 4157' such that movement of the carrier 4520' within the medicament cavity 4157' causes contemporaneous movement of the medicament container 4560' within the medicament cavity 4157'. The proximal end portion 4516' of the needle 4512' is spaced apart from the seal 4523' of the medicament container 4560' when the carrier 4520' is in the first configuration. In the second configuration, the medicament container 4560' releases from the "snap-fit" causing the medicament container 4560' to move distally with respect to the carrier 4520', causing the proximal end portion 4516' of the needle 4512' to pierce the seal 4523'. In this manner, the needle 4512' can be selectively placed in fluid communication with the medicament container 4560' to define a medicament delivery path (not shown).

Figure 43:
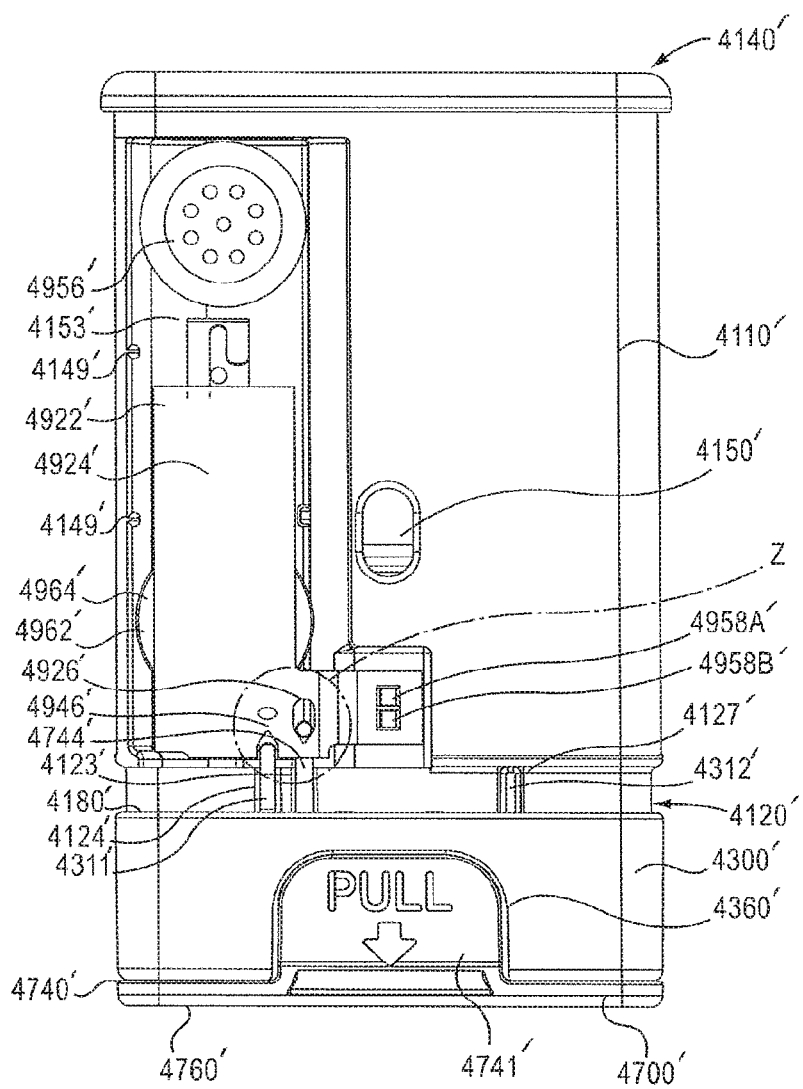
FIG. 43 is a front view of the medical injector illustrated in FIG. 26 in a first configuration showing the electronic circuit system.

FIGS. 36-45 show the electronic circuit system 4900'. The electronic circuit system 4900' of the medical injector 4000' includes an electronic circuit system housing 4170', a printed circuit board 4922', a battery assembly 4962', an audio output device 4956', two light emitting diodes (LEDs) 4958A, 4958B and a battery clip 4910'. As shown in FIG. 43, the electronic circuit system 4900' is configured to fit within the electronic circuit system cavity 4153' of the housing 4110'. Accordingly, as described above, the electronic circuit system 4900' is physically and/or fluidically isolated from the medicament cavity 4157', the gas cavity 4154' and/or the medicament delivery device 4500'. As described herein, the electronic circuit system 4900' is configured to output an electronic output associated with the use of the medical injector 4000'.

The electronic circuit system housing 4170' of the electronic circuit system 4900' includes a distal end portion 4180' and a proximal end portion 4190'. The proximal end portion 4190' includes connection protrusions 4171A and a battery clip protrusion 4173'. The connection protrusions 4171A extend from the proximal end portion 4190' of the electronic circuit system housing 4170', and are configured to be disposed within the connection apertures 4152' of the housing 4110', as described above. In this manner, the electronic circuit system 4900' can be coupled to the housing 4110' within the electronic circuit system cavity 4153'. In other embodiments, the electronic circuit system 4900' can be coupled to the housing 4110' by other suitable means such as an adhesive, a clip and/or the like. As described in more detail herein, the battery clip protrusion 4173' is configured to hold the battery clip 4910' in place.

The proximal end portion 4190' of the electronic circuit system housing 4170' defines multiple sound apertures 4191'. The audible output device 4956' is disposed against the proximal end portion 4190' of the electronic circuit system housing 4170' such that the front face of the audible output device 4956' is disposed adjacent the sound apertures 4191'. In this manner, the sound apertures 4191' are configured to allow sound from an audio output device 4956' to pass from the audio output device 4956' to a region outside of the housing 4110'.

Figure 39:
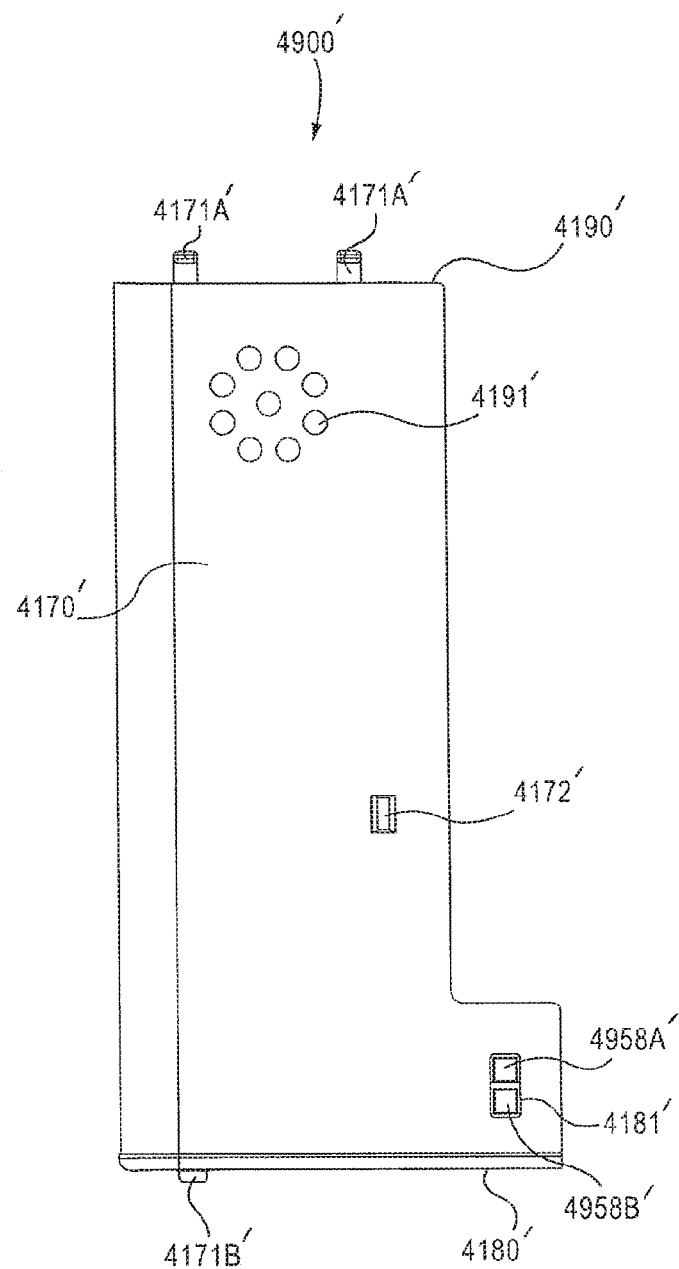
FIG. 39 is a front view of an electronic circuit system housing of the medical injector illustrated in FIG. 36.
Figure 40:
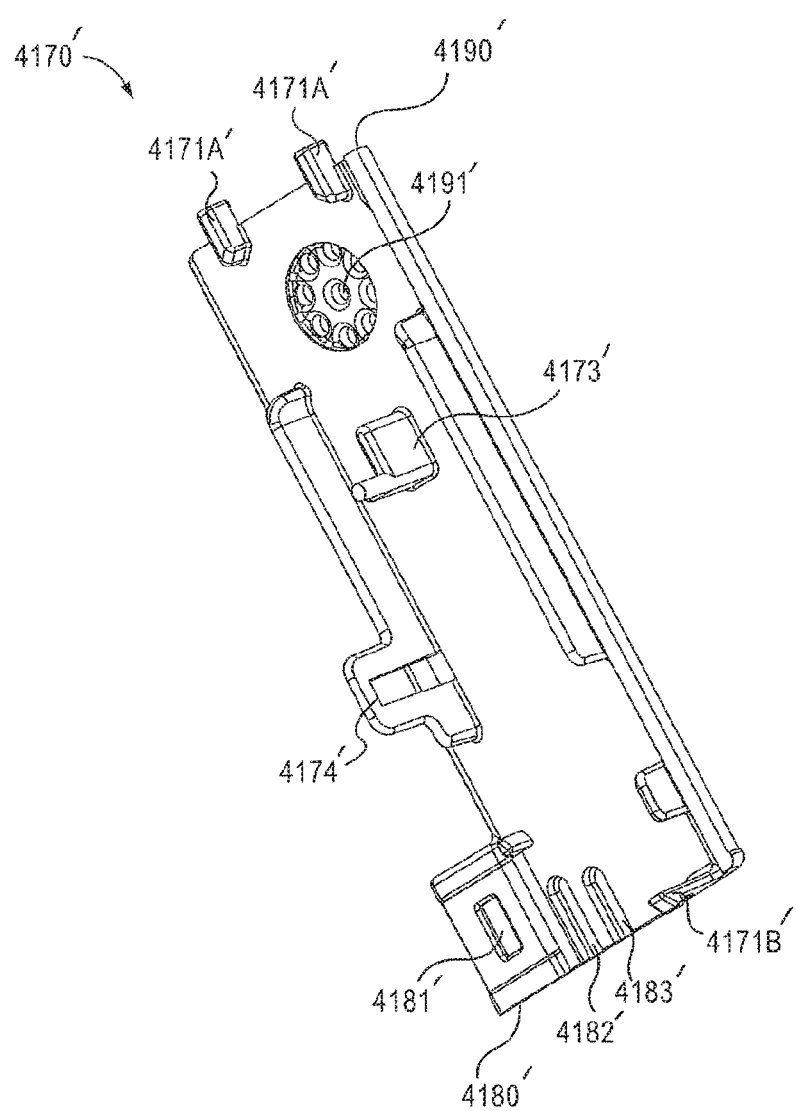
FIG. 40 is a perspective view of the electronic circuit system housing of the medical injector illustrated in FIG. 39.
Figure 41:
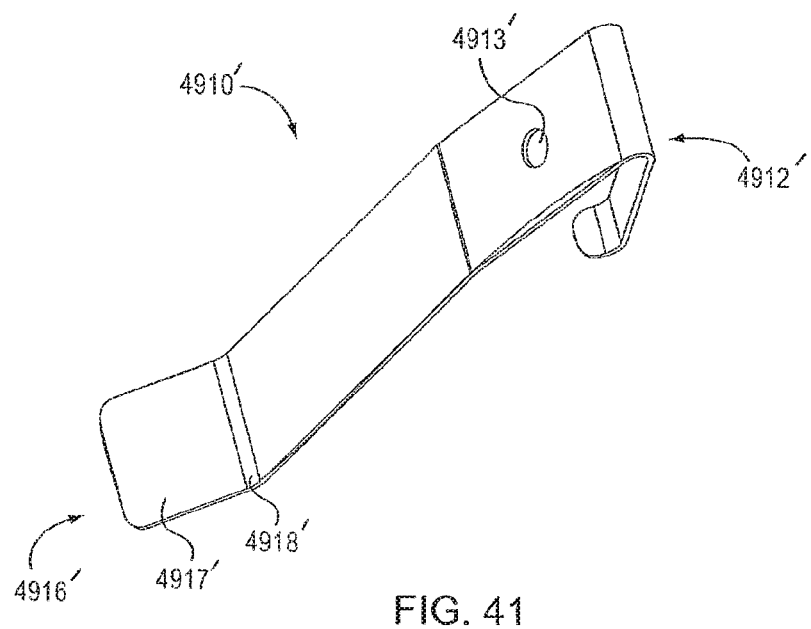
FIG. 41 is a perspective view of a battery clip of the medical injector illustrated in FIG. 36.

As shown in FIGS. 39 and 40, the distal end portion 4180' of the electronic circuit system housing 4170' includes a connection protrusion 4171B, a stiffening protrusion 4174', and defines an LED aperture 4181', an aperture 4172', a safety lock actuator groove 4182', and a base actuator groove 4183'. The LED aperture 4181' is configured to receive the LEDs 4958A, 4958B such that a user can view the LEDs 4958A, 4958B, which are described in more detail herein.

The connection protrusion 4171B extends from the distal end portion 4180' of the electronic circuit system housing 4170', and is configured to attach the electronic circuit system 4900' to the housing 4110', as described above. The stiffening protrusion 4174' is configured to have at least a portion received within and/or accessible via the aperture 4145' in the housing 4110' (see e.g., FIG. 6). The stiffening protrusion 4174' is configured to limit the bending (e.g., buckling) of the electronic circuit system housing 4170' when the electronic circuit system housing 4170' is coupled to the housing 4110'. Moreover, a user can access the stiffening protrusion 4174' via the aperture 4172'. In this manner, for example, the user can disengage the stiffening protrusion 4174' from the aperture 4145'.

The safety lock actuator groove 4182' of the electronic circuit system housing 4170' is configured to be disposed adjacent the safety lock actuator groove 4123' of the distal end portion 4120' of the housing 4110'. In this manner, the safety lock actuator groove 4182' of the electronic circuit system housing 4170' and the safety lock actuator groove 4123' of the distal end portion 4120' of the housing 4110' collectively receive the actuator 4744' of the safety lock 4700', which is described in more detail herein. Similarly, the base actuator groove 4183' of the electronic circuit system housing 4170' is configured to be disposed about the base actuator groove 4124' of the distal end portion 4120' of the housing 4110'. The base actuator groove 4183' of the electronic circuit system housing 4170' and the base actuator groove 4124' of the distal end portion 4120' of the housing 4110' collectively receive the actuator 4311' of the base 4300', which is described in more detail herein.

The printed circuit board 4922' of the electronic circuit system 4900' includes a substrate 4924', a first actuation portion 4926' and a second actuation portion 4946'. The substrate 4924' of the printed circuit board 4922' includes the electrical components necessary for the electronic circuit system 4900' to operate as desired. For example, the electrical components can be resistors, capacitors, inductors, switches, microcontrollers, microprocessors and/or the like.

Figure 46:
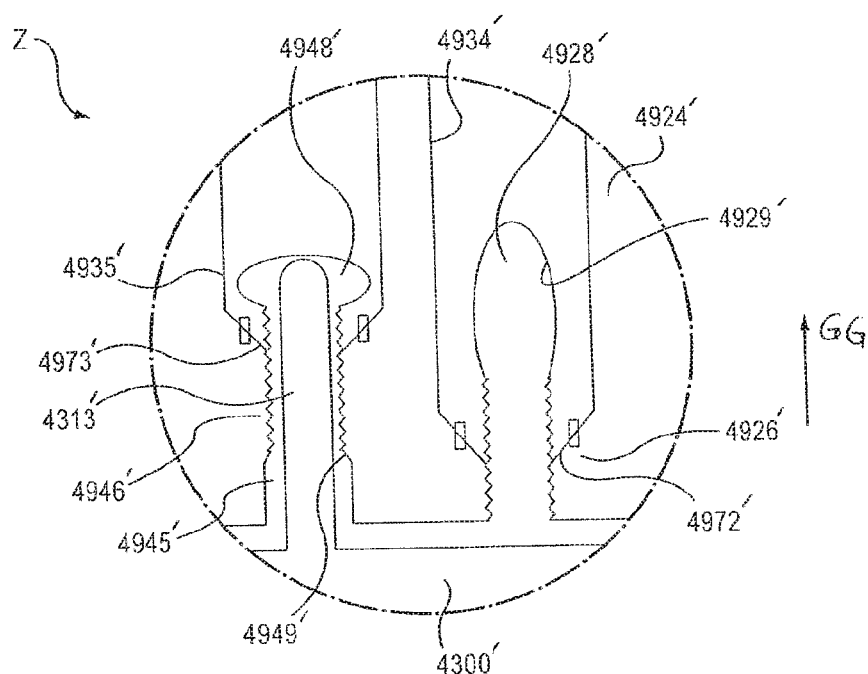
FIGS. 44, 45, and 46 are front views of a portion of the electronic circuit system of the medical injector labeled as Region Z in FIG. 43 in a first configuration, a second configuration, and a third configuration, respectively.
Figure 42:
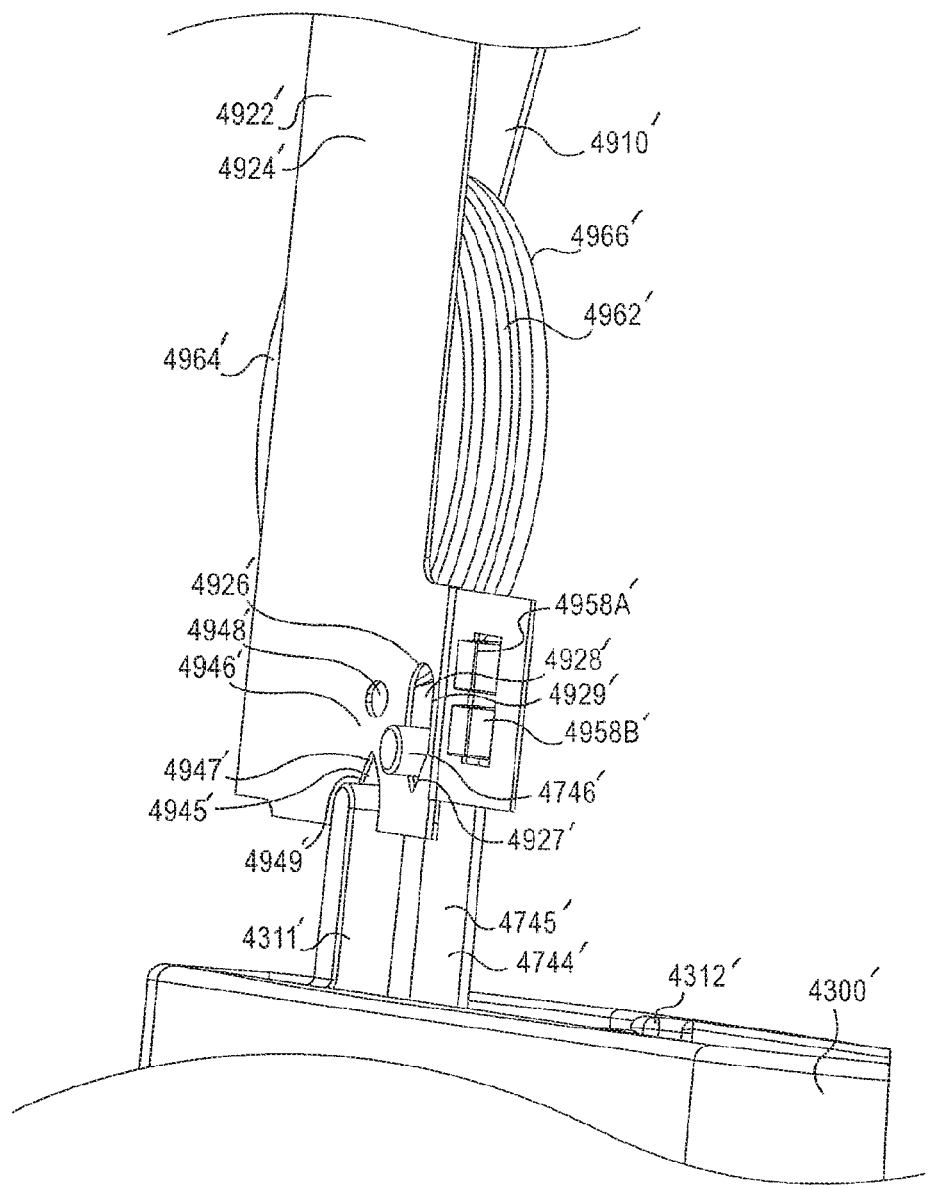
FIG. 42 is a perspective view of a portion of an electronic circuit system of the medical injector illustrated in FIG. 26, in a first configuration.
Figure 44:
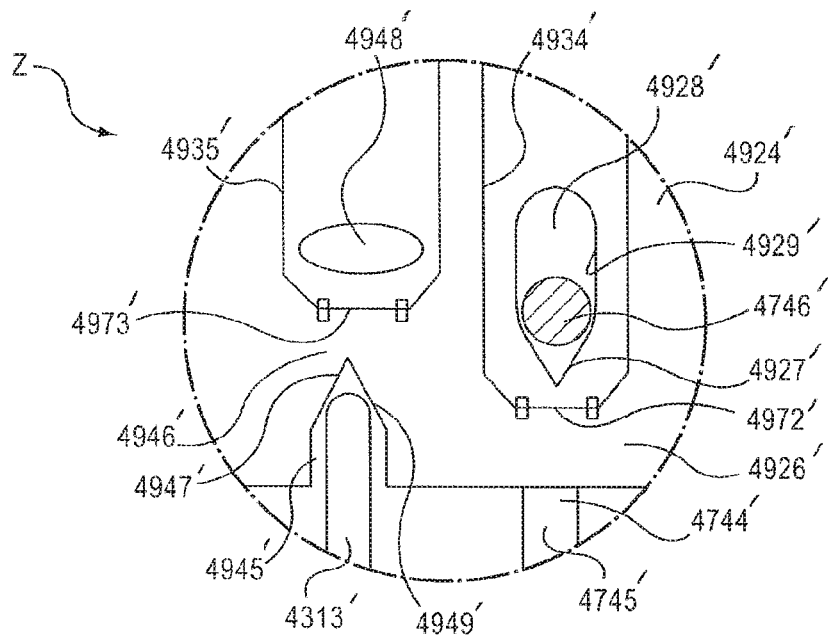
Figure 45:
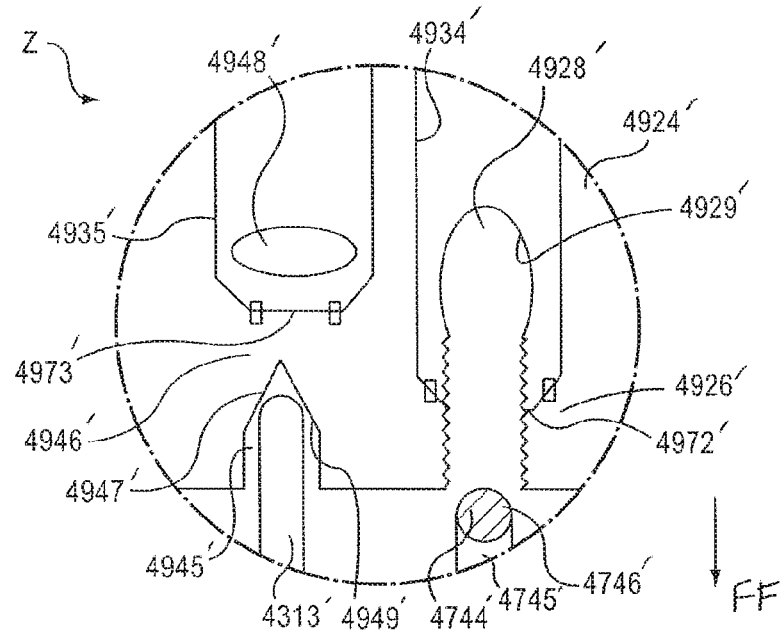

As shown in FIGS. 44-46, the first actuation portion 4926' includes a first electrical conductor 4934' and defines an opening 4928' having a boundary 4929'. The opening 4928' of the first actuation portion 4926' is configured to receive a protrusion 4746' of the actuator 4744' of the safety lock 4700'. The boundary 4929' of the first opening 4928' has a discontinuous shape, such as, for example, a teardrop shape, that includes a stress concentration riser 4927'. The discontinuity and/or the stress concentration riser 4927' of the boundary 4929' can be of any suitable shape to cause the substrate 4924' to deform in a predetermined direction when the protrusion 4746' of the actuator 4744' of the safety lock 4700' is moved relative to the opening 4928', as shown by the arrow FF in FIG. 45.

The opening 4928' is defined adjacent the first electrical conductor 4934' that electronically couples the components included in the electronic circuit system 4900'. The first electrical conductor 4934' includes a first switch 4972', which can be, for example a frangible portion of the first electrical conductor 4934'. In use, when the safety lock 4700' is moved from a first position (see e.g., FIG. 44) to a second position (see e.g., FIG. 45), the actuator 4744' moves in a direction substantially parallel to a plane defined by a surface of the first actuation portion 4926' of the substrate 4924'. The movement of the actuator 4744' causes the protrusion 4746' to move within the first opening 4928', as indicated by the arrow FF in FIG. 45. The movement of the protrusion 4746' tears the first actuation portion 4926' of the substrate 4924', thereby separating the portion of the first electrical conductor 4934' including the first switch 4972'. Said another way, when the safety lock 4700' is moved from its first position to its second position (see e.g., FIG. 33), the actuator 4744' moves irreversibly the first switch 4972' from a first state (e.g., a state of electrical continuity) to a second state (e.g., a state of electrical discontinuity). Said yet another way, when the safety lock 4700' is moved from its first position to its second position, the actuator 4744' disrupts the first electrical conductor 4934'.

The second actuation portion 4946' includes a second electrical conductor 4935' and defines an opening 4945', having a boundary 4949' and a tear propagation limit aperture 4948'. As shown in FIGS. 43-46, the opening 4945' of the second actuation portion 4946' is configured to receive a portion of an actuator 4311' of the base 4300'. The boundary 4949' of the opening 4945' has a discontinuous shape that includes a stress concentration riser 4947'. The discontinuity and/or the stress concentration riser 4947' of the boundary 4949' can be of any suitable shape to cause the substrate 4924' to deform in a predetermined direction when the actuator 4311' of the base 4300' is moved in a proximal direction relative to the opening 4945', as shown by the arrow GG in FIG. 46.

The second electrical conductor 4935' includes a second switch 4973' disposed between the opening 4945' and the tear propagation limit aperture 4948', which can be, for example, a frangible portion of the second electrical conductor 4935'. In use, when the base 4300' is moved from its first position to its second position (see e.g., FIG. 57), the actuator 4311' moves in a proximal direction, substantially parallel to a plane defined by a surface of the second actuation portion 4946' of the substrate 4924'. The proximal movement of the actuator 4311' tears the second actuation portion 4946' of the substrate 4924', thereby separating the portion of the second electrical conductor 4935' including the second switch 4973'. Said another way, when the base 4300' is moved from its first position to its second position, the actuator 4311' moves irreversibly the second switch 4973' from a first state (e.g., a state of electrical continuity) to a second state (e.g., a state of electrical discontinuity). The tear propagation limit aperture 4948' is configured to limit the propagation of the tear in the substrate 4924' in the proximal direction. Said another way, the tear propagation limit aperture 4948' is configured to ensure that the tear in the substrate 4924' does not extend beyond the tear propagation limit aperture 4948'. The tear propagation limit aperture 4948' can be any shape configured to stop the propagation of a tear and/or disruption of the substrate 4924'. For example, the tear propagation limit aperture 4948' can be oval shaped. In other embodiments, the proximal boundary of the tear propagation limit aperture 4948' can be reinforced to ensure that the tear in the substrate 4924' does not extend beyond the tear propagation limit aperture 4948'.

The battery assembly 4962' of the electronic circuit system 4900' comprises two batteries stacked on top of one another. The battery assembly 4962' has a first surface 4964' and a second surface 4966'. The first surface 4964' of the battery assembly 4962' can contact an electrical contact (not shown) disposed on the substrate 4924'. The second surface 4966' of the battery assembly 4962' is configured to contact a contact portion 4918' of a distal end portion 4916' of a battery clip 4910'. When both the electrical contact of the substrate 4924' and the contact portion 4918' of the distal end portion 4916' of the battery clip 4910' contact the battery assembly 4962', the batteries of the battery assembly 4962' are placed in electrical communication with the electronic circuit system 4900'. Said another way, when the electrical contact of the substrate 4924' and the contact portion 4918' of the distal end portion 4916' of the battery clip 4910' contact the battery assembly 4962', the battery assembly 4962' is configured to supply power to the electronic circuit system 4900'.

The battery clip 4910' (shown in FIG. 41) includes a proximal end portion 4912' and a distal end portion 4916'. The proximal end portion 4912' defines a retention aperture 4913'. The retention aperture 4913' is configured to receive the battery clip protrusion 4173' of the electronic circuit system housing 4170'. In this manner, the battery clip protrusion 4173' maintains the position of the battery clip 4910' with respect to the electronic circuit system housing 4170' and/or the battery assembly 4962'.

The distal end portion 4916' of the battery clip 4910' includes a contact portion 4918' and an angled portion 4917'. As described above, the contact portion 4918' is configured to contact the second surface 4916' of the battery assembly 4962' to place the battery assembly 4962' in electrical communication with the electronic circuit system 4900'. The angled portion 4917' of the distal end portion 4916' of the battery clip 4910' is configured to allow a proximal end portion 4236' of a battery isolation protrusion 4235' (see e.g., FIG. 48) to be disposed between the second surface 4966' of the battery assembly 4962' and the contact portion 4918' of the distal end portion 4916' of the battery clip 4910'. When the battery isolation protrusion 4235' is disposed between the second surface 4966' of the battery assembly 4962' and the contact portion 4918' of the distal end portion 4916' of the battery clip 4910', the electrical path between the battery assembly 4962' and the remainder of the electrical circuit system 4900' is severed, thereby removing power from the electronic circuit system 4900'. The contact portion 4918' of the distal end portion 4916' of the battery clip 4910' is biased such that when the battery isolation protrusion 4235' is removed, the contact portion 4918' will move into contact the second surface 4916' of the battery assembly 4962', thereby restoring electrical communication between the battery assembly 4962' and the electronic circuit system 4900'. In some embodiments, the battery isolation protrusion 4235' can be repeatedly removed from between the second surface 4966' of the battery assembly 4962' and the contact portion 4918' of the distal end portion 4916' of the battery clip 4910' and reinserted. Said another way, the battery isolation protrusion 4235' and the battery clip 4910' collectively form a reversible on/off switch.

The audio output device 4956' of the electronic circuit system 4900' is configured to output audible sound to a user in response to a use of the medical injector 4000'. In some embodiments, the audible output device 4956' can be a speaker. In some embodiments, the audible sound can be, for example, associated with a recorded message and/or a recorded speech. In other embodiments, the audible instructions can be an audible beep, a series of tones and/or or the like.

In other embodiments, the medical injector 4000' can have a network interface device (not shown) configured to operatively connect the electronic circuit system 4900' to a remote device (not shown) and/or a communications network (not shown). In this manner, the electronic circuit system 4900' can send information to and/or receive information from the remote device. The remote device can be, for example, a remote communications network, a computer, a compliance and/or adherence monitoring device, a cell phone, a personal digital assistant (PDA) or the like. Such an arrangement can be used, for example, to download replacement processor-readable code from a central network to the electronic circuit system 4900'. In some embodiments, for example, the electronic circuit system 4900' can download information associated with a medical injector 4000', such as an expiration date, a recall notice, updated use instructions or the like. Similarly, in some embodiments, the electronic circuit system 4900' can upload compliance and/or adherence information associated with the use of the medical injector 4000' via the network interface device.

Figure 47:
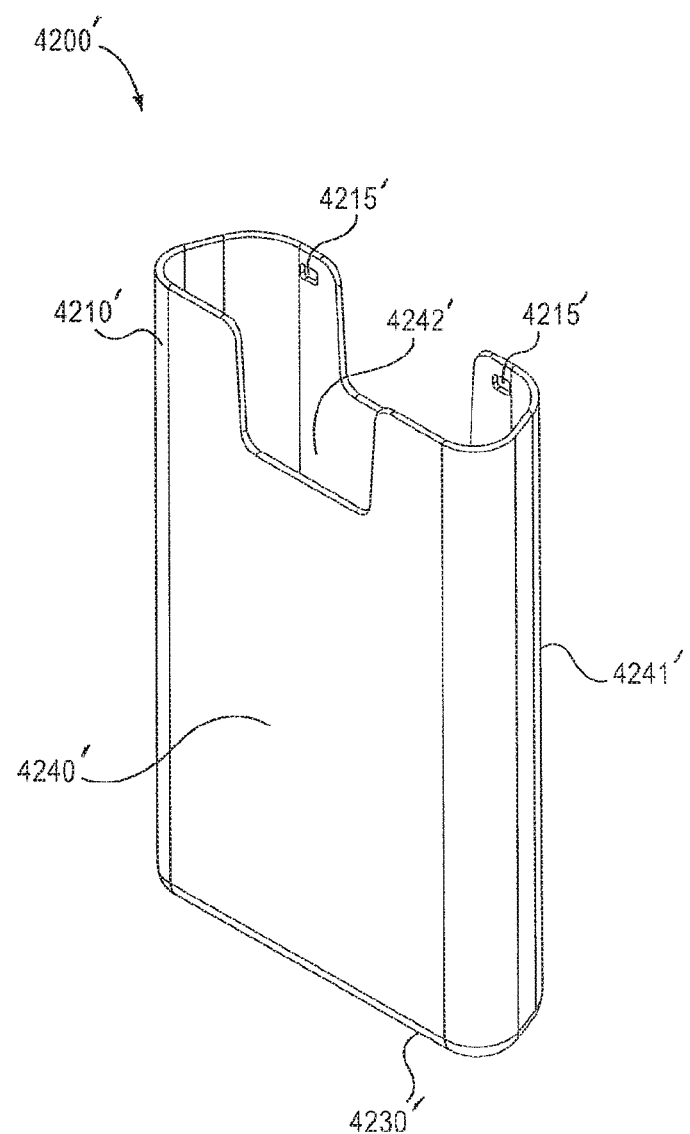
FIGS. 47 and 48 are perspective views of a cover of the medical injector illustrated in FIG. 26.
Figure 48:
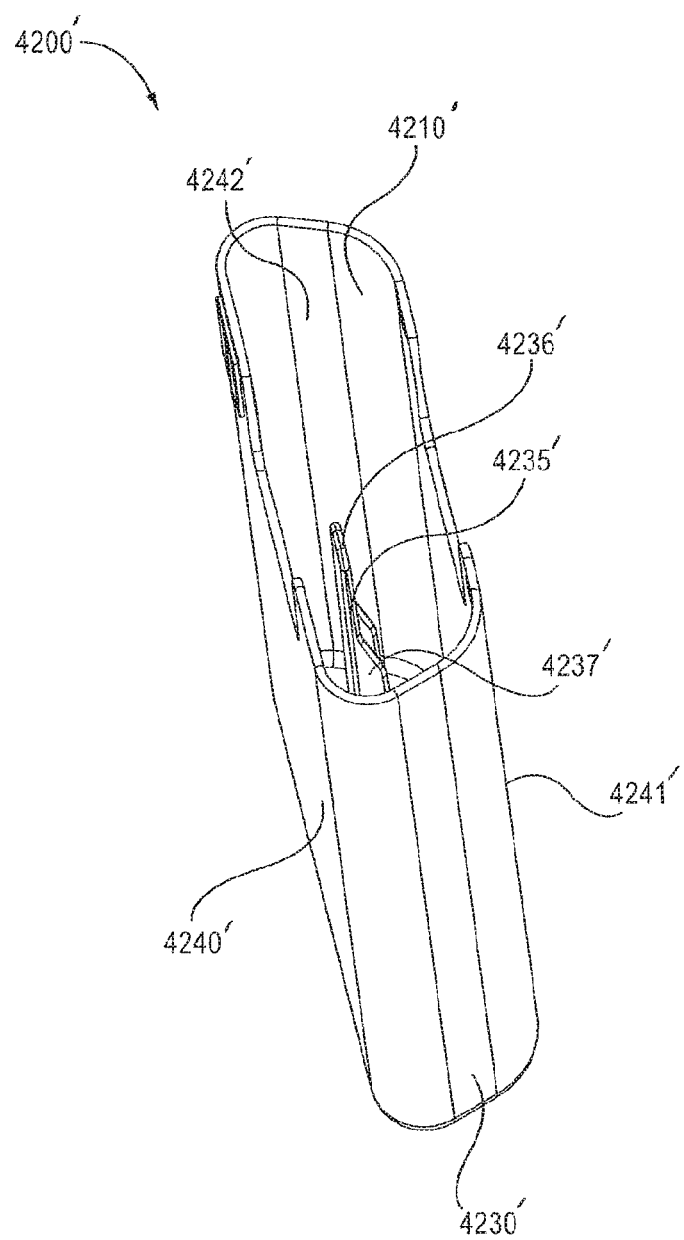
Figure 49:
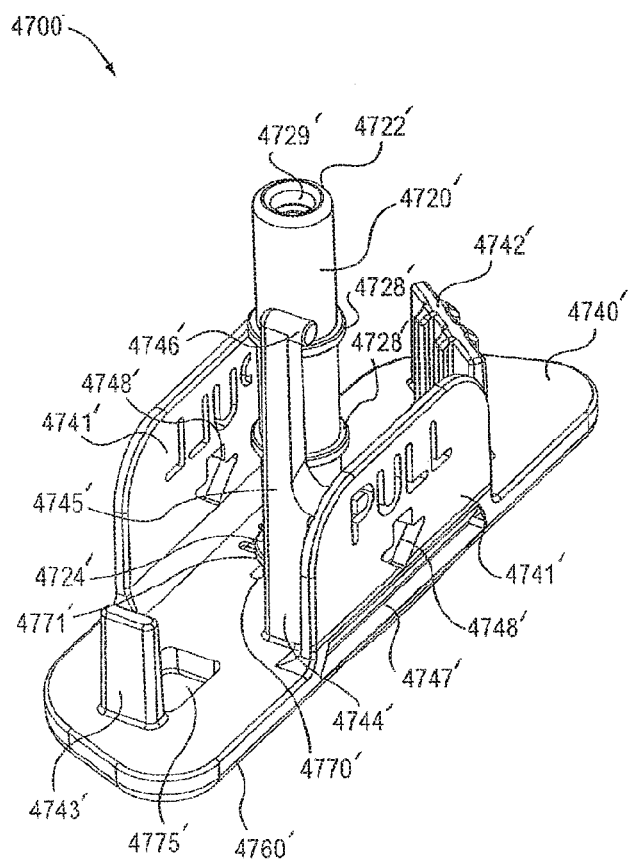
FIG. 49 is a perspective view of a safety lock of the medical injector illustrated in FIG. 26.

FIGS. 47 and 48 show the cover 4200' of the medical injector 4000'. The cover 4200' includes a proximal end portion 4210' and a distal end portion 4230', and defines a cavity 4242'. The cavity 4242' of the cover 4200' is configured to receive at least a portion of the housing 4110'. The proximal end portion 4210' defines apertures 4215' configured to receive the cover retention protrusions 4142' of the housing 4110' (shown in FIGS. 27 and 29). In this manner, the apertures 4215' and the cover retention protrusions 4142' of the housing 4110' removably retain the cover 4200' about at least a portion of the housing 4110'. Said another way, the apertures 4215' and the cover retention protrusions 4142' of the housing 4110' are configured such that the cover 4200' can be removed from a portion of the housing 4110' and then replaced about the portion of the housing 4110'.

The distal end portion 4230' of the cover 4200' includes a battery isolation protrusion 4235'. The battery isolation protrusion 4235' includes a proximal end portion 4236' and a tapered portion 4237'. The proximal end portion 4236' of the battery isolation protrusion 4235' is configured to be removably disposed between the second surface 4966' of the battery assembly 4962' and the contact portion 4918' of the distal end portion 4916' of the battery clip 4910', as described above.

FIGS. 49-52 show the safety lock 4700' of the medical injector 4000'. The safety lock 4700' of the medical injector 4000' includes a proximal surface 4740', a distal surface 4760' opposite the proximal surface 4740' and a needle sheath 4720'. The safety lock 4700' defines a needle sheath aperture 4770' and a battery isolation protrusion aperture 4775'. The battery isolation protrusion aperture 4775' is configured to receive the battery isolation protrusion 4235' of the cover 4200' such that the battery isolation protrusion 4235' can be disposed within the electronic circuit system cavity 4153' or the electronic circuit system 4900', as described above. Similarly stated, the battery isolation protrusion aperture 4775' of the safety lock 4700' is aligned with the battery isolation protrusion aperture 4121' of the housing 4110', such that the battery isolation protrusion 4235' can be disposed within the electronic circuit system cavity 4153' when the cover 4200' is disposed about a portion of the housing 4110'.

The proximal surface 4740' of the safety lock 4700' includes a safety lock protrusion 4742', a stopper 4743', an actuator 4744' and two opposing pull tabs 4741'. As described above, when the safety lock 4700' is in a first (locked) position, the safety lock protrusion 4742' is configured to be disposed in the opening 4554' defined by the extensions 4552' of the distal end portion 4544' of the release member 4540'. Accordingly, the safety lock protrusion 4742' is configured to prevent the extensions 4552' from moving closer to each other, thereby preventing proximal movement of the release member 4540' of the medicament delivery mechanism 4500' and/or delivery of a medicament. The stopper 4743' of the safety lock 4700' is a protrusion extending from the proximal surface 4740' of the safety lock 4700'. The stopper 4743' is configured to contact a portion of the housing 4110' to limit the proximal movement of the safety lock 4700' relative to the housing 4110'. In other embodiments, the stopper 4743' can be any structure configured to limit the proximal movement of the safety lock 4700'.

The actuator 4744' of the safety lock 4700' has an elongated portion 4745' and a protrusion 4746'. The elongated portion 4745' extends in a proximal direction from the proximal surface 4740'. In this manner, the elongated portion 4745' can extend through a safety lock actuator opening 4356' of the base 4300' (see e.g., FIG. 53) and within the safety lock actuator groove 4123' of the housing 4110' and the safety lock actuator groove 4182' of the electronic circuit system housing 4170'. The protrusion 4746' extends in a direction substantially transverse to the elongated portion 4745' and/or substantially parallel to the proximal surface 4740' of the safety lock 4700'. As described above, the opening 4928' of the first actuation portion 4926' is configured to receive the protrusion 4746' of the actuator 4744' of the safety lock 4700'.

The pull tabs 4741' of the safety lock 4700' include a grip portion 4747' and indicia 4748'. The grip portion 4747' of the pull tabs 4741' provides an area for the user to grip and/or remove the safety lock 4700' from the rest of the medicament delivery system 4700'. The indicia 4748' provides instruction on how to remove the safety lock 4700'. In some embodiments, for example, the indicia 4748' can indicate the direction the user should pull the safety lock 4700' to remove the safety lock 4700'.

Figure 51:
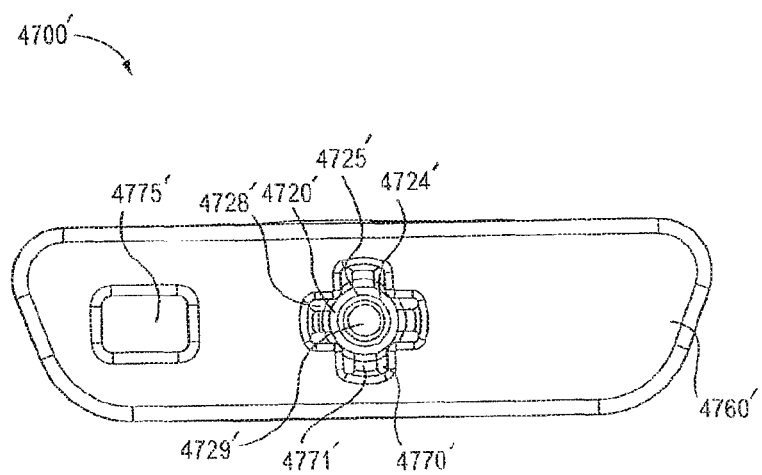
FIG. 51 is a bottom view of the safety lock of the medical injector illustrated in FIG. 49.
Figure 52:
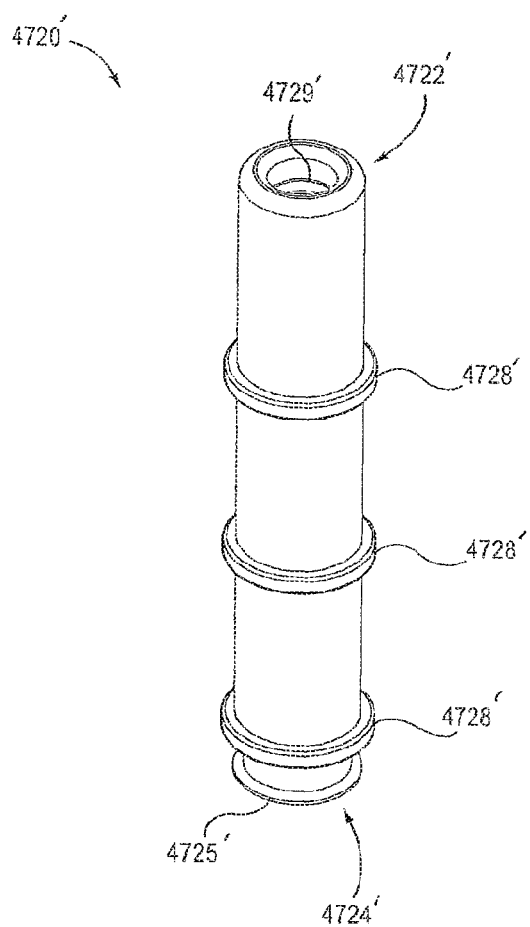
FIG. 52 is a perspective view of a needle sheath of the safety lock of the medical injector illustrated in FIG. 49.

As shown in FIG. 51, the needle sheath 4720' of the safety lock 4700' includes a distal end portion 4724', a proximal end portion 4722' and a plurality of ribs 4728'. The needle sheath 4720' can also define a lumen 4729'. The lumen 4729' of the safety lock 4700' is configured to receive the needle 4512'. In this manner, the needle sheath 4720' can protect the user from the needle 4512' and/or can keep the needle 4512' sterile before the user uses the medical injector 4000'. The proximal end portion 4722' of the needle sheath is configured to contact the distal end portion 4522' of the carrier 4520' of the medicament delivery mechanism 4500'.

Figure 56:
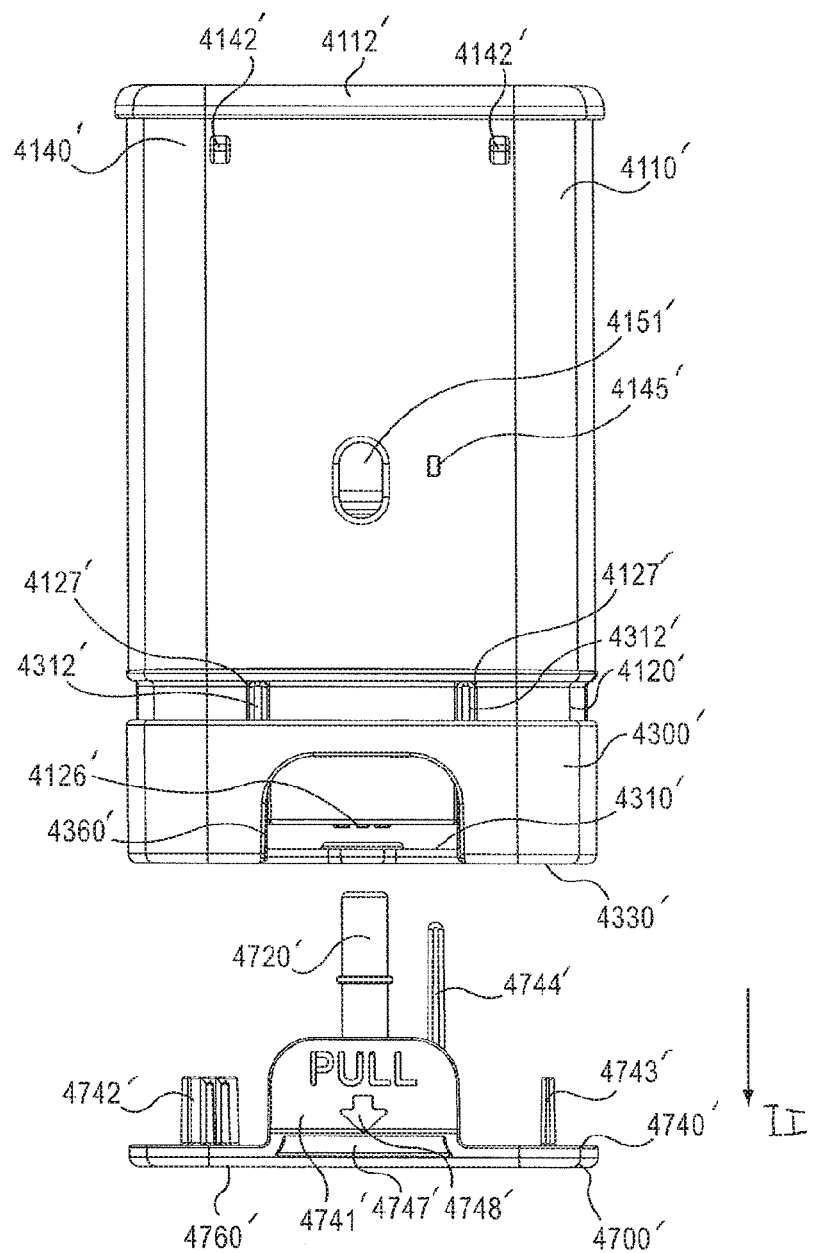
FIG. 56 is a back view of the medical injector illustrated in FIG. 26 in a third configuration.
Figure 57:
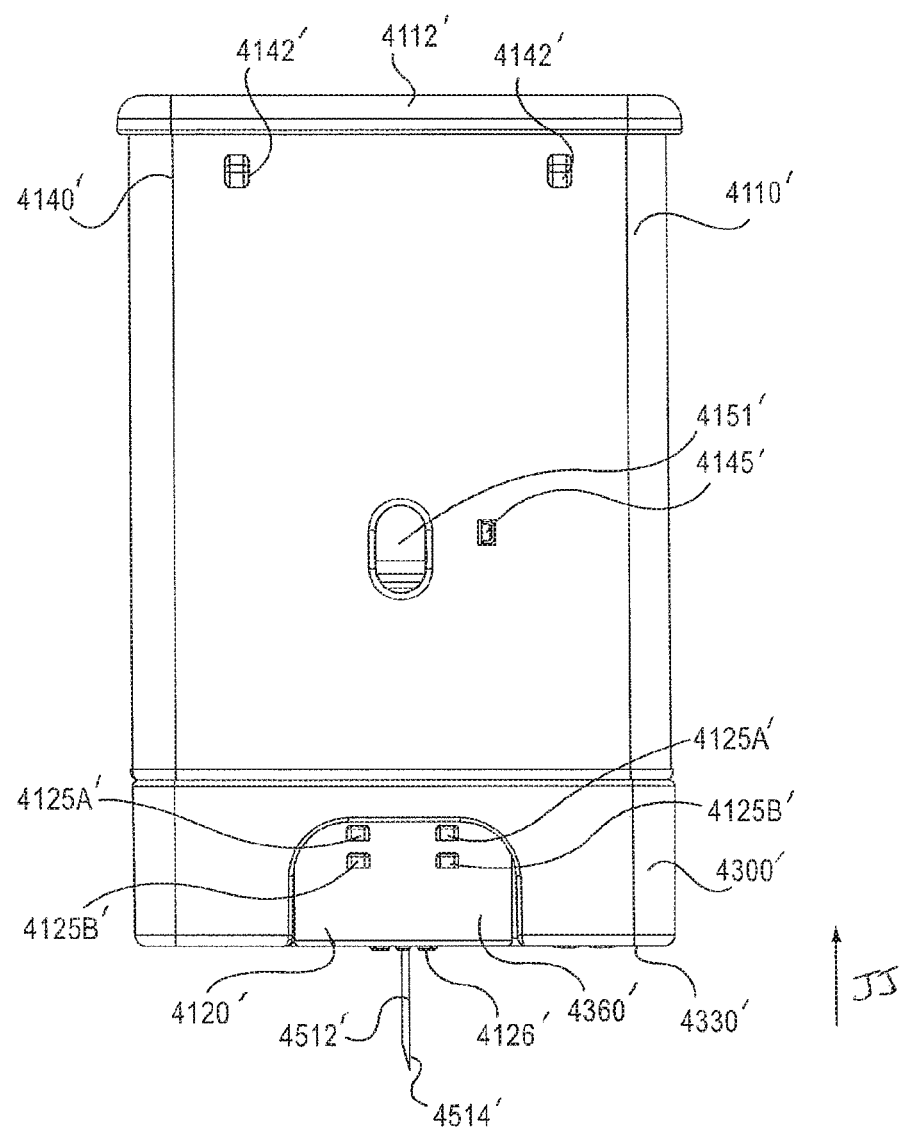
FIG. 57 is a back view of the medical injector illustrated in FIG. 26 in a fourth configuration.

The distal end portion 4724' of the needle sheath 4720' has an angled ridge 4725'. The angled ridge 4725' is configured to allow the proximal end portion 4722' of the needle sheath 4720' to irreversibly move through the needle sheath aperture 4770' of the safety lock 4700' in a distal direction. Said another way, the angled ridge 4725' can be configured in such a way as to allow the proximal end portion 4722' of the needle sheath 4720' to move through the needle sheath aperture 4770' in a distal direction, but not in a proximal direction. The needle sheath aperture 4770' has retaining tabs 4771' configured to engage the proximal end of the angled ridge 4725' when the needle sheath 4720' is moved in a proximal direction. In this manner, the retaining tabs 4771' prevent the proximal movement of the needle sheath with respect to the safety lock 4700'. Further, the retaining tabs 4771' are configured to engage the proximal end of the angled ridge 4725' when the safety lock 4700' is moved in a distal direction. Said another way, as shown in FIG. 56, the needle sheath 4720' is removed from the needle 4512' when the safety lock 4700' is moved in a distal direction with respect to the housing 4110'.

Figure 53:
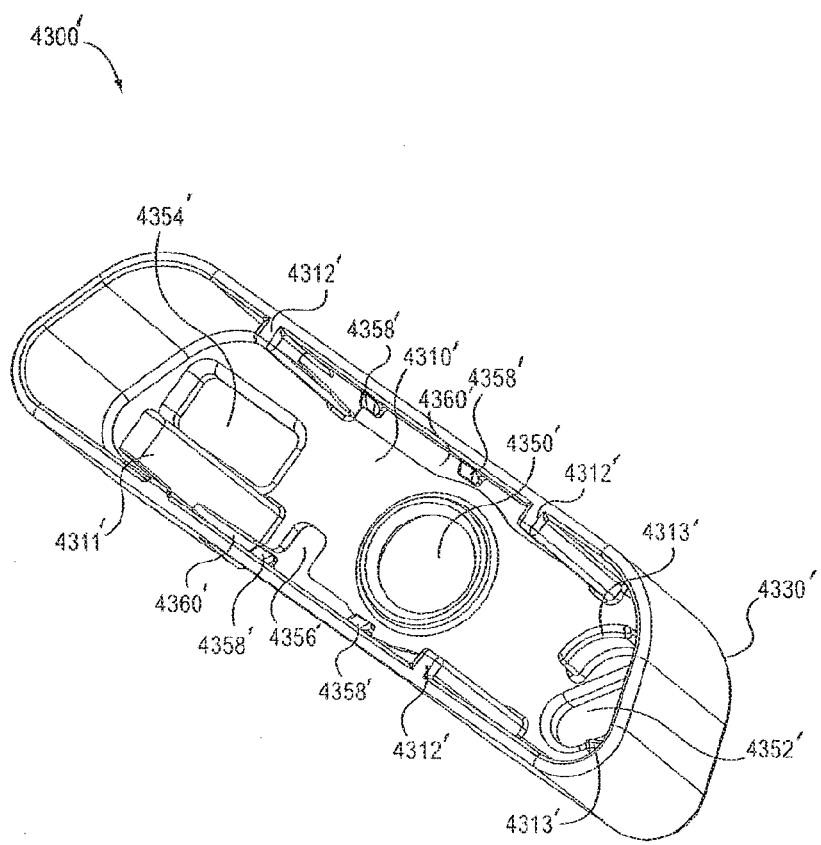
FIG. 53 is a perspective view of a base of the medical injector illustrated in FIG. 26.
Figure 54:
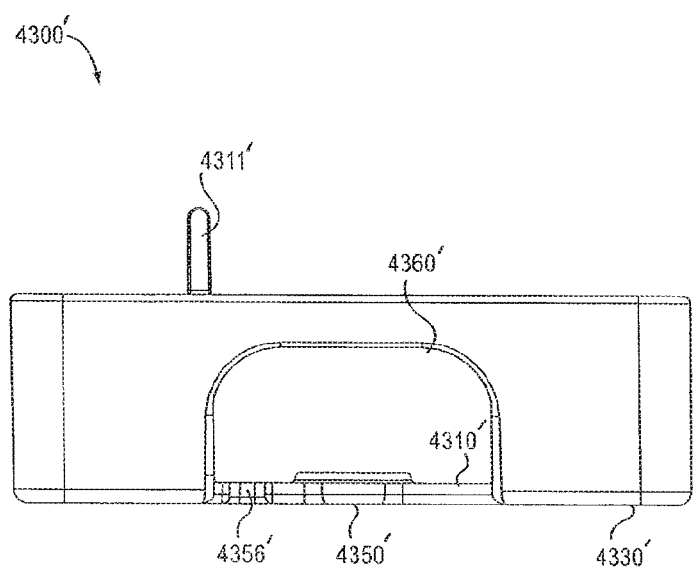
FIG. 54 is a front view of the base of the medical injector illustrated in FIG. 26.

FIGS. 53 and 54 show the base 4300' of the medical injector 4000'. The base 4300' includes a proximal surface 4310', a distal surface 4330' and base connection knobs 4358'. The base 4300' defines a needle aperture 4350', a safety lock protrusion aperture 4352', a battery isolation protrusion aperture 4354', a safety lock actuator opening 4356', and pull tab openings 4360'. The needle aperture 4350' is configured to receive the needle 4512' when the medical injector 4000' is actuated. The safety lock protrusion aperture 4352' of the base 4300' receives the safety lock protrusion 4742' of the safety lock 4700'. The battery isolation protrusion aperture 4354' of the base 4300' receives the battery isolation protrusion 4235' of the cover 4200' and the stopper 4743' of the safety lock 4700'. The safety lock actuator opening 4356' receives the safety lock actuator 4744' of the safety lock 4700'. The pull tab openings 4360' are configured to receive the pull tabs 4741' of the safety lock 4700'.

The proximal surface 4310' of the base 4300' includes an actuator 4311', guide members 4312', and protrusions 4313'. The actuator 4311' is an elongate member configured to engage the substrate 4924' of the electronic circuit system 4900'. As described above, the opening 4945' of the second actuation portion 4946' is configured to receive the actuator 4311' of the base 4300'. The guide members 4312' of the base 4300' are configured to engage and/or slide within the base rail grooves 4127' of the housing 4110', as described above. The protrusions 4313' of the base 4300' are configured to engage the tapered surfaces 4549' of the extensions 4552' of the release member 4540'. As described in further detail herein, when the safety lock 4700' is removed and the base 4300' is moved in a proximal direction with respect to the housing 4110', the protrusion 4313' of the base 4300' are configured to move the extensions 4552' of the release member 4540' closer to each other, actuating the medicament delivery mechanism 4500'. As described above, the base connection knobs 4358' are configured to engage the base retention recesses 4125A, 4125B in a way that allows proximal movement of the base 4300' but limits distal movement of the base 4300'.

Figure 55:
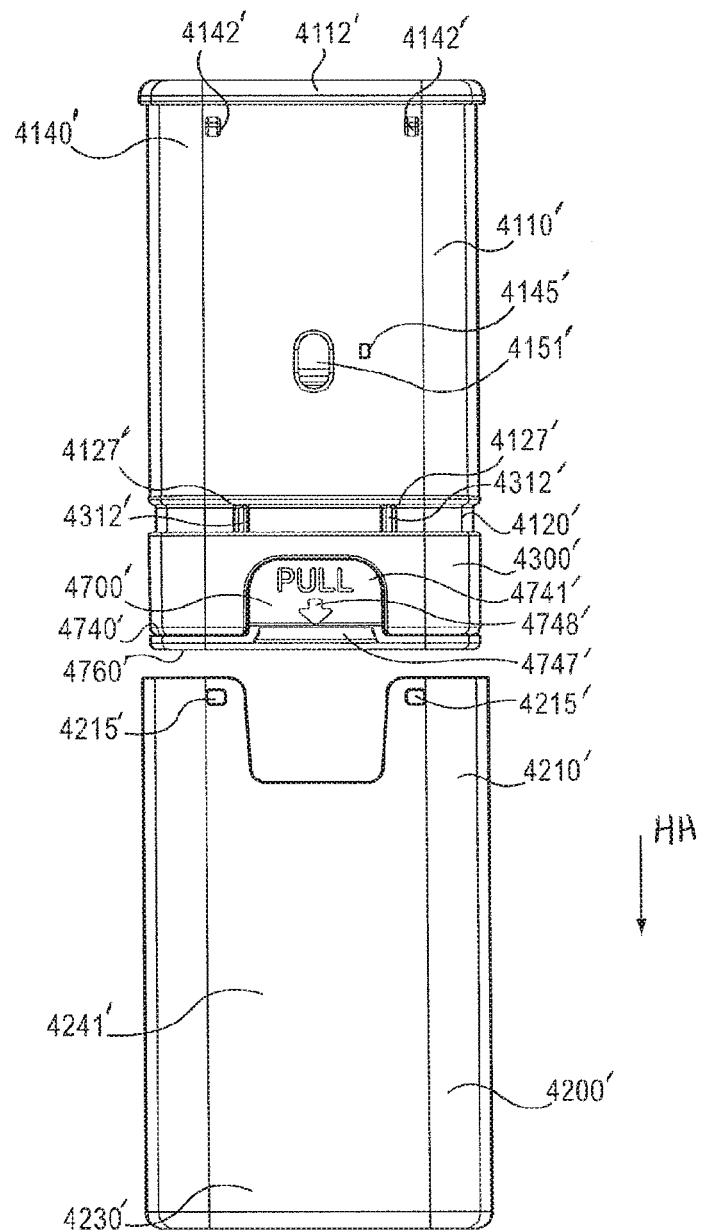
FIG. 55 is a back view of the medical injector illustrated in FIG. 26 in a second configuration.

As shown in FIG. 55, the medical injector 4000' is first enabled by moving the medicament delivery device from a first configuration to a second configuration by moving the cover 4200' from a first position to a second position. The cover 4200' is moved from the first position to the second position by moving it with respect to the housing 4110' in the direction shown by the arrow HH in FIG. 55. When the cover 4200' is moved with respect to the housing 4110' in the direction HH, the battery isolation protrusion 4235' is removed from the area between the battery clip 4910' and the second surface 4966' of the battery assembly 4962'. In this manner, the battery assembly 4962' can be operatively coupled to the electronic circuit system 4900' when the cover 4200' is removed, thereby providing power to the electronic circuit system 4900'.

When power is provided, as described above, the electronic circuit system 4900' can output one or more predetermined electronic outputs. For example, in some embodiments, the electronic circuit system 4900' can output an electronic signal associated with recorded speech to the audible output device 4956'. Such an electronic signal can be, for example, associated with a .WAV file that contains a recorded instruction instructing the user in the operation of the medical injector 4000'. Such an instruction can state, for example, "remove the safety tab near the base of the auto-injector." The electronic circuit system 4900' can simultaneously output an electronic signal to one and/or both of the LEDs 4958A, 4958B thereby causing one and/or both of the LEDs 4958A, 4958B to flash a particular color. In this manner, the electronic circuit system 4900' can provide both audible and visual instructions to assist the user in the initial operation of the medical injector 4000'.

In other embodiments, the electronic circuit system 4900' can output an electronic output associated with a description and/or status of the medical injector 4000' and/or the medicament contained therein. For example, in some embodiments, the electronic circuit system 4900' can output an audible message indicating the type of medicament contained in the medical injector 4000', the expiration date of the medicament, the dosage of the medicament or the like.

As described above, the medical injector 4000' can be repeatedly moved between the first configuration and the second configuration when the cover 4200' is moved repeatedly between the first position and the second position respectively. Said another way, the cover 4200' can be removed and replaced about the housing 4110' any number of times. When the cover 4200' is moved from the second position to the first position, the battery isolation protrusion 4235' is inserted between the battery clip 4910' and the second surface 4966' of the battery assembly 4962', deactivating the electronic circuit system 4900'. When the cover is moved from the first position to the second position a second time, the electronic circuit system 4900' is once again activated. In this manner, the cover 4200' can be removed and the electronic circuit system 4900' can output an electronic output without compromising the sterility of the needle 4512'.

After the cover 4200' is removed from the housing 4110', the medical injector 4000' can be moved from the second configuration to a third configuration by moving the safety lock 4700' from a first position to a second position. The safety lock 4700' is moved from a first position to a second position by moving the safety lock 4700' with respect to the housing 4110' in the direction shown by the arrow II in FIG. 56. When the safety lock 4700' is moved from the first position to the second position, the safety lock protrusion 4742' is removed from between the extensions 4552' of the release member 4540', thereby enabling the medicament delivery member 4500'. Moreover, as shown in FIGS. 44 and 45, when the safety lock 4700' is moved from the housing 4110', the actuator 4744' of the safety lock 4700' moves in the direction FF as shown in FIG. 45, irreversibly moving the first switch 4972' from a first state (e.g., a state of electrical continuity) to a second state (e.g., a state of electrical discontinuity). When the actuator 4744' of the safety lock 4700' moves irreversibly the first switch 4972' of the electronic circuit system 4900' to the second state, the electronic circuit system 4900' can output one or more predetermined electronic outputs. For example, in some embodiments, a processor (not shown) can output an electronic signal associated with recorded speech to the audible output device 4956'. Such an electronic signal can be, for example, associated with a recorded message notifying the user of the status of the medical injector 4000'. Such a status message can state, for example, "The medical injector is now enabled." The electronic circuit system 4900' can also simultaneously output an electronic signal to one and/or both of the LEDs 4958A, 4958B, thereby causing one and/or both of the LEDs 4958A, 4958B to stop flashing, change color or the like.

In some embodiments, the first actuation portion 4926' and the actuator 4744' can be configured such that the actuator 4744' must move a predetermined distance before the actuator 4744' engages the boundary 4929' of the opening 4928'. For example, in some embodiments, the actuator 4744' must move approximately 0.20 inches before the actuator 4744' engages the boundary 4929' of the opening 4928'. In this manner, the safety lock 4700' can be moved slightly without irreversibly moving the first switch 4972' of the electronic circuit system 4900' to the second state. Accordingly, this arrangement will permit the user to inadvertently and/or accidentally move the safety lock 4700' without actuating the electronic circuit system 4900'.

In some embodiments, the electronic circuit system 4900' can be configured to output the status message for a predetermined time period, such as, for example, five seconds. After the predetermined time period has elapsed, the electronic circuit system 4900' can output an audible message further instructing the user in the operation of the medical injector 4000'. Such an instruction can state, for example, "Place the base of the auto-injector against the patient's thigh. To complete the injection, press the base firmly against the patient's thigh." In some embodiments, the electronic circuit system 4900' can simultaneously output an electronic signal to one and/or both of the LEDs 4958A, 4958B, thereby causing one and/or both of the LEDs 4958A, 4958B to flash a particular color. In this manner, the electronic circuit system 4900' can provide both audible and/or visual instructions to assist the user in the placement and actuation of the medical injector 4000'. In some embodiments, the electronic circuit system 4900' can be configured to repeat the instructions after a predetermined time period has elapsed.

As described above, in other embodiments, the medical injector 4000' can have a network interface device (not shown) configured to operatively connect the electronic circuit system 4900' to a remote device (not shown) and/or a communications network (not shown). In this manner, the electronic circuit system 4900' can send a wireless signal notifying a remote device that the safety lock 4700' of the medical injector 4000' has been removed and that the medical injector 4000' has been armed.

After the safety lock 4700' is moved from the first position to the second position, the medical injector 4000' can be moved from the third configuration to a fourth configuration by moving the base 4300' from a first position to a second position. The base 4300' is moved from its first position to its second position by placing the medical injector 4000' against the body of the patient and moving the base 4300' with respect to the housing 4110' in the direction shown by the arrow JJ in FIG. 57. Moving the base 4300' from the first position to the second position causes the protrusions 4313' on the proximal surface 4310' of the base 4300' to engage the tapered surfaces 4549' of the extensions 4552' of the release member 4540', causing the release member 4540' to actuate the medicament delivery mechanism 4500' and deliver a medicament to a body of a patient.

When the base 4300' is moved from the first position to the second position, the medicament delivery mechanism 4500' is actuated such that the puncturer 4541' of the release member 4540' is brought in contact with and/or punctures the frangible seal 4573' of the gas container 4570'. In some embodiments, the movement of the release member 4540' can be caused by a spring (not shown in FIG. 12). After the frangible seal 4573' has been punctured, an actuating portion of a compressed gas can escape from the gas container 4570' and flow via the gas passageway 4144' into the medicament cavity 4157'. The gas applies gas pressure to the movable member 4530' causing the movable member 4530' and the carrier 4520' to move in a distal direction within the medicament cavity 4157'. When the carrier 4520' moves distally within the medicament cavity 4157', the carrier 4520' and the medicament container 4560' are in a first configuration. Accordingly, as described above, the medicament container 4560' is connected to the carrier 4520' by a "snap fit" connection. In this manner, the medicament container 4560' and the needle 4512' contemporaneously move with movable member 4530' and/or the carrier 4520' in a distal direction. As described above, the proximal end portion 4516' of the needle 4512' is connected to the distal end portion 4522' of the carrier 4520' and is spaced from the seal 4523' of the medicament container 4560' when the carrier 4520' is in its first configuration. Said another way, the medicament container 4560' and the needle 4512' do not define a medicament delivery path when the carrier 4520' is in the first configuration. The movement of the needle 4512' in a distal direction causes the proximal end portion 4516' of the needle 4512' to exit the housing 4110' and enter the body of a patient prior to administering a medicament.

After the carrier 4520' and/or the needle 4512' have moved within the medicament cavity 4157' a predetermined distance, the carrier 4520' and the medicament container 4560' are moved from the first configuration to a second configuration. In the second configuration of the carrier 4520', the medicament container 4560' is released from the "snap-fit" allowing the medicament container 4560' and the movable member 4530' to continue to move in a distal direction relative to the carrier 4520'. Said another way, the medicament container 4560' is configured to slidably move within the carrier 4520' when the carrier is moved from the first configuration to the second configuration. As the medicament container 4560' continues to move within the carrier 4520', the proximal end portion 4516' of the needle 4512' contacts and punctures the seal 4523' of the medicament container 4560'. This allows the medicament contained in the medicament container 4560' to flow into the lumen (not shown) defined by the needle 4512', thereby defining a medicament delivery path.

As the medicament container 4560' contacts the distal end of the carrier 4520', the medicament container 4560' stops moving within the carrier 4520' while the movable member 4530' continues to move in a distal direction. This causes the piston portion 4534' of the movable member 4530' to sealingly slide and/or move within the medicament container 4560' containing a liquid medicament. As the piston portion 4534' of the movable member 4530' sealingly slides and/or moves within the medicament container 4560', the piston portion 4534' generates a pressure upon the medicament contained within the medicament container 4560', thereby allowing at least a portion of the medicament to flow out of the medicament container 4560' and into the lumen defined by the needle 4512'. The medicament is delivered to a body of a user via the medicament delivery path defined by the medicament container 4560' and the needle 4512'.

As described above, the actuator 4538' of the base 4300' actuates the electronic circuit 4900' to trigger a predetermined output or sequence of outputs when the base 4520' is moved from its first position to its second position (see, e.g., FIGS. 42-46). When the actuator 4538' is moved in a proximal direction relative to the opening 4945', as shown by the arrow GG in FIG. 46, the electronic circuit system 4900' is actuated to output one or more predetermined electronic outputs. For example, in some embodiments, the electronic circuit system 4900' can output an electronic signal associated with recorded speech to the audible output device 4956'. Such an electronic signal can be, for example, associated with an audible countdown timer, instructing the user on the duration of the injection procedure. Said another way, if it takes, for example, ten seconds to complete an injection, an audible countdown timer can count from ten to zero ensuring that the user maintains the medical injector 4000' in place for the full ten seconds. In other embodiments, the electronic signal can be, for example, associated with a recorded message notifying the user that the injection is complete, instructing the user on post-injection disposal and safety procedures, instructing the user on post-injection medical treatment or the like. Such a status message can state, for example, "The injection is now complete. Please seek further medical attention from a doctor." The electronic circuit system 4900' can also simultaneously output an electronic signal to one and/or both LEDs 4958A, 4958B, thereby causing one and/or both LEDs 4958A, 4958B to stop flashing, change color or the like, to provide a visual indication that the injection is complete. In other embodiments, the electronic circuit system 4900' can send a wireless signal notifying a remote device that the injection is complete. In this manner, a patient's compliance and/or adherence can be monitored.

In some embodiments, the second actuation portion 4946' and the actuator 4538' can be configured such that the base 4500' and/or the actuator 4538' must move a predetermined distance before the actuator 4538' engages the boundary 4949' of the opening 4945'. For example, in some embodiments, the actuator 4538' must move approximately 0.20 inches before the actuator 4538' engages the boundary 4949' of the opening 4945'. In this manner, the base 4700' can be moved slightly without irreversibly moving the second switch 4973' of the electronic circuit system 4900' to the second state. Accordingly, this arrangement will permit the user to inadvertently and/or accidentally move the base 4500' without actuating the electronic circuit system 4900'.

Figure 58:
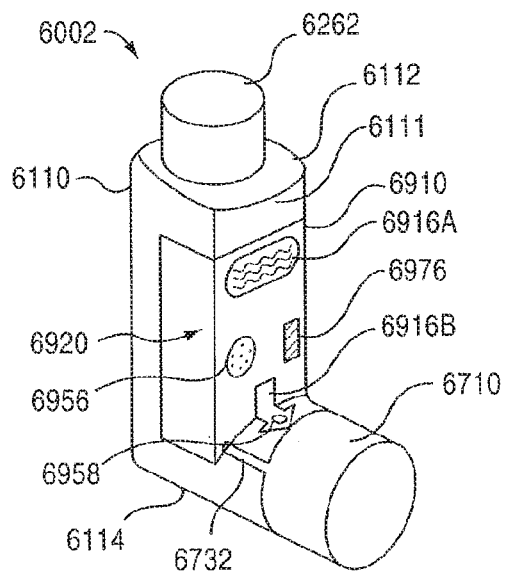
FIGS. 58 and 59 are perspective views of an inhaler according to an embodiment, in a first configuration and a second configuration, respectively.
Figure 59:
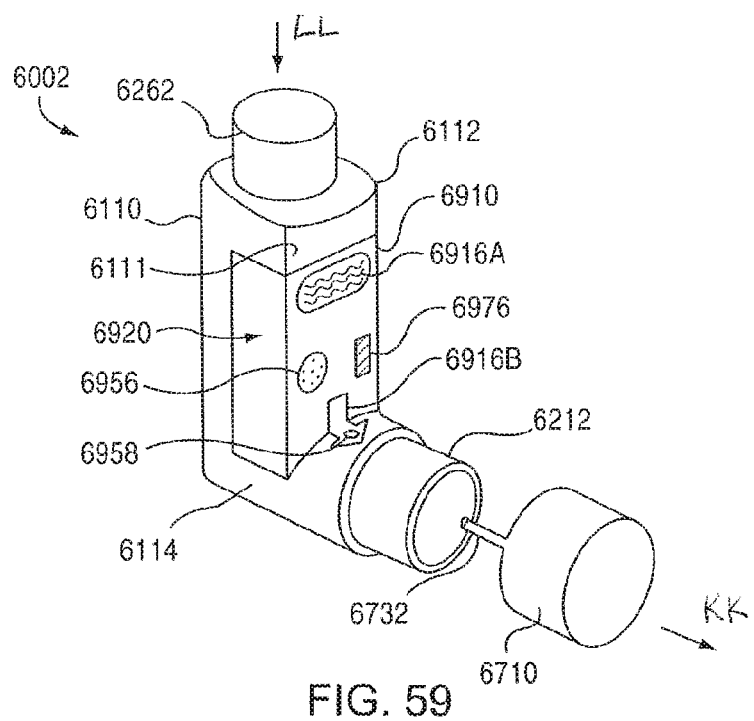

FIGS. 58 and 59 show an inhaler 6002 according to an embodiment. The inhaler 6002 includes a housing 6110 and a medicament container 6262 movably disposed within the housing 6110. The medicament container 6262 includes a metering mechanism (not shown in FIGS. 58 and 59) configured to discharge a predetermined volume of medicament when the inhaler 6002 is actuated.

The housing 6110 has a proximal end portion 6112 and a distal end portion 6114. An label 6910, which includes at least a portion of an electronic circuit system 6920, is disposed on an outer surface 6111 of the housing 6110. As described above, a portion of the label 6910 can include a textual indicia 6916. Similar to the electronic circuit systems shown and described above, the electronic circuit system 6920 is configured to output at least one electronic signal associated with the user of the inhaler 6002. The electronic circuit system 6920 includes a microprocessor (not shown), a microspeaker 6956 and an LED 6958. The electronic circuit system 6920 also includes a motion sensor 6976, the function of which is discussed in more detail below.

The distal end portion 6114 of the housing 6110 includes a mouthpiece 6212 about which a protective cap 6710 is disposed. Prior to use, the inhaler 6002 is first enabled by removing the protective cap 6710, as shown by the arrow KK in FIG. 59. The protective cap 6710 includes an actuator 6732 that actuates the electronic circuit system 6920 to trigger a predetermined output or sequence of outputs when the protective cap 6710 is removed. In some embodiments, the actuator 6732 can include a protrusion that is received by an actuation portion of the electronic circuit system 6920, in a similar manner as described above. In other embodiments, the actuator 6732 can be configured to engage a microswitch that can be repeatedly moved between a first state and a second state.

When actuated, the electronic circuit system 6920 can output one or more predetermined electronic outputs. For example, in some embodiments, the electronic circuit system 6920 can output an audible message via the microspeaker 6956 instructing the user to "vigorously shake the inhaler for five seconds." The processor can simultaneously enable the motion sensor 6976.

Upon receiving a predetermined input from the motion sensor 6976, which can be any sensor suitable for detecting the rapid motion of the inhaler 6002, the processor can then send an electronic signal to produce a second audible message. Such a message can state, for example, "the inhaler is now sufficiently shaken and is ready for use." In some embodiments, the electronic circuit system 6920 can also output an instruction associated with the correct placement of the inhaler 6002. For example, the electronic circuit system 6920 can output an audible message stating "please place the mouthpiece in your mouth and firmly press down on the medicament container." The electronic circuit system 6920 can also simultaneously output a signal to the LED 6958 to provide a visual indication of where the mouthpiece 6212 is located.

After the inhaler 6002 is enabled and placed within the mouth of the patient, the inhaler 6002 is actuated by moving the medicament container 6262 distally within housing 6110, as illustrated by arrow LL in FIG. 59. In some embodiments, the medicament container 6262 can include an actuator (not shown) that actuates the electronic circuit 6920, in a manner similar to those described above, to trigger a predetermined output or sequence of outputs. For example, in some embodiments, the processor can output an electronic signal associated with recorded speech to the microspeaker 6956. Such an electronic signal can be, for example, associated with a recorded message notifying the user that the medicament delivery is complete, instructing the user on post-inhalation procedures, instructing the user on post-inhalation medical treatment or the like. Such a status message can state, for example, "The delivery of medication is now complete."

In some embodiments, an electronic circuit system of a medicament delivery device can include a network interface device. Similarly stated, in some embodiments, the auto-injector 4002 and/or the auto-injector 4000' can be configured to send electronic signals to and/or receive electronic signals from a communications network and/or a remote device. The remote device can be, for example, a compliance and/or adherence monitoring device, a computer, a cell phone, a personal digital assistant (PDA) or the like. In this manner, any of the device described herein (e.g., the auto-injector 4000) can facilitate electronic and/or automatic compliance and/or adherence monitoring associated with its use.

Figure 60:
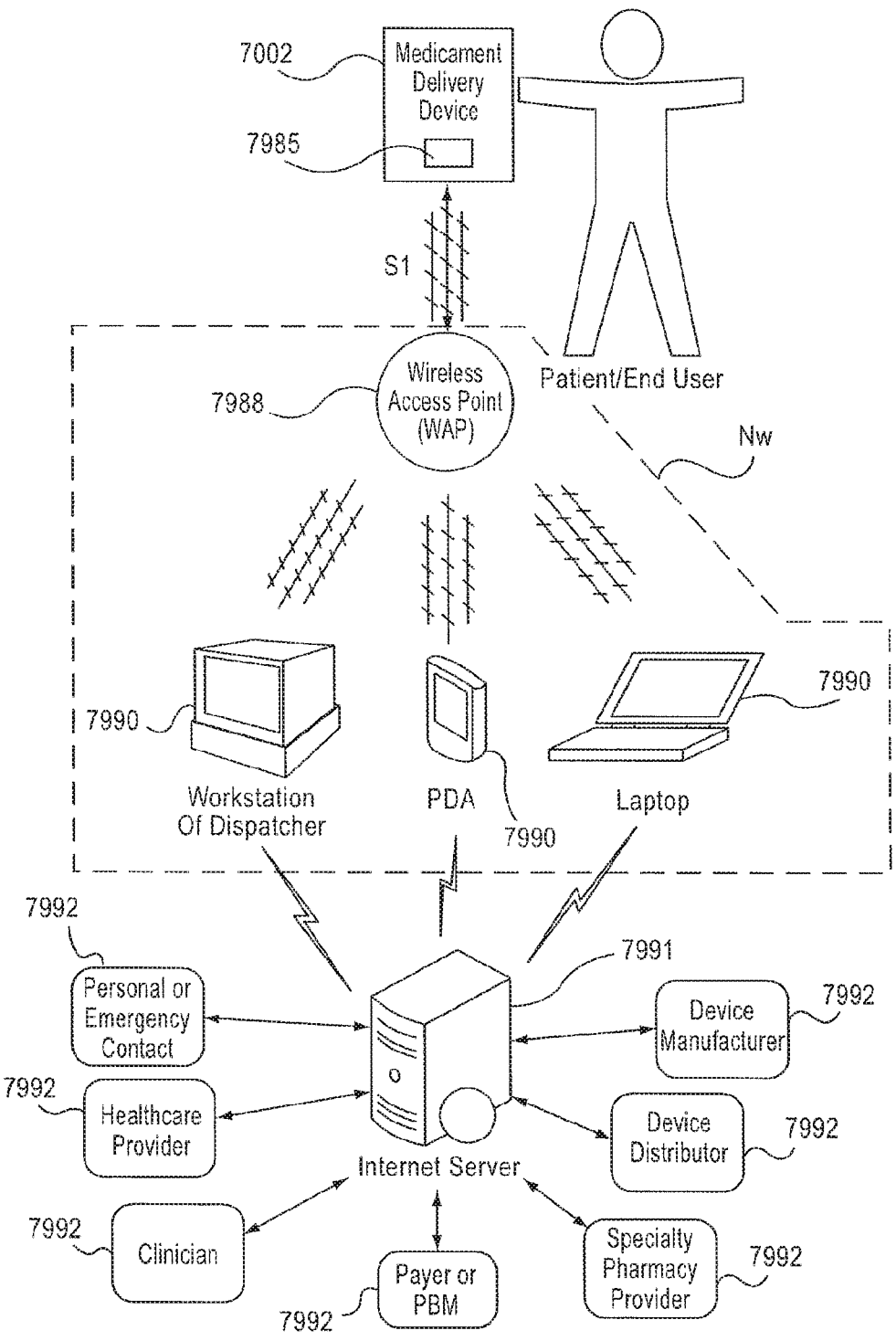
FIG. 60 is a schematic illustration of a medicament delivery device according an embodiment.

In some embodiments, for example, a medicament delivery device can include a network interface device configured to send and/or receive electrical signals via a wireless network. For example, FIG. 60 is a schematic illustration of a medicament delivery device 7002 according an embodiment that includes a wireless communications system 7985. The wireless communications system 7985 is configured to send and/or receive one or more electronic signals S1 to a variety of communications devices 7990 via a wireless communications network $N_W$. The wireless communication network $N_W$ includes a wireless access point (WAP) 7988 configured to operatively connect the communications devices 7990 and the wireless communications system 7985 on the medicament delivery device 7002 to form the wireless communications network $N_W$. As described herein, the communications devices 7990 can include, for example, a laptop computer, a personal digital assistant, a compliance and/or adherence monitoring device, a stand-alone processor, a workstation and/or the like. Moreover, as shown in FIG. 60, the communications devices 7990 can be configured to communicate electronically to an internet server 7991 by sending electronic signals to and/or receiving electronic signals from the internet server. In this manner, the wireless communications system 7985 can transmit information associated with the medicament delivery device 7002 to and/or receive information associated with the medicament delivery device 7002 from any number of third party devices 7992 located anywhere in the world.

In use, the wireless communications system 7985 can be used to send and/or receive information associated with the medicament delivery device 7002. Such information can include, for example, information associated with the frequency with which medicament delivery device 7002 is used (e.g., a compliance and/or adherence log), the functionality of the medicament delivery device 7002 after use (e.g., the number of doses remaining), the date and/or time of use, a parameter measuring the success of the latest use of the medicament delivery device 7002, an expiration date of the medicament delivery device 7002 and/or the medicament contained therein, a status of the medicament delivery device 7002 and/or the medicament contained therein, instructions for using the medicament delivery device 7002, the need for additional medical devices, the need for additional drug dosages, and/or any other information that may be useful to users and/or medical professionals associated with the medicament delivery device 7002. For example, in some embodiments, the wireless communications system 7985 can send one or more signals S1 including information related to a user's compliance and/or adherence to the user's home computer, mobile computing device (e.g., mobile phone) and/or a compliance and/or adherence monitoring device. In this manner, the user can use their home computer and/or a mobile computing device (e.g., mobile phone) to track their compliance and/or adherence with a prescribed medication regimen or other usage of the medicament delivery device 7002. In other embodiments, the wireless communications system 7985 can send one or more signals S1 including information related to a user's compliance and/or adherence to a third party. Such third parties can include, for example, a health care provider, an emergency contact, a manufacturer of the medicament delivery device 7002, a pharmaceutical benefits manager (PBM), a specialty pharmacy, a payor (e.g., an insurance company), a clinical trial administrator, an on-line support group or forum, and/or a pharmaceutical company. For example, in some embodiments, the wireless communications system 7985 can send one or more signals S1 including information related to a user's compliance and/or adherence to the user's health care provider. In some embodiments, for example, the one or more signals S1 can be related to the successful (or unsuccessful) delivery of a vaccine to the user. In this manner, the health care provider can ensure that the user successfully self-administered the vaccine.

The wireless communications system 7985 can include any hardware, software and/or firmware suitable for wireless communication. For example, in some embodiments, the wireless communications system 7985 can include a microprocessor, a transmitter, a receiver, a transceiver, a microchip, a radio chipset, a wireless interface card (WIC), a host controller interface (HCI), a universal asynchronous receiver/transmitter (UART), a power source (e.g., a battery), one or more sensors, a transponder, an antenna, a crystal, a circuit board, a liquid crystal display (LCD), a Small Computer System Interface (SCSI and ports), a FireWire (or other IEEE 1394 interfaces), a data uplink, a data downlink, a point-to-point link, a fiber optic link, a storage device (e.g., hard drive, flash drive or the like), a personal computer cards, a docking stations, a parallel and/or bit-serial connections, a Universal Serial Bus (USB) port or other serial ports, a light emitting diode (LEDs), a speaker, an amplifier, radiofrequency identification (RFID) devices and/or other common electronic components used for wireless communication. The electronic components can be operatively coupled to form the wireless communications system 7985 by any suitable circuitry. In some embodiments, the wireless communications system 7985 can include the components used for wireless communication on a single chip, such as, for example, the Bluetooth™ radio chip LMX9830 manufactured by National Semiconductor.

As described above, the wireless access point WAP is configured to establish the wireless network $N_W$ and to transmit electronic signals between the medicament delivery device 7002 (which can be referred to as a wireless client device), wireless communications devices 7990 (which can be referred to as other wireless client devices) and/or other third party devices 7992. In some embodiments, the wireless communications devices 7990 and/or other third party devices 7992 can include, for example, laptops (computers), personal digital assistants (PDAs), wireless IP phones, servers, routers, and other wireless enabled network devices. Although the wireless access point WAP is shown and described as being distinct from the wireless communications system 7985, in some embodiments, the wireless communications system 7985 can include the functionality of a wireless access point. In this manner, the medicament delivery device 7002 can be utilized as a wireless access point. In yet other embodiments, the wireless communications system 7985 can send and/or receive electronic signal S1 without the use of a wireless access point. In such embodiments, which can be referred to as peer-to-peer networks or ad-hoc networks, the wireless communications system 7985 can communicate directly with the wireless communications devices 7990 and/or other third party devices 7992.

The wireless communication system 7985 can employ any suitable protocol or protocols for sending and/or receiving the electronic signals S. Such protocols can include, for example, Wi-Fi, Bluetooth™, Zigbee, Wi-Max, 802.XX, HomeRF, any protocols associated with Radio Frequency Identification (RFID) transmission and/or a combination thereof. In some embodiments, the wireless communications system 7985 can employ a protocol having heightened security, such as for example, varying levels of encryption. In this manner any information associated with the medical records of a user can be protected against unauthorized access.

In addition to encryption, in some embodiments, the information transmitted and/or received by the wireless communication system 7985 can be in a format configured to prevent the identification of the user. For example, in some embodiments, the information transmitted and/or received by the wireless communication system 7985 can be associated with a unique identification number known only by certain parties, such as, for example, the end user and the end user's physician.

The wireless communications network $N_W$ can have any suitable range. For example, in some embodiments, the wireless communications network $N_W$ can be a wireless local area network (WLAN). A WLAN can be suitable in certain conditions in which the communications devices 7990 are confined to a limited geographical area, such as, for example, within a hospital, a nursing home or a triage unit. In other embodiments, the wireless communications network $N_W$ can be a wireless metropolitan area network (WMAN). A WMAN can be suitable in certain conditions in which the communications devices 7990 are used within a predefined area that cannot easily be covered by a WLAN, such as, for example, within a city. In yet other embodiments, the wireless communications network $N_W$ can be a wireless wide area network (WWAN).

Although the arrangement shown in FIG. 60 shows the wireless communication system 7985 sending information to and/or receiving information from the third party devices 7992 via the wireless access point 7988 and the wireless communications devices 7990, in other embodiments, the wireless communication system 7985 can transmit information to and/or receive information from the third party devices 7992 directly. For example, in some embodiments, third party devices 7992 can be included within the wireless communications network $N_W$, which can be, for example, a wireless wide area network (WWAN).

The medicament delivery device 7002 can be any device suitable for delivering one or more doses of a medicament into a patient's body. As described herein, such devices can include, for example, auto-injectors, pen injectors, inhalers, transdermal patches, pre-filled syringes (PFS), syringes, catheters, stents, implantable vehicles, topical vehicles, pill dispensers or the like. In some embodiments, for example, the medicament delivery device 7002 can be a single-dose device typically used in emergency situations or to administer vaccines. For example, in some embodiments, the medicament delivery device 7002 can be a single-use medical injector, similar to auto-injector 4002 shown and described above with reference to FIGS. 5-25. In such embodiments, the wireless communications system 7985 can be configured to send automatically data to a workstation and/or a compliance and/or adherence monitoring device during the various stages of operation of the medicament delivery device 7002. In this manner, the details of each stage of operation of the medicament delivery device 7002 can be electronically and/or automatically recorded to track patient compliance and/or adherence. Such details can include, for example, a time stamp associate with the removal of a safety mechanism (i.e., the "arming" of the medicament delivery device), a time stamp associated with the actuation of the medicament delivery device, an indicator associated with the validity of the medicament delivery event and/or the like.

In other embodiments, the medicament delivery device 7002 can be a chronic-care medicament delivery device containing multiple doses of medicament configured to be delivered on a regular schedule. In some embodiments, for example, the medicament delivery device 7002 can be a chronic-care pen injector used for injectable pharmaceuticals that require daily, weekly and/or monthly injections, such as, for example, insulin or human growth hormone (HgH). In such embodiments, the wireless communication system 7985 can track the usage of the pen injector and transmit the use information to the patient's physician, specialty pharmacy, payor (e.g., an insurance company), PBM, clinical trial administrator or other provider. In this manner, for example, the patient's physician can ensure that the therapy regime is effective.

In yet other embodiments, the medicament delivery device 7002 can be a single-use and/or disposable chronic-care medicament delivery device. As described in more detail herein, in such embodiments the medicament delivery device 7002 can be included within a kit containing the desired number of doses of medicament.

Figure 61:
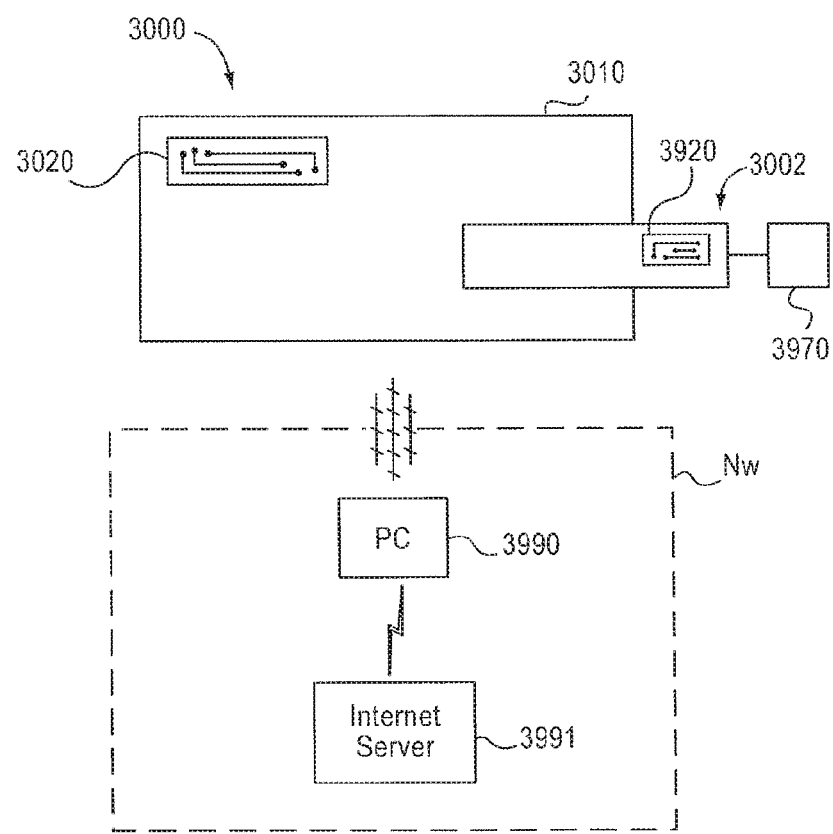
FIGS. 61-63 are schematic illustrations of a medical system according to an embodiment, in a first configuration, a second configuration and a third configuration, respectively.
Figure 62:
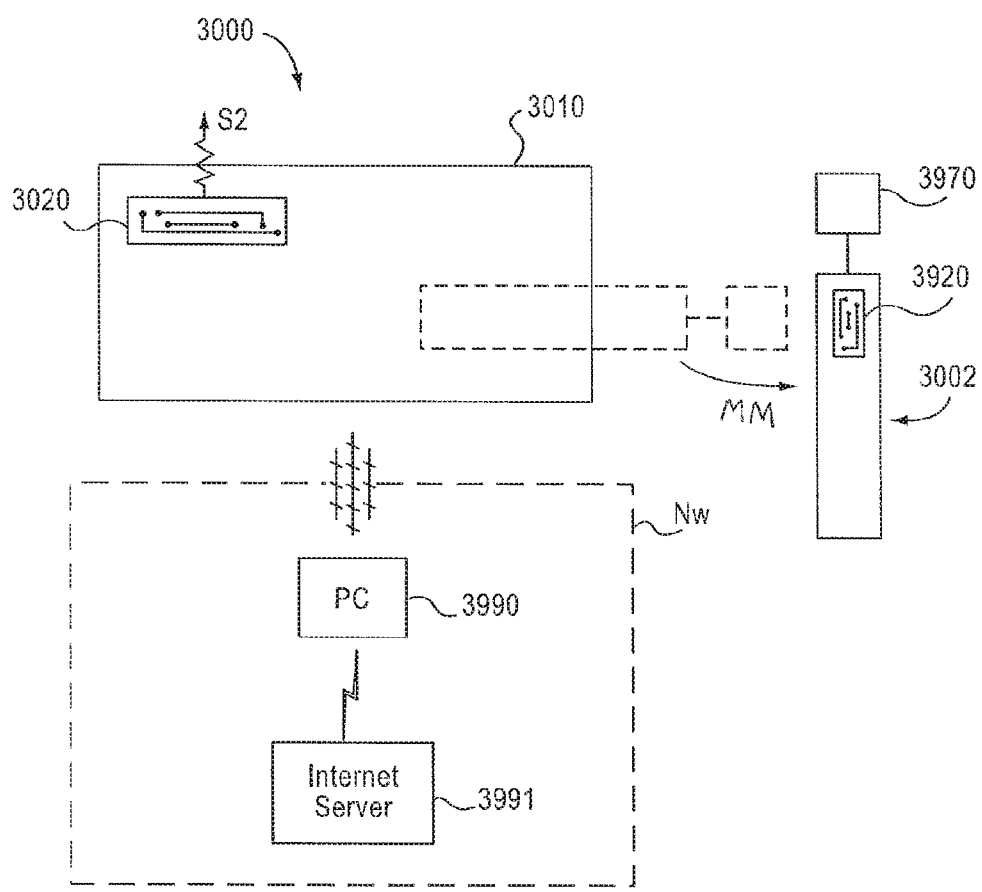
Figure 63:
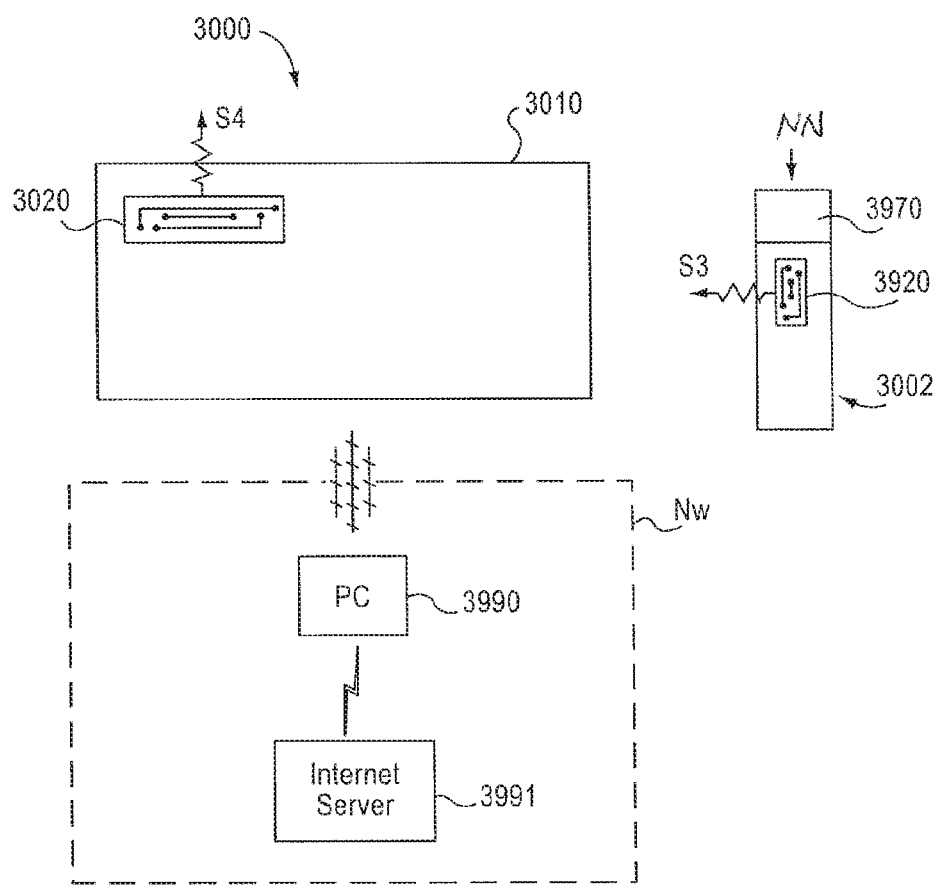

As described above, in some embodiments, a medicament delivery device can be configured to produce and/or output an electrical signal when the medicament delivery device is actuated. In this manner, patient compliance data, such as, for example, the frequency of use, the date and time of use and/or a parameter measuring the success and/or validity of the use of the medicament delivery device can be monitored based on the actuation of the medicament delivery device, rather than on the removal of a safety interlock from the medicament delivery device. For example, FIGS. 61-63 are schematic illustrations of a medical system 3000 according to an embodiment, in a first configuration, a second configuration and a third configuration, respectively. The medical system 3000 includes a medicament delivery device 3002 and a container 3010. As shown in FIG. 61, the container 3010 is configured to receive at least a portion of the medicament delivery device 3002. For example, in some embodiments, the container 3010 can include a recessed portion, a retainer, and/or any other suitable structure that matingly receives at least a portion of the medicament delivery device 3002.

The container 3010 includes an electronic circuit system 3020 configured to output at least electronic signals S2 and S4, as described in more detail herein. The electronic circuit system 3020 can include any suitable electronic components operatively coupled to produce and/or output the electronic signal S2 and S4, and/or to perform the functions described herein. The electronic circuit system 3020 is operatively coupled to the communications network $N_W$, which includes at least a personal computer (PC) 3990 or other processor, and an internet server 3991. In some embodiments, for example, the electronic circuit system 3020 can include a wireless communications device, similar to the wireless communications system 7985 shown and described above with reference to FIG. 60, to wirelessly connect the electronic circuit system 3020 to the PC 3990 and/or the communications network $N_W$. In other embodiments, the electronic circuit system 3020 can be operatively coupled to the PC 3990 and/or the communications network $N_W$ via a wired connection. In this manner, as described in more detail herein, the electronic circuit system 3020 of the container 3010 can transmit information associated with the medical system 3000 to and/or receive information associated with the medical system 3000 from any number of remotely located third party devices (not shown in FIGS. 61-63).

The medicament delivery device 3002 can be any device for delivering a medicament into a body, such as, for example, a medical injector (which can include an auto-injector, a pen injector, a multiple-use injector, a syringe or the like), an inhaler or the like. The medicament delivery device 3002 includes an actuator 3970 and an electronic circuit system 3920. The actuator 3970 is movable between a first position (FIGS. 61 and 62) and a second position (FIG. 63). When the actuator 3970 is moved from the first position to the second position, the actuator 3970 initiates the delivery of the medicament into the body. In some embodiments, the actuator 3970 can be configured to release a spring, an energy storage member, or the like, to initiate medicament delivery when the actuator 3970 is moved from the first position to the second position. For example, in some embodiments, the actuator can be similar to the base 4520 shown and described above with reference to FIGS. 5-25.

The electronic circuit system 3920 of the medicament delivery device 3002 is configured to output at least an electronic signal S3 (see FIG. 63) when the actuator 3970 is moved from the first position to the second position. The electronic circuit system 3920 of the medicament delivery device 3002 can include any suitable electronic components operatively coupled to produce and/or output the electronic signal S3 and/or to perform the functions described herein. In some embodiments, for example, the electronic circuit system 3920 of the medicament delivery device 3002 can be similar to the electronic circuit system 4920 shown and described above with reference to FIGS. 5-25.

The medical system 3000 can be used to manage the patient's medication regimen and/or track the patient's compliance and/or adherence in following the prescribed medication regimen. When the medical system 3000 is in the first configuration (i.e., the "storage configuration"), as shown in FIG. 61, at least a portion of the medicament delivery device 3002 is disposed within the container 3010, and the electronic circuit system 3020 of the container 3010 is operatively coupled to the communications network $N_W$, and/or the personal computer (PC) 3990. In some embodiments, when the medical system 3000 is in the first configuration, the electronic circuit system 3020 can optionally output one or more electronic signals (not shown in FIG. 61) associated with the medication regimen and/or the medicament delivery device 3002. Such electronic signals can include, for example, a visual and/or an audible output reminding the patient of the date and time of the next dosage, indicating the expiration date of the medicament delivery device, providing instructions in the use of the medicament delivery device, providing instructions for monitoring compliance, adherence, or the like.

To move the medical system 3000 from the first configuration to the second configuration (i.e., a "pre-delivery" configuration), the medicament delivery device 3002 is removed from the container 3010, as shown by the arrow MM in FIG. 62. When the medicament delivery device 3002 is removed from the container 3010, the electronic circuit system 3020 of the container 3010 produces the first electronic signal S2. The first electronic signal S2 can be associated with the prescribed medication regimen (including, for example, compliance and/or adherence data), an identification of the medicament delivery device 3002, a status of the medicament delivery device 3002, a use instruction associated with the medicament delivery device 3002, a status of the container 3010 (including, for example, an indication of whether the electronic circuit system 3020 of the container 3010 is connected to the network $N_W$, the remaining battery life of a battery powering the electronic circuit system 3020, or the like), a use instruction associated with the container 3010 and/or the like. In some embodiments, for example, the first electronic signal S2 can include a visual output, an audible output and/or a haptic output that instructs and/or provides cues to a user in the use of the container 3010 to track the patient's compliance and/or adherence. In other embodiments, the first electronic signal S2 can include a communications signal that can be transmitted via the PC 3990 and the internet server 3991 to a remotely located third party device (not shown in FIGS. 61-63).

To move the medical system 3000 from the second configuration to the third configuration (i.e., a "post-delivery" configuration), the medicament delivery device 3002 is actuated by moving the actuator 3970 from the first position (FIG. 62) to the second position (FIG. 63), as shown by the arrow NN in FIG. 63. When the actuator 3970 is moved from the first position to the second position, actuation of the medicament delivery device is initiated. Said another way, the actuator 3970 is configured to initiate delivery of the medicament when the actuator 3970 is moved from the first position to the second position. As described above, the actuator 3970 can be configured to release a spring, an energy storage member, or the like, to initiate medicament delivery when the actuator 3970 is moved from the first position to the second position.

When the actuator 3970 is moved from the first position to the second position, the electronic circuit system 3920 of the medicament delivery device 3002 outputs the second electronic signal S3. Said another way, when actuator 3970 is moved from the first position to the second position, the actuator 3970 actuates the electronic circuit system 3920 of the medicament delivery device 3002 such that the electronic circuit system 3920 produces and/or outputs the second electronic signal S3. In some embodiments, the movement of the actuator 3970 produces an input that is received by the electronic circuit system 3920, thereby triggering the electronic circuit system 3920 to produce and/or out the second electronic signal S3. Said another way, in some embodiments, the movement of the actuator 3970 changes the state of a switch (not shown in FIGS. 61-63) within the electronic circuit system 3920, thereby triggering the electronic circuit system 3920 to produce and/or output the second electronic signal S3. Such a switch can be either reversible or irreversible, as described above. For example, in some embodiments, the movement of the actuator 3970 can separate, tear, deform and/or sever an electrical conductor (not shown in FIGS. 61-63) within the electronic circuit system 3920. For example, in some embodiments, the actuator 3970 can include a protrusion (not shown in FIGS. 61-63) configured to be received within and sever a portion of the electronic circuit system 3920, similar to the protrusion 4730 shown and described above with reference to FIGS. 23-25. In other embodiments, the movement of the actuator 3970 can electronically couple and/or decouple a power source (not shown in FIGS. 61-63) to a portion of the electronic circuit system 3920. For example, in some embodiments, the actuator 3970 can include a battery isolation tab (not shown in FIGS. 61-63) configured to isolate a battery from a portion of the electronic circuit system 3920, similar to the battery isolation tab 4860 shown and described above with reference to FIGS. 16, 18 and 21.

The second electronic signal S3 is received by the electronic circuit system 3020 of the container 3010, which then produces the third electronic signal S4. The third electronic signal S4 is associated with the second electronic signal S3.

In this manner, the electronic circuit system 3020 of the container 3010 and the electronic circuit system 3920 of the medicament delivery device 3002 can cooperatively monitor the patient's compliance and/or adherence in using the medicament delivery device 3002. By utilizing two electronic circuit systems, the electronic circuit system 3920 and the electronic circuit system 3020 can be cooperatively designed to provide the desired functionality. For example, in some embodiments, the container 3010 can be a reusable compliance tracking device and the medicament delivery device 3002 can be a single-use, disposable device. In such an arrangement, the electronic circuit system 3020 of the container 3010 can include complicated circuit elements, circuit elements having a higher cost, and/or circuit elements having higher power consumption (e.g., speakers, long-range wireless communications systems and the like). Conversely, the electronic circuit system 3920 of the medicament delivery device 3002 can include fewer circuit elements, circuit elements having a lower cost, and/or circuit elements having lower power consumption. In some embodiments, for example, the electronic circuit system 3920 of the medicament delivery device 3002 can include a transceiver (not shown in FIGS. 61-63) that consumes less than approximately 100 mA (at a supply voltage of approximately 1.8 volts) when outputting the second electronic signal S3. In other embodiments, the electronic circuit system 3920 of the medicament delivery device 3002 can include a transceiver (not shown in FIGS. 61-63) that consumes less than approximately 20 mA (at a supply voltage of approximately 1.8 volts) when outputting the second electronic signal S3. Such an arrangement can facilitate the use of the electronic circuit system 3920 on a single-use, disposable medicament delivery device.

The second electronic signal S3 can be any suitable communications signal (e.g., a radio frequency signal) that can be received by the electronic circuit system 3020 of the container 3010. For example, in some embodiments, the second electronic signal S3 can be a short-range radio frequency signal having a range of approximately 100 meters or less. In some embodiments, the second electronic signal S3 can be a BLUETOOTH™-compatible electronic signal (for example, a short-range radio frequency signal having a frequency between approximately 2400 MHz and 2480 MHz), including either a class 1(i.e., having a maximum permitted power of less than 100 mW), class 2 (i.e., having a maximum permitted power of less than 2.5 mW) or class 3 (i.e., having a maximum permitted power of less than 1 mW) signal. Said another way, in some embodiments, the electronic circuit system 3920 of the medicament delivery device 3002 and the electronic circuit system 3020 of the container 3010 can be BLUETOOTH™-enabled circuits. In this manner, the medicament delivery device 3002 can electronically communicate with the container 3010 using low-cost circuit elements and/or using circuit elements having minimal power consumption.

The third electronic signal S4 can be any suitable electronic signal that can be produced and/or output by the electronic circuit system 3020 of the container 3010. For example, in some embodiments, the third electronic signal S4 can be output to an audio output device and/or a video output device (not shown in FIGS. 61-63) within the electronic circuit system 3020. In this manner, the electronic circuit system 3020 of the container 3010 can produce an audible and/or a visual output associated with the actuation of the medicament delivery device 3002. For example, in some embodiments, the third electronic signal S4 can be output to a speaker of the types shown and described above, thereby providing the user with a message associated with the use of and/or the compliance (and/or adherence) with the medicament delivery device 3002. In some embodiments, the third electronic signal S4 can be associated with a message instructing the user on post-injection disposal, safety procedures, post-injection medical treatment or the like. Such a message can state, for example, "THE DOSAGE OF XXX HAS BEEN SUCCESSFULLY ADMINISTERED. PLEASE SEEK FURTHER MEDICAL ATTENTION FROM A DOCTOR IF THE FOLLOWING SYMPTOMS OCCUR . . . . " In other embodiments, the third electronic signal S4 can be associated with a message related to procedures for tracking compliance and/or adherence with the medication regimen. Such a message can state, for example, "THE SUCCESSFUL DOSAGE OF XXX HAS BEEN RECORDED TO YOUR ELECTRONIC COMPLIANCE LOG. NO FURTHER ACTION IS REQUIRED." In other embodiments, such a message can state, "PLEASE ENSURE THAT YOU RECORD THE CORRECT DOSAGE IN YOUR ELECTRONIC LOGBOOK." In yet other embodiments, such a message can state, "PLEASE DO NOT EAT OR DRINK UNTIL XX P.M." In yet other embodiments, such a message can state, "THE COMPLIANCE MONITOR IS CURRENTLY DISCONNECTED FROM THE NETWORK. PLEASE ENSURE THAT THE COMPLIANCE MONITOR IS CONNECTED TO YOUR HOME COMPUTER."

In some embodiments, the third electronic signal S4 can be a communications signal (e.g., a radio frequency signal) that can be transmitted from the electronic circuit system 3020 of the container 3010 to the PC 3990 and/or the communications network $N_W$. Such transmission can occur using any suitable method and/or protocol. The third electronic signal S4 can be transmitted, for example, in the form of an e-mail, a phone call, a data stream or the like.

In some embodiments, for example, the third electronic signal S4 can be associated with the patient's compliance and/or adherence in using the medicament delivery device 3002. For example, in some embodiments, the third electronic signal S4 can be sent via the communications network $N_W$ to the patient's pharmacy to automatically order additional pre-filled medicament delivery devices and/or replacement cartridges for the medicament delivery device. In other embodiments, the third electronic signal S4 can be sent via the communications network $N_W$ to a health care provider, thereby allowing the health care provider to remotely monitor the patient's medication regimen. In yet other embodiments, the third electronic signal S4 can be sent via the communications network $N_W$ to a clinical trial administrator, thereby allowing the clinical trial administrator to ensure that the clinical trial protocols are being properly followed.

Figure 64:
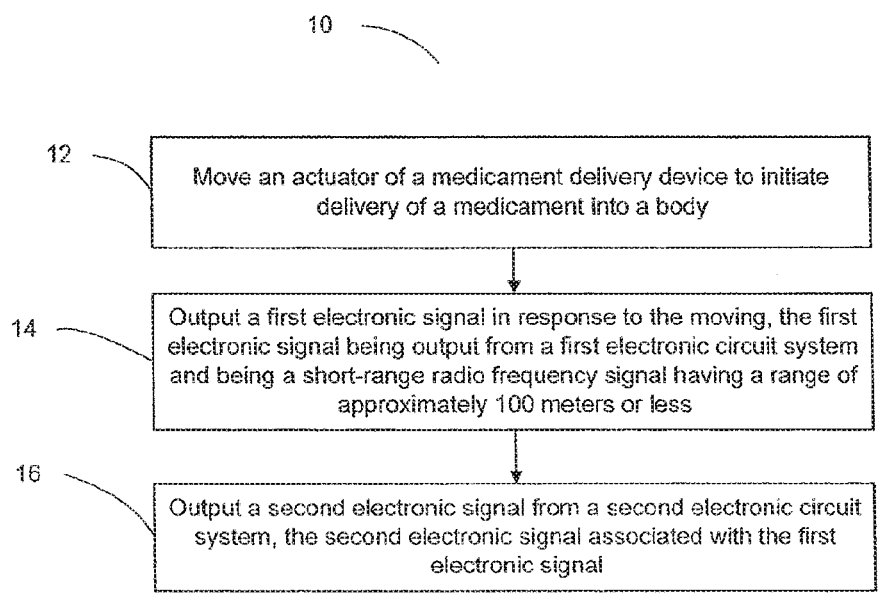
FIG. 64 is a flow chart of a method according to an embodiment.
Figure 65:
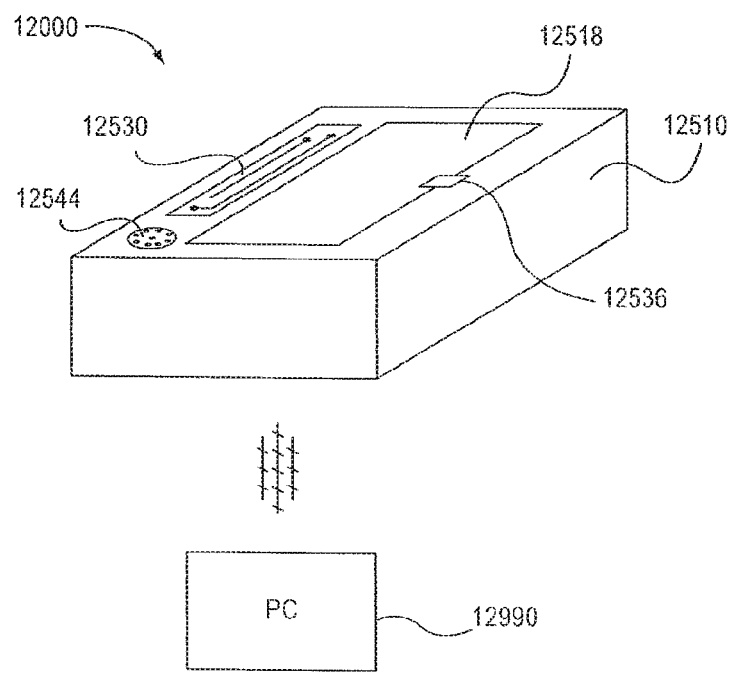
FIGS. 65-68 are perspective views of a medical system according to an embodiment, in a first configuration, a second configuration, a third configuration, and a fourth configuration, respectively.

FIG. 64 is a flow chart of a method 10 according to an embodiment. The method includes moving an actuator on a medicament delivery device to initiate delivery of a medicament into a body, 12. The actuator can be any suitable actuator configured to initiate the delivery of medicament into the body, as described above. For example, in some embodiments, the actuator can be configured to release a spring, an energy storage member, or the like, to initiate medicament delivery when the actuator is moved. In some embodiments, the method can optionally include moving one or more safety locks before the actuator is moved. Such safety locks can be similar to the safety lock 4710 shown and described above with reference to FIGS. 5-26, and can be configured to prevent the actuator from being moved.

A first electronic signal is then output from a first electronic system in response to the movement of the actuator, 14. The first electronic signal is a short-range radio frequency signal having a range of approximately 100 meters or less. In some embodiments, for example, the first electronic signal can be a BLUETOOTH™-compatible electronic signal (for example, a short-range frequency signal having a frequency between approximately 2400 MHz and 2480 MHz), including either a class 1(i.e., having a maximum permitted power of less than 100 mW), class 2 (i.e., having a maximum permitted power of less than 2.5 mW) or class 3 (i.e., having a maximum permitted power of less than 1 mW) signal. In other embodiments, the first electronic signal can be a short-range signal produced by a radio frequency identification ("RFID") tag within the first electronic circuit system. In this manner, the first electronic circuit system can produce and/output the first electronic signal using electronic devices having a low power consumption, as described above. As described in more detail herein, in some embodiments, the first electronic circuit system can be devoid of a battery.

The first electronic circuit system can be any suitable electronic circuit system of the types shown and described herein. For example, in some embodiments, at least a portion of the first electronic circuit system can be disposed on the housing of the medicament delivery device. In other embodiments, at least a portion of the first electronic circuit system can be disposed on a portion of the medicament delivery device that is removably coupled to the housing of the medicament delivery device (e.g., a removable protective sheath, a removable safety lock or the like). In some embodiments, for example, a medicament delivery device can include a protective sheath that includes a first portion of the first electronic circuit system, and a housing that includes a second portion of the first electronic circuit system. In such embodiments, the first portion of the first electronic circuit system can include a processor configured to control the second portion of the first electronic circuit system and/or a battery configured to provide power to the second portion of the first electronic circuit system. Similarly, the second portion of the first electronic circuit system can include a processor configured to control the first portion of the first electronic circuit system and/or a battery configured to provide power to the first portion of the first electronic circuit system.

A second electronic signal is then output from a second electronic circuit system, 16. The second electronic signal is associated with the first electronic signal. Similarly stated, the second electronic circuit system outputs the second electronic signal in response to the first electronic signal. In some embodiments, for example, the second electronic signal can include information associated with and/or included within the first electronic signal, such as, for example, the date and time when the first electronic signal was received by the second electronic circuit system. In other embodiments, the second electronic signal can include information identifying the contents of the medicament delivery device (e.g., the amount and type of medicament contained therein), an expiration date of the medicament delivery device, or the like.

As described above, the second electronic signal can be any suitable electronic signal that can be produced and/or output by the second electronic circuit system. For example, in some embodiments, the second electronic signal can be output to an audio output device and/or a video output device. In other embodiments, the second electronic signal can be a communications signal (e.g., a radio frequency signal) that can be transmitted from the second electronic circuit system to the user's computer, a communications network $N_W$, and/or a remotely located device.

Figure 66:
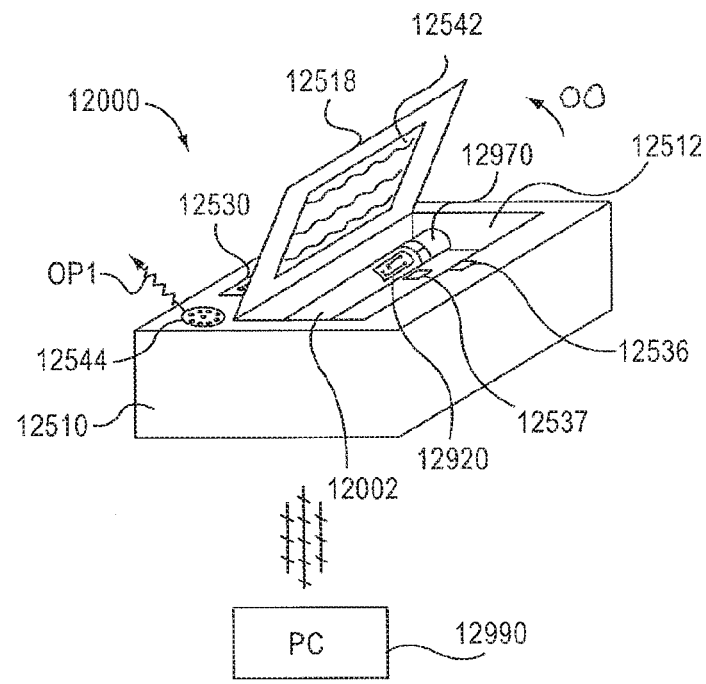

FIGS. 65-68 show a medical system 12000 according to an embodiment, in a first configuration, a second configuration, a third configuration, and a fourth configuration, respectively. The medical system 12000 includes a medicament delivery device 12002 (see e.g., FIG. 66) and a compliance monitoring device 12510 (also referred as an adherence monitoring device). As shown in FIG. 66, the compliance monitoring device 12510 includes a hinged lid 12518, an electronic circuit system 12530, a first switch 12536 and a second switch 12537. Additionally, the compliance monitoring device 12510 defines an internal region 12512 within which the medicament delivery device 12002 can be contained.

The electronic circuit system 12530 of the compliance monitoring device 12510 is configured to produce and/or output one or more electronic outputs and/or electronic signals of the type described above. As described in more detail below, the electronic circuit system 12530 includes a speaker 12544 and an LCD screen 12542. Moreover, similar to the container 3010 shown and described above with reference to FIGS. 61-63, the electronic circuit system 12530 of the compliance monitoring device 12510 is operatively coupled to a personal computer (PC) 12990. In this manner, as described in more detail herein, the electronic circuit system 12530 of the compliance monitoring device 12510 can transmit information associated with the medical system 12000 to and/or receive information associated with the medical system 12000 from any number of remotely located third party devices (not shown in FIGS. 65-68) via the PC 12990.

Figure 67:
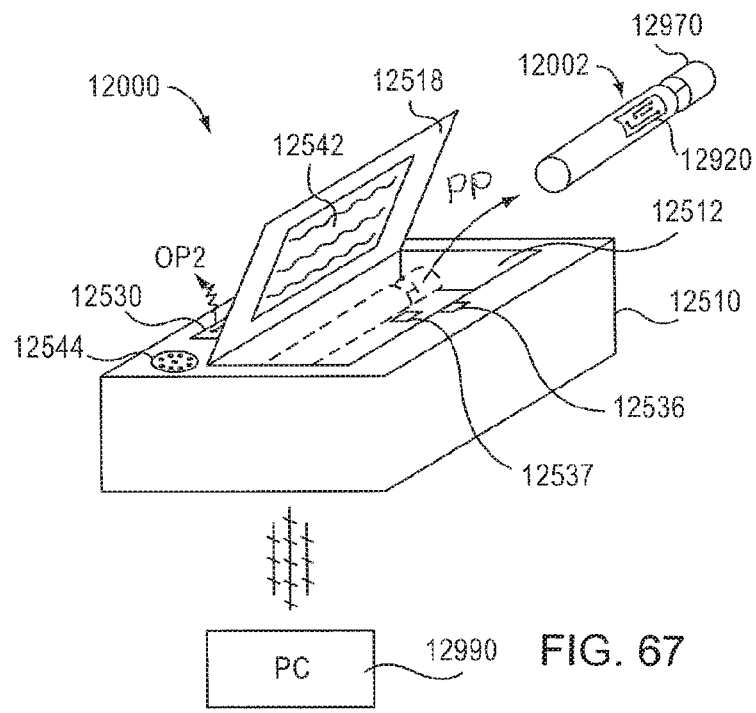
Figure 68:
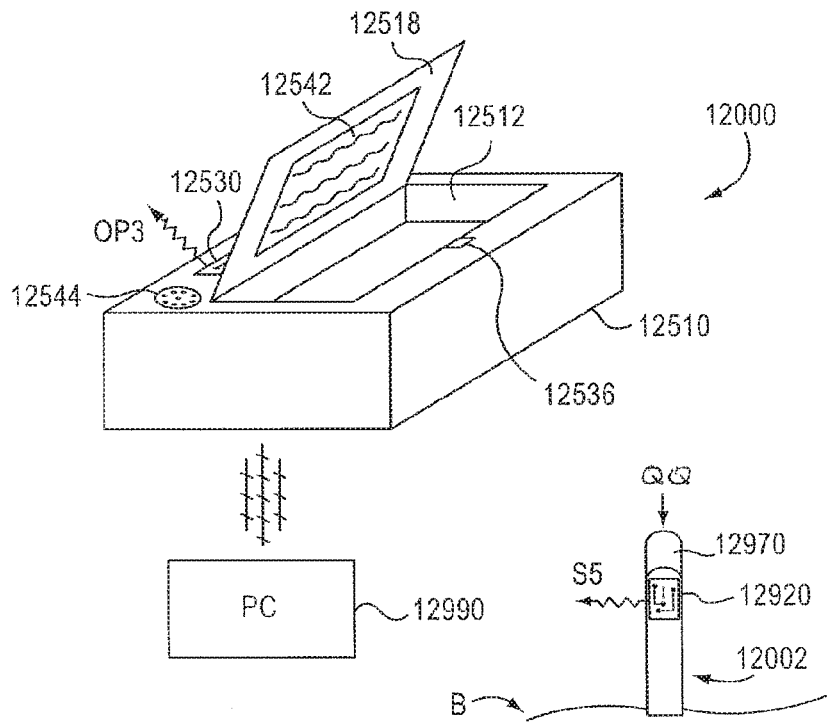

The hinged lid 12518 has a first position (see FIG. 65) and a second position (see FIGS. 66-68). When the hinged lid 12518 is in the first position, the hinged lid 12518 covers the internal region 12512 of the compliance monitoring device 12510. Conversely, when the hinged lid 12518 is in the second position, at least a portion of the internal region 12512 of the compliance monitoring device 12510 is exposed. Said another way, when the hinged lid 12518 is in the second position, the medicament delivery device 12002 can be removed from the internal region 12512 of the compliance monitoring device 12510.

The electronic circuit system 12530 of the compliance monitoring device 12510 is operatively coupled to the first switch 12536 and the second switch 12537. The first switch 12536 is configured to move between a first state (e.g., closed) and a second state (e.g., opened) when the hinged lid 12518 moves between its first position and its second position, as indicated by arrow OO in FIG. 66. The electronic circuit system 12530 is configured to produce and/or output a first output OP1 via the speaker 12544 when the first switch 12536 is moved from its first state to its second state. The first output OP1 can be a recorded speech output associated with an identification of the medicament delivery device 12002, an identification of patient symptoms (e.g., instructions for assessing the physical condition of the patient), an instruction for using the medicament delivery device 12002, an instruction for using the compliance monitoring device 12510, a message guiding the patient in procedures for adhering to the prescribed medication regimen, a status of the compliance monitoring device 12510 and/or a status of the patient's compliance and/or adherence with the prescribed medication regimen. For example, in some embodiments the first output OP1 can state "YOU HAVE ACTIVATED THE ALLERGIC REACTION RESPONSE KIT. THIS KIT INCLUDES AN AUTO-INJECTOR CONTAINING EPINEPHRINE. BEFORE USING THIS AUTO-INJECTOR, PLEASE ENSURE THAT THE PATIENT IS EXHIBITING THE FOLLOWING SYMPTOMS . . . . " In other embodiments, the first output OP1 can state "YOUR NEXT DOSAGE IS NOT DUE UNTIL XX P.M. PLEASE DO NOT ADMINISTER THE DOSE AT THIS TIME." In yet other embodiments, the first output OP1 can state "BECAUSE THE MEDICAMENT HAS BEEN REFRIGERATED FOR STORAGE, THE MEDICAMENT IS CURRENTLY TOO COLD. THE CURRENT TEMPERATURE OF THE MEDICAMENT IS XX DEGREES, PLEASE LEAVE THE MEDICAMENT AT ROOM TEMPERATURE FOR XX MINUTES BEFORE ADMINISTERING THE DOSE." In yet other embodiments, the first output OP1 can state "THIS IS THE LAST DOSE IN THE CURRENT PRESCRIPTION. AFTER ADMINISTERING THIS DOSE, PLEASE CONTACT YOUR HEALTH CARE PROVIDER FOR FURTHER ADVICE." Although described as an audible output, in other embodiments, the first output OP1 can be any type of electronic output as described herein.

The second switch 12537 is configured to move between a first state (e.g., closed) and a second state (e.g., opened) when the medicament delivery device 12002 is removed from the internal region 12512 of the compliance monitoring device 12510, as indicated by the arrow PP in FIG. 67. The electronic circuit system 12530 of the compliance monitoring device 12510 is configured to output a second output OP2 via the speaker 12544 and/or the LCD screen 12542 when the second switch 12537 is moved from its first state to its second state. The second output OP2 can be, for example, a recorded speech output and/or a video output associated with an identification of the medicament delivery device 12002, an identification of patient symptoms (e.g., instructions for assessing the physical condition of the patient), an instruction for using the medicament delivery device 12002, an instruction for using the compliance monitoring device 12510, a status of the compliance monitoring device 12510 and/or a status of the patient's compliance and/or adherence with the prescribed medication regimen. For example, in some embodiments the second output OP2 can be an audio-visual output via both the speaker 12544 and the LCD screen 12542 providing step-by-step instructions for using the medicament delivery device 12002 and/or the compliance monitoring device 12510.

The medicament delivery device 12002 can be any device for delivering a medicament into a body, of the types shown and described herein. The medicament delivery device 12002 includes an actuator 12970 and an electronic circuit system 12920. The actuator 12970 is movable between a first position (FIG. 67) and a second position (FIG. 68). When the actuator 12970 is moved from the first position to the second position, the actuator 12970 initiates the delivery of the medicament into the body. In some embodiments, the actuator 12970 can be similar to the base 4520 shown and described above with reference to FIGS. 5-25.

The electronic circuit system 12920 of the medicament delivery device 12002 is configured to output at least an electronic signal S5 (see FIG. 68) when the actuator 12970 is moved from the first position to the second position. The electronic circuit system 12920 of the medicament delivery device 12002 can include any suitable electronic components operatively coupled to produce and/or output the electronic signal S5 and/or to perform the functions described herein. In some embodiments, for example, the electronic circuit system 12920 of the medicament delivery device 3002 can be similar to the electronic circuit system 4920 shown and described above with reference to FIGS. 5-25.

The medical system 12000 can be used to manage the patient's medication regimen and/or track the patient's compliance and/or adherence in following the prescribed medication regimen in a similar manner as described above with reference to the medical system 3000. To move the medical system 12000 from a storage configuration (FIG. 65) to a pre-delivery configuration (FIG. 67), the hinged lid 12518 is moved, as shown by the arrow OO in FIG. 66, and the medicament delivery device 12002 is removed from the compliance monitoring device 12510, as shown by the arrow PP in FIG. 67. As described above, the movement of the hinged lid 12518 produces an input to the electronic circuit system 12530 via the first switch 12536. The input from the first switch 12536 triggers the electronic circuit system 12530 to produce and/or output the first output OP1, as discussed above. Similarly, when the medicament delivery device 12002 is removed from the internal region 12512 of the compliance monitoring device 12510, the second switch 12537 produces an input to the electronic circuit system 12530. The input from the second switch 12537 triggers the electronic circuit system 12530 to produce and/or output the second output OP2, as discussed above.

To administer the medication (i.e., to move the medical system 12000 to a post-delivery configuration, as shown in FIG. 68), the medicament delivery device 12002 is first positioned adjacent a portion of a body B of a patient. Although the portion of the body B is shown as being a surface, such as, for example, the skin, in other embodiments, the portion of the body B can be any suitable location for delivering the medicament (e.g., the mouth, the nasal passages, or the like). The medicament delivery device 12002 is then actuated by moving the actuator 12970 from the first position (FIG. 67) to the second position (FIG. 68), as shown by the arrow QQ in FIG. 68.

When the actuator 12970 is moved from the first position to the second position, the electronic circuit system 12920 of the medicament delivery device 12002 outputs the electronic signal S5. Said another way, when actuator 12970 is moved from the first position to the second position, the actuator 12970 actuates the electronic circuit system 12920 of the medicament delivery device 12002 such that the electronic circuit system 12920 produces and/or outputs the electronic signal S5. The actuator 12970 can actuate the electronic circuit system 12920 in any manner as described herein. The electronic signal S5 can be any suitable communications signal, as described herein.

In a similar manner as described above with reference to the medical system 3000, the electronic signal S5 is received by the electronic circuit system 12530 of the compliance monitoring device 12510, which then produces the third electronic output OP3. The third electronic output OP3 is associated with the electronic signal S5. For example, the third electronic output OP3 can include a date and time stamp documenting when the electronic signal S5 was received. In some embodiments, the third electronic output OP3 can include information included within the electronic signal S5, such as a unique identification of the medicament delivery device 12002. In this manner, the electronic circuit system 12530 of the compliance monitoring device 12510 and the electronic circuit system 12920 of the medicament delivery device 12002 can cooperatively monitor the patient's compliance and/or adherence in using the medicament delivery device 12002. As described above, in some embodiments, the third electronic output OP3 includes a communications signal (e.g., a radio frequency signal) that can be transmitted from the electronic circuit system 12530 of the of the compliance monitoring device 12510 to the PC 12990.

Although the electronic circuit system 12530 of the compliance monitoring device 12510 is shown and described as receiving the electronic signal S5 from medicament delivery device 12002 in real-time when the medicament delivery device 12002 is actuated, in other embodiments, the electronic signal S5 can be received by the electronic circuit system 12530 of the compliance monitoring device 12510 at any time after the medicament delivery device 12002 has been actuated. For example, in some embodiments, the electronic signal S5 can be a short-range radio frequency signal having a range of approximately 100 meters or less. Accordingly, in certain instances, the medicament delivery device 12002 may be actuated when the medicament delivery device 12002 is out of transmission range for transmitting the electronic signal S5 to the compliance monitoring device 12510. In some such embodiments, for example, the electronic circuit system 12530 of the compliance monitoring device 12510 and/or the electronic circuit system 12970 of the medicament delivery device 12002 can be configured to detect when the medicament delivery device is in range (e.g., when the patient returns home) and then transmit the electronic signal S5. In other such embodiments, the electronic circuit system 12530 of the compliance monitoring device 12510 can include a scanner (e.g., an optical scanner or the like; not shown in FIGS. 65-68) such that the patient can scan the medicament delivery device 12002 when in proximity to the compliance monitoring device 12510 such that the electronic circuit system 12970 of the medicament delivery device 12002 can transmit the electronic signal S5 to the electronic circuit system 12530 of the compliance monitoring device 12510.

Figure 69:
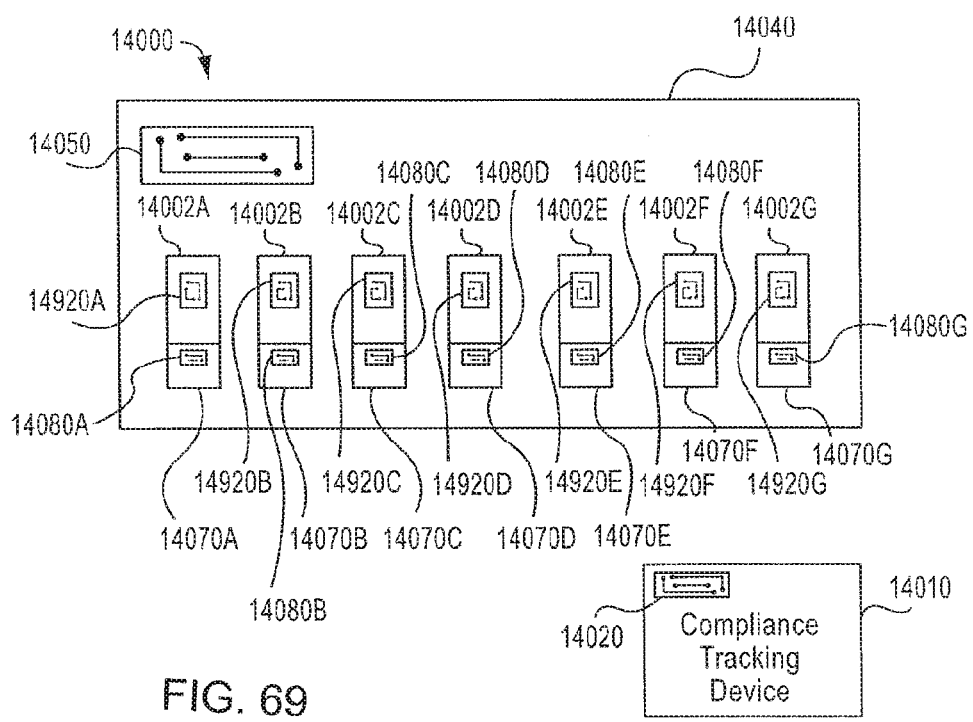
FIG. 69 is a schematic illustration of a medical system according to an embodiment.

Although the medical system 12000 is shown and described above as including one medicament delivery device 12002, in other embodiments, a medical system can include multiple medicament delivery devices. Such a system can be used, for example, as a part of a chronic-care medication regimen and/or a multi-dose vaccination regimen. For example, a medical system having multiple medicament delivery devices can be used to manage insulin delivery, the delivery of multiple doses of a vaccine, or the delivery of other medicaments (e.g., to treat Multiple Sclerosis, anemia, Rheumatoid Arthritis, Osteoporosis or the like), which can require daily, weekly and/or monthly injections. FIG. 69 is a schematic illustration of a medical system 14000 according to an embodiment, that includes multiple medical injectors 14002A-14002G. Because the medical system 14000 is similar in many respects to the medical systems shown and described above, the medical system 14000 is shown in only one configuration. The medical system 14000 includes a container 14040, a compliance tracking device 14010 (also referred to as an adherence tracking device) and multiple medical injectors 14002A-14002G. The compliance tracking device 14010 is similar to the compliance monitoring device 12510 shown and described above, except that the medical injectors 14002A-14002G need not be disposed within the compliance tracking device 14010. The compliance tracking device 14010 includes an electronic circuit system 14020, which can be operatively coupled to a computer, a communications network, or the like, as discussed above.

The medical injectors 14002A-14002G can be, for example, single-use, disposable auto-injectors of the types shown and described herein. In some embodiments, the medical injectors 14002A-14002G can include the same dosage of a medicament, and can be prescribed as a part of a chronic-care medicament regimen, clinical trial, multi-dose vaccine or the like. In other embodiments, the medical injectors 14002A-14002G can include the different dosages and/or different medicament compositions. For example, in a kit including a vaccine, a first medical injector can include a first dose of a vaccine and the remaining medical injectors can include subsequent boosters.

Each of the medical injectors 14002A-14002G includes a removable cover 14070A-14070G, a first electronic circuit system 14920A-14920G and a second electronic circuit system 14080A-14080G. The removable covers 14070A-14070G can be, for example, protective needle guards, safety locks, or any other protective device. As shown in FIG. 69, each of the second electronic circuit systems 14080A-14080G is coupled to the corresponding removable cover 14070A-14070G. The first electronic circuit systems 14920A-14920G are coupled to the medicament injectors 14002A-14002G, as shown and described above. The first electronic circuit systems 14920A-14920G and the second electronic circuit systems 14080A-14080G can each be similar in function and design to the electronic circuit systems shown and described above. By utilizing two electronic circuit systems on each medical injector (e.g., the first electronic circuit system 14920A and the second electronic circuit system 14080A), the first electronic circuit systems 14920A-14920G and the second electronic circuit systems 14080A-14080G can be cooperatively designed to provide the desired functionality, as described above. In other embodiments, however, each medical injector 14002A-14002G can include only a single electronic circuit system.

The container 14040 includes an electronic circuit system 14050, and is configured to receive and/or hold at least a portion of each of the medical injectors 14002A-14002G. For example, in some embodiments, the container 14040 can include multiple recessed portions, retainers, and/or any other suitable structure that matingly receives at least a portion of each medical injector 14002A-14002G. In some embodiments, the medical injectors 14002A-14002G can be arranged within the container 14040 in a specific order and/or orientation. Such an arrangement can be used, for example, to facilitate the medication regimen. Said another way, in some embodiments, the medical injectors 14002A-14002G can be arranged in the order reflecting the order in which they are to be administered by the user. In other embodiments, however, the medical injectors 14002A-14002G can be arranged within the container 14040 randomly. Moreover, in some embodiments, the container 14040 can be configured to receive different types of medical injectors. This can allow the container 14040 to be used in both current and future therapeutic regimens for a patient.

The electronic circuit system 14050 of the container 14040 can be similar to the electronic circuit systems shown and described above, and can, for example, transmit and/or receive electronic signals from the electronic circuit system 14020 of the compliance monitor, the first electronic circuit systems 14920A-14920G and/or the second electronic circuit systems 14080A-14080G. In some embodiments, the electronic circuit system 14050 of the container 14040 can include an RFID tag encoded with information associated with the medical injectors 14002A-14002G, the medication regimen or the like. In this manner, the electronic signals output and/or produced by the electronic circuit system 14050 of the container 14040 can include information characterizing the medical injectors 14002A-14002G and/or the medication regimen. Such information can include, for example, the number of medical injectors, the amount and type of medicament contained within each medical injector, an expiration date of each medical injector or the like. In this manner, when a patient receives a container 14040 for use, the electronic circuit system 14050 of the container 14040 can be electronically encoded with information that can received by the compliance tracking device 14010. Accordingly, when the patient electronically couples the container 14040 to the compliance tracking device 14010 (e.g., by wired connection or a wireless connection), the container 14040 and the compliance tracking device 14010 can electronically and/or automatically update the patient compliance and/or adherence data associated with the medication regimen.

In use, a container 14040 can include the medical injectors required to administer a predetermined medication regimen. For example, in some embodiments the container 14040 can be "loaded" by a pharmacy and delivered to the patient. The container 14040 is then operatively coupled to the compliance tracking device 14010. Said another way, the electronic circuit system 14050 of the container 14040 can be electronically coupled to the electronic circuit system 14020 of the compliance tracking device 14010. In this manner, the electronic information included within the electronic circuit system 14050 of the container 14040 can be received by the electronic circuit system 14020 of the compliance tracking device 14010 to initialize and/or update a compliance and/or adherence tracking schedule associated with the patient's medication regimen.

The compliance tracking device 14010 can then produce and/or output one or more electronic outputs, as described above. Such outputs can include, for example, visual and/or audible outputs reminding the patient of the date and time of the next dosage, indicating the expiration date of the medicament delivery device, providing instructions in the use of the medicament delivery device, a status of the compliance tracking device 14010, a use instruction associated with the compliance tracking device 14010 and/or the like.

To administer a dosage, the patient removes the appropriate medical injector (e.g., medical injector 14002A) from the container 14040. In some embodiments, the removal of the medical injector 14002A triggers the electronic circuit system 14050, the first electronic circuit system 14920A and/or the second electronic circuit system 14080A to output an electronic signal, as described above. Similarly, when the patient removes the removable cover 14070A to place the medical injector 14002A in a "ready" position, the first electronic circuit system 14920A and/or the second electronic circuit system 14080A can output an electronic signal, as described above. Finally, when the patient actuates the medical injector 14002A, the first electronic circuit system 14920A and/or the second electronic circuit system 14080A can output an electronic signal, as described above. In this manner, the medical injectors 14002A-14002G, the container 14040 and the compliance tracking device 14010 can cooperatively monitor the patient's compliance and/or adherence in adhering to the medication regimen.

Figure 70:
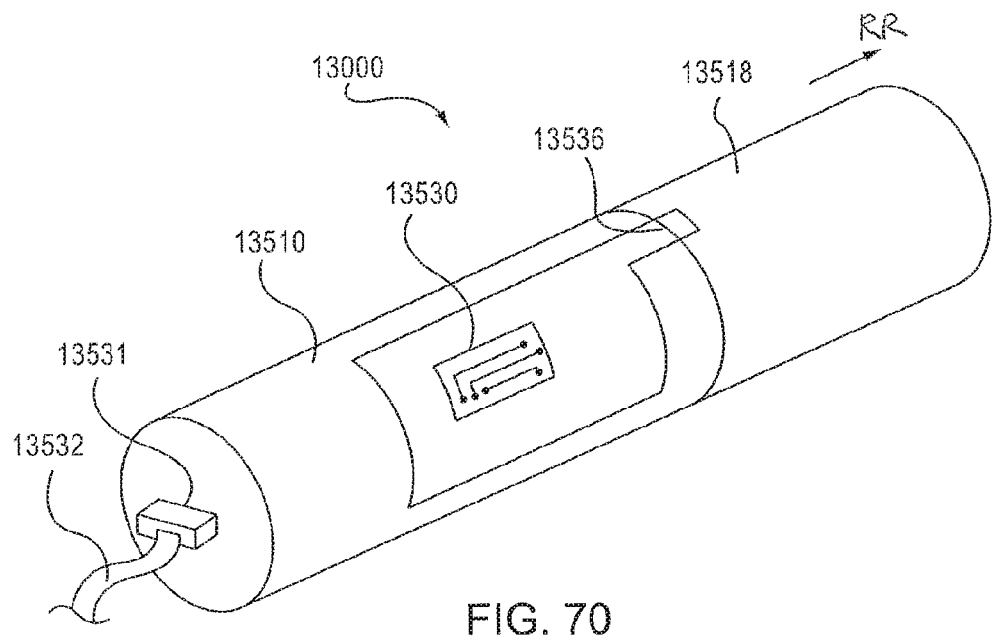
FIGS. 70-72 are perspective views of a medical system according to an embodiment, in a first configuration, a second configuration, and a third configuration, respectively.
Figure 71:
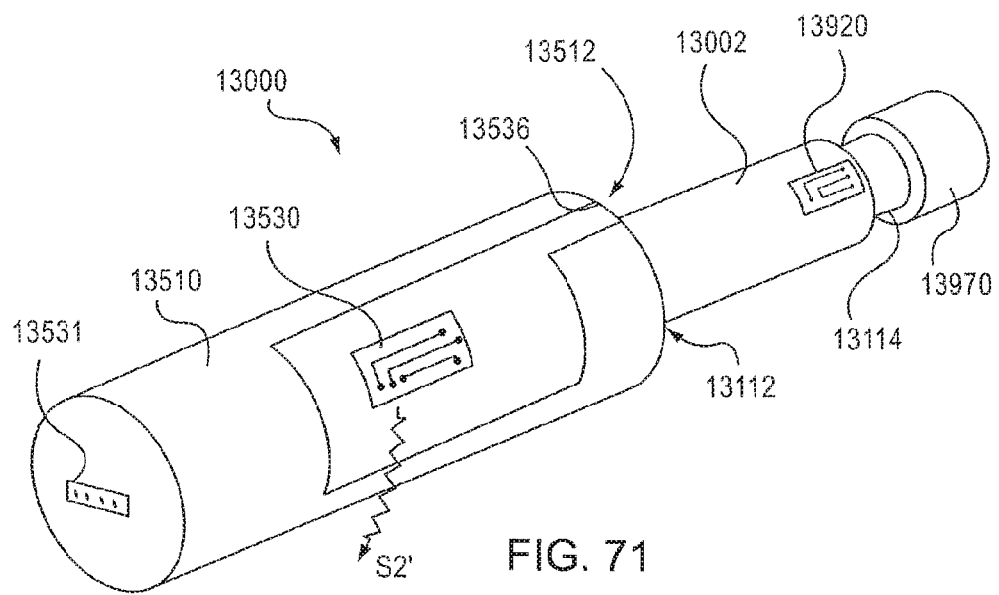
Figure 72:
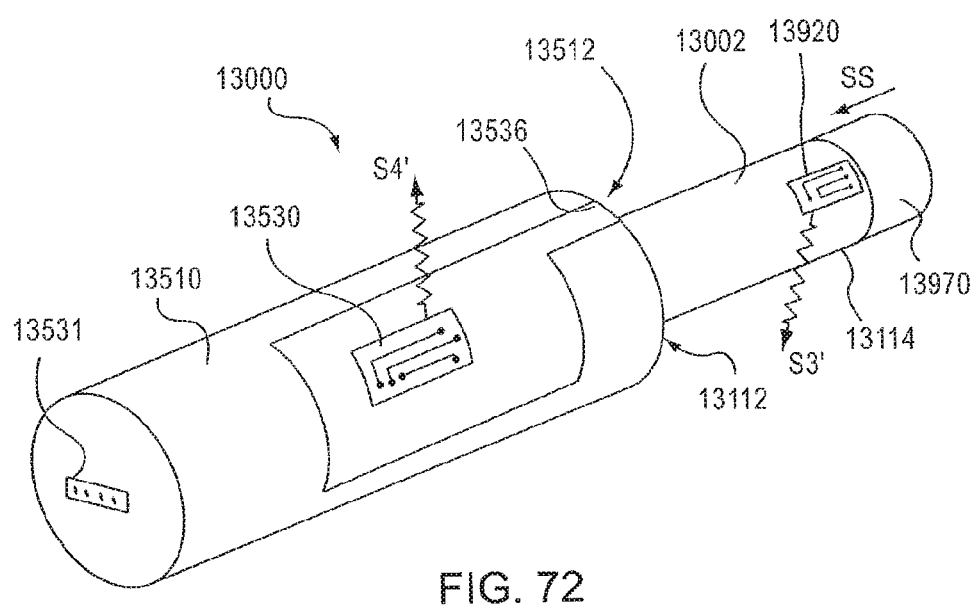

Although the medical system 3000 is shown and described above as including a medicament delivery device 3002 that is removed from a container 3010 during the medicament delivery event, in other embodiments, a medical system can include a medicament delivery device that remains at least partially disposed within the container during a medicament delivery event. For example, FIGS. 70-72 show a medical system 13000 according to an embodiment in a first configuration, a second configuration and a third configuration, respectively. The medical system 13000 includes a medicament delivery device 13002 and a container 13510. As shown in FIGS. 71 and 72, the medicament delivery device 13002 has a proximal end portion 13112 and a distal end portion 13114. The distal end portion 13114 includes an actuator 13970 configured to initiate the delivery of medicament from the medicament delivery device 13002, as described above. The medicament delivery device 13002 also includes an electronic circuit system 13920. The electronic circuit system 13920 of the medicament delivery device 13002 can include similar components and can have similar functionality as any of the electronic circuit systems described herein.

The container 13510 defines an internal region 13512 (see FIGS. 71 and 72) and a cover 13518 (FIG. 70). The container 13510 also includes an electronic circuit system 13530. As shown in FIGS. 71 and 72, the proximal end portion 13112 of the medicament delivery device 13002 is disposed within the internal region 13512 of the container 13510. In some embodiments, the internal region 13512 of the container 13510 can include a recessed portion, a retainer, and/or any other suitable structure that matingly receives at least a portion of the proximal end portion 13112 of the medicament delivery device 13002. In this manner, the medicament delivery device 13002 can be maintained within the container 13510 during use.

The cover 13518 is removably coupled to the container 13510. When the cover 13518 is coupled to the container 13510, the distal end portion 13114 of the medicament delivery device 13002 is within the cover 13518. In this manner, the cover 13518 can protect the medicament delivery device 13002 and/or prevent the inadvertent use thereof. In some embodiments, the cover 13518 can be coupled to the container 13510 via an interference fit, a threaded coupling, a mating protrusion and recess coupling, or the like.

The electronic circuit system 13530 of the container 13510 includes at least a switch 13536 and a communications port 13531. The switch 13536, which can be similar to the switch 12536 shown and described above, produces an electronic input to the electronic circuit system 13530 when the cover 13518 is removed from the container 13510. Said another way, the electronic circuit system 13530 is configured to produce and/or output one more electronic signals when the switch 13536 changes states in response to the cover 13518 being removed from the container 13510. For example, as shown in FIG. 71, in some embodiments, the electronic circuit system 13530 is configured to produce and/or output a first electronic signal S2' when the switch 13536 changes states (e.g., when the cover 13518 is removed from the container 13510). The first electronic signal S2' can be similar to any of the electronic signals and/or outputs described herein.

The communications port 13531 can be any suitable port for operatively coupling the electronic circuit system 13530 of the container 13510 to a remote device, such as a compliance monitoring device, a PC, a battery charger, or the like (not shown in FIGS. 70-72). The remote device can be coupled to the communications port 13531 via an electronic cable 13532 configured to be matingly coupled to the communications port 13531. In some embodiments, the internal region 13512 of the container 13510 can include a port and/or electronic coupling (not shown in FIGS. 70-72) such that the electronic circuit system 13920 of the medicament delivery device 13002 can be operatively coupled to the electronic circuit system 13530 of the container 13510 when the proximal end portion 13112 of the medicament delivery device 13002 is disposed within the container 13510. In this manner, the container 13510 can function as a docking station for the medicament delivery device 13002. Said another way, the electronic circuit system 13920 of the medicament delivery device 13002 can be powered by and/or use certain components of the electronic circuit system 13530 of the container 13510. Such an arrangement can facilitate the use of a low-cost electronic circuit system on a single-use, disposable medicament delivery device.

To move the medical system 13000 from the first configuration to the second configuration (i.e., a "pre-delivery" configuration), the cover 13518 is removed from the container 13510, as shown by the arrow RR in FIG. 70. When the cover 13518 is removed from the container 13510, the electronic circuit system 13530 of the container 13510 produces the first electronic signal S2'. The first electronic signal S2' can be associated with the prescribed medication regimen (including, for example, compliance and/or adherence data), an identification of the medicament delivery device 13002, a status of the medicament delivery device 13002, a use instruction associated with the medicament delivery device 13002, a status of the container 13510, a use instruction associated with the container 13510 and/or the like. In some embodiments, for example, the first electronic signal S2' can include a visual output, an audible output and/or a haptic output that instructs and/or provides cues to a user in the use of the container 13510 to track the patient's compliance and/or adherence. In other embodiments, the first electronic signal S2' can include a communications signal that can be transmitted via the port 15531 and/or by wireless transmission to a remote device (not shown in FIGS. 70-72).

To move the medical system 13000 from the second configuration to the third configuration (i.e., a "post-delivery" configuration), the medicament delivery device 13002 is actuated by moving the actuator 13970 as shown by the arrow SS in FIG. 72. The patient can move the actuator 13970, for example, by gripping the container 13510 and pressing the distal end portion 13114 of the medicament delivery device 13002 against the body. When the actuator 13970 is moved from the first position to the second position, actuation of the medicament delivery device is initiated. Moreover, when the actuator 3970 is moved, the electronic circuit system 13920 of the medicament delivery device 13002 outputs the second electronic signal S3'.

The second electronic signal S3' is received by the electronic circuit system 13530 of the container 13510, which then produces the third electronic signal S4'. As described above, the third electronic signal S4' is associated with the second electronic signal S3'. The electronic signals S3' and S4' can be similar to the electronic signals S3 and S4 described above with reference to FIGS. 61-63. For example, in some embodiments, the electronic signal S3' can include a time stamp associated with the actuation of the medicament delivery device 13002, and the electronic signal S4' can include information associated with the dosage, contents and/or status of the medicament delivery device 13002.

In this manner, the electronic circuit system 13530 of the container 13510 and the electronic circuit system 13920 of the medicament delivery device 13002 can cooperatively monitor the patient's compliance and/or adherence in using the medicament delivery device 13002. By utilizing two electronic circuit systems, the electronic circuit system 13920 and the electronic circuit system 13530 can be cooperatively designed to provide the desired functionality. For example, in some embodiments, the container 13530 can be a reusable compliance and/or adherence tracking device and the medicament delivery device 13002 can be a single-use, disposable device. Upon completion of the injection, the patient can subsequent re-load the container 13510 with next medicament delivery device 13002, as prescribed.

Figure 73:
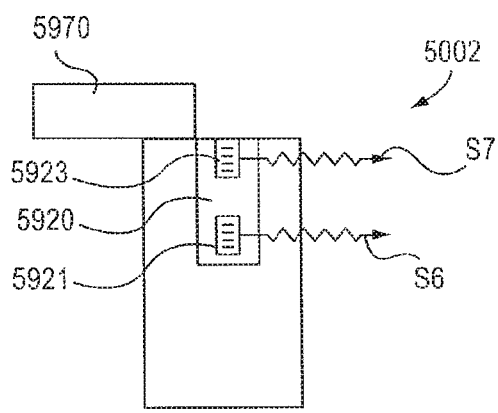
FIGS. 73 and 74 are schematic illustrations of a medicament delivery device according to an embodiment, in a first configuration and a second configuration, respectively.

Although the electronic circuit systems disposed on the medicament delivery devices are shown and described above as outputting an electronic signal in response to the movement of an actuator, in other embodiments, an electronic circuit system can be configured to prevent, eliminate, reduce and/or alter the transmission of an electronic signal in response to the actuation of the medicament delivery device. For example, FIGS. 73 and 74 are schematic illustrations of a medicament delivery device 5002 according to an embodiment, in a first configuration and a second configuration, respectively.

The medicament delivery device 5002, which can be medical injector (e.g., an auto-injector, a pen injector, a multiple-use injector, a syringe or the like), an inhaler or the like, includes an actuator 5970 and an electronic circuit system 5920. The actuator 5970 is movable between a first position (FIG. 73) and a second position (FIG. 74). When the actuator 5970 is moved from the first position to the second position, the actuator 5970 initiates the delivery of the medicament into the body. In some embodiments, for example, the actuator 5970 can be configured to release a spring, an energy storage member, or the like, to initiate medicament delivery when the actuator 5970 is moved from the first position to the second position.

The electronic circuit system 5920 includes at least a first RFID tag 5921 and a second RFID tag 5923. The first RFID tag 5921 is configured to output a first electronic signal S6, which can be received by a compliance and/or adherence monitoring device (not shown in FIGS. 73 and 74) of the types shown and described herein. Similarly, the second RFID tag 5923 is configured to output a second electronic signal S7, which can be received by a compliance and/or adherence monitoring device. The first electronic signal S6 has an electronic characteristic (e.g., frequency, amplitude, etc.) that is different from an electronic characteristic of the second electronic signal S7. In this manner, a receiving device (e.g., a compliance and/or adherence monitoring device) can distinguish the first electronic signal S6 from the second electronic signal S7.

Figure 74:
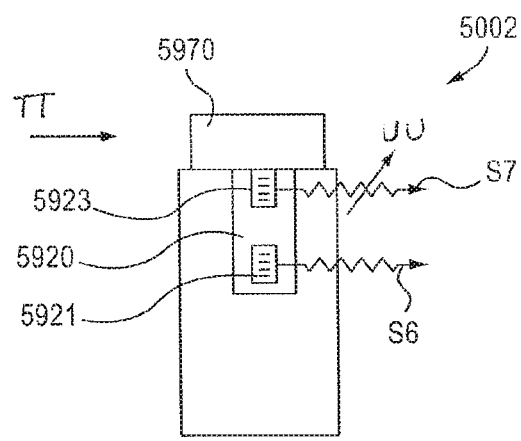

To deliver a dose of medicament, the patient moves the actuator 5970 from the first position to the second position, as shown by the arrow TT in FIG. 74. When the actuator 5970 is moved from the first position to the second position, actuation of the medicament delivery device 5002 is initiated. Said another way, the actuator 5970 is configured to initiate delivery of the medicament when the actuator 5970 is moved from the first position to the second position.

When the actuator 5970 is moved from the first position to the second position, the actuator 5970 eliminates, blocks, and/or alters the second electronic signal S7, as indicated by the arrow UU in FIG. 74. In this manner, the receiving device (e.g., a compliance and/or adherence monitoring device) can receive electronic feedback from the electronic circuit system 5920 corresponding to the actuation of the medicament delivery device 5002. Moreover, the electronic feedback (i.e., the elimination, blockage, and/or alteration of the second electronic signal S7) is provided without requiring the patient to execute any additional steps, other than those required to actuate the medicament delivery device 5002. In this manner, the medicament delivery device 5002 is configured to electronically and/or automatically track the details of its use.

When the actuator 5970 is moved from the first position to the second position, the first electronic signal S6 is not changed. Accordingly, the first electronic signal S6 can function as a validation signal to the receiving device during the actuation of the medicament delivery device 5002. Said another way, the electronic signal S6 can provide feedback associated with the functionality of the electronic circuit system 5920 (e.g., that the first electronic circuit system 5920 is within the transmission range of the receiving device, that the first electronic circuit system is receiving power, etc.).

The actuator 5970 can eliminate, block, and/or alter the second electronic signal S7 by any suitable mechanism. For example, in some embodiments, the movement of the actuator 5970 produces an input that is received by the electronic circuit system 5920, thereby triggering the electronic circuit system 5920 to eliminate, block, and/or alter the second electronic signal S7 output by the second RFID tag 5923. Said another way, in some embodiments, the movement of the actuator 5970 can change the state of a switch (not shown in FIGS. 73 and 74) within the electronic circuit system 5920 thereby triggering the electronic circuit system 5920 to eliminate, block, and/or alter the second electronic signal S7 output by the second RFID tag 5923.

In other embodiments, the movement of the actuator 5970 can disrupt at least a portion of the second RFID tag 5923, thereby eliminating, blocking, and/or altering the second electronic signal S7. For example, in some embodiments, the movement of the actuator 5970 can separate, tear, deform and/or sever a portion of the second RFID tag 5923. In other embodiments, the movement of the actuator 5970 can electronically shield a portion of the second RFID tag 5923, thereby eliminating, blocking, and/or altering the second electronic signal S7. For example, in some embodiments, the actuator 5970 can include a shield portion configured to be disposed about the second RFID tag 5923 when the actuator is in the second position. Such a shield can, for example, block the signal S7 from being output by the second RFID tag 5923.

In other embodiments, the movement of the actuator 5970 can electronically decouple a power source (not shown in FIGS. 73 and 74) from a portion of the electronic circuit system 5920 and/or the second RFID tag 5923. For example, in some embodiments, the actuator 5970 can include a battery isolation tab (not shown in FIGS. 73-74) configured to isolate a battery from a portion of the electronic circuit system 5920. In other embodiments, the actuator 5970 can include a shield portion configured to be disposed about the second RFID tag 5923 when the actuator is in the second position. In this manner, the shield can prevent the second RFID tag 5923 from receiving power from a remote source (e.g., a master RFID tag disposed on the receiving device).

As described herein, the first electronic signal S6 and/or the second electronic signal S7 can include information characterizing the first medicament delivery device 5002. For example, in some embodiments, the first electronic signal S6 and/or the second electronic signal S7 can be associated with the contents of the medicament delivery device 5002 (e.g., the amount and type of medicament contained therein), an expiration date of the medicament delivery device 5002, a dosage of the medicament delivery device 5002 and/or a use instruction associated with the medicament delivery device 5002. In this manner, the receiving device (not shown in FIGS. 73 and 74) can produce the electronic outputs associated with information contained within the first electronic signal S6 and/or the second electronic signal S7. Said another way, this arrangement allows the receiving device to produce an electronic output that is unique to the medicament delivery device 5002.

In some embodiments, the first RFID tag 5921 and/or the second RFID tag 5923 can be passive RFID tags. In such an arrangement, the first RFID tag 5921 and/or the second RFID tag 5923 can be powered remotely by a parent RFID tag, which can be disposed, for example on a compliance and/or adherence monitoring device (not shown in FIGS. 73 and 74). In this manner, the electronic circuit system 5920 of the medicament delivery device 5002 can be devoid of a power supply (e.g., a battery or any other energy storage device). Accordingly, the electronic circuit system 5920 can be a simple, low-cost circuit system 5920 that is suitable for use on a single-use, disposable medicament delivery device.

Figure 75:
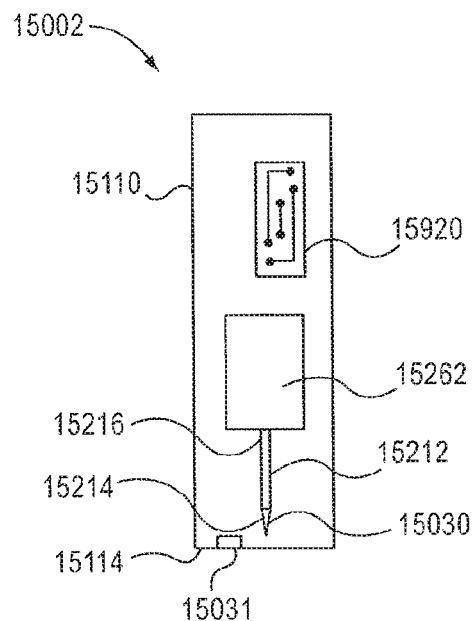
FIGS. 75 and 76 are schematic illustrations of a medicament delivery device according to an embodiment, in a first configuration and a second configuration, respectively.
Figure 76:
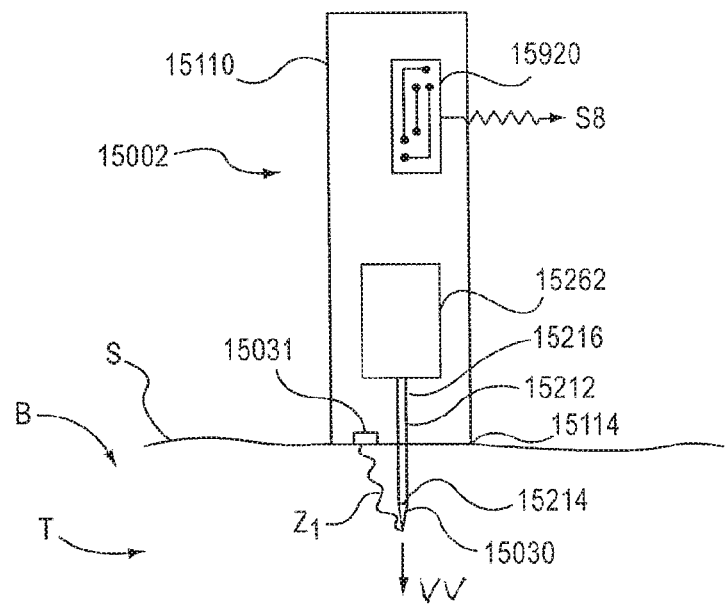

Although the medicament delivery devices are shown and described above as outputting an electronic signal in response to the movement of an actuator, in other embodiments, a medicament delivery device can include any suitable means for providing feedback associated with a dosage administration event. Moreover, although the electronic circuit system 1920 shown and described above with reference to FIGS. 1-3 include a proximity sensor 1974 to provide feedback associated with the validity of an injection event, in other embodiments, a medicament delivery device can include any suitable feedback mechanism for providing feedback associated with the validity of a medicament delivery event. For example, FIGS. 75 and 76 are schematic illustrations of a medical injector 15002 according to an embodiment, in a first configuration and a second configuration, respectively.

The medical injector 15002, which can be, for example, a single-use, disposable auto-injector of the types shown and described herein, includes a housing 15110, a medicament container 15262, a needle 15212, and an electronic circuit system 15920. The housing 15110 has a proximal end portion 15112 and a distal end portion 15114. The medicament container 15262 is disposed within the housing 15110. Although the medicament container 15262 is shown as being movably disposed within the housing 15110, in other embodiments, the medicament container 15262 can be fixedly disposed within the housing 15110.

The needle 15212 includes a proximal end 15216 and a distal end 15214, and is configured to be in fluid communication with the medicament container 15262. In this manner, the medicament within the medicament container 15262 can be conveyed into a body during an injection event via the needle 15212. The needle 15212 is movably disposed within the housing 15110 between a first position (FIG. 75) and a second position (FIG. 76). When the needle 15212 is in the first position, the distal end 15214 of the needle is disposed within the housing 15110. When the needle 15212 is in the second position, the distal end 15214 of the needle is disposed outside of the housing 15110. Accordingly, when the medical injector 15002 is actuated, the needle 15212 can be moved between the first position and the second position to penetrate the patient's skin S (see FIG. 76) and/or provide a passageway for delivering the medicament into the patient's body B.

The electronic circuit system 15920 is includes at least a first electrode 15030 and a second electrode 15031. The first electrode 15030 is disposed at the distal end 15214 of the needle 15212. The second electrode 15031 is disposed at the distal end portion 15114 of the housing 15110. The electronic circuit system 15920 is configured to output an electronic signal S8 associated with an impedance between the first electrode 15030 and the second electrode 15031. The electronic signal S8 can be any suitable communications signal, of the types described herein, configured to be received by a compliance and/or adherence monitoring device (not shown in FIGS. 75 and 76) of the types shown and described herein. In this manner, as described in more detail below, the electronic circuit system 15920 can provide electronic and/or automatic feedback associated with the validity and/or administration of an injection event based on the impedance between the first electrode 15030 and the second electrode 15031.

To deliver a dose of medicament, the patient first places the distal end portion 15114 of the housing against the skin S of the body B. In some embodiments, the second electrode 15031 can include a proximity sensor, similar to the proximity sensor 1974 shown and described above with reference to FIGS. 1-3. Accordingly, in such embodiments, the electronic circuit system 15920 can produce one or more electronic outputs indicating that the medical injector 15002 is properly positioned and ready to be actuated. The patient then actuates the medical injector 15002 thereby causing the needle to move from the first position to the second position, as shown by the arrow VV in FIG. 76. Accordingly, the needle penetrates the patient's skin S to provide a passageway for delivering the medicament into the patient's body B.

During the above-described injection event, the electronic circuit system 15920 is configured to measure the impedance $Z_1$ between the first electrode 15030 and the second electrode 15031. The electronic circuit system 15920 can then produce and/or output the electronic signal S8, which is associated with the impedance $Z_1$. In some embodiments, the electronic signal S8 can be processed, either by the electronic circuit system 15920 or by a compliance and/or adherence monitoring device (not shown in FIGS. 75 and 76) to characterize the validity of the injection event. For example, based on the impedance $Z_1$, the known depth of penetration of the needle 15212 (i.e., the distance between the distal end 15114 of the housing 15110 and the distal end 15214 of the needle 15212), and/or the characteristic impedance of various types of bodily tissue, a compliance and/or adherence monitoring device can determine whether the needle 15212 was disposed within bodily tissue T during the injection event. Said another way, because bodily tissue T has a characteristic impedance that is different from a characteristic impedance of other materials (e.g., a pillow, drywall, clothing materials or the like), the compliance and/or adherence monitoring device can evaluate the validity of the injection event based on the impedance $Z_1$ and/or the known depth of penetration of the needle 15212. Moreover, because different types of bodily tissue can have different characteristic impedance values, in some embodiments, the compliance and/or adherence monitoring device can evaluate whether the injection occurred within fatty tissue, muscle tissue, bone tissue or the like. For example, many vaccines are intended to be delivered into muscle tissue of a patient. If a patient inadvertently delivers the vaccine into a tissue other than muscle tissue (e.g., fatty tissue), the electronic circuit system 15920 can output an electronic signal notifying the user to contact a medical professional. In other embodiments, the electronic circuit system can output a communication signal that is sent over a communications network directly to a medical professional to notify the medical professional that the vaccine was improperly administered.

Figure 77:
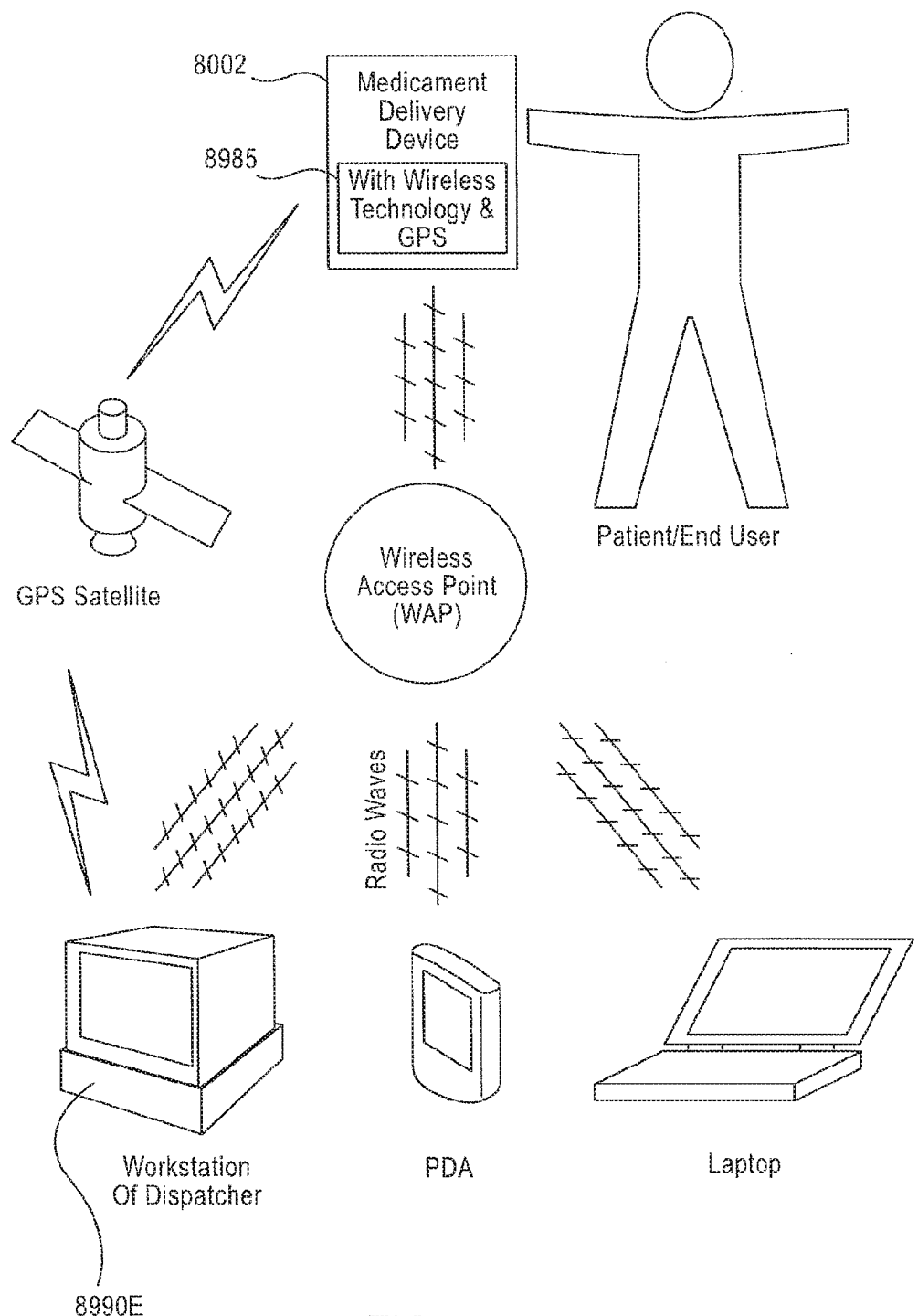
FIG. 77 is a schematic illustration of a medicament delivery device according an embodiment.

Although the medicament delivery devices, containers and/or compliance tracking devices shown and described above can be configured to send and/or receive electronic signals associated with a wide range of information, in some embodiments, a medicament delivery device, a container and/or a compliance tracking device can include a wireless communications system configured to transmit a location of the medicament delivery device. Such embodiments, can be particularly appropriate, for example, when the medicament delivery device is a single-dose device for use in emergency situations. For example, FIG. 77 is a schematic illustration of a medicament delivery device 8002 according an embodiment that includes a wireless communications system 8985 configured to communicate electronically directly with an emergency response dispatcher 8990E, via wireless network $N_W$ as described above. Moreover, the wireless communications system 8985 includes a Global System for Mobile Communications and/or Global Positioning System (GPS) enabled feature, which can include a transmitter, a receiver, software, hardware and/or other electronics (not shown in FIG. 77) to transmit the geographical location of the medicament delivery device 8002 to the emergency response dispatcher 8990E. In this manner, when the medicament delivery device 8002 is used, it can be configured to automatically notify emergency response personnel (Emergency Medical Technicians, Fire, Police and the like).

Figure 78:
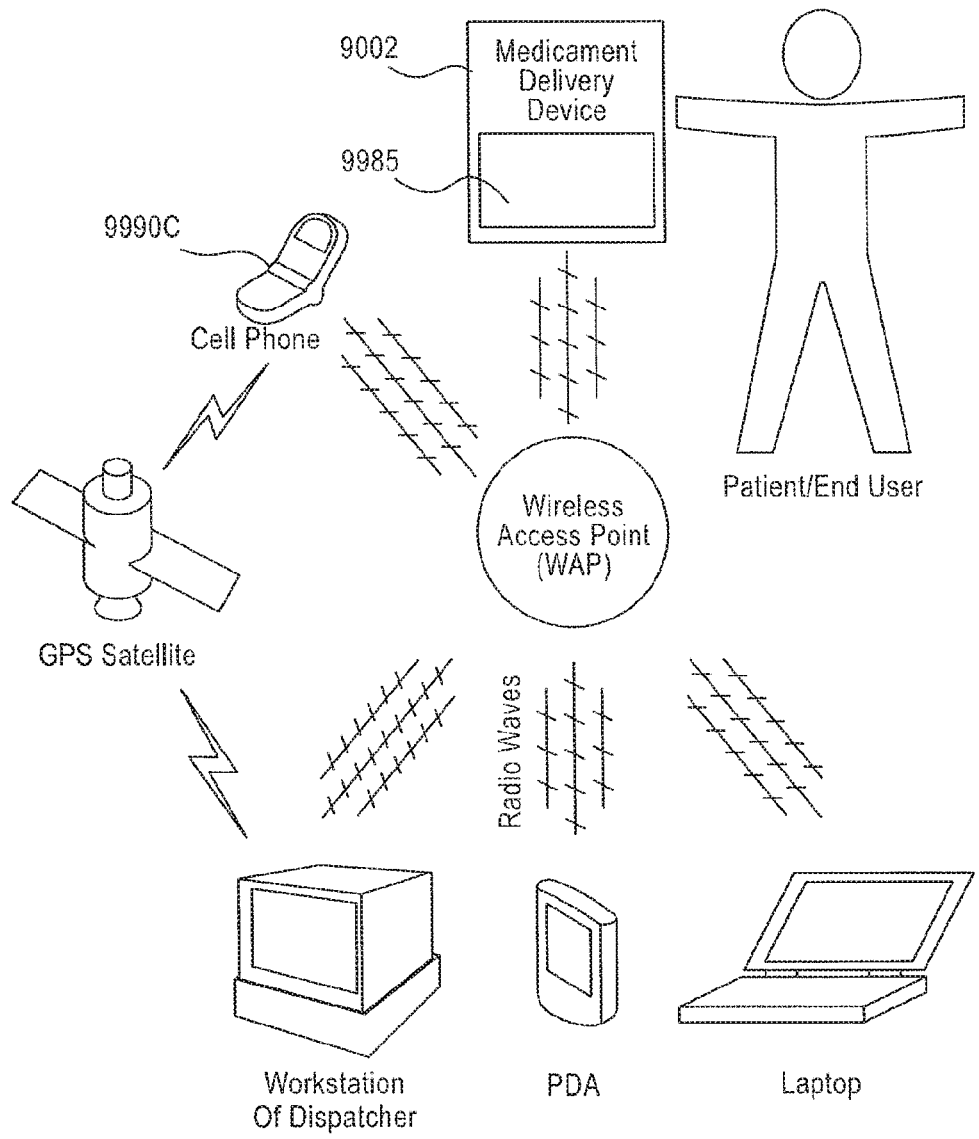
FIG. 78 is a schematic illustration of a medicament delivery device according an embodiment.

In some embodiments, a wireless communications system can be configured to transmit the geographical location of the medicament delivery device to an emergency response dispatcher via a wireless communications device that is GPS-enabled. For example, FIG. 78 is a schematic illustration of a medicament delivery device 9002 according an embodiment that includes a wireless communications system 9985 configured to transmit the geographical location of the medicament delivery device 9002 via a wireless communications device 9990C that is GPS-enabled. For example, in some embodiments, the GPS-enabled wireless communications device 9990C can be a cellular phone. In this manner, when the medicament delivery device 9002 is actuated, the wireless communications system 9985 transmits data to the GPS-enabled cell phone 9990C, as described above. The GPS-enabled cell phone 9990C automatically dials an emergency number such as, for example, 911 (emergency dispatcher), and/or sends information associated with the location of the medicament delivery device 9002 and/or the end user location through GPS satellite positioning or network based positioning (using cell phone towers).

Figure 79:
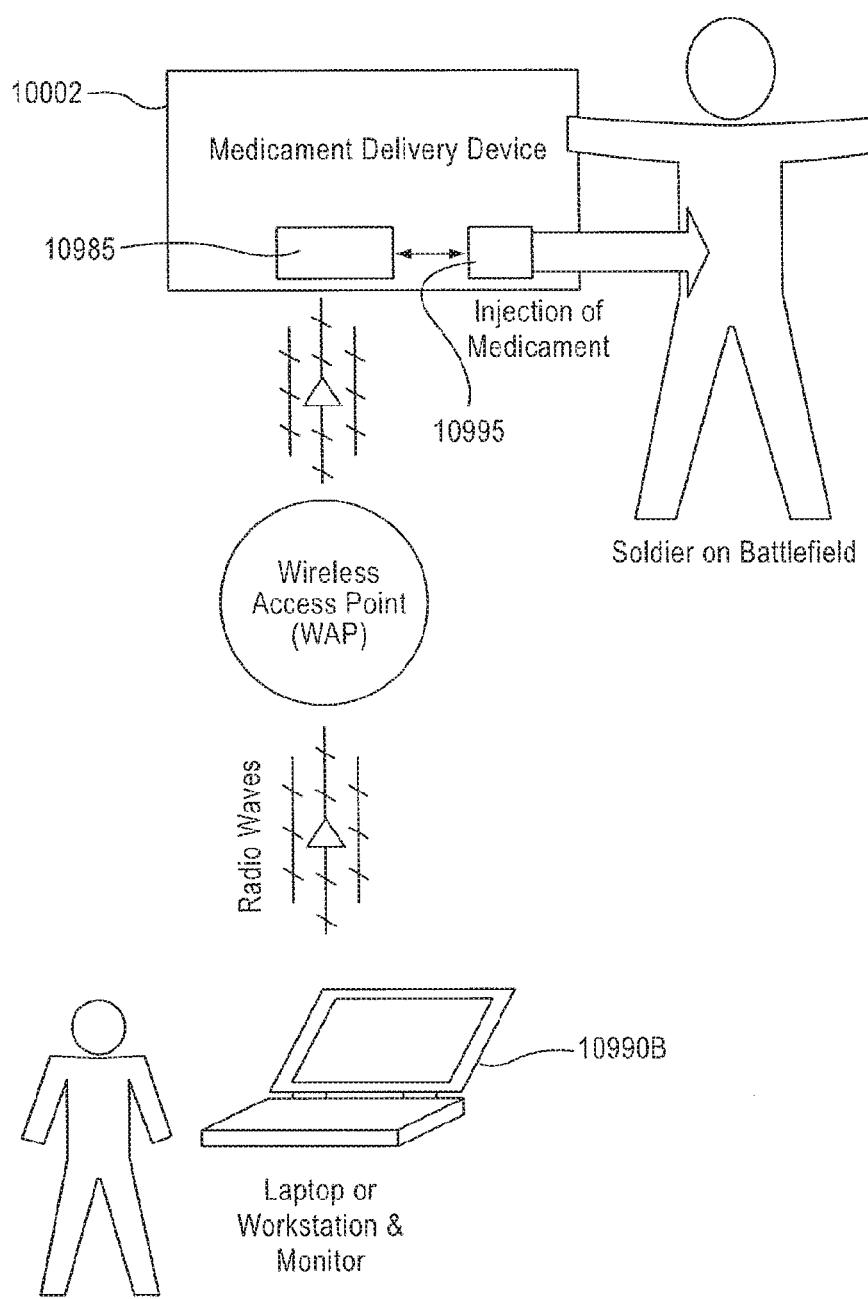
FIG. 79 is a schematic illustration of a medicament delivery device according an embodiment.

Although the wireless communications systems are shown and described above as being configured to send and/or receive electronic signals associated with a wide range of information, in some embodiments, a wireless communications system can be configured to send and/or receive electronic signals associated with the actuation of a medicament delivery device. More particularly, in some embodiments a wireless communications system can be employed to remotely trigger various functions of a medicament delivery device. For example, FIG. 79 is a schematic illustration of a medicament delivery device 10002 according to an embodiment that includes such functionality. The medicament delivery device 10002 includes a wireless communications system 10985 and an actuator 10995. The wireless communications system 10985, which can be any suitable system of the type shown and described above is operatively coupled to the actuator 10995. The actuator 10995 can be any suitable mechanism configured to receive an input from the wireless communications system 10985 and, based upon the input, trigger a function of the medicament delivery device 10002. For example, in some embodiments, the actuator 10995 can be integrated into the wireless communications system 10985. The actuator can include, for example, a programmable logic controller (PLC) and/or solenoid that allow the data received via the wireless communications system 10985 to be converted into an action to actuate the medicament delivery device 10002. For example, in some embodiments, as described in more detail herein, the medicament delivery device 10002 can be a gas-powered auto-injector and the actuator 10995 can be configured to move a compressed gas cylinder to actuate the auto-injector.

In use, the remote actuation feature of the medicament delivery device 10002 can be advantageous in circumstances in which the user of such a device is not able to actuate the medicament delivery device 10002 and/or there are no other individuals present to actuate the medicament delivery device 10002. For example, in certain situations, soldiers on a battlefield can carry the medicament delivery device 10002, which can contain one or more medicaments. Such medicaments can be formulated to relieve acute pain (e.g., morphine), mitigate the effects of exposure to a nerve agent and/or prevent seizures secondary to such exposure. The wireless communications system 10985 can be configured to send information to and/or receive information from a battlefield monitor station 10990B located in a secure area. In this manner, the battlefield monitor station 10990B can monitor and/or be in communication with the soldiers on the battlefield.

When a critical incident occurs requiring the use of the medicament delivery device 10002, monitoring personnel can send a signal from the battlefield monitor station 10990B to the medicament delivery device 10002 on the soldier requiring medical attention. The wireless communications system 10985 can receive the signal and process the signal into "activation" data, which can then be transmitted to the actuator 10995 to trigger the actuation of the medicament delivery device 10002 and subsequent delivery of the required medication and/or agent. To ensure that the medicament is delivered in the desired location within the soldier's body, the medicament delivery device 10002 can be placed in a predetermined orientation relative to the soldier. For example, in some embodiments, the medicament delivery device 10002 can be retained within a specific pocket of the soldier's uniform.

Figure 80:
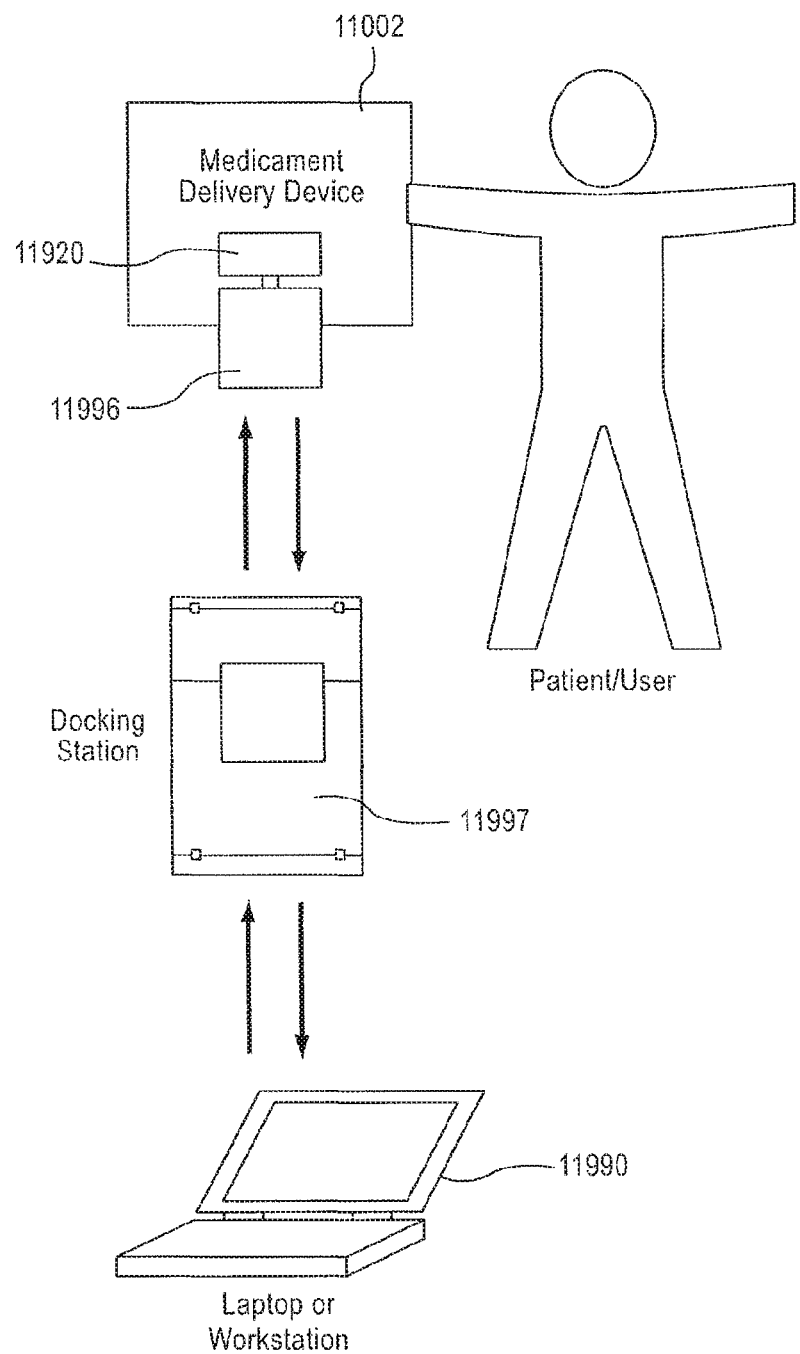
FIG. 80 is a schematic illustration of a medicament delivery device according an embodiment.

Although the medicament delivery devices have been shown and described above as including a wireless communications system, in some embodiments, a medicament delivery device can send signals to and/or receive signals from various communications devices using a combination of communications networks. For example, in some embodiments, a medicament delivery device can send signals to and/or receive signals from various communications devices using any suitable combination of wireless networks and wired networks. For example, FIG. 80 is a schematic illustration of a medicament delivery device 11002 according to an embodiment that includes an electronic circuit system 11920 and an electronic communications port 11996. The electronic circuit system 11920 can be any electronic circuit system of the type shown and described herein. For example, the electronic circuit system 11920 can be configured to monitor the status of the medicament delivery device 11002, actuate the medicament delivery device 11002, provide instructions for using the medicament delivery device 11002 or the like.

The electronic communications port 11996 can be any device configured to be operatively coupled to a docking station 11997, which is in turn operatively coupled via a communications network N to a communications device 11990. The docking station 11977 can be, for example, a compliance and/or adherence monitoring device and/or a container of the types shown and described herein. The communications device 11990 can be any communications device of the type shown and described above (e.g., a physician's computer, PDA, an insurer's computer, etc.). In this manner, the electronic circuit system 11920 can send electronic signals to and/or receive electronic signals from the communications device 11990 via the communications network N and the docking station 11997. Moreover, as described herein, the docking station 11997 can include an electronic circuit system (not shown in FIG. 80) to store, process and/or produce electronic signals associated with the use of the medicament delivery device 11002. The communications network N can be any suitable communications network, and can include, for example, wired networks.

In some embodiments, the electronic communications port 11996 can be a serial bus port such as a USB ports or any another method of connecting the electronic circuit system 11920 to the docking station 11997 and/or the communications device 11990 to transfer data. The electronic circuit system 11920, the electronic communications port 11996 and/or the docking station 11997 can include any electronic components (including hardware, firmware and/or software) configured to facilitate electronic communication. For example, in some embodiments, the electronic circuit system 11920, the electronic communications port 11996 and/or the docking station 11997 can include Small Computer System Interface (SCSI and ports), FireWire (or other IEEE 1394 interfaces), data uplink, point-to-point link, fiber optic links, hard drives, pc cards, circuit boards, uplinks, downlinks, docking stations, parallel and bit-serial connections, and the like.

In some embodiments, the use of a wired communication system used as a part of the communications path, can improve the reliability of the information being transferred and could ensure that the information is transferred at the right time and efficiently. For example, after a patient uses the medicament delivery device 11002, the user can place the device into the docking station 11997 connected to the user's workstation (i.e., the communications device 11990 to trigger the transfer of information.

Moreover, as described above, in some embodiments, the communications device 11990 can include software and/or hardware to download the information from the medicament delivery device to the workstation and transmit such information to a third party such as the patient's/user's health care provider (not shown in FIG. 80). As described above, such information could include the location where the device was activated, time of day, dosage and route of administration, frequency of device usage, functionality of the device once used, expiration date of the device, device status, medicament status, and any adverse event experienced by the user following the use of the device. Moreover, as described above, after the information is sent, the user can be notified that the information was sent successfully by receiving electronic confirmation from the communications device 11990 and/or the third party devices. The illustrated communication system also allows the patient to connect to his or her workstation and download information to the medicament delivery device. Such information can include, for example, updated dosing information, updated use instructions, critical software updates, and other information that would be useful to the patient. The medicament delivery device could also connect to other devices other than just a workstation or docking station such as a mini USB drive to transfer the information.

The electronic circuit systems shown and described above can include one or more electronic components operatively coupled to perform the functions described herein For example, the electronic circuit systems shown and described herein (including those included as a part of the medicament delivery devices, the containers, and the compliance and/or adherence monitoring devices shown and described herein) can be similar to the electronic circuit system 1920 shown and described above with reference to FIG. 3. Although the medical devices shown and described above include one electronic circuit system, in some embodiments, a medical device can include multiple electronic circuit systems configured to perform the functions described herein.

Any of the medicament delivery devices shown and described herein can be used to self-administer a dose of a vaccine. Similarly stated, any of the medicament delivery devices shown and described herein can be used to administer a dose of a vaccine at a location other than an office staffed by a medical professional (e.g., a doctor's office, vaccination clinic or the like) and/or by a person who is not a medical professional (e.g., the recipient of the vaccine, a parent of the recipient or the like). For example, in some embodiments, a medicament delivery device for self-administration of a vaccine can be similar to the auto-injector 4000' shown and described above with reference to FIGS. 26 through 57. As described above, the auto-injector 4000' includes the housing 4110', the medicament container 4560' disposed within the housing, an activation mechanism 4500', a cover 4200' and an electronic circuit system 4900'.

The medicament container 4560' can contain a single dose of a vaccine. Such vaccines can include, for example, an influenza A vaccine, an influenza B vaccine, an influenza A (H1N1) vaccine, a hepatitis A vaccine, a hepatitis B vaccine, a *haemophilus influenzae* Type B (HiB) vaccine, a measles vaccine, a mumps vaccine, a rubella vaccine, a polio vaccine, a human papilloma virus (HPV) vaccine, a tetanus vaccine, a diptheria vaccine, a pertussis vaccine, a bubonic plague vaccine, a yellow fever vaccine, a cholera vaccine, a malaria vaccine, a smallpox vaccine, a pneumococcal vaccine, a rotavirus vaccine, a varicella vaccine and/or a meningococcus vaccine.

As described above, the activation mechanism 4500' includes an energy storage member (i.e., the gas container 4570') configured to produce a force to inject and/or deliver the dose of the vaccine into a body. By producing the force to inject the vaccine via an energy storage member, the vaccine can be exposed to a force and/or a pressure within a predetermined range. Similarly stated, because the energy storage member can be configured to produce a force independent of characteristics of the user (e.g., independent of how the user manipulates the auto-injector), the force and/or pressure at which the vaccine is injected can be maintained within a predetermined range, controlled and/or limited. Controlling and/or limiting the injection force and/or pressure in this manner can minimize damage to the vaccine or vaccine combination, excipients (e.g., albumin) and/or the adjuvants (e.g., alum) within the vaccine product that can otherwise reduce the stability and/or potency of the vaccine.

In some embodiments, for example, the activation mechanism 4500' can include a mechanism to release (or vent) a portion of the pressurized gas during an injection event to an area outside of the housing 4110'. Said another way, in some embodiments, the activation mechanism 4500' can control and/or limit the force and/or pressure at which the vaccine is injected. Such mechanisms can include, for example, a gas release valve, an aperture or the like. For example, in some embodiments, the injection force and/or pressure can be controlled by controlling the gas pressure using any of the pressure release mechanisms shown and described in U.S. patent Ser. No. 11/566,422, entitled "Devices, Systems and Methods for Medicament Delivery," filed on Dec. 4, 2006, which is incorporated herein by reference in its entirety.

As described above, the electronic circuit system 4900' is coupled to the housing 4110' such that the protrusion 4235' of the cover 4200' electrically isolates the battery assembly 4962' from a portion of the electronic circuit system 4900' when the cover 4200' is disposed about the housing 4110'. Thus, in use when cover 4200' is removed from about the housing 4110', the protrusion 4235' is removed from between the battery assembly 4962' and the electronic circuit system 4900' such that the battery assembly 4962' is placed in electrical communication with the electronic circuit system 4900'. Said another way, in use the electronic circuit system 4900' is actuated when the cover 4200' is removed from about the housing 4110'. In other embodiments, the electronic circuit system 4900' can be actuated by a switch that is manipulated by the user, a switch that is remotely actuated (as described above) or any other suitable manner.

Although the cover 4200' is shown as having an open end and receiving a portion of the housing 4110', in other embodiments, the cover 4200' can substantially enclose the housing 4110'. For example, in some embodiments, an auto-injector can be contained within a cover, sheath and/or container similar to the container 13510 shown and described with reference to FIGS. 70-72. In such embodiments, for example, the cover, sheath and/or container within which a portion of the housing is disposed can include an electronic circuit system configured to cooperatively function with the electronic circuit system disposed on the housing of the device.

As described above, when actuated, the electronic circuit system 4900' can produce a recorded speech output. Moreover, when the activation mechanism 4500' is actuated, the electronic circuit system 4900' can produce a signal, such as, for example, a wireless signal validating the injection event. In this manner, the auto-injector 4000' can provide instructions for the use of the auto-injector 4000' and the administration of the overall vaccine regimen (e.g., for regiments requiring multiple doses), as well as produce a signal in response to the actuation of the device. The signal can include any information related to compliance and/or adherence as described herein, such as, for example, an indication of the validity of the injection, an indication of the time period within which the next dose should be administered or the like. In some embodiments, for example, the signal can be configured to be received by an electronic calendar to automatically schedule a time for a subsequent dose of the vaccine. Thus, the auto-injector 4000' can facilitate the administration of the vaccine at a location other than an office staffed by a medical professional and/or by a person who is not a medical professional.

As described above, some vaccines have historically been administered at a location staffed by a medical professional and/or by a medical professional to, among other reasons, ensure that the stability of the vaccine has not been compromised. Vaccine stability can be related to the temperature at which the vaccine is stored prior to administration. More particularly, because some vaccines include antigens that are bound to various adjuvants, the effectiveness or potency of the vaccine is maintained by storing the vaccine within a predetermined range of temperatures. For example, if a vaccine is maintained at a temperature higher than the recommended storage temperature range, denaturation and/or degradation of the antigens within the vaccine can result, thereby reducing the effectiveness or potency of the vaccine. Conversely, if a vaccine is stored at temperatures below freezing, ice crystal formation within the vaccine can damage the antigens and/or adjuvants therein, which also reduces the effectiveness or potency of the vaccine. The systems, policy and/or methods of maintaining the vaccine within the storage temperature range during manufacture, shipment and storage is often referred to as the "cold chain."

In some embodiments, the recorded speech output upon actuation of the electronic circuit system 4900' and/or the signal produced by the auto-injector 4000' in response to its actuation can be associated with the stability of the vaccine contained therein. In this manner, the auto-injector 4000' can provide information related to the stability of the vaccine to the user to reduce the likelihood of administering a vaccine having a compromised stability. Additionally, the auto-injector 4000' can provide information related to the stability of the vaccine to a third party (e.g., a medical professional, an insurance company or the like) to report the administration of a vaccine having a compromised stability. In some embodiments, for example, the electronic circuit system 4900' can include a temperature sensor to track the history of the temperature of the medicament delivery device. In some such embodiments, a temperature sensor can include a quantitative sensor that can track the vaccine temperature as a function of time. In this manner, the electronic circuit system 4900' can calculate a stability parameter to characterize the stability of the vaccine. The stability parameter can be a quantitative value, such as, for example, an integrated temperature history of the vaccine, or a qualitative value, such as, for example, an indicator that the vaccine has been stored outside of a predetermined temperature range for a certain amount of time.

In some embodiments, the temperature sensor can be a non-electronic sensor that relies on a reaction or material change to characterize the stability of the vaccine, or degradation thereof as a result of the temperature history of the vaccine. For example, in some embodiments, the temperature sensor can be a temperature sensitive color strip that can indicate the temperature history of the medicament using various colors to indicate different temperatures and/or temperature ranges at which the medicament has been stored. In some embodiments, the non-electronic temperature sensor can be optically interrogated by the electronic circuit system 4900' to produce the stability parameter and/or to produce the recorded speech output and/or the signal associated with the stability of the vaccine. In other embodiments, the non-electronic temperature sensor can be visually inspected by the user. In such embodiments, the recorded speech output can provide instructions to assist the user in reading and/or interpreting the non-electronic temperature sensor.

Although many of the medicaments and vaccines shown and described above have been in liquid form, in some embodiments, an auto-injector can include a lyophilized vaccine that is reconstituted prior to administration. Similarly stated, in some embodiments, an auto-injector can include a first portion of the vaccine stored as a dry component and second portion of the vaccine stored as liquid diluent. In some such embodiments, the electronic circuit system can include multiple temperature sensors (e.g., one to monitor the temperature history of the dry component and one to monitor the temperature history of the diluent).

Moreover, for some lyophilized vaccines, the stability of the vaccine can also be related to the amount of time elapsed after the dry component and the diluent have been mixed. For example, the mumps vaccine should be used within six hours of being reconstituted. Accordingly, in some embodiments, the recorded speech output and/or the signal produced by the auto-injector 4000' can be associated with the actuation of a mixing mechanism. For example, in some embodiments, the electronic circuit system 4900' can produce a recorded speech output instructing the user that the vaccine has been mixed and should be administered within six hours. The electronic circuit system can also include a timer to provide audible warnings (e.g., subsequent recorded speech outputs, beeps or the like) indicating an amount of time remaining before the stability of the vaccine may be compromised. In some embodiments, the electronic circuit system 4900' can calculate a stability parameter that is related to the amount of time elapsed after actuation of the mixing mechanism.

In some embodiments, an auto-injector can include an automated mixing mechanism, such as the type of mixing mechanisms disclosed in U.S. patent application Ser. No. 11/692,359, entitled "Devices, Systems and Methods for Medicament Delivery," filed Mar. 28, 2007, which is incorporated herein by reference in its entirety. In other embodiments, an auto-injector can include a non-automated mixing mechanism.

In addition to providing instructions and/or signals associated with the stability, effectiveness and/or potency of the vaccine, in some embodiments, a medicament delivery device can produce a signal associated with an administration of a vaccine. For example, as described above, in some embodiments, a medicament delivery device can produce a signal in response to actuation of the device. Such signals can include, for example, a recorded speech output confirming the actuation of the device to the user, a wireless signal confirming the actuation of the device to a remotely located party, a light output or the like. In this manner, the medicament delivery device can provide and indication of the patient's compliance and/or adherence with the vaccination regimen.

In some embodiments, for example, an auto-injector, such as for example, the auto-injector 4000', can include a needle configured to inject a vaccine into a portion of the body. The electronic circuit system (e.g., electronic circuit system 4900') can be configured to produce a signal upon actuation of the auto-injector 4000' that includes information associated with a characteristic of the portion of the body within which the vaccine is injected. The characteristic can include, for example, the density of the body tissue within which the vaccine was injected. In this manner, the signal can provide information associated with the validity and/or effectiveness of the vaccination. The signal produced by the electronic circuit system can be any signal of the types shown and described herein (e.g., a recorded speech output, a wireless signal or the like). In this manner, the auto-injector can provide information related to the validity of the injection event to the user and/or a medical professional to identify improper and/or ineffective vaccinations. For example, procedures for administering the Hepatitis B vaccine specify that the vaccine should be injected into the thigh, and not the buttocks. An auto-injector configured to administer the Hepatitis B vaccine can therefore include an electronic circuit system to produce one or more recorded speech instructions to identify the thigh as the point for injection. The electronic circuit system can also produce one or more signals to indicate whether the vaccine was injected into the thigh, based on the sensed characteristic of the bodily tissue.

In some embodiments, the electronic circuit system can include a sensor configured to detect a characteristic of a portion of the body in which the injection is administered. The sensor can be an optical sensor or an impedance sensor of the types shown and described above. Moreover, in some embodiments, an electronic circuit system can include an ultrasonic transmitter and receiver configured measure the density of the tissue in which the vaccine was injected.

In some embodiments, a medicament delivery device can include a mechanism configured to disarm and/or lock the device under certain conditions to prevent the vaccine from being delivered. For example, in some embodiments, an auto-injector can include a disarming mechanism to prevent the injection of a vaccine when the stability of the vaccine has been compromised. In other embodiments, an auto-injector can include a disarming mechanism to prevent the injection of a vaccine when the vaccine has been exposed to light, excessive humidity or microwave radiation.

In some embodiments, a medicament delivery device can include a disarming mechanism that irreversibly and/or permanently prevents the device from administering the vaccine. Similarly stated, in some embodiments, a disarming device can irreversibly prevent an activation mechanism from producing the force to deliver a dose of the vaccine. For example, in some embodiments, the medicament delivery device can be irreversibly and/or permanently disabled in response to the temperature sensor indicating that the vaccine and/or medicament has been stored above a predetermined temperature for a certain amount of time. In other embodiments, the medicament delivery device can be irreversibly and/or permanently disabled in response to a timer indicating that the vaccine and/or medicament has been mixed for longer than a predetermined period of time.

Figure 81:
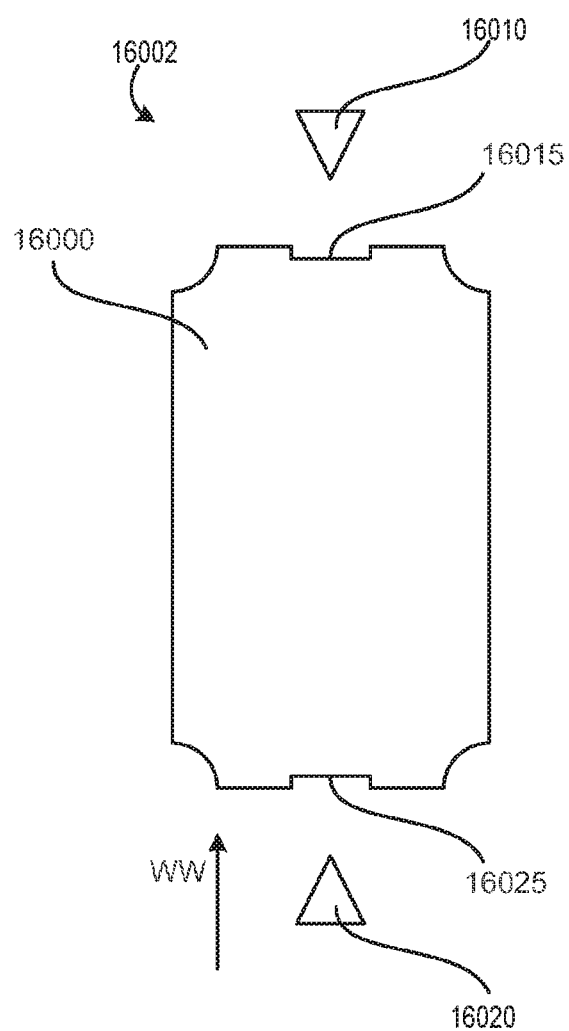
FIG. 81 is a schematic illustration of a portion of a medicament delivery device according to an embodiment.

The disarming mechanism can be any suitable mechanism configured to prevent and/or limit the delivery of the medicament and/or the vaccine into the body. In some embodiments, for example, an auto-injector can be disabled by releasing the actuation energy stored in an energy storage member. In some embodiments, for example, compressed gas contained in the compressed gas cylinder can be released to the atmosphere to prevent the actuation of the medicament delivery device. For example, FIG. 81 is a schematic illustration of a portion of an auto-injector 16002 according to an embodiment. Auto-injector 16002 can be any of the auto-injectors shown herein. The auto-injector 16002 includes a compressed gas cylinder 16000. The compressed gas cylinder 16000 includes a first frangible seal 16015 and a second frangible seal 16025. The first frangible seal 16015 is configured to be punctured by a first puncturing mechanism 16010 when the user actuates the auto-injector, as described above. When the first puncturing mechanism 16010 punctures the first frangible seal 16015, the contents of the compressed gas cylinder 16000 are expelled, causing the delivery of a medicament, as described above.

The second frangible seal 16025 is configured to be punctured by a second puncturing mechanism 16020 when the temperature of the medicament contained within the auto-injector is above a threshold temperature for a certain amount of time. In some embodiments, for example, thermal expansion can cause the second puncturing mechanism 16020 to move in the direction shown by the arrow WW in FIG. 81. This causes the second puncturing mechanism 16020 to puncture the second frangible seal 16025, expelling the contents of the compressed gas cylinder 16000. When the second frangible seal 16025 is punctured, the contents of the compressed gas cylinder 16000 are expelled to a region outside of the housing (e.g., via a vent pathway) such that the auto-injector is not actuated and the medicament is not delivered. In this manner, the auto-injector is irreversibly disabled, and a patient will be unable to use the medicament. Although the second puncturing mechanism 16020 is shown and described as puncturing the second frangible seal 16025 of the gas cylinder 16000, in other embodiments, the second puncturing mechanism 16020 can puncture a frangible seal within the device housing to place the gas chamber within the device in fluid communication with a region outside of the housing. In this manner, by venting or "short circuiting" the gas upon actuation of the device, the delivery of the vaccine can be prevented.

Figure 82:
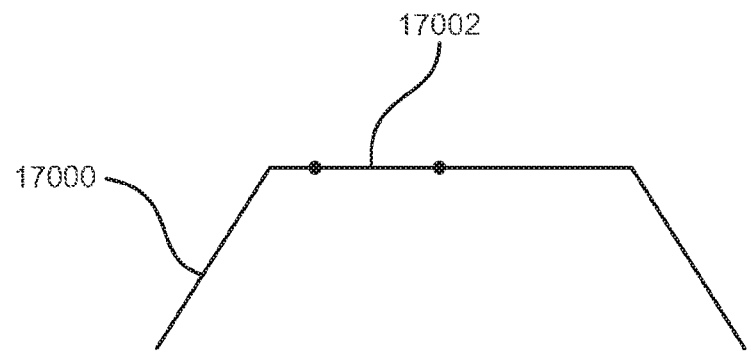
FIGS. 82-83 are schematic illustrations of a portion of an electronic circuit system of a medicament delivery device, according to an embodiment.
Figure 83:
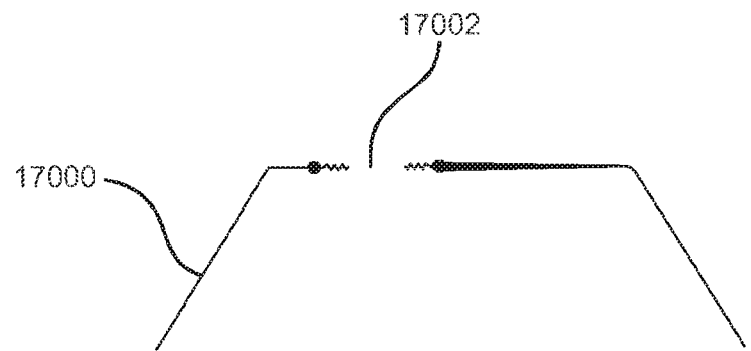

In other embodiments, a medicament delivery device can be disabled electronically. For example, FIGS. 82 and 83 show an electrical conductor 17000 on a circuit board of an electronic circuit system of an auto-injector in a first configuration and a second configuration, respectively. The auto-injector can be similar to the auto-injectors described above. A portion 17002 of the electrical conductor 17000 and/or the substrate upon which the electrical conductor is disposed is constructed of a heat sensitive material, such as a shape memory material. When the electrical conductor 17000 and/or the substrate reaches a certain temperature, the ends of the heat sensitive portion 17002 of the electrical conductor 17000 separate, moving the electrical conductor 17000 from the first configuration (FIG. 82) to the second configuration (FIG. 83). This "fusible link" in the circuit can be used to trigger an indicator and/or a signal that the medicament has been exposed to temperatures above a threshold temperature. Such a signal can include, for example, an audible, visual, or haptic indicator on the device itself, or a wireless communications signal sent to a remote location to prompt a doctor and/or a healthcare provider to contact the patient.

In some embodiments, such an arrangement can be used to disable the auto-injector by puncturing the compressed gas container or by another method. In some embodiments, for example, the discontinuity of the electronic trace 17000 on the electronic circuit system can actuate a spring to move the second puncturing mechanism 16025 in the direction shown by the arrow WW in FIG. 81, causing the second puncturing mechanism 16020 to puncture the second frangible seal 16025. In other embodiments, the discontinuity of the electronic trace 1700 can cause the compressed gas cylinder to be moved in a direction substantially opposite the direction shown by the arrow WW in FIG. 81 such that the second puncturing mechanism punctures the second frangible seal. In still other embodiments, the discontinuity of the electronic trace 1700 can change the state of an electronic switch that controls a valve attached to the compressed gas cylinder. In such an embodiment, the electronic circuit system can cause the valve to open when the medicament reaches a certain temperature threshold. This releases the contents of the compressed gas cylinder and disables the auto-injector.

In other embodiments, a medicament delivery device can include a disarming mechanism that is reversible. For example, in some embodiments, an auto-injector can include a disarming mechanism to temporarily and/or reversibly prevent the injection of a vaccine when device has been placed against a portion of the body having characteristics (e.g., tissue density) unsuitable for administration of the vaccine. In such an embodiment, the auto-injector can be enabled (e.g., the disarming mechanism can be reversed) when the auto-injector is positioned against a portion of the body having characteristics suitable for administration of the vaccine. In other embodiments, an auto-injector can temporarily and/or reversibly prevent injection when the device is located outside of a predefined location and/or more than a predetermined distance away from a calibration point. For example, in some embodiments, an auto-injector can have a reversible lock-out feature configured to prevent actuation of the device if the device has been removed from a self-administration vaccine clinic.

Similarly, in some embodiments, an electronic circuit system can include a temperature sensor configured to sense the temperature of the medicament contained within the medicament delivery device such that the electronic circuit system can output an instruction, a status message and/or an electronic signal to a compliance and/or adherence tracking device when the medicament is too cold for effective and/or pain free delivery. For example, in some embodiments, when the medicament is too cold for effective delivery, the electronic circuit system can reversibly prevent the injection of a medicament until the temperature of the medicament has reached a predetermined value. Moreover, the electronic circuit system can also output a message, such as, for example, "MEDICAMENT IS TOO COLD—PLEASE ALLOW TO THE DEVICE TO WARM UNTIL THE READY INDICATOR IS HEARD." Similarly, in some embodiments, the electronic circuit system can output a message and/or a signal based upon the feedback from the temperature sensor, for example, indicating when the medicament will be at the appropriate temperature for delivery. For example, in some embodiments, the electronic circuit system can output a message stating "THE CURRENT MEDICAMENT TEMPERATURE IS XX DEGREES. PLEASE ALLOW THE MEDICAMENT TO STAND AT ROOM TEMPERATURE FOR APPROXIMATELY XX MINUTES BEFORE ADMINISTERING THE DOSE. PLEASE DO NOT MICROWAVE OR OTHERWISE HEAT THE MEDICAMENT." Similarly, in some embodiments, the electronic circuit system can output an electronic signal to a compliance and/or adherence tracking device so that the temperature data can be stored and/or transmitted to a remote device, as described herein. In some embodiments, when the temperature of the medicament reaches an appropriate temperature for delivery, the electronic circuit system can output a message and/or a signal indicating that the medicament is at an appropriate temperature and is ready to be delivered. In such an embodiment, the message and/or the signal can be an audible alarm, a visual indication, a haptic indication and/or the like.

Although the disarming mechanisms described above act on the activation mechanism and/or the electronic circuit system to temporarily or permanently disable the device, in other embodiments, a medicament delivery device can include a housing and a cover that cooperatively prevent the medicament delivery device from being actuated under certain conditions. For example, in some embodiments, the cover 4200' of the auto-injector 4000' can receive a portion of the housing 4110' such that when the auto-injector is at a temperature outside of a certain temperature range, the cover 4200' cannot be removed from the housing 4110'. In this manner, the cover 4200' prevents actuation of the auto-injector 4000'. For example, in some embodiments, the cover retention protrusions 4142' of the housing 4110' and the corresponding openings 4215' on the cover 4200' (see e.g., FIG. 27) are sized, configured and/or constructed from materials having different coefficients of thermal expansion such that an interference fit between the protrusions 4142' and the openings 4215' substantially prevents the cover 4200' from being removed from the housing 4110' when the auto-injector is at a temperature outside of a predefined temperature range. In other embodiments, the cover 4200' can include a locking member constructed, at least in part, from a material that changes phase, shape and/or size when exposed to certain levels and/or types of radiation (e.g., microwave radiation). In this manner, when the auto-injector is exposed to certain levels and/or types of radiation, the locking member can change configurations to substantially prevent the cover 4200' from being removed from the housing 4110'.

Although the "lock-out" covers described above include substantially mechanical and/or chemical mechanisms for maintaining the cover 4200' about the housing 4110', in other embodiments, a cover, container and/or sheath can include an electrical or electro-mechanical mechanism for substantially preventing the housing from being removed from the cover. For example, in some embodiments, an auto-injector can be contained within a cover, sheath and/or container similar to the container 13510 shown and described with reference to FIGS. 70-72, which includes an electronic circuit system. In such embodiments, for example, the cover, sheath and/or container can include a locking mechanism that is controlled and/or actuated by the electronic circuit system of the cover, sheath and/or container.

Figure 84:
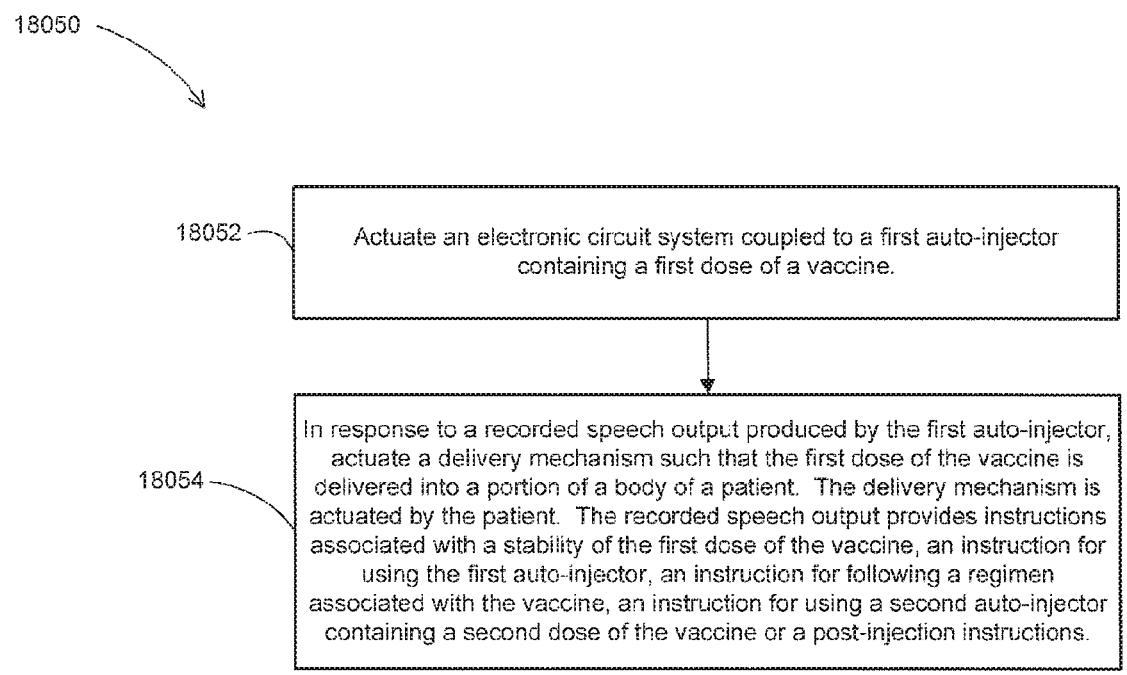
FIG. 84 is a flow chart of a method of self-administering a vaccine according to an embodiment.

FIG. 84 is a flow chart illustrating a method 18050 of self-administering a vaccine, according to an embodiment. The method includes actuating an electronic circuit system coupled to a first auto-injector containing a first dose of a vaccine, at 18052. The auto-injector can be any of the auto-injectors shown and described herein. In response to a recorded speech output produced by the first auto-injector, a delivery mechanism is actuated such that the first dose of the vaccine is delivered into a portion of a body of a patient, at 18054. The delivery mechanism is actuated by the patient and/or a non-medical professional. The recorded speech output includes instructions associated with a stability of the first dose of the vaccine, an instruction for using the first auto-injector, an instruction for following a regimen associated with the vaccine, an instruction for using a second auto-injector containing a second dose of the vaccine and/or a post-injection instruction.

Figure 85:
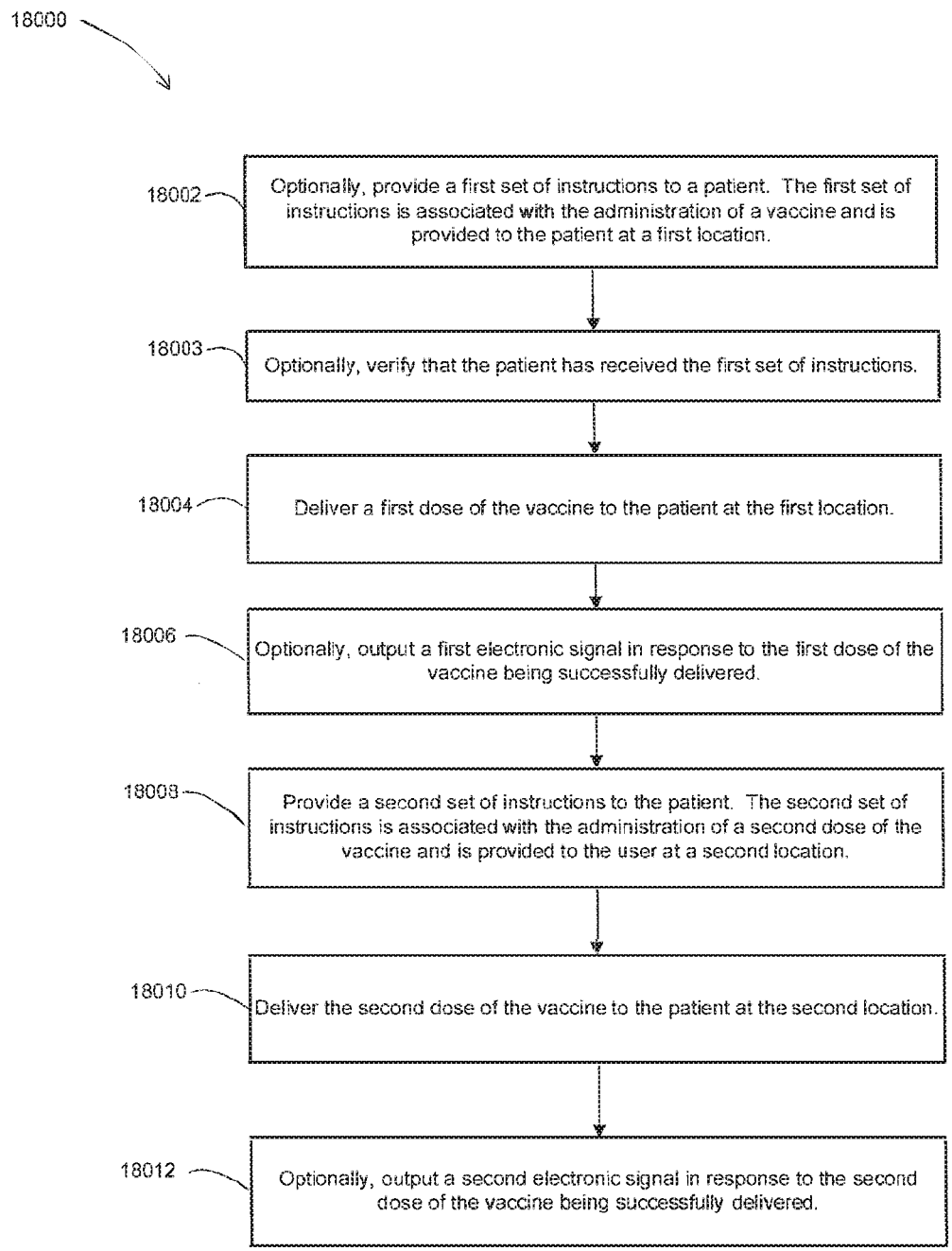
FIG. 85 is a flow chart of a method according to an embodiment.

FIG. 85 is a flow chart illustrating a method 18000 of delivering a vaccine to a patient, according to an embodiment. The method 18000 includes optionally providing a first set of instructions to a patient, 18002. The first set of instructions is associated with the administration of a vaccine and is provided to the patient at a first location. The first location can be any location appropriate for delivery of a vaccine. In some embodiments, for example, the first location can be a doctor's office, a pharmacy, a hospital, a medical clinic and/or the office of a similar medical professional. In other embodiments, the first location is the patient's home, or any other location different than a medical professional's office.

The first set of instructions can include any suitable instruction associated with the administration of the vaccine to the user. In some embodiments, for example, the first set of instructions can include general instructions regarding the vaccination regimen. In such embodiments, the first set of instructions can describe what the vaccine prevents, possible adverse reactions to the vaccine (e.g., anaphylaxis, side effects and/or the like) and/or warnings associated with administering the vaccine. In other embodiments, the first set of instructions can be associated with the use of a medicament delivery device. For example, in some embodiments, the first set of instructions can be similar to the instructions for using an auto-injector, as shown and described herein. In still other embodiments, the first set of instructions can be part of a registration and/or purchase process, as described in further detail herein.

The first set of instructions can be provided to the patient in any manner. In some embodiments, for example, the first set of instructions can be manually provided by a medical professional, such as a doctor, a pharmacist, and/or the like. Said another way, a medical professional can orally and/or through written instructions, instruct a patient in the use of the medicament delivery device and/or the overall vaccination regimen.

In other embodiments, the first set of instructions can be automatically provided to the patient by an electronic device. The electronic device can be operatively coupled to a communication network, as described herein. In some embodiments, the communications network can be similar to the wireless communications network $N_W$, shown and described with reference to FIG. 60. In such embodiments, the electronic device (e.g., any of the devices 7990 shown and described above) within the communications network can receive the first set of instructions via the network $N_W$ from another device (e.g., the server 7991) within the communications network. In this manner the electronic device can provide the first set of instructions to the patient. In some embodiments, for example, the first set of instructions can be sent to the patient's home computer and/or a mobile computing device (e.g., mobile phone), which can then display the first set of instructions on a monitor and/or audibly provide the first set of instructions to the patient. In other embodiments, the first set of instructions can be sent to the medicament delivery device that will be used to deliver a dose of the vaccine.

In some embodiments, the first set of instructions can be automatically provided to the patient by the medicament delivery device that will be used to deliver a dose of the vaccine. In some embodiments, the medicament delivery device can be similar to the auto-injectors described herein (e.g., 1002, 4002, etc.). In other embodiments, the first set of instructions can be automatically provided to the patient by a simulated medicament delivery device (e.g., a trainer). In yet other embodiments, the first set of instructions can be automatically provided to the patient by a container configured to house and/or contain the medicament delivery device. For example, such a container can be similar to the containers shown and described above (e.g., container 14040 shown and described with reference to FIG. 69).

In some embodiments, the first set of instructions can be provided to the patient as part of a vaccination registration and/or purchase process. In some embodiments, for example, a patient can enter registration information into a registration device such as a kiosk and/or computer located at a first location (e.g., doctor's office, pharmacy and/or the like). The registration information can include, for example, insurance information, personal information, medical history information, scheduling information, payment information and/or the like. Once a patient enters the registration information, the registration device (e.g., kiosk, computer, or the like) can provide the patient with the first set of instructions in one or more of the manners described herein. In some embodiments, after the patient has received the first set of instructions, the kiosk can distribute the medicament delivery devices needed to self-administer the vaccine, as described in detail herein. In other embodiments, the kiosk can notify a medical professional that the registration is complete and/or the first set of instructions has been delivered, and that the patient is ready to see the medical professional to receive further instruction and/or the first dose of the vaccine.

The first set of instructions can be provided to the user in any suitable format. In some embodiments, for example, the first set of instructions can be provided to the patient by an electronic signal communicated to an output device included within the kiosk, container, medicament delivery device, and/or the like. Similar to the electronic signals described above, the electronic signal can be associated with, for example, a visual output, an audio output, a haptic output and/or the like. In other embodiments, the first set of instructions can be provided to the user in a non-electronic format, such as by a written instructions sheet.

In some embodiments, the method optionally includes verifying that the first set of instructions was received, 18003. For example, in some embodiments, the first set of instructions can be followed by a series of questions (e.g., a quiz) to verify that the patient has received and/or understood the first set of instructions. In some embodiments, for example, after the first set of instructions is delivered to the patient, the patient must correctly answer a series of questions before she can receive the medicament delivery device or devices containing the vaccine. In other embodiments, after the first set of instructions is delivered to the patient by a container and/or a medicament delivery device, the user must answer a series of questions before the container and/or the medicament delivery device is enabled. Said another way, in some embodiments, the medicament delivery device used to self-administer the vaccine is not enabled until it receives a signal confirming that the user has received and understood the first set of instructions.

The first dose of the vaccine is then delivered to the patient at the first location, 18004. The first dose can be delivered by any method suitable to deliver a vaccine. For example, the first dose can be delivered by a medicament delivery device such as an auto-injector, a pen injector, an inhaler, a transdermal delivery system or the like, such as those described herein. In other embodiments, the first dose of the vaccine can be delivered by a syringe or taken orally. In some embodiments, the medicament delivery device used to deliver the first dose is prefilled with the vaccine. In some embodiments, for example, the medicament delivery device used to deliver the first dose can be a pre-filled, electronic auto-injector of the same type used to deliver a second and/or subsequent doses of the vaccine. In other embodiments, the medicament delivery device can be filled at the first location (e.g., by a medical professional) prior to delivering the vaccine to the patient.

In some embodiments, a medical professional can administer the first dose of the vaccine to the patient. This allows the medical professional to monitor the patient for possible allergic and/or adverse reactions to the vaccine. If a patient does not have an allergic and/or adverse reaction to a first dose of a vaccine, the probability of the patient having an allergic and/or adverse reaction to a subsequent dose of the vaccine may be substantially reduced. Moreover, in certain instances, the medical professional can deliver the first dose using a medicament delivery device of the type that the patient will use to self-administer a second dose and/or subsequent doses. In this manner, the medical professional can provide instructions for and/or a demonstration of the use of the medicament delivery device when the first dose is delivered. In other embodiments, the patient can self-administer the first dose of the vaccine or have someone other than a medical professional administer the vaccine.

A first electronic signal is then optionally output in response to the first dose of the vaccine being delivered, 18006. The first electronic signal can be any signal associated with the actuation of the medicament delivery device used to convey the first dose of the vaccine. The first electronic signal can be any signal of the types shown and described herein. For example, the first electronic signal can be a visual output, an audio output, a haptic output and/or an output configured to be sent to a communications network and/or the like.

In some embodiments, for example, the first electronic signal can be sent via a communications network to a remote location (e.g., a location different than the first location). In this manner, regardless of whether the first dose is delivered by a medical professional or self-administered by the patient, the first electronic signal can be used to monitor the patient's compliance and/or adherence. In some embodiments, the first electronic signal can be sent wirelessly from the medicament delivery device. In other embodiments as described herein, a user can physically and electrically connect the medicament delivery device to a home computer or mobile phone (e.g., an iPhone®) to send the first electronic signal. In some embodiments, the patient can self-monitor their compliance and/or adherence to the prescribed regimen on their home computer or mobile phone.

A second set of instructions is then provided to the patient, 18008. The second set of instructions is associated with the administration of a second dose of the vaccine and is provided to the user at a second location. In some embodiments, the second set of instructions can be automated. Said another way, the second set of instructions can be provided to the user without significant human intervention (i.e., without human intervention other than the user initiating the second set of instructions). In some embodiments, for example, a user can initiate the second set of instructions by pushing a button, removing a medicament delivery device from a kit, beginning the delivery process with one of the medicament delivery devices, and/or the like.

In some embodiments, the second set of instructions can be initiated automatically by a signal, alarm and/or reminder provided by a compliance tracking monitor and/or any other suitable device. The compliance tracking monitor can be any of the types shown and described above (e.g., the compliance and/or adherence tracking monitors described above with reference to FIGS. 61-63 and/or FIG. 69). In such an embodiment, for example, a reminder to administer the vaccine can be triggered at a certain time and/or after a certain time period. For example, when the time period arrives for the patient to receive the second dose of the vaccine, a reminder to administer the vaccine can be sent to the patient. The reminder can be sent to any device connected to a communications network such as, for example, the medicament delivery device that will be used to deliver the second dose, a home computer, a personal digital assistant, a mobile phone and/or the like. In other embodiments, the reminder can be triggered locally on a medicament delivery device, a home computer, personal digital assistant, a mobile phone and/or the like. In this manner, for example, the medicament delivery device does not need to be connected to a communications network to remind the patient. In some embodiments, for example, the reminder can include an audible alarm, a visual alarm or the like configured to notify the user that the time period for administering the vaccine is approaching and/or is ending. The reminder can include and/or initiate the second set of instructions. In this manner the medicament delivery device and/or a vaccination self-administration system can ensure that the patient is administering the vaccine at the prescribed times and/or within the prescribed intervals.

The second set of instructions can be delivered to the patient in any manner described above with respect to the first set of instructions. In some embodiments, for example, the second set of instructions can be automatically provided to the patient by a device within a communications network, such as a computer. In some embodiments, the second set of instructions can be automatically provided to the patient by the medicament delivery device and/or a container of a kit. Similar to the first set of instructions, in some embodiments, the second set of instructions can be provided to the patient by an electronic signal communicated to an output device included within the container, medicament delivery device, and/or the like. Similar to the electronic signals described above, the electronic signal can be, for example, a visual output, an audio output, a haptic output and/or the like. In other embodiments, the second set of instructions can be provided to the user in writing by, for example, a manual.

The second dose of the vaccine is then delivered to the patient at the second location, 18010. In some embodiments, the second location can be a home of the patient and/or a place other than the office of a medical professional. In this manner, the patient need not visit a physician's office to receive the second dose of the vaccine.

The second dose can be delivered by any method suitable to deliver a vaccine. In some embodiments, for example, the patient can self-administer the second dose of the vaccine or have someone other than a medical professional administer the vaccine. For example, the second dose can be delivered by a medicament delivery device such as an auto-injector, a pen injector, an inhaler, a transdermal delivery system or the like, such as those described above. In some embodiments, the second dose of the vaccine can be delivered by the same medicament delivery device used to deliver the first dose of the vaccine. In other embodiments, the second dose of the vaccine can be delivered by a different medicament delivery device than the medicament delivery device used to deliver the first dose of the vaccine. For example, in some embodiments, the medicament delivery device used to deliver the second dose and/or subsequent doses of the vaccine can be part of a kit such as kit 14000 shown and described in FIG. 69. The kit can contain multiple medicament delivery devices containing the first dose and/or any subsequent doses required by the vaccine.

In some embodiments, the medicament delivery device is prefilled with the second dose of the vaccine. In such an embodiment, the patient can receive a medicament delivery device containing the second dose of the vaccine from a medical practitioner at the same time the first dose of the vaccine is administered and/or the first medicament delivery device is received. In other embodiments, the patient can have a medical professional (e.g., a pharmacist) fill the medicament delivery device with the second dose of the vaccine prior to delivering the second dose of the vaccine. In some embodiments, a medical practitioner, such as a pharmacist, can send the medicament delivery device containing the second dose of the vaccine via mail.

A second electronic signal is then optionally output in response to the second dose of the vaccine being delivered, 18012. In some embodiments, the second electronic signal can be any signal that conveys that the second dose of the vaccine has been administered. In such an embodiment, for example, the second electronic signal can be a visual output, an audio output, a haptic output, an output configured to be sent to a communications network and/or the like.

In some embodiments, the second electronic signal can be used to monitor the patient's compliance and/or adherence with the vaccination regimen. In some embodiments, for example, the second electronic signal can be sent through a communications network to a remote location, such as a doctor's office, a hospital, and/or a pharmacy. In some embodiments, the second electronic signal can be sent wirelessly from the medicament delivery device used to deliver the second dose of the vaccine. In other embodiments, a user physically and electrically connects the medicament delivery device to a home computer and/or a mobile computing device (e.g., mobile phone) to send the second electronic signal. In some embodiments, the patient can monitor their compliance on their home computer and/or a mobile computing device (e.g., mobile phone).

Although the method 18000 is shown and described as including delivering a second dose of the vaccine, in other embodiments, any number of doses subsequent to the first dose can be delivered according to the illustrated method. Similarly, although the method 18000 is shown and described as including delivering a second set of instructions, in other embodiments, any number of instructions or sets of instructions subsequent to the first set of instructions can be delivered according to the illustrated method.

Figure 86:
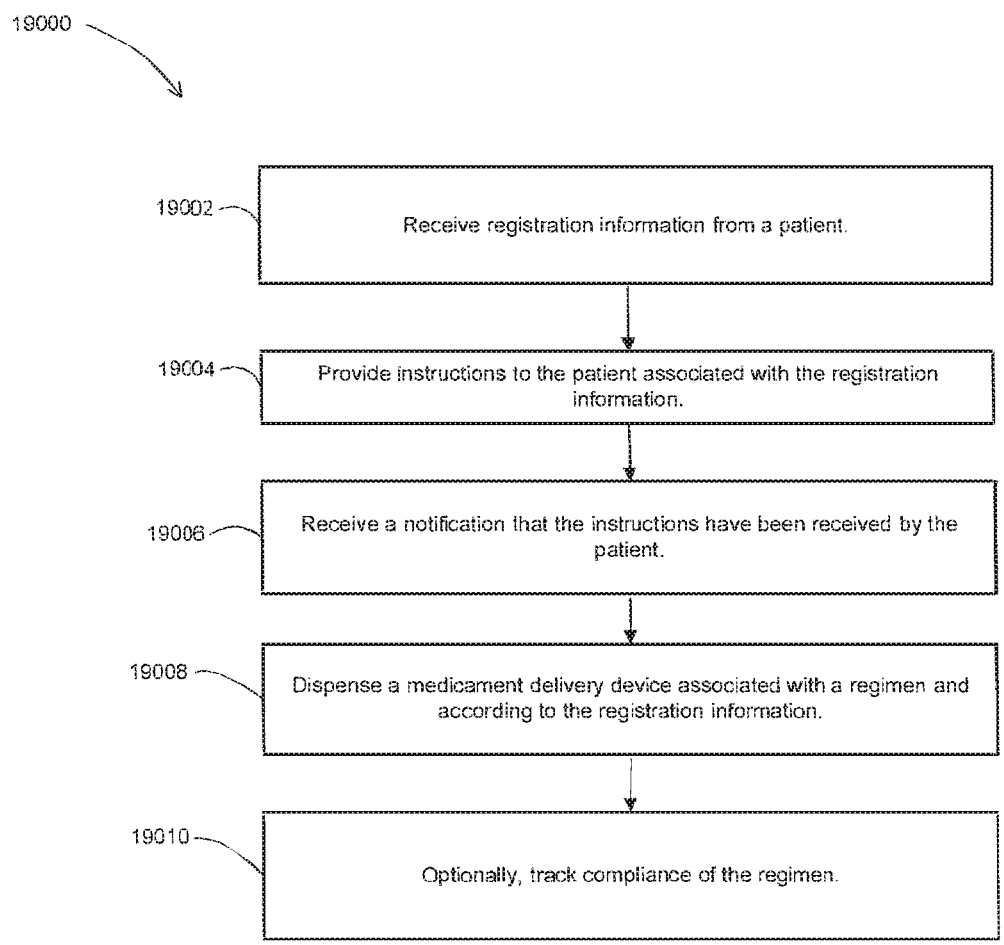
FIG. 86 is a flow chart of a method according to an embodiment.

FIG. 86 is a flow chart of a method 19000 of providing and/or dispensing a medicament delivery device to a patient, according to an embodiment. The method 19000 includes receiving registration information from a patient, 19002. Registration information can be received by any device and/or system of the types shown and described herein. In some embodiments, for example, a patient can enter registration information into a registration device such as a kiosk and/or computer located at a first location (e.g., doctor's office, pharmacy and/or the like), as described above. In other embodiments, the registration device can be a home computer, a personal data assistant, a mobile computing device (e.g., mobile phone) and/or the like connected to a network configured to transmit the registration information to a doctor's office, hospital, pharmacy, insurance company and/or the like. In yet other embodiments, the registration device can be a registration and/or dispensing device, of the type shown and described below with reference to FIG. 87.

In some embodiments, for example, the registration device can be any combination of devices configured to perform the functions as described herein. For example, in some embodiments, the registration device can be the user's cell phone or other portable device that is operatively coupled to a central database that receives and/or stores the registration information. In this manner, the registration information can be received regardless of the physical location of the patient. Similarly stated, in this manner, the registration information can be received without requiring that the patient visit a specific location, such as, for example, a kiosk. The central database can be, for example, a database managed by an entity associated with the medicament and/or therapeutic regimen (e.g., an insurance company, a device manufacturer, a pharmaceutical company, a physician's office or the like). In some embodiments, the central database can include or be linked to multiple different databases, such as for example, a personal health record management database (e.g., Microsoft HealthVault, Google Health Data, or the like).

The registration information can be any information used by a medical practitioner and/or a pharmacist when dispensing a medicament to a patient. In some embodiments, for example, the registration information can include insurance information, personal information, medical history information, scheduling information, payment information and/or the like. In other embodiments, the registration information can include a prescription, an authorization and/or a security code indicating that the patient is authorized to receive the medicament delivery device and/or the medicament associated with the medicament delivery device.

The registration information can be received in any suitable format. For example, in some embodiments, the patient can enter the registration information into an electronic device via a keyboard, a touch screen, a microphone or the like. The patient can enter the registration information in response to a series of prompts and/or questions requesting the registration information. In other embodiments, the registration information can be received electronically via a bar code, a magnetic strip, a proximity chip and/or the like that can be scanned and read by the electronic device receiving the registration information. For example, in some embodiments, the patient's prescription can be included in a secured and/or encrypted (i.e., tamper-proof) bar code configured to be read by an electronic device. In this manner, the registration device can verify that the correct medicament is dispensed to the patient and/or that the patient is authorized to receive the medicament delivery device.

Instructions associated with the registration information, a therapeutic regimen, a vaccination regimen, and/or a medicament delivery device are then provided to the patient, 19004. The instructions associated with the registration information can be provided by any device configured to provide instructions of the types shown and described herein. In some embodiments, the instructions can be automatically provided to the patient by the electronic device that receives the registration information (i.e., the registration device). In other embodiments, the instructions can be automatically provided to the patient by an electronic device different than the registration device. In some embodiments, for example, the instructions can be automatically provided to the patient by the patient's home computer and/or a mobile computing device (e.g., mobile phone).

The instructions can be provided to the user in any suitable format. In some embodiments, for example, the instructions can be provided to the patient via an electronic signal communicated to an output device included within the registration device. Similar to the electronic signals described above, the electronic signal can be associated with, for example, a visual output, an audio output, a haptic output and/or the like. In other embodiments, the first set of instructions can be provided to the user in writing. In some embodiments, for example, the registration device can dispense written instructions (e.g., a manual).

The instructions can be any instructions associated with the registration information, a therapeutic regimen, a vaccination regimen, and/or a medicament delivery device that may be used to deliver the vaccine. In some embodiments, for example, the instructions can include general instructions regarding the vaccination regimen. In such embodiments, the instructions can describe what the vaccine prevents, possible adverse reactions to the vaccine (e.g., anaphylaxis, side effects and/or the like) and/or warnings associated with administering the vaccine. In other embodiments, the instructions can be associated with the use of a medicament delivery device. For example, in some embodiments, the instructions can be similar to the instructions for using an auto-injector, as described herein.

A notification is then received that the patient received the instructions, 19006. The notification can be received by any suitable device associated with the registration process and/or the dispensing of the medicament. In some embodiments, for example, the registration device can receive the notification. For example, in some embodiments, the patient's cell phone can receive the notification and then transmit the notification to a central location via a network as shown and described herein. In other embodiments, a medical practitioner can receive the notification. In yet other embodiments, an electronic device including a database that is accessible by multiple parties (e.g., a physician, an insurance company, a pharmacy or the like) can receive the notification. The database can be any suitable database of the types described above.

The notification can be any notification indicating that the patient has received and/or understood the instructions. In some embodiments, for example, the notification can be a series of questions (i.e., a quiz) to verify that the patient has received and/or understood the first set of instructions. In other embodiments, the notification can be an oral indication provided by the patient (e.g., via a microphone). In yet other embodiments, the notification can be a written form that is signed by the patient.

A self-administered medicament delivery device associated with a regimen is dispensed according to the registration information, 19008. The medicament delivery device can be any of the medicament delivery devices described herein and can be dispensed in any manner. In some embodiments, for example, the self-administered medicament delivery device can be dispensed by the registration device. In such embodiments, the registration device can operate similar to any suitable dispensing device (e.g., a vending machine, an automated teller machine or the like), as described in further detail herein. In still other embodiments, the medicament delivery device can be delivered to the patient via mail.

Although shown and described above as being a self-administered medicament delivery device, any medicament can be dispensed. In some embodiments, for example, pills and/or other medications can be dispensed according to the method 19000.

Compliance and/or adherence of the regimen is then optionally tracked, 19010. Compliance and/or adherence can be tracked by any means capable of showing that the patient has followed the regimen. In some embodiments, for example, the medicament delivery device can output an electronic signal that conveys that a dose of the vaccine has been successfully administered. In some embodiments, for example, the electronic signal can be sent through a communications network to a remote location, such as the registration device, a doctor's office, a hospital, and/or a pharmacy. This enables a medical practitioner to remotely monitor the patient. In some embodiments, the electronic signal can be sent wirelessly from the medicament delivery device used to deliver the dose of the vaccine.

Figure 87:
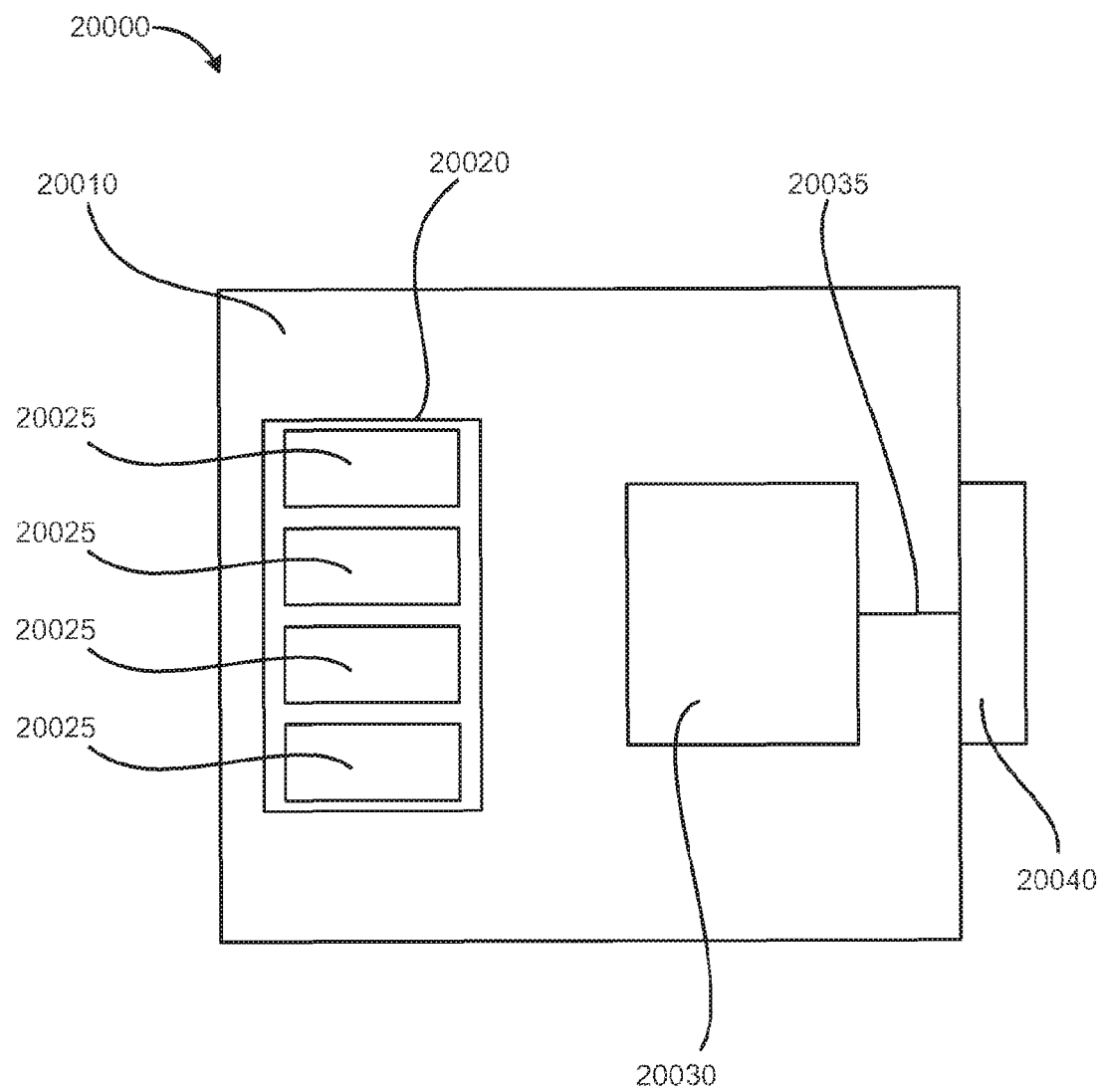
FIG. 87 is a schematic illustration of a medicament delivery device dispenser, according to an embodiment.

FIG. 87 is a schematic illustration of a dispensing device 20000 configured to dispense a medicament delivery device 20025 to a patient. The dispensing device 20000 can dispense the medicament delivery device 20025 according to any suitable method, such as, for example, the method 19000 shown and described above. The dispensing device 20000 includes a housing 20010, a medicament storage container 20020, multiple medicament delivery devices 20025, a processor 20030, an input/output connection 20035 and a user interface device 20040. The housing 20010 can be any housing configured to store and dispense medicament delivery devices.

The medicament delivery devices 20025 are stored within the medicament storage container 20020. The medicament delivery devices 20025 can be any of the medicament delivery devices described herein. In some embodiments, the medicament storage container 20020 can include various types of medicament delivery devices. In some embodiments, for example, the medicament storage container 20020 includes auto-injectors, pen injectors, inhalers, transdermal delivery systems and/or the like. In other embodiments, the medicament storage container 20020 can include multiple medicament delivery devices 20025 of the same type, but that contain different medicaments and/or dosages of a medicament.

The medicament contained within the medicament delivery devices 20025 can be any medicament. In some embodiments, for example, the dispensing device dispenses prescription medication. In other embodiments, the dispensing device dispenses behind-the-counter medication (i.e., medication that does not require a prescription, but that has certain restrictions on its distribution), over-the-counter medication, and/or the like. Although the medicament is shown as being contained within a medicament delivery device 20025, in other embodiments, the medicament can be contained within any container that is suitable for being dispensed via the dispensing device 20000 (pill bottles, vials, blister packs or the like).

The dispensing device 20000 can be placed in any suitable location. For example, in some embodiments, the dispensing device 20000 can be placed at a doctor's office, pharmacy, vaccination clinic or other location at which a medical professional is typically present. In other embodiments, however, the dispensing device 20000 can be placed at a location at which a medical professional is not present, such as, for example, a shopping center, stadium or the like. In this manner, the dispensing device 20000 can facilitate self-administration of medicaments, such as, for example, the self-administration of a vaccine as a part of a mass vaccination program.

The medicament storage container 20020 can be any suitable storage container that can store the medicament delivery devices 20025. In some embodiments, for example, the medicament storage container 20020 can monitor and/or maintain the temperature of the medicament in the medicament delivery devices. This ensures that the medicament to be dispensed is not ineffective and/or harmful because of exposure to a temperature above a predetermined threshold, as described in further detail herein. In some embodiments, for example, when the temperature within the medicament storage container 20020 exceeds a threshold value for at least a predetermined time period, the processor 20030 can produce a signal indicating that the medicament may be compromised. Such a signal can be transmitted, for example, to a remote location (e.g., a pharmacy) to prompt a user to retrieve the compromised medicament, determine the cause of the increase in temperature or the like. In this manner, the dispensing device 20000 can ensure that compromised medicaments are not dispensed. Similarly, in some embodiments, the medicament storage container 20020 can track the expiration date of the medicament delivery devices 20025 contained therein, as described above with reference to the containers described herein.

The user interface device 20040 is coupled to and/or contained within the housing 20010 and is operatively coupled to the processor by the input/output connection 20035. The user interface device 20040 can be any device configured to provide and/or receive information (e.g., registration information) from the patient and/or provide information to the user regarding the medicament delivery device 20025. In some embodiments, for example, the user interface device can be a touch-screen LCD monitor. In other embodiments, the user interface device can include a monitor, such as an LCD, CRT, or the like, and a user input device such as a mouse, a keyboard, a microphone, a fingerprint reader, a card reader, and/or the like.

The information received by the user interface device 20040 from the patient can be any information associated with receiving a medicament delivery device 20025. In some embodiments, for example, the information can be registration information including, for example, insurance information, personal information, medical history information, scheduling information, payment information, prescription information, other information that identifies the medicament the patient will be receiving, identifies the identity of the patient, and/or the like. In some embodiments, the user interface device 20040 can receive biometric information associated with the patient to verify the identity of the patient. In some embodiments, a prescription can include a bar code, a magnetic strip, a proximity chip and/or the like that can be scanned and read by the registration device. In this manner, the registration device can verify that the correct medicament is dispensed to the patient and/or that the prescription is valid. In other embodiments, for example, the information can be answers to a series of questions (e.g., a quiz) to verify that the patient has received and/or understands how to operate the medicament delivery device.

Similarly, the information provided to the patient by the user interface device 20040 can be any information associated with a therapeutic regimen, a vaccination regimen, the medicament delivery device 20025 and/or the medicament within the medicament delivery device. In some embodiments, for example, the information provided to the patient can be questions regarding registration, instructions on how to use the medicament delivery device, questions regarding the patient's understanding of how to use the medicament delivery device, information regarding the medicament such as possible side effects and/or allergic reactions, and/or the like.

In some embodiments, the information provided to the patient by the user interface device 20040 can be any information associated with the patient's personal medical history, payment history and/or transactional history. For example, in some embodiments, the information provided to the patient can be a summary of all recent prescriptions dispensed to the patient by a particular pharmacy. In other embodiments, the information provided to the patient can be a summary of the patient's medical history as provided to a particular doctor. In yet other embodiments, the information provided to the patient can be a summary of the patient's insurance coverage as related to the transaction. For example, in some embodiments, the information provided to the patient can include the amount of the transaction cost that will be paid by the patient's insurance company and the amount of the transaction cost for which the patient is responsible.

The input/output connection 20035 can be any device configured to electrically couple the user interface device 20040 with the processor 20030. In some embodiments, for example, the input/output connection 20035 is a cable such as a D-sub cable, a High-Definition Multimedia Interface (HDMI) cable, a digital visual interface (DVI) cable and/or the like. In other embodiments, the input/output connection 20035 is an electrical trace on a printed circuit board.

The processor 20030 can be any processor configured to receive and process information from the user interface device 20040. The processor 20030 is also configured to send data to the user interface device 20040. The processor 20030 receives information from the patient via the user interface device 20040 and the input/output connection 20035 and causes a medicament delivery device to be dispensed to the patient, as further described herein. In some embodiments, the processor 20030 includes or is coupled to a network interface device, such as, for example, a wireless transceiver. In this manner, the dispensing device 20000 can be operatively coupled to a communications network, as described herein.

In use, the dispensing device 20000 operates similar to the method 19000 shown and described in relation to the flow chart of FIG. 86. Specifically, a patient can interact with the user interface device 20040 to input and/or receive information related to dispensing a medicament delivery device. In response to the interaction between the user interface device 20040 and the patient, the dispensing device 20000 dispenses a medicament delivery device, or a kit containing multiple medicament delivery devices to the patient.

While the dispensing device 20000 is shown as dispensing medicament delivery devices, in other embodiments, the dispensing device can dispense any medication. In some embodiments, for example, the dispensing device can dispense pills and/or the like.

While the dispensing device 20000 is shown and described above as dispensing a medicament delivery device, in other embodiments, the dispensing device 20000 can provide a location where the patient can self-administer the medicament within the dispensed medicament delivery device. For example, the dispensing device 20000 can be disposed at and/or provide a location for the delivery of a dosage of a vaccination, as described above with reference to the method 18000. The location can be, for example, the first location (e.g., a doctor's office) and/or the second location (e.g., the patient's home), as described above with reference to the method 18000.

In some embodiments, the dispensing device 20000 can dispense and/or provide medical accessories (e.g., sanitary wipes, bandages, latex gloves or the like) associated with the use of the medicament delivery device and/or the administration of a dosage of the medicament. In this manner, the dispensing device 20000 can facilitate the use of and/or provide a suitable location for the use of the dispensed medicament delivery device. In some embodiments, the dispensing device 20000 can include a waste receptacle and/or a waste container (not shown in FIG. 87) configured to receive the medicament delivery device and/or the medical accessories after the medicament delivery device has been used. In this manner, the dispensing device 20000 can minimize the spread of biohazard waste and/or minimize the hazards (e.g., needle sticks) associated with used medicament delivery devices. In some embodiments, the waste receptacle can track receipt of the used medicament delivery device.

In some embodiments, the dispensing device 20000 can transmit a signal to a device within a communications network indicating that a medicament delivery device has been dispensed and/or received within a waste receptacle. Such a signal can be any communication signal of the types shown and described herein. In this manner, the dispensing device 20000 can track the patient's compliance and/or adherence in using the dispensed medicament delivery device. In some embodiments, for example, the dispensing device 20000 can transmit a signal to a device within a communications network associated with the actuation of the dispensed medicament delivery device, as described above.

In some embodiments, the user interface device 20040 of the dispensing device 20000 can include a communications portal that allows the patient to communicate with a human being at any time during the dispensing of and/or use of the medicament delivery device. For example, in some embodiments, the user interface device 20040 can include a phone with which the patient can communicate with a medical health professional (e.g., a doctor or a pharmacist), an emergency medical technician (e.g., via a 911 call) or the like at any time during the transaction. In other embodiments, the user interface device can include a monitor and keyboard with which the patient can communicate with a medical health professional via a "live on-line chat."

Figure 88:
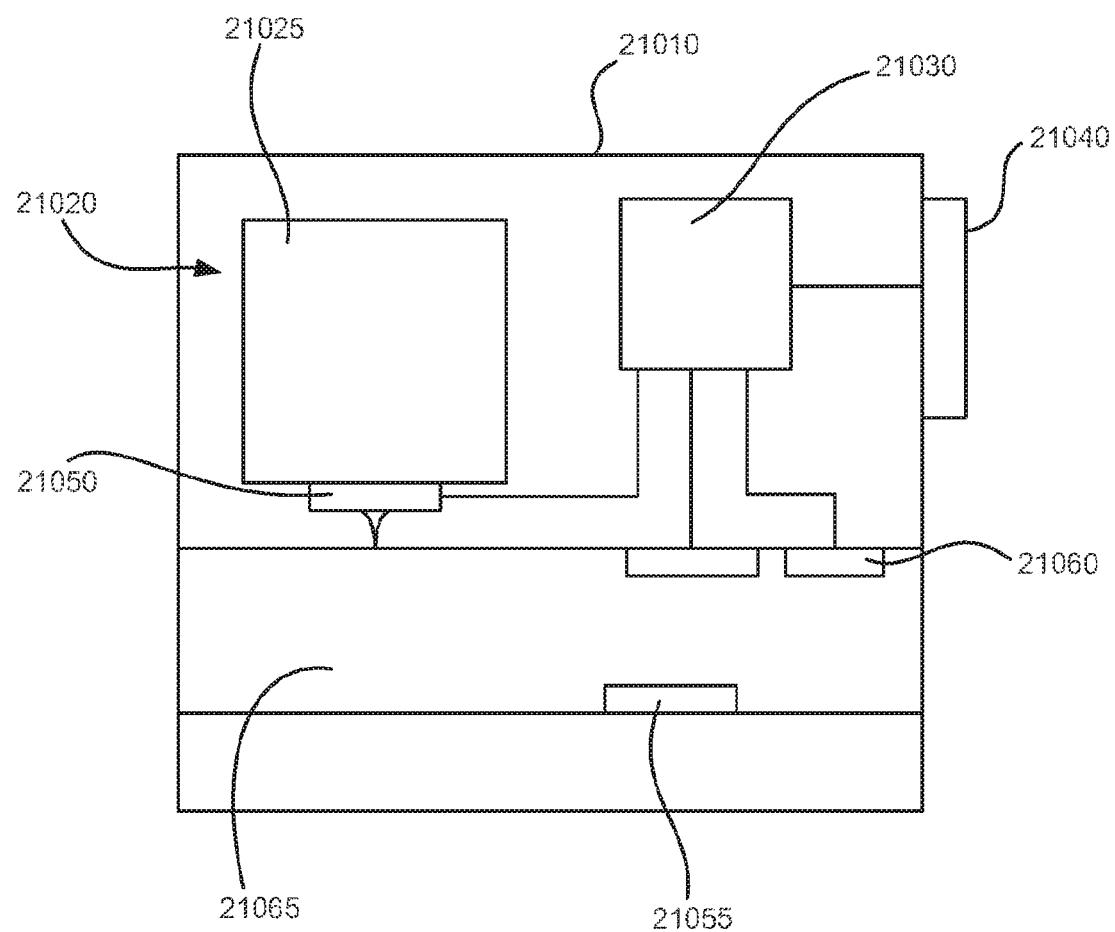
FIG. 88 is a schematic illustration of a medicament dispenser according to an embodiment.

Although the dispensing device 20000 is shown and described above as dispensing a medicament delivery device and/or providing a location for the use of the medicament delivery device, in other embodiments, a dispensing device can automatically and/or semi-automatically administer a vaccination or other medicament. For example, FIG. 88 is a schematic illustration of a dispensing device 21000 according to an embodiment. The dispensing device 21000 includes a housing 21010, a medicament delivery module 21020, a processor 21030, and a user interface device 21040. The housing 21010 can be any housing configured to store and dispense a medicament as described herein.

The housing 21010 includes an administration portion that includes a sensor 21060 and a restraining mechanism 21050, and defines an opening 21065. The opening 21065 is configured to receive a portion of a patient's body within which the medicament is to be delivered. For example, in some embodiments, the opening 21065 is configured to receive a portion of the patient's leg such that the medicament can be delivered into the portion of the patient's leg via an intramuscular injection.

The sensor 21060, which is operatively coupled to the processor 21030, is configured to produce a signal associated with a bodily characteristic when the portion of the patient's body is disposed within the opening 21065. For example, in some embodiments, the sensor 21060 is configured to produce a signal associated with the patient's pulse and/or blood pressure when a portion of the patient's leg is disposed within the opening 21065. In other embodiments, the sensor 21060 is configured to produce a signal associated with an impedance of the patient's bodily tissue when a portion of the patient's leg is disposed within the opening 21065. In this manner, the sensor can provide input to the processor 21030 regarding the patient's health and/or the portion of the patient's body within which the medicament is to be delivered. In yet other embodiments, the sensor 21060 is configured to measure a variable associated with bodily tissue (e.g., the circumference and/or thickness of the portion of the patient's body where the medication is being administered) when said portion is disposed within opening 21065. In this manner, the sensor can provide input to the processor 21030 regarding the measurement of the portion of the patient's body where the drug is being administered to ensure that the medicament is delivered in the correct location (e.g., intramuscular versus subcutaneous administration).

The restraining mechanism 21055 is configured to limit movement of the portion of the patient's body when the portion of the patient's body is disposed within the opening 21065. In this manner, when the medicament is being delivered into the portion of the patient's body, the patient cannot inadvertently move, thereby causing improper delivery of the medicament and/or harm to the portion of the patient's body. The restraining mechanism 21055 can be any suitable mechanism for limiting the movement of a portion of a body within the opening 21065. In some embodiments, for example, the restraining mechanism 21055 can be an inflatable member configured to expand within the opening 21065, thereby constricting the size of the opening 21065 to limit movement of a portion of the body within the opening 21065.

The restraining mechanism 21050 is operatively coupled to the processor 21030. In this manner, the restraining mechanism 21050 can be actuated automatically when the portion of the patient's body is disposed within the opening 21065 in the desired position and/or orientation. For example, in some embodiments, the restraining mechanism 21050 can be actuated automatically after the patient has answered a prompt requesting confirmation that the patient is ready to begin the medicament delivery. In other embodiments, the restraining mechanism 21050 can be actuated automatically in response to a signal from the sensor 21060 indicating that the portion of the patient's body is positioned properly within the opening 21065.

The medicament delivery module 21020 is disposed within the housing 21010 and includes a storage container 21025 and an actuator 21050. The storage container 21025 is configured to store any suitable medicament of the types described herein. In some embodiments, the storage container 21025 can contain multiple different types of medicaments. In some embodiments, the storage container 21025 can include pre-filled containers of medicament, such as, for example, any of the containers, vials, ampules and/or cartridges shown and described herein. In this manner, the container 21025 can contain medicaments in different predetermined dosages.

The storage container 21025 can be any suitable storage container that can store the medicaments described herein. In some embodiments, for example, the storage container 21025 can monitor and/or maintain the temperature of the medicament. This ensures that the medicament to be dispensed is not ineffective and/or harmful because the medicament has been exposed to a temperature above a predetermined threshold, as described in further detail herein. In some embodiments, for example, when the temperature within the storage container 21025 exceeds a threshold value for at least a predetermined time period, the processor 21030 can produce a signal indicating that the medicament may be compromised. Such a signal can be transmitted, for example, to a remote location (e.g., a pharmacy) to prompt a user to retrieve the compromised medicament, determine the cause of the increase in temperature or the like. Similarly, in some embodiments, the storage container 21025 and/or the processor 21030 can track the expiration date of the medicament contained within the storage container 21025.

The actuator 21050 can be any suitable actuator for initiating the delivery of the medicament into a patient's body. In some embodiments, for example, the actuator 21050 can include a needle configured to be moved by an energy storage member to convey the medicament into the patient's body. For example, in some embodiments, the actuator 21050 can include a compressed gas container, a movable member and a needle of the types shown and described above. In other embodiments, the energy storage member can include a spring. Although the actuator 21050 is shown as including a needle through which the medicament can be delivered, in other embodiments, the actuator 21050 can include any suitable device for delivering the medicament into the body of the patient, such as for example, a nozzle, a transdermal patch or the like.

As shown in FIG. 88, the actuator 21050 is operatively coupled to the processor 21030. In this manner, the processor 21030 can initiate the actuator 21050, either automatically (e.g., in response to a signal from the sensor 21060) or semi-automatically (e.g., in response the patient providing an input to the processor 21030).

The user interface device 21040 can be any device configured to provide and/or receive information (e.g., input from the sensor 21060, registration information or the like) from the patient and/or provide information to the patient regarding the medicament delivery and/or the dispensing device 21000. In some embodiments, for example, the user interface device 21040 can include a touch-screen LCD monitor. In other embodiments, the user interface device 21040 can include a monitor, such as an LCD, CRT, or the like, and a user input device such as a mouse, a keyboard, a microphone, a fingerprint reader, a card reader, and/or the like.

In use, the dispensing device 21000 can deliver a medicament directly into the patient's body. The patient can first receive instructions and/or provide registration information via the user interface 21040, as described above. After the dispensing device 21000 has verified the patient information, the appropriate dosage and/or any other desired information, the dispensing device 21000 can provide instructions and/or information to the patient, as described above. The instructions can include, for example, instructions on how to use the dispensing device 21000 to automatically or semi-automatically administer a dosage of a medicament into the patient. In some embodiments, for example, the instructions can include an audible instruction stating "REGISTRATION IS NOW COMPLETE, TO PROCEED WITH THE DELIVERY, PLEASE INSERT YOUR THIGH INTO THE OPENING BELOW THE TOUCH SCREEN."

The user can then insert a portion of the body (e.g., an arm, a thigh, a finger or the like) into the opening 21065 of the housing 21010. The sensor 21060 can provide feedback to the processor 21030 regarding the location of the portion of the body within the opening 21065, a characteristic of the patient's body or the like, as described above. When the portion of the body is disposed within the opening 21065 in a desired location and/or orientation, the restraining mechanism 21055 can limit the movement of the portion of the body within the opening 21065.

The delivery of the medicament can occur either automatically or via input by the patient. In some embodiments, for example, the actuator 21050 can be triggered automatically by the processor 21030 in response to an input from the sensor 21060. In other embodiments, after the sensor 21060 has verified the positioning of the portion of the body within the opening 21065, the actuator 21050 can be triggered via patient input from the user interface 21040.

The processor 21030 can then trigger the actuator 21050 move a medicament delivery member (e.g., a needle, a nozzle, or the like) into contact with a portion of the patient's body. The actuator 21050 can then initiate the delivery of the medicament via the medicament delivery member.

While various embodiments of the invention have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

For example, although the components included in the electronic circuit system 4920 (e.g., the microprocessor 4950, the LEDs 4958A and 4958B or the like) are shown and described as being operatively coupled by electrical conductors 4934, in other embodiments, the components can be operatively coupled without being physically connected. For example, in some embodiments, at least a portion of the components included in an electronic circuit system can be inductively coupled. In other embodiments, at least a portion of the components included in an electronic circuit system can be evanescently coupled.

Although the switches 4972A and 4972B are shown and described as being "tear-through" switches that are monolithically formed from the electrical conductors 4934, in other embodiments, a switch can be formed separately from the electrical conductors 4934. For example, in some embodiments, an electrical circuit system can include a series of first electrical conductors having a first set of characteristics (e.g., the width, height, material from which the conductor is fabricated or the like) and a switch constructed from a second electrical conductor having a second set of characteristics different than the first set of characteristics. In other embodiments, a switch can be a separate component, such as, for example, a microswitch, that is mounted to the printed circuit board. In yet other embodiments, an electrical circuit system can include a "pop-out" switch that includes a biasing member to bias the switch in a predetermined state. In yet other embodiments, an electrical circuit system can include a switch that is disposed at a location other than on a printed circuit board.

Similarly, although the switches 4972A and 4972B are shown and described as being irreversibly movable from a first state to a second state, in other embodiments, a switch can be reversibly movable between a first state and a second state. Moreover, in yet other embodiments, a switch can have more than two distinct states.

Although the actuators 4732, 4539 are shown and described as being configured to move in a direction substantially parallel to the surface of the substrate 4924, in other embodiments, an actuator can be configured to actuate an electronic circuit system by moving in any direction. For example, in some embodiments a circuit actuator can be moved in a direction substantially normal to a portion of an electronic circuit system.

Similarly, although the actuators 4732, 4539 are shown and described as actuating the switches 4972A and 4972B by tearing and/or deforming a portion of the substrate 4924, in other embodiments, a switch can be moved from a first state to a second state without deforming the substrate. For example, in some embodiments, an electronic circuit system can include a printed circuit board having a substrate and a frangible switch tab disposed on the substrate. An electrical conductor and/or a switch can be disposed on the frangible switch tab, such that when the switch tab is removed from the substrate the switch is moved from a first state to a second state. In this manner, the switch can be actuated without tearing and/or deforming a portion of the substrate.

Although the actuators 4732, 4539 are shown and described as being included on the safety lock 4710 and the base 4520, respectively, in other embodiments, the actuators can be included on any component of a medicament delivery device. For example, in some embodiments, an auto-injector can include a start button having an actuator configured to actuate an electronic circuit system. In other embodiments, an auto-injector can include a movable member configured to move a medicament container and/or a needle within a housing of the auto-injector, the movable member including an actuator configured to actuate an electronic circuit system.

Although the safety lock 4710 is shown and described as being removed from the housing 4110 of the auto-injector 4002 when in its second position, in other embodiments, a safety lock can remain coupled to the housing of an auto-injector when in its second position. For example, in some embodiments, a safety lock can be moved from its first position to its second position by rotating a portion of the safety lock.

Certain components of the auto-injector 4002 are shown and described as being coupled together via protrusions and mating openings. The protrusions and/or openings can be disposed on any of the components to be coupled together and need not be limited to only a certain component. For example, the safety lock 4710 is shown and described as including an actuator 4732 having a protrusion 4730 configured to be received within an opening 4928A defined by the substrate 4924. In some embodiments, however, the protrusions can be disposed on the substrate 4924 and the mating openings can be defined by the actuator 4732. In other embodiments, such components can be coupled together in any suitable way, which need not include protrusions and mating openings. For example, in some embodiments, an actuator can be operatively coupled to an actuation portion of a substrate via mating shoulders, clips, adhesive or the like.

Although the energy storage member included within the activation mechanism 4500' is shown and described as being a pressurized gas container 4570', in other embodiments, the activation mechanism 4500' can include any suitable energy storage member. For example, in some embodiments, an energy storage member can include a spring, a gas spring, a battery, a capacitor, a container including separate components that, when mixed, produce a pressurized fluid, or the like.

Although the medicament containers are shown and described above as having various shapes and/or configurations, in other embodiments, a medicament delivery device can include any suitable medicament container. For example, in some embodiments, a medicament container can be a vial, a cartridge, a pre-filled syringe, an ampule, or any other suitable container for storing a vaccine or medicament. In other embodiments, a medicament container can be configured to store a lyophilized vaccine and a diluent for reconstituting the vaccine. In yet other embodiments, a medicament delivery device can include more than one medicament container.

Although the medical system 14000 shown as including a container 14040, a compliance tracking device 14010 and multiple medical injectors 14002A-14002G, each having at least one electronic circuit system (see e.g., electronic circuit systems 14050, 14020, 14080 and 14920), in some embodiments, a medical system can include only a container having multiple medical injectors. In such embodiments, the container can be a tray or other device configured to hold the medical injectors. The container can also perform the functions of the compliance monitoring device 14010, as described above. Moreover, in some embodiments, a medical injector can include a sheath similar to sheath 14070, wherein the sheath performs the electronic functions of the compliance monitoring device 14010 and/or the container 14050, as described above.

Although the electronic circuit systems are shown and described above as outputting recorded speech in English, in other embodiments, the electronic circuit system can output recorded speech in any language. In yet other embodiments, the electronic circuit system can output recorded speech in multiple languages.

Although some of the electronic circuit systems are shown and described above as including a proximity sensor, in other embodiments, an electronic circuit system can include any suitable sensor for providing feedback to the electronic circuit system. For example, in some embodiments, an electronic circuit system can include a pressure sensor configured to sense the internal gas pressure within a gas-powered auto-injector. In this manner, the electronic circuit system can output an instruction, a status message, and/or an electronic signal to a compliance tracking device when the internal gas pressure crosses a predetermined threshold. For example, in some embodiments, when the internal gas pressure rapidly increases, the electronic circuit system can output a message, such as, for example, "Internal gas chamber has been successfully punctured—injection is in process."

Although the electronic circuit systems (e.g., the electronic circuit system 4900') are shown and described above as having a single battery assembly (e.g., battery assembly 4962') configured to selectively supply power to the electronic circuit system, in other embodiments, an electronic circuit system can have more than one power source. For example, in some embodiments, an electronic circuit system can include a first power source configured to provide power to a first portion of an electronic circuit system to produce a recorded speech output, a light output, a wireless signal output or the like when the device is in use. As described above the first power source can be selectively isolated from the electronic circuit system to prevent discharge of the energy during storage of the device. In such embodiments, the electronic circuit system can also include a second power source configured to provide power to a second portion of the electronic circuit system such that the second portion of the electronic circuit system can monitor the temperature history of the vaccine during storage of the device.

Although the medicament delivery device 5002 is shown and described above as having an electronic circuit system 5920 including a first RFID tag 5921 and a second RFID tag 5923, in other embodiments, a medicament delivery device can have an electronic circuit system 5920 including only one RFID tag. Similarly, although the signal S6 output by the first RFID tag 5921 is shown and described above as having a characteristic different from the signal S7 output by the second RFID tag 5923, in other embodiments, the signal S6 can be the same as the signal S7.

As discussed above, an electronic signal can be associated with a message instructing the user on post-injection disposal, safety procedures, post-injection medical treatment or the like. Such a message can state, for example, "THE DOSAGE OF XXX HAS BEEN SUCCESSFULLY ADMINISTERED. PLEASE SEEK FURTHER MEDICAL ATTENTION FROM YOUR HEALTHCARE PROVIDER IF THE FOLLOWING SYMPTOMS OCCUR . . . . " In some embodiments, for example, an HPV vaccine is self-administered to a patient using a medicament delivery device. Subsequent to the patient self-administering the vaccine, the electronic signal can instruct the patient to contact a medical professional or emergency medical services (such as 911) if the patient experiences symptoms of an allergic reaction to the vaccine such as difficulty breathing, wheezing (bronchospasm), hives, a rash, itching burning, a fever and/or the like.

In other embodiments, a kit can include multiple medicament delivery devices each containing a dose of a medicament (such as an HPV vaccine). Such a kit can include three medicament delivery devices corresponding to the three doses of the HPV vaccine. An initial dose of the HPV vaccine is followed up by a second dose two months after the initial dose is administered, and a third dose six months after the initial dose is administered. In some embodiments, the first dose is administered by a medical practitioner. In such an embodiment, the medical practitioner trains the patient on the use of the medicament delivery device so the patient can self-administer the subsequent doses. In other embodiments, a pharmacy delivers the kit to the patient and the patient self-administers the first dose of the vaccine using audio instructions of the medicament delivery device and/or printed instructions contained within the kit. The second and third doses can then be self-administered by the patient. As discussed above, compliance and/or adherence can be monitored by the patient and/or a medical practitioner through electronic circuit signals.

In some embodiments, a kit also includes a medicament delivery device containing epinephrine. In such an embodiment, an electronic signal associated with a message instructing the user on post-injection disposal might state, for example, "THE DOSAGE OF XXX HAS BEEN SUCCESSFULLY ADMINISTERED. PLEASE USE THE MEDICAMENT DELIVERY DEVICE CONTAINING EPINEPHRINE IF THE FOLLOWING SYMPTOMS OCCUR . . . . " If, for example, the medicament is a dose of a medication known to cause severe allergic reactions in a portion of the patient population, the symptoms might be difficulty breathing, wheezing (bronchospasm), hives, a rash, and/or the like. Including a medicament delivery device containing epinephrine in the kit allows a patient to self-administer a dose of epinephrine to combat a possible allergic reaction to the vaccine.

Although some of the medicament delivery devices are shown and described above as delivering various vaccines, such as HPV, in other embodiments a medicament delivery device can be used to deliver any vaccine, such as, for example, vaccines for influenza (including H5N1 and other variants). In some embodiments, a medicament delivery device can be used to deliver any treatment and/or vaccine associated with pandemic preparedness. In some embodiments, for example, the medicament delivery device can be used to deliver a Tetnaus-Diphtheria-Pertussis (TDP) vaccine, a hepatitis A vaccine, a hepatitis B vaccine, a HiB vaccine, an influenza vaccine, a Measles-Mumps-Rubella (MMR) vaccine, a polio (inactivated) vaccine, a pneumococcal vaccine, a rotavirus vaccine, a varicella (chicken pox) vaccine, a meningococcus vaccine, various vaccines for travelers and/or the like.

In some embodiments, a medicament delivery device can include an electronic circuit system having a thermoelectric cooler. In this manner, the device can maintain and/or regulate a temperature of the device and/or the medicament contained therein.

Although various embodiments have been described as having particular features and/or combinations of components, other embodiments are possible having a combination of any features and/or components from any of embodiments where appropriate. For example, in some embodiments, a medicament delivery device can include an electronic circuit system configured to produce a first electronic signal when the device is actuated, similar to the medicament delivery device 3002, and a second electronic signal based upon the impedance between various portions of the device, similar to the medicament delivery device 15002.

What is claimed is:
1. An apparatus, comprising:
 a container including a side wall defining a volume within which a medical injector can be disposed, a shape of the volume corresponding to a shape of the medical injector, the container including a lid movably coupled to the container, the lid configured to cover the volume when the lid is in a first position, the volume being exposed to allow access to the medical injector when the lid is in a second position; and an electronic circuit system coupled to the container, the electronic circuit system including a first switch, a second switch, a light output device, an audible output device, and a wireless communication module, the first switch configured to be actuated when the lid is moved from the first position to the second position, the second switch disposed within the volume such that the second switch extends from the side wall of the container, the medical injector in contact with a portion of the side wall of the container when the medical injector is within the volume, the second switch configured to move from a first state to a second state when the medical injector is removed from within the volume, the electronic circuit system configured to transmit, via the wireless communication module, a first wireless signal, the first wireless signal being a short-range radio frequency signal indicating that the container is within a transmission range of a remote computing device, the electronic circuit system configured to transmit, via the wireless communication module, a second wireless signal in response to the second switch moving from the first state to the second state, the second wireless signal being a short-range radio frequency signal indicating that the medical injector has been removed, the electronic circuit system configured to receive, via the wireless communication module, a third wireless signal and produce, in response to the third wireless signal, at least one of a visual output from the light output device or an audible output from the audible output device.

2. The apparatus of claim 1, wherein the medical injector is a single-use autoinjector, the shape of the single-use autoinjector being non-circular.

3. The apparatus of claim 1, wherein the lid is hingedly coupled to the container.

4. The apparatus of claim 1, wherein the wireless communication module includes at least one of a microprocessor, a transmitter, a receiver, a transceiver, or a radio chipset.

5. The apparatus of claim 1, wherein the second wireless signal includes information that, when received by the remote computing device, causes the remote computing device to send a location signal associated with a location associated with the container.

6. The apparatus of claim 1, wherein the second wireless signal includes information that, when received by the remote computing device, causes the remote computing device to output an instruction associated with the medical injector.

7. The apparatus of claim 1, wherein the electronic circuit system includes a temperature sensor, the electronic circuit system configured to transmit, via the wireless communication module, a fourth wireless signal, the fourth wireless signal being a short-range radio frequency signal indicating a temperature of the container.

8. The apparatus of claim 1, wherein at least one of the first wireless signal or the second wireless signal is encrypted.

9. The apparatus of claim 1, wherein the second switch is configured to be reversibly moved between the first state and the second state.

10. The apparatus of claim 1, wherein the second switch includes a biasing member configured to bias the second switch towards one of the first state or the second state.

11. The apparatus of claim 1, wherein the container defines the volume within which one and only one medical injector can be disposed, the apparatus further comprising:

the medical injector, the medical injector being an autoinjector including an injector housing and a medicament container containing epinephrine disposed within the injector housing, the injector housing in contact with the portion of the side wall of the container when the medical injector is within the volume, a length of the portion of the side wall being greater than a length of the injector housing, the first wireless signal and the second wireless signal each being transmitted independently from an actuation of the autoinjector, at least one of the first wireless signal or the second wireless signal includes a unique identification associated with the autoinjector.

12. The apparatus of claim 11, wherein the second switch is configured to be reversibly moved between the first state and the second state.

13. An apparatus, comprising:

a container defining a volume within which a medical injector can be disposed, a shape of the volume corresponding to a shape of the medical injector, the container including a lid movably coupled to the container, the lid configured to cover the volume when the lid is in a first position, the volume being exposed to allow access to the medical injector when the lid is in a second position; and an electronic circuit system coupled to the container, the electronic circuit system including a switch, a light output device, an audible output device, a temperature sensor, and a wireless communication module, the switch configured to move from a first state to a second state when the medical injector is removed from the volume, the electronic circuit system configured to transmit, via the wireless communication module, a first wireless signal, the first wireless signal being a short-range radio frequency signal indicating that the container is within a transmission range of a remote computing device, the electronic circuit system configured to transmit, via the wireless communication module, a second wireless signal in response to the switch moving from the first state to the second state, the second wireless signal being a short-range radio frequency signal indicating that the medical injector has been removed, the second wireless signal including information that, when received by the remote computing device, causes the remote computing device to output an instruction associated with the medical injector, the electronic circuit system configured to transmit, via the wireless communication module, a third wireless signal, the third wireless signal being a short-range radio frequency signal indicating a temperature of the container.

14. The apparatus of claim 13, wherein the medical injector is a single-use autoinjector having a distal end portion, a proximal end portion, and defining a longitudinal axis therebetween, the shape of the single-use autoinjector in a plane normal to the longitudinal axis being non-circular.

15. The apparatus of claim 14, wherein the volume defined by the container is elongated such that when the lid is in the second position, the single-use autoinjector can be removed from the volume by moving the single-use autoinjector along the longitudinal axis such that the proximal end portion is removed from the volume before the distal end portion is removed from the volume.

16. The apparatus of claim 13, wherein:

the medical injector is a single-use autoinjector; and the container defines a recess configured to receive a protrusion of the single-use autoinjector to limit movement of the single-use autoinjector when the single-use autoinjector is disposed within the volume of the container.

17. The apparatus of claim 13, wherein the second wireless signal includes information that, when received by the remote computing device, causes the remote computing device to send a location signal associated with a location associated with the container.

18. The apparatus of claim 13, wherein:

the switch is a first switch; and the electronic circuit system includes a circuit board and a second switch coupled to the circuit board, a portion of the lid configured to engage the second switch when the lid is moved between the first position and the second position to actuate the second switch, the electronic circuit system configured to produce an electronic output when the second switch is actuated.

19. An apparatus, comprising:

an autoinjector including a housing and a medicament container disposed within the housing;

a compliance monitor housing including a side wall defining a volume within which the autoinjector can be disposed, the compliance monitor housing including a lid configured to retain the autoinjector within the volume; and an electronic circuit system coupled to the compliance monitor housing, the electronic circuit system including a first switch, a second switch, a light output device, an audible output device, and a wireless communication module, the first switch configured to be actuated when the lid is opened to expose the volume, the second switch coupled to the side wall of the compliance monitor housing, the autoinjector in contact with a portion of the side wall of the compliance monitor housing when the autoinjector is within the volume, the second switch configured to move from a first state to a second state when the autoinjector is removed from the compliance monitor housing, the electronic circuit system configured to transmit, via the wireless communication module, a first wireless signal, the first wireless signal being a short-range radio frequency signal indicating that the compliance monitor housing is within a transmission range of a remote computing device, the electronic circuit system configured to transmit, via the wireless communication module, a second wireless signal in response to the second switch moving from the first state to the second state, the second wireless signal being a short-range radio frequency signal, the electronic circuit system configured to receive, via the wireless communication module, a third wireless signal and produce, in response to the third wireless signal, at least one of a visual output from the light output device or an audible output from the audible output device.

20. The apparatus of claim 19, wherein the wireless communication module includes at least one of a microprocessor, a transmitter, a receiver, a transceiver, or a radio chipset.

21. The apparatus of claim 19, wherein the second wireless signal includes information that, when received by the remote computing device, causes the remote computing device to send a location signal associated with a location associated with the compliance monitor housing.

22. The apparatus of claim 19, wherein the second wireless signal includes information that, when received by the remote computing device, causes the remote computing device to output an instruction associated with the autoinjector.

23. The apparatus of claim 19, wherein the electronic circuit system includes a temperature sensor, the electronic circuit system configured to transmit, via the wireless communication module, a fourth wireless signal, the fourth wireless signal being a short-range radio frequency signal indicating a temperature of the compliance monitor housing.

24. The apparatus of claim 19, wherein the second switch extends from the sidewall of the compliance monitor housing, the second switch including a biasing member configured to bias the second switch towards one of the first state or the second state.

* * * * *